US012233120B2

(12) United States Patent
Carver, III et al.

(10) Patent No.: US 12,233,120 B2
(45) Date of Patent: *Feb. 25, 2025

(54) **PROTEINS AND IMMUNIZING COMPOSITIONS CONTAINING *PASTEURELLA* PROTEINS AND METHODS OF USE**

(71) Applicant: VAXXINOVA US, INC., Willmar, MN (US)

(72) Inventors: Charles Nelson Carver, III, Willmar, MN (US); Daryll Emery, Willmar, MN (US)

(73) Assignee: Vaxxinova US, Inc., Willmar, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,917

(22) Filed: May 31, 2023

(65) Prior Publication Data

US 2023/0414739 A1 Dec. 28, 2023

Related U.S. Application Data

(63) Continuation of application No. 17/191,913, filed on Mar. 4, 2021, now Pat. No. 11,696,945, which is a continuation of application No. 16/484,332, filed as application No. PCT/US2018/017682 on Feb. 9, 2018, now Pat. No. 10,967,056.

(60) Provisional application No. 62/457,599, filed on Feb. 10, 2017.

(51) Int. Cl.
| | | |
|---|---|---|
| *A61K 39/02* | (2006.01) | |
| *A61K 39/102* | (2006.01) | |
| *A61K 39/39* | (2006.01) | |
| *C07K 14/285* | (2006.01) | |
| *C07K 16/12* | (2006.01) | |
| *G01N 33/569* | (2006.01) | |
| *A61K 39/00* | (2006.01) | |

(52) U.S. Cl.
CPC ........... *A61K 39/102* (2013.01); *A61K 39/39* (2013.01); *C07K 14/285* (2013.01); *C07K 16/1242* (2013.01); *G01N 33/56911* (2013.01); *A61K 2039/552* (2013.01); *A61K 2039/55566* (2013.01); *G01N 2333/285* (2013.01)

(58) Field of Classification Search
None
See application file for complete search history.

(56) References Cited

U.S. PATENT DOCUMENTS

| | | | |
|---|---|---|---|
| 5,587,166 | A | 12/1996 | Donachie |
| 6,027,736 | A | 2/2000 | Emery |
| 9,308,247 | B2 | 4/2016 | Narayanan |
| 2009/0123500 | A1 | 5/2009 | Emery |

FOREIGN PATENT DOCUMENTS

| | | |
|---|---|---|
| EP | 0694560 A2 | 1/1996 |
| EP | 2431382 A1 | 3/2012 |
| JP | 9-505085 | 5/1997 |
| JP | 2002-541790 | 12/2002 |
| WO | WO 95/25742 | 9/1995 |
| WO | WO 1996/01620 A1 | 1/1996 |
| WO | WO 00/61724 | 10/2000 |
| WO | WO 2000/61724 A2 | 10/2000 |
| WO | WO 2001/37810 A2 | 5/2001 |
| WO | WO 2007/006101 A1 | 1/2007 |
| WO | WO 2011/125015 A2 | 10/2011 |
| WO | WO 2017/011340 A2 | 1/2017 |

OTHER PUBLICATIONS

American Type Culture Collection, Budapest Treaty on the International Recognition of the Deposit of Microorganisms for the Purposes of Patent Procedure., Deposited on Behalf of : Willmar Poultry Co., Inc., Serotype A: 3,4.
Angen et al., "Taxonomic relationships of the [*Pasteurella*] *haemolytica* complex as evaluated by DNA-DNA hybridizations and 16s rRNA sequencing with proposal of *Mannheimia haemolytica* gen. nov., comb. Nov., *Mannheimia granulomatis* comb. Nov., *Mannheimia glucosida* sp. Nov., *Mannheimia ruminalis* sp. Nov. and *Mannheimia varigena* sp. Nov." 1999, *Int'l J. Systematic Bacteriology* 49:67-86.
Arnold et al., "The Swiss-Model workspace: a web-based environment for protein structure homology modelling", 2006, *Bioinformatics Original Paper* 22(2):195-201.
Bagos et al., "A hidden Markov Model method, capable of predicting and discriminating β-barrel outer membrane proteins", 2004, *BMC Bioinformatics* 5:29.
Boulianne et al., "Production of functional chimaeric mouse/human antibody", Dec. 13, 1984, *Nature* 312:643-646.
Brüggmann et al., "Production of human antibody repertoires in transgenic mice", 1997, *Current Opinion in Biotechnology* 8:455-458.
Carver, "Vaccination with Siderophore Receptors and Porins Protects against Fowl Cholera Challenge by Heterologous Serotypes," Western Poultry Disease Conference. Sacramento, California, Mar. 20-22, 2017.
"Chapter 2.3.9. Fowl Cholera," in *OIE Terrestrial Manual* 2015, pp. 1-11.
Confer et al, "Intranasal Vaccination of Rabbits with Pasteurella multocida A:3 Outer Membranes that Express Iron-Regulated Proteins" Mar. 2013 *AJVR*, 62(5): 697-703.
Database Geneseq [Online] Feb. 2, 2012 (Feb. 2, 2012), "Drug delivery related pore-forming protein, SEQ 10 2985." XP055474131, retrieved from EBI accession No. GSP: AZQ49682 Database accession No. AZQ49682.

(Continued)

*Primary Examiner* — Jennifer E Graser
(74) *Attorney, Agent, or Firm* — Mueting Raasch Group

(57) ABSTRACT

The present invention provides isolated proteins isolatable from a *Pasteurella* spp. such as *P. multocida*. Also provided by the present invention are compositions that include one or more of the proteins, and methods for making and methods for using the proteins.

15 Claims, 41 Drawing Sheets

Specification includes a Sequence Listing.

(56) References Cited

OTHER PUBLICATIONS

Database JPO Proteins [Online] Sep. 26, 2013 (Sep. 26, 2013), "JP 2013121347-A/107: Anti-Bacterial Vaccine Compositions.", XP055474134, retrieved from EBI accession No. JPOP:DL676647 Database accession No. DL676647.

Daugherty et al., "Polymerase chain reaction facilitates the cloning, CDR-grafting, and rapid expression of a murine monoclonal antibody directed against the CD18 component of leukocyte integrins", Mar. 1991, Nucleic Acids Research, 19(9):2471-2476.

Glisson et al, "Cross-Protection Studies with Pasteurella multocida Bacterins Prepared from Bacteria Propagated in Iron-Depleted Medium" Apr. 1993 *Avian Diseases*, 37(4): 1074-1079.

Jones et al., "Replacing the complementarity-determining regions in a human antibody with those from a mouse", May 1986, *Nature* 321:522-525.

Ikeda et al, "Antigenically Related Iron-Regulated Outer Membrane Proteins Produced by Different Somatic Serotypes of Pasteurella multocida" Sep. 1988 *Infection and Immunity*, 56(9):2499-2502.

Keler et al., "Metachromatic Assay for the Quantitative Determination of Bacterial Endotoxins", Oct. 1985, *Analytical Biochemistry* 156:189-193.

Liu et al., "Zinc Sequestration by the Neutrophil Protein Calprotectin Enhances *Salmonella* Growth in the Inflamed Gut", 11:227-239.

Lomize et al., "OPM database and PPM web server: resources for positioning of proteins in membranes", Sep. 2011, *Nucleic Acids Research*, 40:.

Lonberg et al., "Antigen-specific human antibodies from mice comprising four distinct genetic modifications", Apr. 1994, *Nature* 368:856-859.

Lobuglio et al., "Mouse/human chimeric monoclonal antibody in man: Kinetics and immune response", Jun. 1989, *Proc. Natl. Acad. Sci.*, 86:4220-4224.

Mikayama et al., "Molecular Cloning and Functional Expression of a cDNA encoding Glycosylation-Inhibiting Factor", *Proc. Natl. Acad. Sci.*, vol. 90, 10056-10060, Nov. 1993.

Mietinen, "Proportion of Disease Caused or Prevented by a Given Exposure, Trait or intervention", 1974, *Am. J. Epidemiology*, 99(5):325-332.

Morrison et al., "Chimeric human antibody molecules: Mouse antigen-binding domains with human constant region domains", 1984, *Proc. Natl. Acad. Sci.* 81:6851-6855.

Petersen et al., "SignalP 4.0: discriminating signal peptides from transmembrane regions", Oct. 2011, *Nature Methods*, 8(10):785-786.

Patent Application No. PCT/US2018/017682, filed Feb. 9, 2018; [International Search Report / Written Opinion] issued Aug. 16, 2018; 21pages.

Patent Application No. PCT/US2018/017682, filed Feb. 9, 2018; [International Preliminary Report on Patentability] issued Aug. 22, 2019; 14 pages.

Queen et al., "A humanized antibody that binds to the interleukin 2 receptor", Dec. 1989, *Proc. Natl. Acad. Sci.*, 86:10029-10033.

Rice et al., "EMBOSS: The European Molecular Biology Open Software Suite" Jun. 2000, *TIG* 16(6).

Riechmann et al., "Reshaping human antibodies for therapy" Mar. 1988, *Nature*, 332:323-327.

Roier et al, "Immunogenicity of Pasteurella multocida and Mannheimia haemolytica outer membrane vesicles" Jul. 2013 *International Journal of Medical Microbiology*, 303(5):247-256.

Rudinger et al., "Characteristics of the Amino Acids as Components of a Peptide Hormone Sequence," Peptide Hormones, Biol. Council, pp. 507, Jun. 1976.

Stork et al., "An Outer Membrane Receptor of *Neisseria meningitidis* Involved in Zinc Acquisition with Vaccine Potential", Jul. 2010, *PLoS Pathogens*, 6(7).

"Supplemental Assay Method for Potency Testing of Fowl Cholera (*Pasteurella multocida*) Bacterins, Type 1," in *United States Department of Agriculture Center for Veterinary Biologics Testing Protocal*. SAM 607.03, p. 1-11.

Tatusova et al., "BLAST 2 Sequences, a new tool for comparing protein and nucleotide sequences", 1999, *FEMS Microbiology Letters* 174:247-250.

Taylor et al., "A transgenic mouse that expresses a diversity of human sequence heavy and light chain immunoglobulins" 1992, *Nucleic Acids Research*, 20:23):6287-6295.

Wilson et al., "Comparison of DNA Fingerprinting and serotyping for Identification of Avian *Pasteurella multocida* Isolates", Feb. 1993, *J. Clin. Microbiology*, 31(2):255-259.

Office Action issued in Japan for Application No. 2019-543050 dated Jan. 19, 2022 (15 pages). English translation included.

Office Action issued in Europe for Application No. 18708005.6-1112 dated Jul. 30, 2020 (8 pages).

Office Action issued in Europe for Application No. 18708005.6-1112 dated Mar. 25, 2021 (4 pages).

FIG. 3

| Protein ID | MW | Description | Vaccine Strain MS061130 type A: 3x4 | X73: type A:1 | p1059 type A:3 |
|---|---|---|---|---|---|
| 1 | 128,216 | Putative Ton-B dependent hemine receptor | Present | Present | Present |
| 2 | 114,216 | Outer membrane receptor protein, mostly Fe transport | Present | Present | Absent |
| 3 | 109,900 | Outer membrane receptor protein, mostly Fe transport | Absent | Present | Absent |
| 4 | 109,863 | Outer membrane receptor protein, mostly Fe transport | Present | Absent | Present |
| 5 | 104,901 | Outer membrane receptor protein, mostly Fe transport | Absent | Present | Present |
| 6 | 91,308 | Outer membrane receptor protein, mostly Fe transport | Absent | Present | Absent |
| 7 | 90,917 | Outer membrane receptor protein, mostly Fe transport | Absent | Present | Present |
| 8 | 90,887 | Outer membrane receptor protein, mostly Fe transport | Absent | Present | Absent |
| 9 | 90,601 | Outer membrane receptor protein, mostly Fe transport | Present | Absent | Present |
| 10 | 89,635 | TonB-dependent hemoglobin receptor | Present | Present | Present |
| 11 | 88,107 | Outer membrane receptor protein, mostly Fe transport | Absent | Present | Absent |
| 12 | 84,792 | Outer membrane receptor protein, mostly Fe transport, HemR | Absent | Absent | Present |
| 13 | 81,394 | PfhR | Present | Present | Present |
| 14 | 59,543 | Heme binding protein A HbpA | Absent | Present | Present |

FIG. 6

| MW | % Identity | MS | x-73 | p1059 | p1662 | 1121 | 1135 | 1138 | 1558 | 1696 | gonz2 | gonz4 | gonz5 | gonz6 |
|---|---|---|---|---|---|---|---|---|---|---|---|---|---|---|
| 109,862 | | (+) | (-) | (+) | (+) | (+) | (-) | (+) | (-) | (-) | (-) | (+) | (+) | (-) |
| 109,900 | 97% | (-) | (+) | (-) | (-) | (-) | (+) | (-) | (+) | (+) | (-) | (-) | (-) | (+) |
| 92,670 | | (-) | (-) | (-) | (-) | (-) | (+) | (-) | (-) | (-) | (+) | (+) | (-) | (-) |
| 91,308 | >93% | (+) | (+) | (-) | (+) | (+) | (-) | (+) | (+) | (+) | (-) | (-) | (+) | (+) |
| 89,631 | 99% | (+) | (-) | (-) | (-) | (-) | (+) | (-) | (-) | (-) | (+) | (+) | (-) | (+) |
| 84,910 | 99% | (-) | (-) | (+) | (-) | (-) | (+) | (-) | (+) | (+) | (-) | (-) | (-) | (-) |
| 81,332 | 99% | (-) | (+) | (-) | (-) | (+) | (-) | (+) | (-) | (-) | (-) | (+) | (-) | (+) |

FIG.8-1.

SEQ ID NO:1

```
ATGCGTACAACAACAATAAAATTTTCTGCAATTACATTGGCATTATTGAGTTATTGTGGGCTAT
TTTGGCGGATAGTCATCAAGAGGCGACTGAACTTGATACGATTACCGTTTCTTCTCAACAAGATG
AGATGAATATTAAAGAGAAAAAAGTCGGTGAAACTGTGAAAACGGCGAGTCAATTGAAACGCCAG
CAAGTACAGGATAGTCGTGATCTTGTGCGCTATGAAACCGGTGTGACTGTGGTAGAAGCTGGACG
TTTTGGGTCGAGCGGTTATGCCATTCGTGGTGTGGATGAGAACCGAGTGGCAATTACAGTAGATG
GCTTACATCAAGCAGAAACCCTTTCTTCTCAAGGTTTTAAAGAATTATTTGAAGGTTACGGCAAT
TTTAACAATACCCGAAATAGTGTGGAAATTGAGACGTTGAAAGTCGCTAAAATCGCGAAAGGTGC
TGATTCTGTAAAAGTGGGTAGTGGTTCTTTGGGAGGCGCTGTACTTTTTGAAACAAAAGATGCCA
GAGATTTCCTGACTGAAAAGATTGGCATATCGGCTATAAAGCGGGCTACTCAACGGCAGATAAT
CAGGGATTAAATGCAGTGACTCTTGCAGGTCGCTATCAAATGTTTGATGCATTGATTATGCATTC
TAAGCGACATGGACATGAATTAGAAAATTATGACTATAAAAATGGCAGAGATATTCAAGGGAAAG
AAAGAGAGAAAGCGGATCCTTATACGATTACGAAAGAAAGTACATTAGTGAAATTCTCTTTTTCG
CCAACAGAAAATCATCGTTTTACAGTCGCTTCTGATACTTATCTTCAGCATTCCCGCGGACATGA
TCTTTCATACAATCTTGTTGCAACAACACATATTCAGTTAGATGAGAAAGAATCTCGTCATGCAA
ATGATCTGACAAAACGTAAAAATGTTTCCTTTACTTATGAAATTATACTGTTACGCCATTTTGG
GATACGCTCAAGTTAAGCTATTCACAACAAAGAATTACAACAAGAGCAAGAACAGAAGATTACTG
TGATGGTAATGAAAAATGTGACTCTTATAAGAATCCTTTAGGGCTTCAATTAAAAGAGGGAAAAA
TCGTTGATCGTAATGGCGATCCTGTTAATTTGAAGCTTGTTGATGGTAAACATCAAGTTGTAGAT
AAAGCTGGTAAGCCTTTTGATGTAGCCTCTGGAACTAATTATGCGGCTTTCTCAGGTAAAGAATT
AAGTCCTTCTTCTTTTTGGTTAGATTGCTCTATTTTTGATTGTTCTAAGCCTATCAATACTTATA
AATATCGCTATACCTCTTCGGAGCCAACTTTGCAGCAAATTACTTTAAATAAAACCATGGAAATT
AATGGAAAGACATTTGCTACTTATGATGGGCGTGGACACTATATTATTTTACCAAATTCTAAAGG
TTACTTGCCTTTGGATTATAAAGAGCGTGATTTAAATACAAAGACGAAACAAATTAATTTAGATT
TAACAAAAGCATTTACTCTCTTTGAGATTGAAAATGAACTTTCCTATGGTGGTGTTTACGCGAAA
ACGACCAAGGAAATGGTGAATAAAGCAGGATATTATGGGCGTAATCCTACTTGGTGGGCGGAGAG
AACGTTAGGGCAATCATGGGGAAAATTGAGAGAGTGTAAGACAAGTTCTTCATATAATGGGATGC
TATGTCCTCGTCATGAACCATTAACCTCCTTCTTAATTCCGGTAGAAGCAACAACTAAGTCTTTA
TATTTTGCAGACAATATCAAGTTGCACAATATGTTAAGTGTAGATTTAGGTTATCGTTATGATGA
TATTAAATATCAGCCAGAATATATTCCTGGTGTGACACCTAAAATTGCAGATGATATGGTAAAAG
GGTTATTTATTCCATTACCTGAAGGTGAAAAAGTAACTGTAGGGACAATGGTATTCACAAAACCA
CTCACTCAGGCGCAAATTCGTAAGAATGCGGAGGAAAATATTGCTTATATTGCACAAGAAAACG
CTTTAAGAAACATTCTTATTCTCTTGGTGCAACGTTCGATCCTCTGAATTTTTACGAGTACAAG
TAAAATATTCAAAGGGTTTAGGGCCCCGACTTCGGATGAACTTTATTTTACCTTTAAGCATCCA
GATTTTACGATTTTACCGAACCCCGTGTTGAAACCAGAGGAAGCAAAAATCAAGAGATTGCATT
AACAGTGCACGATAATTGGGGATTTGTTAGCACAAGTGTTTTCCAAACAAAGTATCGTCATTTTA
TTGATTTAGCGTATTTAGGTTCAAGAAATTTATCGAATTCCGTGGGAGGGCAGGCACAAGCAAGA
GATTCCAAGTTTATCAAAATGTCAATGTCGATAATGCCAAGGTTAAAGGACTTGAAATTAATGC
ACGTTTGAATTTGGGATATTTCTGGCATGTGTTGGATGGATTTAATACGAGCTATAAATTCACTT
ACCAACGTGGTCGTTTGGATGGCGATCGTCCAATGAATGCGATTCAGCCTAAAGCTTCTGTTTTT
GGTTTAGGCTATGATCATAAAGAAAATAAATTTGGCGCTGATTTATATATCACACGTGTGAGTGA
```

FIG.8-2.

```
AAAAAAGCGAAAGACACTTATAATATGTTCTATAAAGAACAGGGATATAAAGATAGTGCTGTTCG
TTGGAGAAGTGATGACTATACGCTAGTTGATGCGGTTGGTTATATTAAACCGATTAAGAATTTAA
CGTTACAGTTTGGCGTTTATAATTTGACAGACCGTAAATACTTGACATGGGAATCTGCTCGTTCG
ATTAAACCATTTGGTACAAGTAATTTAATTAATCAGAAAACAGGCGCAGGAATTAATCGTTTTTA
CTCACCAGGTCGTAATTTTAAATTTAGTGCCGAAATTACCTTCTAA
```

SEQ ID NO:2

```
MRTTTIKFSAITLALLSYCGAILADSHQEATELDTITVSSQQDEMNIKEKKVGETVKTASQLKRQ
QVQDSRDLVRYETGVTVVEAGRFGSSGYAIRGVDENRVAITVDGLHQAETLSSQGFKELFEGYGN
FNNTRNSVEIETLKVAKIAKGADSVKVGSGSLGGAVLFETKDARDFLTEKDWHIGYKAGYSTADN
QGLNAVTLAGRYQMFDALIMHSKRHGHELENYDYKNGRDIQGKEREKADPYTITKESTLVKFSFS
PTENHRFTVASDTYLQHSRGHDLSYNLVATTHIQLDEKESRHANDLTKRKNVSFTYENYTVTPFW
DTLKLSYSQQRITTRARTEDYCDGNEKCDSYKNPLGLQLKEGKIVDRNGDPVNLKLVDGKHQVVD
KAGKPFDVASGTNYAAFSGKELSPSSFWLDCSIFDCSKPINTYKYRYTSSEPTLQQITLNKTMEI
NGKTFATYDGRGHYIILPNSKGYLPLDYKERDLNTKTKQINLDLTKAFTLFEIENELSYGGVYAK
TTKEMVNKAGYYGRNPTWWAERTLGQSWGKLRECKTSSSYNGMLCPRHEPLTSFLIPVEATTKSL
YFADNIKLHNMLSVDLGYRYDDIKYQPEYIPGVTPKIADDMVKGLFIPLPEGEKVTVGTMVFTKP
LTQAQIRKNAEENIAYIAQEKRFKKHSYSLGATFDPLNFLRVQVKYSKGFRAPTSDELYFTFKHP
DFTILPNPVLKPEEAKNQEIALTVHDNWGFVSTSVFQTKYRHFIDLAYLGSRNLSNSVGGQAQAR
DFQVYQNVNVDNAKVKGLEINARLNLGYFWHVLDGFNTSYKFTYQRGRLDGDRPMNAIQPKASVF
GLGYDHKENKFGADLYITRVSEKKAKDTYNMFYKEQGYKDSAVRWRSDDYTLVDAVGYIKPIKNL
TLQFGVYNLTDRKYLTWESARSIKPFGTSNLINQKTGAGINRFYSPGRNFKFSAEITF*
```

FIG. 9-1.

SEQ ID NO:3

ATGGAATCCGCAAAAAATCCACTCAAAAAGACGACACTTGCACTCCTCTGTTGTTCTACCGCCTT
CTCGCTTTCCGCAAAAACCGATACGAACGCCGATAAAAATCACTTTCTGACGGAAATTGTCGTGT
ATGCGGATCAAAATAAATCAATGAGTTCAACACAGAGTGTCACTCAAGATGACATGAAAAAAGC
CCTGTCACAAATGGTAATATTACTGACTATTTACGTTCAAATCCGCATGTGCGTTATGAGAATAG
CGATCAAATGGATTGCAACGAGGTGAAATTAAACCCGAAACATTTCAATTAATGGTGCAGATT
ATCAGCAGACCACTTTTTTTGTCGATAATGTAAATATCAATAATGATATGGGATTTGGTAGTGAT
CTTTTTGACGGCACCATGGCAACAGTCCCCTTTGCCAATCATTCTCAAGGCTACTTTTTTGATGC
CAATCTGCTCTCTTCAATTGTAGTGCATGACAGTAATGTTTCTGCCAGCTTAGGAGGATTTGCGG
GGGGAGCCGTCGTGGCGAAAACCAAACAATATGATGGGAAAGATCGGTTAAAATTTAGTTATCGT
ACAACTGATGCCTCATGGGCAAAATTTAAAGTAGAAGACAAAGATCTTGAACGTTTTAAAAATGC
GATTCCTGAAGGATCGGTCGCCGAATTTCAACCTAAGTATTCTAAACACTTTTTCAATATCACGG
CAGAAAAAGGGTTAAGTGAAATTTAGGTATGGTGATCGGATTAAGTCGTAGAACATCAAGTATC
CAACAATCACGTCAAATTAATCCACAAGGTGATCGTGATAAACAAACACATACAAGACGTTCAGA
CAATGCGTTACTGAATTTTAATCTGACACCAAACGACAAACACCGTTTCGAACTCGGTTTCAGAT
ACTCAAATTATCGTGAGCGTAAATTCTTTAATACTAATATAGACAGTAATGTTTTTGACTATCAC
CGTGCTTATGGTGTGACTTTCTCTTGGATAAACGCCCTTCAGTCTGGCATTCTCACGACGACACT
CGCCTATGATAACTTTGATGACACGAGAAAATCAGCGTCAACTTATATGAAAACGACGCTCACTG
AAGAGGGTGAGGAATATACCGAAGGTGGAATGGGTAACAGTCAATTGAACCAAAAAAATTTACAT
ACGTCACTTGAATATGCGATGAATCCTTTTAATTTAGGTTCAATAGAACACTCTGTATCATTAGG
CGGTATTTATCAAGCAACGAAATATCGCTTTACGCGACATTCAGATGCAGTCGGTGAATTGTATA
CTCCTGATTGGTTAAATGGTAATACAGATAAACTTATATTGACGCAACGTAACATAGCCAAAAAA
GGGACCGTAAAAACACGTTATCAAAATATCGCACTTTACGTGGAAGATTTAATGACGTGGAAAAA
TCTCGAATTTCGGGCGGGACTTCGTCTTGAACGTGATGATTATTTAAAAAACACGAATTTGGCGC
CAAGAACCGTTTTTCGTTATAAACCATTTGAAGACACCGCATTCAGTGTGGGTTGGAACCGTTAC
TACGGACGTTCCTTTGCCTCAATGAAATTATCTGAAGGTATCTTCAAATTAGATGGTCATGATAC
CTTCCGTTACAAAGACCTTAGCCAATTTAAAACCCCTTATTCAGACGAACTGAGCTTTGGTGTAG
AACAATATGTTGCTAATCTCGCCTTTCACTTGAAATACATTTTACGTGATAACAAACAACGTATT
GTTTTACAAGAAGAAGAGGTCATGTTAAATGGAGAAAGGAAAAAACTCCGCTATTACCAACGAGG
AAAAGACTACAAAACGAATGTGTTAACCTTCCAAATTAACACACAAGCGCCTTGGGAGCTTGGTC
CAACACGCTGGACAAGTGCAGTGGCATTTGATTGGTTAGATAGCAAAGCTATCGATCATGGCAGG
GGCTATAACGGTTCGACACCTGTGATTTAGACGGGAAATTAATGACTTATGAGCAAATGTTGAA
AAAAGTCAATGCTTACAAAGAAACATGGGGTCTACGTTTAAATCTTGACATGTTTGTTCCAATAT
TTGATCTTTCTTGGGCTAATACAATCTATGTCAAACCACCAACAACCTTAACCGAACGCGTTAGC
AGTAATACACCTGAGGTATATCGTAGCTATGATTATGGTACTTATACACAATGGGATACCAGTCT
TCGCTGGCAGCCAACTTTCGCAGAAAACACCGTCCTTATATTAAATTAGATGTACTTAATGTGT
TAAATAAAACACGTAAAGGCGCGGGTCCAAATGGACAAGATCTCGGCATCTACACCCCCGGTCGT
GAGTTCTGGCTTGAAGTTGGTTACGAATTCTAA

FIG. 9-2.

SEQ ID NO:4

```
MESAKNPLKKTTLALLCCSTAFSLSAKTDTNADKNHFLTEIVVYADQNKSMSSTQSVTQDDMKKS
PVTNGNITDYLRSNPHVRYENSDQNGLQRGEIKPENISINGADYQQTTFFVDNVNINNDMGFGSD
LFDGTMATVPFANHSQGYFFDANLLSSIVVHDSNVSASLGGFAGGAVVAKTKQYDGKDRLKFSYR
TTDASWAKFKVEDKDLERFKNAIPEGSVAEFQPKYSKHFFNITAEKGLSENLGMVIGLSRRTSSI
QQSRQINPQGDRDKQTHTRRSDNALLNFNLTPNDKHRFELGFRYSNYRERKFFNTNIDSNVFDYH
RAYGVTFSWINALQSGILTTTLAYDNFDDTRKSASTYMKTTLTEEGEEYTEGGMGNSQLNQKNLH
TSLEYAMNPFNLGSIEHSVSLGGIYQATKYRFTRHSDAVGELYTPDWLNGNTDKLILTQRNIAKK
GTVKTRYQNIALYVEDLMTWKNLEFRAGLRLERDDYLKNTNLAPRTVFRYKPFEDTAFSVGWNRY
YGRSFASMKLSEGIFKLDGHDTFRYKDLSQFKTPYSDELSFGVEQYVANLAFHLKYILRDNKQRI
VLQEEEVMLNGERKKLRYYQRGKDYKTNVLTFQINTQAPWELGPTRWTSAVAFDWLDSKAIDHGR
GYNGSTPVILDGKLMTYEQMLKKVNAYKETWGLRLNLDMFVPIFDLSWANTIYVKPPTTLTERVS
SNTPEVYRSYDYGTYTQWDTSLRWQPTFAEKHRPYIKLDVLNVLNKTRKGAGPNGQDLGIYTPGR
EFWLEVGYEF*
```

FIG. 10-1.

SEQ ID NO:5

ATGTCATTCAAACATAAAACACTGGCGCTTTTTGTCGCACATGCTTGCTGCACTTCTGCCTTAGC
AGAAAACGTGGCTACCACGTTAGAACCCATCGTGGTTTCTGATCTCAGTCATACCACGCTGAACC
TTGATCAAAATAAGCTTGAAAAGAAAGTCCAAAAGATTTAAAAGCTATTTTTGCCACAACGCCA
AATATTAATGTTATCCATACGGGACATGCACAATTAGGCGATATTGAAATTCGCGGTATGGGAAG
CAGCCGAGAAATCTTTGCTACCGGCGCAAACCGCGTCACAATGGAATTAGACGGTATGGACATTA
GCCCGAGTTTTTATTTTGGACACAGCTCACGCCATGGTCGGCAATATTTTGATCCCAGTGATCTA
AAACGTGTTGAGATTCATAAGGTCCAAACAGTCAAGGCGTGGCAGGGCATGTTCGTTTCCAAAC
GAAAGATCCTCGTGATTATCTCTTGCCTAACCAACGTACAGGTGCACAACTTCGTGCTGGCTATT
TAGGCGATAGTGATGCTTATTATGTTGGGATAACTGGTGCCACTTTATTGGATGAACACAGTAGT
GCTTTAGTGAGCTATACACGACGCTGGTTTAATGAATTTAATAATAAGGGAGGCTTGGATGTCAC
AGGTAGTCAACGTACTAAAAGCAATCCTTCCAGTGGTTATAGTAATGCAGTGAACAGTAAATTAC
GCTATTCACCAAATGACCGCCATAAATTTACGCTGAATTTGCAACATTATGATTTAAAACGCACC
GCCTATTTAGAAGATAGCTTAGGAACAACGACAACACGACGTGGCACAAAAACAGTTCATCATAA
TACCAACATTCAGAAAAATCAGCGTCATGCTATTGCTTTCAGTCATGACATGCAACAAACCACGG
CATTTTTTGATCACCTGCACTGGCAAATTGCGTTACAACAAACGAAAAGCACGAGCCGTAATACA
GGGGCAGTCACGAATACATCAGCATCTCCTCCCCAAGTACGCCAAAATTTAGCCAAGAGCGTTC
ACTTGATGGCTTTAAAACCAAAACCATCAGCTTAAAAACGGAATTCAATAAAAGCATTGGGCAAC
ATGTCGTACATGAACTTCACTATGGACTAAAATTACAATATAGCCAAATGCAAGCTTTACGCCAA
ACACAATCCCTAAACGAACAAGGGAGTAACACTCGAACCAGCGCCTTTTCCCGACACAGCAACA
ATGGCAAAGTAAACTCCATCTTTCCGATCGGATCAGTTTTGGTAAATCTGGTTTAAGCTTGACAC
CATCCATACATCTCACACAGATTAGAATCAAACCGAAAACAGAAAATGTATCGAAGAAAAACCGT
GAACAATTATTTACTTACAAGGATACCGCCATTGGTTACGGTCTGCGTGTTGATTATGCACTCAA
TGAAGCGAATTTACTGAGTCTGAACTATCAGCACGCCACTCGCTTACCCGGCTATGGTGAAAACA
ATGCGCAAAGCTATGGACACTGGCCAGCAAAACCGAACCCTCATCTACAGCCAGAAACCTCAGAT
GGTATTGAATTAAGTTGGCGTAGTGCGGGGCGATTGGTCAACAAACCACGACCTTGTTCTATAA
CCGTTACAATGACTTAATTTATCTCGATACCACGGCATGTTATGCTGACCGAACAGGTCAAGTGC
CTTGTGATTTAGCAAATGAAAAGGACGTAGTTATAGCTATGGAATAGAATTCGACGGTAAACTC
AATCTTGATACGATCGGCTTCGCTCAAGGAACATATTTAAATGCTGGCTTCGCTTACAGCAAAGG
GAAGACCGCGAACAAGCAACCACAAGGACGTCTTGATCCCCTAACAGGCTTTGTCGGTCTTGGCT
ACCAACAGCCAATGGATGTTTGGGGCATTGAAGGTAAACTGAAATTTGCCGCGAAGAAAAAACT
AAAGACTTACCCGCCAATCAAGGTTTTGAAGGCTTACCGGGCTATGCTGTAGTTGATCTTACCGC
CTATTATAATGTGACGAAACAGCTTTATCTTGGCATCGGCATCTATAATGTGCTAGATAAAAAAT
ATGCTCGCTGGGCAATGGCAAGAGGCGACATTAAACATGGTAACTATGACAAGCACACTGAAGCA
GGTCGTCATTTTGGTGCCAATATTCGTTACCACTTTTAA

SEQ ID NO:6

MSFKHKTLALFVAHACCTSALAENVATTLEPIVVSDLSHTTLNLDQNKLEKESPKDLKAIFATTP
NINVIHTGHAQLGDIEIRGMGSSREIFATGANRVTMELDGMDISPSFYFGHSSRHGRQYFDPSDL
KRVEIHKGPNSQGVAGHVRFQTKDPRDYLLPNQRTGAQLRAGYLGDSDAYYVGITGATLLDEHSS
ALVSYTRRWFNEFNNKGGLDVTGSQRTKSNPSSGYSNAVNSKLRYSPNDRHKFTLNLQHYDLKRT

FIG. 10-2.

```
AYLEDSLGTTTTRRGTKTVHHNTNIQKNQRHAIAFSHDMQQTTAFFDHLHWQIALQQTKSTSRNT
GAVTNTSASPPPSTPKFSQERSLDGFKTKTISLKTEFNKSIGQHVVHELHYGLKLQYSQMQALRQ
TQSLNEQGSNTRTSAFFPTQQQWQSKLHLSDRISFGKSGLSLTPSIHLTQIRIKPKTENVSKKNR
EQLFTYKDTAIGYGLRVDYALNEANLLSLNYQHATRLPGYGENNAQSYGHWPAKPNPHLQPETSD
GIELSWRSAGAIGQQTTTLFYNRYNDLIYLDTTACYADRTGQVPCDLANEKGRSYSYGIEFDGKL
NLDTIGFAQGTYLNAGFAYSKGKTANKQPQGRLDPLTGFVGLGYQQPMDVWGIEGKLKFAAKKKT
KDLPANQGFEGLPGYAVVDLTAYYNVTKQLYLGIGIYNVLDKKYARWAMARGDIKHGNYDKHTEA
GRHFGANIRYHF*
```

FIG. 11-1.

SEQ ID NO:7

```
ATGCGTACAACAACAATAAAATTTTCTGCAATTACATTGGCATTATTGAGTTATTGTGGGGTCAT
TTTGGCGGATAGTCATCAAGAGGCGACTGAACTTGATACGATTACCGTTTCTTCTCAACAAGATG
AGATGAATATTAAAGAGAAAAAAGTCGGTGAAACTGTGAAAACGGCGAGTCAATTGAAACGCCAG
CAAGTACAGGATAGTCGTGATCTTGTGCGCTATGAAACCGGTGTGACTGTGGTAGAAGCTGGACG
TTTTGGGTCGAGCGGTTATGCCATTCGTGGTGTGGATGAGAACCGAGTGGCAATTACAGTAGATG
GCTTACATCAAGCAGAAACCCTTTCTTCTCAAGGTTTTAAAGAATTATTCGAAGGTTACGGCAAT
TTTAACAATACCCGAAATAGTGTGGAAATTGAGACGTTGAAAGTCGCTAAAATCGCGAAAGGTGC
TGATTCTGTAAAAGTGGGTAGTGGTTCTTTGGGAGGCGCTGTACTTTTTGAAACAAAAGATGCCA
GAGATTTCCTGACTGAAAAGATTGGCATATCGGCTATAAAGCGGGCTACTCAACGGCAGATAAT
CAGGGATTAAATGCAGTGACTCTTGCAGGTCGCTATCAAATGTTTGATGCATTGATTATGCATTC
TAAGCGACATGGACATGAATTAGAAAATTATGACTATAAAAATGGCAGAGATATTCAAGGGAAAG
AAAGAGAGAAAGCGGATCCTTATACGATTACGAAAGAAAGTACATTAGTGAAATTCTCTTTTTCG
CCAACAGAAAATCATCGTTTTACAGTCGCTTCTGATACTTATATACAACGTTCTCGTGGCCATGA
TCGCTCTTATTCTTTACAGCCTCAATCTAATTATTTCACATATGACGAGAAAGAATCGCGTCATG
CAAATGATTTGACAAAACGTAAAAATGTTTCTTTTACTTATGAAAACTATAGCGTAACTCCATTT
TGGGATACGCTAAAATTGAGTTATTCACAACAAAAGATCAGAACAAGAGCAAGAACAGAAGATTA
TTGTGATGGTAATGAAAAATGTGATTCTTATAAAAATCCATTAGGGCTTCAGTTGAAAGATGGCA
AAATTGTTGATCCAGAGGGAAATCAGATTACTTTAAAAGGAACAGGATTTAATACAGAAATAGTT
GATAAAAATGGTAACCCATTTCCTACGACATCTGGTACTAATAATGCAGCATTTAGTAATAATAT
TCAGTTAGGACCTAAAGAATTTTGGTTAGATTGTTCTCTTTTTGATTGTACTCAGCCATTTACTG
TTTATAACTATCAAAATGGTCAATATACGCCAAAACAAGTTGAGTTATCTGAAGAAATCACTGTC
AATGGTAAATTATATAAAACAGCTAAAGAAGAAAGAGGTGTTAGGAACTATTTAATTTTACCTAA
TTCAAAAGGTTATTTACCATATGATTACAAAGAAAGAGATCTTGATTCAAATACAAAACAAATCA
ATTTGGATTTAACAAAAACATTTTCGACTTTTAATATAGAAAATGAATTATTATACGGTGCCATT
TATTCACGTACAGAGAAGAAAATGGTTAATAAAGCAGGTTACGATGGGAGAAATCCTACATGGTG
GGCTGATAGAATTTTAGGGAAGAGTACGAATTGTAACTATAATGGACTGAAATGTCCTCGTCATG
AACCTTTAACTTCTTTCTTAATTCCAGTAGAAGCGACAACCAAGTCTCTATATTTTTCAGATAAT
ATCAAATTACACAACATGTTGAGTGTAGATTTAGGTTATCGTTATGACGATATTAAATATCAACC
AGAATATATTCCTGGTGTAACACCTAAAATTGCAGATGATATGGTGAAAGGTATTTTTATTCCAT
TACCTAAGGGAGAAAAAGTAACAACACCTTGGGGGGCCGAATATACAAAACCACTCACACAGGAA
CAAATTCGTAAGAATGCGGAGGAAAATATTGCTTATATTGCACAAGAAAAACGCTTTAAAAAACA
TTCTTATTCTCTTGGTGCAACGTTCGATCCTCTGAATTTTTTACGAGTACAAGTAAAATATTCAA
AAGGGTTTAGAGCCCCGACTTCGGATGAACTTTATTTTACCTTTAAGCATCCAGATTTTACGATT
TTACCGAACCCCGTGTTGAAACCAGAGGAAGCAAAAAATCAAGAGATTGCATTAACAGTGCACGA
TAATTGGGGATTTGTTAGCACAAGTGTTTTCCAAACAAAGTATCGTCATTTTATTGATTTAGCGT
ATTTAGGTTCAAGAAATTTATCGAATTCCGTGGGAGGGCAGGCACAAGCAAGAGATTTCCAAGTT
TATCAAAATGTCAATGTCGATAATGCCAAGGTTAAAGGACTTGAAATTAATGCACGTTTGAATTT
GGGATATTTCTGGCATGTGTTGGATGGATTTAATACGAGCTATAAATTCACTTACCAATGTGGTC
GTTTGGATGGCGATCGTCCAATGAATGCGATTCAGCCTAAAGCTTCTGTTTTTGGTTTAGGCTAT
GATCATAAAGAAAATAAATTTGGCGCTGATTTATATATCACACGTGTGAGTGAGAAAAAAGCGAA
AGACACCTATAATATGTTCTATAAGAACAGGGGTATAAAGATAGTGCTATTCGTTGGAGAAGTG
ATGACTATACGCTAGTTGATGCGGTTGGTTATATTAAACCGATTAAGAATTTAACGTTACAGTTT
```

FIG. 11-2.

GGCGTTTATAATTTGACAGACCGTAAATACTTGACATGGGAATCTGCTCGTTCGATTAAACCATT
TGGTACAAGTAATTTAATTAATCAGAAAACAGGCGCAGGAATTAATCGTTTTTACTCACCAGGTC
GTAATTTTAAATTTAGTGCCGAAATTACCTTCTAA

SEQ ID NO:8

MRTTTIKFSAITLALLSYCGVILADSHQEATELDTITVSSQQDEMNIKEKKVGETVKTASQLKRQ
QVQDSRDLVRYETGVTVVEAGRFGSSGYAIRGVDENRVAITVDGLHQAETLSSQGFKELFEGYGN
FNNTRNSVEIETLKVAKIAKGADSVKVGSGSLGGAVLFETKDARDFLTEKDWHIGYKAGYSTADN
QGLNAVTLAGRYQMFDALIMHSKRHGHELENYDYKNGRDIQGKEREKADPYTITKESTLVKFSFS
PTENHRFTVASDTYIQRSRGHDRSYSLQPQSNYFTYDEKESRHANDLTKRKNVSFTYENYSVTPF
WDTLKLSYSQQKIRTRARTEDYCDGNEKCDSYKNPLGLQLKDGKIVDPEGNQITLKGTGFNTEIV
DKNGNPFPTTSGTNNAAFSNNIQLGPKEFWLDCSLFDCTQPFTVYNYQNGQYTPKQVELSEEITV
NGKLYKTAKEERGVRNYLILPNSKGYLPYDYKERDLDSNTKQINLDLTKTFSTFNIENELLYGAI
YSRTEKKMVNKAGYDGRNPTWWADRILGKSTNCNYNGLKCPRHEPLTSFLIPVEATTKSLYFSDN
IKLHNMLSVDLGYRYDDIKYQPEYIPGVTPKIADDMVKGIFIPLPKGEKVTTPWGAEYTKPLTQE
QIRKNAEENIAYIAQEKRFKKHSYSLGATFDPLNFLRVQVKYSKGFRAPTSDELYFTFKHPDFTI
LPNPVLKPEEAKNQEIALTVHDNWGFVSTSVFQTKYRHFIDLAYLGSRNLSNSVGGQAQARDFQV
YQNVNVDNAKVKGLEINARLNLGYFWHVLDGFNTSYKFTYQCGRLDGDRPMNAIQPKASVFGLGY
DHKENKFGADLYITRVSEKKAKDTYNMFYKEQGYKDSAIRWRSDDYTLVDAVGYIKPIKNLTLQF
GVYNLTDRKYLTWESARSIKPFGTSNLINQKTGAGINRFYSPGRNFKFSAEITF*

FIG. 12-1.

SEQ ID NO:9

```
ATGCAAAAACAGCAACCTTATCCCATTCACCTTGGGATTTTTTTGATGTTGGGTTTACCAACATG
GGCGTTCAGTCAAGCTAATTTAGAGAAATCAACAATCAATAAATTGGAAACGATTTTGGTCAATG
AGAGTGAAGAGAAAAATAAATTCGATGAGAATTTGATCAAAACTTATCTGTCTTCGGGTTCTTAT
TCTTATTTATCGCAATCGGATATCAGTACGTTCAGAGGTAGCTCGGTAGGGGATTTCCTCTCTGG
TGTACCAGGAGTTATTGTGGGAAATAAGCGTAATAGCGGCGCTTTATCCGTTAATATTCGAGGAA
TTGCGAATGAAAATCGTGTGCCTGTTTGGATAGATAAAGGTCTACAATCGGTACCCTCTTACCAA
GGTTATGCAGGTTCTTCAACTCGAACCTATTTAGATCCCGATTTGATCAGCCAAGTCGAGATTGA
AAAGGTCCCTCTTTGCAAATGGACGCAACAGGCGCGACGGGAGGGGTAGTGAGAGTAGAGACTT
TACGTTGGCAAGATATTATTCCTCAAGGGAAAAATTGGGGCGTGCGTTTGAAACTAGGGACGATG
ACTAACACCGTATCACCTCCCCCTTATTATACAAGAGGAGGATATCAAACTAAGTATATTAGTAA
ATGTCTTTCTAATGATACTGGTTTATGTCAAACACAAACATATGCACCAAATGCACGCTATTCTT
CTCATGGCTTTGATTTGAATGCATACAATTATAGCCTGGCTTTTGCTAATAAATGGCAAAATGCT
GATCTTGTACTTGCGTATGCAAAACGTAAACAGGGCAACTATTTTGTTGGGCGTCATGGACAAAC
CCCAGTGATTGAATCCATTGAATTTGAGGAAGATTCAGTAGAAGTCAAAGAGCCTCGCGTTCATG
AAGAGGTTGAAATTGGTTCATTAACATTTAAAGAAATCGCAGCACCTTATATCGACCGGGTGAA
GAAGCCCTGAATACCTCACAAGATAATACCTCTTATCTCGCTAAAATAAATGTCTACAATGATGT
TCATCGTTTAGGGTTAGCGTATCGCCATTATCATAGCCGTTTTGGTGAGATTATGAGCTCAATTT
TGAATTTCAGAGCGTATGGCGCATTGCAAGGTGAAGGGACAGAAGTCAAAGTCGATAGCTATCAT
GCAAATTATAGCTATAACCCAACGACACCTTATGTGAATTTGAATGTTAATGCATATTTTACTGA
CAGTGATTCGTCTAATTTTACCCCATTTATTGAAGAATATGGTTACTCTTTATCCAGTCGTCATG
CCCATTTTCTGGTTTCTAAGCAGAAAGGGTTAAGTATTGAAAATACTAGCATTTTCCAGCTTAAC
GACAAACCGTTTAGTTTAAAATATGGTCTTGCGCATAGTTATGAACGGATTTATCAACCACGTAA
TGCTCAAGCACGTGTGAGAGCTAAAGGGTATCCAGAAGATGCGATTGGTCCACTTTATATTCGAG
ATGGTAAGCGTAAAGAATGGAGCGCTTTTGTTGCTGCGAACTATCCAATCACTTCGTGGTTAAAA
GCCGACATCGGGCTACGTTATCTTCAATCTACTATTTATGATTATATTGTGAGAACGGAAAGAGT
GAATATTGGAGGGGCACTTGTGCCTAATCCAAATGGATCCGGTAATATTTGGGTGGAAAAATATA
AAGATGTTGTGCATAAACAGGCGCCAGTGAAAAATAAAGGCATGTCGCCAATTGTGATGCTCACA
TTTGAACCTATTAACGGAGTACAAATTTATACGAAATATGCAGAAGCATTGCGTTCGCCAAGTTT
ATTCCAAGCAACTAAAGGCTGGTCCATGAGTGCGACGGCAGATAATCTAGAACAATTGAGACCTG
AACGAGCCCAAAATTGGGAGGCGGGTATTAACTTGTTTTATGAAAATCTAGGTGGTAAGGACAAT
ATTCTTGGTTTTAAATTGGCGTATTTTAATAATAGGATAAAAGATTATTTGACGCGGAGTTATTC
GCCTAAAGATAAGGTGACGCAGACAATTAATATACAAAGTGCACAATTTAAAGGAATTGAGTTAT
CAGCGTATTATGATATGGGGAAATTTTACGCAAAATTAGCTGGTACATATTACACAAAAACGAAA
TTTTGTTTAACAGCAGAACAAGCAGGCAAAGGAGAGCAATGTAATTCAGGTTATGTATATCGTAG
TAATTTAAATAATGCCGTTCCTCCGCGTTTAAATTTACATGCGACTTTAGGAACCCGTTTGTTTG
AACAAAAACTCGATATTGGTGCGCGCTATAGTTACTACAGTAAGCGATTAGTACCAGTGCTTTCT
GCAGAACGTTTTGTTAACACATCAAGTATTGAGTGGGCGCCTTATTCCTTAGTAGATTTATATGC
CAATTACAATGTGTCTAATAACCTAAAACTTACGATGACCATGGATAATGTGTTTAATCGCTATT
ATTTAGATATCAATAATATGGGATTAAATACCGCACCGGGTAGAACATTGCATTTAGGATTAGAA
TATCGGTTTTAG
```

Fig. 12-2.

SEQ ID NO:10

MQKQQPYPIHLGIFLMLGLPTWAFSQANLEKSTINKLETILVNESEEKNKFDENLIKTYLSSGSY
SYLSQSDISTFRGSSVGDFLSGVPGVIVGNKRNSGALSVNIRGIANENRVPVWIDKGLQSVPSYQ
GYAGSSTRTYLDPDLISQVEIEKGPSLQMDATGATGGVVRVETLRWQDIIPQGKNWGVRLKLGTM
TNTVSPPPYYTRGGYQTKYISKCLSNDTGLCQTQTYAPNARYSSHGFDLNAYNYSLAFANKWQNA
DLVLAYAKRKQGNYFVGRHGQTPVIESIEFEEDSVEVKEPRVHEEVEIGSLTFKENRSTLYRPGE
EALNTSQDNTSYLAKINVYNDVHRLGLAYRHYHSRFGEIMSSILNFRAYGALQGEGTEVKVDSYH
ANYSYNPTTPYVNLNVNAYFTDSDSSNFTPFIEEYGYSLSSRHAHFLVSKQKGLSIENTSIFQLN
DKPFSLKYGLAHSYERIYQPRNAQARVRAKGYPEDAIGPLYIRDGKRKEWSAFVAANYPITSWLK
ADIGLRYLQSTIYDYIVRTERVNIGGALVPNPNGSGNIWVEKYKDVVHKQAPVKNKGMSPIVMLT
FEPINGVQIYTKYAEALRSPSLFQATKGWSMSATADNLEQLRPERAQNWEAGINLFYENLGGKDN
ILGFKLAYFNNRIKDYLTRSYSPKDKVTQTINIQSAQFKGIELSAYYDMGKFYAKLAGTYYTKTK
FCLTAEQAGKGEQCNSGYVYRSNLNNAVPPRLNLHATLGTRLFEQKLDIGARYSYYSKRLVPVLS
AERFVNTSSIEWAPYSLVDLYANYNVSNNLKLTMTMDNVFNRYYLDINNMGLNTAPGRTLHLGLE
YRF*

FIG. 13-1.

SEQ ID NO:11

```
ATGAAATATCCCTTAAGCTATAAAAATATAGCAAGGTCCATTCCTTTTCTCTCATTCATTGCGTT
TCCTCTGTATGCGCAAGAAACGACTGAATTAGAACAAATTACAGTACAAGAAAGCGCAACCGCTG
AAGTGAACAAAACCTCACCAACAGTGATCAGCAAAAGCGCCACGACCATTCAAAACGAAATGATT
CGAGACACCAGAGATTTAGTCCGCTACACAACGGATGTAGGGATTAGCGATAATGGGCGTTTTTT
GAAAGGCTTTGCGATGCGAGGCGTTGAAGATAACCGCGTTGGTATCAGTATTGATGGTGTTTCTT
TGCCTGATTCAGAAGAAAACTCACTGTATGCGCGTTATGGTAACTTTAATAATTCCCGCCTAAGC
ATTGATCCTGAATTAATTCAAACCATTGATATTGTACGCGGCTCAGATTCCTTTAATGCAGGCAG
CGGTTCATTAGGTGGCGGTGTGAATTATAACACTTTAGATCCACAACATATTGTTAAAACAGGTA
ATTCCGTTGGTGCTTTACTACGAGGCAGTTATGCCAGTAAAAATCGTGAATGGGTTCGTACTTTA
GGGATAGGCTATGTTGGCGAAAAATTTGATGCCTTATTGATGTATTCACAACGCACAGGGCACGA
GTTTAAAAGTCGTGGTTCAGGTCCTGAATTTCGGTATTCCAGTAGCCAGCATCCCGATCCTGTGA
CACAACGCTTCCACAATTATCTCGCTAAATGAATTATCAAATTAATGACAAACAACGTATTGGT
TTAACGCTGAATGGGCAAACAGGGGGGCGTTACATTGATGAGCGTTCTTATACGTTAATGGGCTC
ACAATGGCGTGAAGCCGATGATCAAAACGAACGGTTGAATGCAAACTTATATTATATTTATGCAC
CAAGCACGGGATGGTTAGCCTACAGTAAATTTGATTTAGATTATCAAAAGACCGATCTAGCAGCA
GTTAACTATAAAGGCGGACGCCATTTCACGACAGATGCTAAAGAGCTGAACGAAATTTATGATCG
CCGTATGAAAACCGTGTTTACGCGCGGCAGTGTAGAACTCAATGCACAACCTGTACATTTCTATG
GTGAACATACTTTAACCATCAAAGGCTATGTTAGTCAGCGTGATTTCAAAAATATCAATCAAGAT
CGTATCGGTATTGGCACAAACTACGACACACAATACCACTATACGATTCAATATCCTATTAGAAC
CAAGCAGTACGGGCTTTCTTTGAAAGATCATGTGCGCTGGAATGATACCTTCTCAAGCCATTTAG
GTTTACGTTATGACCATACAAAACTAAAACCAAAGGAACTCAATGCACCTTGTAGCAAAGCCTGT
TTAGAAGAAGGAAAACCTAAACCGACCCGTTTCTCTACCGTTAGCACATTTGCGGGATTTGAGGC
ACAACTCAGCCCCTCATGGATGTTAGGCTACAATATTAGCACCGGTTATCGTGTACCAACGGCTT
CAGAAATGTTCTTCAGCTTTACCAATGCGTATGGCACGTGGAAATCTAACCCGAGCTTGAAACCC
GAAAAAGTATTAACCATACACTCTCTTTGAAAGGCAATAGTGAAAAAGGCTTGCTTGATCTCAC
CCTCTATCAAACAAACTATCGTCATTTCTTATTTGAACAAGAAAGTTTAATTCAACGTACCGAAA
TGCGCTATGGACGCCCTTATACTTACCAAAGCCAAGAACAACAAATGGTGAACTTAGATAAAGCA
AAAATTTATGGTGTGGAATTGAAAACCCATGTCAATTTAGATCAGATGATCGCTGTGATACCACA
AGGCTTTAAGTTCTACGCCGCGCTCGGTTATAGCAAAGGTAAACTCTCGAATAACGCCAGCCTAC
TTTCCATTCAACCGCTTAAAATTATTCTGGGGTTGGATTATGAAGCAACAAACGGCAAATGGGCT
ATTTTCAACCGCCTAACCTATTTGGGTGAAAAAGAGCTAGTGATGCGAAAGTGTATGAAATTAA
ACGTCGCTGTACTGAATTTGTGACAGAAACAGATCCTTGGACTGGTCAACAAATTACTCGCTGTA
AAAAACGGGAATTGTATCCAGATTTATCTACTTATAAACACTTAAATAAATCTGCTTTTGTGTTT
GATACTTTTGGTTATTACAAGATCACGGACGATATCACGTTCCGAGCTGGCATTTATAATCTGTT
TAATAAAAAATACCACACTTGGGATGCCTTACGTGGTATTAATGCCAATAGTACGTTAAATTCAG
TTGACCGTGAAGGGAAAGGGTTACAACGCTTCTATGCGCCCGGACGTAACTATGCGGCTTCCCTT
GAAATCCGTTTCTAA
```

FIG. 13-2.

SEQ ID NO:12

```
MKYPLSYKNIARSIPFLSFIAFPLYAQETTELEQITVQESATAEVNKTSPTVISKSATTIQNEMI
RDTRDLVRYTTDVGISDNGRFLKGFAMRGVEDNRVGISIDGVSLPDSEENSLYARYGNFNNSRLS
IDPELIQTIDIVRGSDSFNAGSGSLGGGVNYNTLDPQHIVKTGNSVGALLRGSYASKNREWVRTL
GIGYVGEKFDALLMYSQRTGHEFKSRGSPEFRYSSSQHPDPVTQRFHNYLAKMNYQINDKQRIG
LTLNGQTGGRYIDERSYTLMGSQWREADDQNERLNANLYYIYAPSTGWLAYSKFDLDYQKTDLAA
VNYKGGRHFTTDAKELNEIYDRRMKTVFTRGSVELNAQPVHFYGEHTLTIKGYVSQRDFKNINQD
RIGIGTNYDTQYHYTIQYPIRTKQYGLSLKDHVRWNDTFSSHLGLRYDHTKLKPKELNAPCSKAC
LEEGKPKPTRFSTVSTFAGFEAQLSPSWMLGYNISTGYRVPTASEMFFSFTNAYGTWKSNPSLKP
EKSINHTLSLKGNSEKGLLDLTLYQTNYRHFLFEQESLIQRTEMRYGRPYTYQSQEQQMVNLDKA
KIYGVELKTHVNLDQMIAVIPQGFKFYAALGYSKGKLSNNASLLSIQPLKIILGLDYEATNGKWA
IFNRLTYLGEKRASDAKVYEIKRRCTEFVTETDPWTGQQITRCKKRELYPDLSTYKHLNKSAFVF
DTFGYYKITDDITFRAGIYNLFNKKYHTWDALRGINANSTLNSVDREGKGLQRFYAPGRNYAASL
EIRF*
```

FIG. 14-1.

SEQ ID NO:13

```
ATGGATAAAAATTTAATGAAGGGATGTGTATTCTTATCAATAGTCGGTTGCGGTATCCAAATAGG
GCTAGCATCAAATCCAAATCCTCCAGATGTGGATGAGTTATTACCTATTATTGTGAATGCTGATG
AAGATAATAAATTACCAGGTCGTTCTGTATTAAAACAGAAAAATATCGATCAACAACAAGCAGAT
AATGCTGCTGACTTAATAAATATTTTGCCTGGTGTAAATATGGCGGGAGGATTTCGCCCTAGTGG
TCAAACATTAAATATTAATGGAATGGGTGATGCTGAAGATGTTAGAGTTCAACTAGACGGCGCAA
CAAAAAGTTTCGAAAAATATCAACAAGGCTCTATTTTTATTGAACCTGAGTTATTAAGAAAGGTG
ACAGTAGACAAGGAAATTATTCTCCTCAATATGGCAATGGTGGCTTTGCTGGTACTGTAAAATT
TGAAACAAAAGATGCAACTGATTTTTTGAAAGAAAATCAGAAAATAGGTGGATTATTTAAATATG
GAATAATAGCAATAATAACCAAAAAACTTATAGTACAGCCCTAGTTTTACAGAATGAACAAAAA
AATATTGATTTGTTATTATTTGGTTCTGTAAGAAATGCAAGCAATTATACAAGACCTGATAAAAG
TAAAATTCTTTTTTCAAAAAACAATCAAAAAGTGGATTAATAAAAGTAAATTGGCAAATTACTC
CTGAACATTTATTAACTTTATCCAGTGTTTATGGCATTCATAAAGGGTGGGAACCTTGGGCAGCA
AAAAGAGATGTGATGTCGAGACCAACAGAAACAGAAATAAAACACTATGGGATTGATGTTGCGTG
GAAACGTAAACTTGTTTATCGAGATCAAAAAGATGAAAGTTATTCATTGAAATATCGCTATTTAC
CTGAAAATAATAAGTGGATTAATTTATCTGTTCAGCTGAGTTATAGTAAAACAGAACAGAATGAT
ACTCGCCATGAGAAAGTCACTTCTTCATTCCTAGGTACATTAGGAAATAAAAGTTGGATAACTTA
TTCAGATCTTACTTTTGATATAAGTAACACAAGTACTCTAAATATTGGGCGTGCTGAGCATGAAC
TACTATTTGGTTTACAGTGGTTAAAAAATAAAAGAAATACCCTTATGTATCATAAAGGGGAGTC
AAGAAGGCAGACTATAATTATGGCTATTTTCAGCCTTATTATATGCCTTCTGGACGCCAGTATAC
ACAAGCATTTTATTTACAAGATCAAATAAAATGGCAGAATTTCCTCTTTACAGGAGGGATAAGAT
ATGACCATATCAATAATATAGGGCAGAAAAATTTAGCGCCACGATATAATGATATCTCTGCAGGA
CATGATTATAGCCAGAAAAATTATAATGGTTGGTCTTATTATTTAGGTCTTAAGTATGATGTAAA
TCATTATTTAAGTTTATTTACGAATTTTAGTAAAACTTGGCGAGCCCCTGTTATTGATGAACAGT
ATGAGACACAATATAGTCAAGCTTCTGTATCTGCGACTTCTTTAAATTTAGAAAAAGAAATGATT
AATCAAACCAGAGTGGGTGGAATTATTACTCTCAATCATCTATTTCAGGAAAATGATGCTTTTCA
ATTTAGAACTACTTATTTTTACAATCGCGGCAAGAATGAAATCTTCAAAACGAGAGGAGTTAATT
GCGTAGAAAATGCTTTAGATGTTGATAATAGTGTTTGTCCTAAAATTATTAGTAATTACCGTAAT
TTACCTGGTTATGTTATTCAAGGAGCGGAATTAGAAGCTTATTATCAATCATCGTATTTATTTGG
TGGACTGACATATTCTTATGTAAAAGGAAAACGCGATACTTCACCAAGAAATCCATGGAGTAAAA
CATCTACATGGATCGCAGAAACATCACCTAGAAAAGCAATCGCTACTTTAGGTTTTAATATTCCG
GAATATTATTTTACGGCAGGTTGGCGTGCTGAGTTTGTGAGAAAGCAAGATAGATCACCACTATC
TAATGATTCTAAAGCATCATATTGGGCATTACCTTCTTCAAAAGGATATAGCCTACATAGTGTAT
TCTTCTCTTGGAGTCCTACAAAGATTAAAGGAATGAATTTCAAAGTTACTGTTGATAATTTATTT
AACCGACCCTATTATCCTTACTTAGGAGAATTAGCTTCAGGAACAGGTAGGAATGTCAAATTTAG
CCTGACTCAGCAATTTTAA
```

FIG. 14-2.

SEQ ID NO:14

MDKNLMKGCVFLSIVGCGIQIGLASNPNPPDVDELLPIIVNADEDNKLPGRSVLKQKNIDQQQAD
NAADLINILPGVNMAGGFRPSGQTLNINGMGDAEDVRVQLDGATKSFEKYQQGSIFIEPELLRKV
TVDKGNYSPQYGNGGFAGTVKFETKDATDFLKENQKIGGLFKYGNNSNNNQKTYSTALVLQNEQK
NIDLLLFGSVRNASNYTRPDKSKILFSKNNQKSGLIKVNWQITPEHLLTLSSVYGIHKGWEPWAA
KRDVMSRPTETEIKHYGIDVAWKRKLVYRDQKDESYSLKYRYLPENNKWINLSVQLSYSKTEQND
TRHEKVTSSFLGTLGNKSWITYSDLTFDISNTSTLNIGRAEHELLFGLQWLKNKRNTLMYHKGGV
KKADYNYGYFQPYYMPSGRQYTQAFYLQDQIKWQNFLFTGGIRYDHINNIGQKNLAPRYNDISAG
HDYSQKNYNGWSYYLGLKYDVNHYLSLFTNFSKTWRAPVIDEQYETQYSQASVSATSLNLEKEMI
NQTRVGGIITLNHLFQENDAFQFRTTYFYNRGKNEIFKTRGVNCVENALDVDNSVCPKIISNYRN
LPGYVIQGAELEAYYQSSYLFGGLTYSYVKGKRDTSPRNPWSKTSTWIAETSPRKAIATLGFNIP
EYYFTAGWRAEFVRKQDRSPLSNDSKASYWALPSSKGYSLHSVFFSWSPTKIKGMNFKVTVDNLF
NRPYYPYLGELASGTGRNVKFSLTQQF*

FIG. 15-1.

```
WP_053521090.1      -----------VLLMLSQPTNQPTNQPTNQNSNASEQLEQINVLGSDNNNDNTPPKIAET
1121_HgbA_968aa     MRTTTIKFSAITLALLSYCGA-----ILADSHQEATELDTITVSSQQDEMNIKEKKVGET
WP_005756141.1      MRTTTIKFSAITLALLSYCGA-----ILADSHQEATELDTITVSSQQDEMNIKEKKVGET
AAQ14873.1          MRTTTIKFSAITLALLSYCGV-----ILADSHQEATELDTITVSSQQDEMNIKEKKVGET
WP_061405928.1      MRTTTIKFSAITLALLSYCGA-----ILADSHQEATELDTITVSSQQDEMNIKEKKVGET
                              .* :**           :. : : :*: *.* ..::: : .   *:.**

WP_053521090.1      VKTASQLKRQQVQDSRDLVRYETGVTVVEAGRFGSSGYAIRGVDENRVAITVDGLHQAET
1121_HgbA_968aa     VKTASQLKRQQVQDSRDLVRYETGVTVVEAGRFGSSGYAIRGVDENRVAITVDGLHQAET
WP_005756141.1      VKTASQLKRQQVQDSRDLVRYETGVTVVEAGRFGSSGYAIRGVDENRVAITVDGLHQAET
AAQ14873.1          VKTASQLKRQQVQDSRDLVRYETGVTVVEAGRFGSSGYAIRGVDENRVAITVDGLHQAET
WP_061405928.1      VKTASQLKRQQVQDSRDLVRYETGVTVVEAGRFGSSGYAIRGVDENRVAITVDGLHQAET
                    ************************************************************

WP_053521090.1      LSSQGFKELFEGYGNFNNTRNSVEIETLKVAKIAKGADSVKVGSGSLGGAVLFETKDARD
1121_HgbA_968aa     LSSQGFKELFEGYGNFNNTRNSVEIETLKVAKIAKGADSVKVGSGSLGGAVLFETKDARD
WP_005756141.1      LSSQGFKELFEGYGNFNNTRNSVEIETLKVAKIAKGADSVKVGSGSLGGAVLFETKDARD
AAQ14873.1          LSSQGFKELFEGYGNFNNTRNSVEIETLKVAKIAKGADSVKVGSGSLGGAVLFETKDARD
WP_061405928.1      LSSQGFKELFEGYGNFNNTRNSVEIETLKVAKIAKGADSVKVGSGSLGGAVLFETKDARD
                    ************************************************************

WP_053521090.1      FLTEKDWHIGYKAGYSTADNQGLNAVTLAGRYQMFDALIMHSKRHGHELENYDYKNGRDI
1121_HgbA_968aa     FLTEKDWHIGYKAGYSTADNQGLNAVTLAGRYQMFDALIMHSKRHGHELENYDYKNGRDI
WP_005756141.1      FLTEKDWHIGYKAGYSTADNQGLNAVTLAGRYQMFDALIMHSKRHGHELENYDYKNGRDI
AAQ14873.1          FLTEKDWHIGYKAGYSTADNQGLNAVTLAGRYQMFDALIMHSKRHGHELEIYDYKNGRDI
WP_061405928.1      FLTEKDWHIGYKAGYSTADNQGLNAVTLAGRYQMFDALIMHSKRHGHELENYDYKNGRDI
                    ************************************************* ********

WP_053521090.1      QGKEREKADPYTITKESTLVKFSFSPTENHRFTVASDTYLQHSRGHDFSYNLVKTTYINK
1121_HgbA_968aa     QGKEREKADPYTITKESTLVKFSFSPTENHRFTVASDTYLQHSRGHDLSYNLVATTHIQL
WP_005756141.1      QGKEREKADPYTITKESTLVKFSFSPTENHRFTVASDTYLQHSRGHDLSYNLVATTHIQL
AAQ14873.1          QGKEREKADPYTITKESTLVKFSFSPTENHRFTVASDTYLQHSRGHDLSYNLVATTYIQL
WP_061405928.1      QGKEREKADPYTITKESTLVKFSFSPTENHRFTVASDTYLQHSRGHDLSYNLVATTHIQL
                    ********************************************** ***** ** :*:

WP_053521090.1      DEEELRHTNDLTKRKNVSFTYENYTVTPFWDTLKLSYSQQRITTRARTEDYCDGNEKCDS
1121_HgbA_968aa     DEKESRHANDLTKRKNVSFTYENYTVTPFWDTLKLSYSQQRITTRARTEDYCDGNEKCDS
WP_005756141.1      DEKESRHANDLTKRKNVSFTYENYTVTPFWDTLKLSYSQQRITTRARTEDYCDGNEKCDS
AAQ14873.1          DEKESRHANDLTKRKNVSFTYENYTVTPFWDTLKLSYSQQRITTRARTEDYCDGNEKCDS
WP_061405928.1      DEKESRHANDLTKRKNVSFTYENYTVTPFWDTLKLSYSQQRITTRARTEDYCDGNEKCDS
                    **:.* **:***************************************************

WP_053521090.1      YKNPLGLQLKNGQIVDRDGNPVNLKLINGRHKVVDKNNKLFGLTDEDNNAAFDGKQLGLS
1121_HgbA_968aa     YKNPLGLQLKEGKIVDRNGDPVNLKLVDGKHQVVDKAGKPFDVASGTNYAAFSGKELSPS
WP_005756141.1      YKNPLGLQLKEGKIVDRNGDPVNLKLVDGKHQVVDKAGKPFDVASGTNYAAFSGKELSPS
AAQ14873.1          YKNPLGLQLKEGKIVDRNGDPVNLQLVDGKHQVVDKAGKPFDVTSGTNYAAFSGKQLGPS
WP_061405928.1      YKNPLGLQLKEGKIVDRNGDPVNLQLVDGKHQVVDKAGKPFDVTSGTNYAAFSGKQLGPS
                    **********:.*:****:*:***:*:.*:*:****..* *..:*.**:***.**:*. *

WP_053521090.1      GFWFDCTVFDCDKPVRTYKYKYSSSNPAVENVELNKFMQVNGKRFATYEDKIQSSEKRYV
1121_HgbA_968aa     SFWLDCSIFDCSKPINTYKYRYTSSEPTLQQITLNKTMEINGKTFATYDG-----RGHYI
WP_005756141.1      SFWLDCSIFDCSKPINTYKYRYTSSEPTLQQITLNKTMEINGKTFATYDG-----RGHYI
AAQ14873.1          YFWLECTVFDCSKPVTTYKYRYSTETPVKEDIQLNKTMEVNGKTFATYDMG---RERRYI
WP_061405928.1      YFWLDCTVFDCSKPVTTYKYRYSTETPVKEDIQLNKTMEVNGKTFATYDMG---RERRYI
                    **::*::***.**: ****:*:.:: *. :: *** *::*** ****;        . :*
```

FIG. 15-2.

```
WP_053521090.1    ILPNSKGYLPLDYKERDLNTKTKQINLDLTKAFTLFEIENELSYGGVYAKTTKEMVNKAG
1121_HgbA_968aa   ILPNSKGYLPLDYKERDLNTKTKQINLDLTKAFTLFEIENELSYGGVYAKTTKEMVNKAG
WP_005756141.1    ILPNSKGYLPLDYKERDLNTKTKQINLDLTKAFTLFEIENELSYGGVYAKTTKEMVNKAG
AAQ14873.1        ILPNSQGYLPLDYKERDLNTKTKQINLDLTKAFTLFEIENELSYGGVYAKTTNGVVNKAG
WP_061405928.1    ILPNSQGYLPLDYKERDLNTKTKQINLDLTKAFTLFEIENELSYGGVYAKTTKEMVNKAG
                  *****:*****************************************:.:*****

WP_053521090.1    YYGRNPTWWAERTLGQDLSGNQHNCNTNSSYNGMLCPRHEPLTSFLIPVEATTKSLYFSD
1121_HgbA_968aa   YYGRNPTWWAERTLGQSW-GKLRECKTSSSYNGMLCPRHEPLTSFLIPVEATTKSLYFAD
WP_005756141.1    YYGRNPTWWAERTLGQSW-GKLRECKTSSSYNGMLCPRHEPLTSFLIPVEATTKSLYFAD
AAQ14873.1        YYGRNPTWWAERTLGQSWNGTLRECKTSSSYNGMLCPRHEPLTSFLIPVEATTKSLYFAD
WP_061405928.1    YYGRNPTWWAERTLGQSWNGTLRECKTSSSYNGMLCPRHEPLTSFLIPVEATTKSLYFAD
                  ****************.  *.:::*:*.*****************************:*

WP_053521090.1    NIKLHNMLSVDLGYRYDDIKYQPEYIPGVTPKIADDMVKGIFIPLPKGEKIKIGNYETTK
1121_HgbA_968aa   NIKLHNMLSVDLGYRYDDIKYQPEYIPGVTPKIADDMVKGLFIPLPEGEKVTVGTMVFTK
WP_005756141.1    NIKLHNMLSVDLGYRYDDIKYQPEYIPGVTPKIADDMVKGLFIPLPEGEKVTVGTMVFTK
AAQ14873.1        NIKLHNMLSVDLGYRYDDIKYQPEYIPGVTPKIADDMVKGLFIPLPEGEKVTVGTVVFTK
WP_061405928.1    NIKLHNMLSVDLGYRYDDIKYQPEYIPGVTPKIADDMVKGLFIPLPEGEKVTVGTVVFTK
                  ****************************************:*****:***:.:*.  **

WP_053521090.1    PLTPEQIRKNAEENIAYIAQEKRFKKHSYSLGATFDPLNFLRVQVKYSKGFRAPTSDELY
1121_HgbA_968aa   PLTQAQIRKNAEENIAYIAQEKRFKKHSYSLGATFDPLNFLRVQVKYSKGFRAPTSDELY
WP_005756141.1    PLTQAQIRKNAEENIAYIAQEKRFKKHSYSLGATFDPLNFLRVQVKYSKGFRAPTSDELY
AAQ14873.1        PLTPEQIRKNAEENIAYIAQGKRFKKHSYSLGTTFDPLNFLRVQVKYSKGFRAPTSDELY
WP_061405928.1    PLTPEQIRKNAEENIAYIAQEKRFKKHSYSLGATFDPLNFLRVQVKYSKGFRAPTSDELY
                  ***  *************** *********** **************************

WP_053521090.1    FTFKHPDFTILPNPVLKPEEAKNQEIALTVHDNWGFVSTSVFQTKYRHFIDLAYLGSRNL
1121_HgbA_968aa   FTFKHPDFTILPNPVLKPEEAKNQEIALTVHDNWGFVSTSVFQTKYRHFIDLAYLGSRNL
WP_005756141.1    FTFKHPDFTILPNPVLKPEEAKNQEIALTVHDNWGFVSTSVFQTKYRHFIDLAYLGSRNL
AAQ14873.1        FTFKHPDFTILPNPVLKPEEAKNQEIALTVHDNWGFVSTSVFQTKYRHFIDLAYLGSRNL
WP_061405928.1    FTFKHPDFTILPNPVLKPEEAKNQEIALTVHDNWGFVSTSVFQTKYRHFIDLAYLGSRNL
                  ************************************************************

WP_053521090.1    SNSVGGQAQARDFQVYQNVNVDNAKVKGLEINARLNLGYFWHVLDGFNTSYKFTYQRGRL
1121_HgbA_968aa   SNSVGGQAQARDFQVYQNVNVDNAKVKGLEINARLNLGYFWHVLDGFNTSYKFTYQRGRL
WP_005756141.1    SNSVGGQAQARDFQVYQNVNVDNAKVKGLEINARLNLGYFWHVLDGFNTSYKFTYQRGRL
AAQ14873.1        SNSVGGQAQARDFQVYQNVNVDNAKVKGLEINARLNLGYFWHVLDGFNTSYKFTYQRGRL
WP_061405928.1    SNSVGGQAQARDFQVYQNVNVDNAKVKGLEINARLNLGYFWHVLDGFNTSYKFTYQRGRL
                  ************************************************************

WP_053521090.1    DGDRPMNAIQPKASVFGLGYDHKENKFGADLYITRVSEKKAKDTYNMFYKEEKKKDSAIH
1121_HgbA_968aa   DGDRPMNAIQPKASVFGLGYDHKENKFGADLYITRVSEKKAKDTYNMFYKEQGYKDSAVR
WP_005756141.1    DGDRPMNAIQPKASVFGLGYDHKENKFGADLYITRVSEKKAKDTYNMFYKEQGYKDSAVR
AAQ14873.1        DGDRPMNAIQPKASVFGLGYDHKENKFGADLYITRVSEKKAKDTYNMFYKEQGYKDSAIR
WP_061405928.1    DGDRPMNAIQPKASVFGLGYDHKENKFGADLYITRVSEKKAKDTYNMFYKEQGYKDSAVR
                  ***************************************************:  ****::

WP_053521090.1    WRSDDYTLVDFVTYIKPVKNVTLQFGIYNLTDRKYLTWESARSIKPFGTSNLINQQTGAG
1121_HgbA_968aa   WRSDDYTLVDAVGYIKPIKNLTLQFGVYNLTDRKYLTWESARSIKPFGTSNLINQKTGAG
WP_005756141.1    WRSDDYTLVDAVGYIKPIKNLTLQFGVYNLTDRKYLTWESARSIKPFGTSNLINQKTGAG
AAQ14873.1        WRSDDYTLVDAVGYIKPIKNLTLQFGVYNLTERKYLTWESARSIKPFGTSNLINQKTGAG
WP_061405928.1    WRSDDYTLVDAVGYIKPIKNLTLQFGVYNLTDRKYLTWESARSIKPFGTSNLINQKTGAG
                  **********  *  *:**:**:*****:*****:*********************:****

WP_053521090.1    INRFYSPGRNYKLSAEITF-
1121_HgbA_968aa   INRFYSPGRNFKFSAEITF*
WP_005756141.1    INRFYSPGRNFKFSAEITF-
AAQ14873.1        INRFYSPGRNFKFSAEITF-
WP_061405928.1    INRFYSPGRNFKLSAEITF-
                  **********:*:******
```

FIG. 16-1.

```
ESQ71136.1        MEKIDMESAKNPLKKTTLALLCCSTAFSLSAKTDTNADKNHFLTEIVVYADQNKSMSSTQ
WP_014391205.1    ------MESAKNPLKKTTLALLCCSTAFSLSAKTDTDSDKNHFLTEIVVYADQNKSMSSTQ
WP_016534044.1    ------MEYAKNPLKKTTLALLCCSTAFSLSAKTDTNADKNHFLTEIVVYADQNKSMSSTQ
1121_FepA_790aa   ------MESAKNPLKKTTLALLCCSTAFSLSAKTDTNADKNHFLTEIVVYADQNKSMSSTQ
WP_005756883.1    ------MESAKNPLKKTTLALLCCSTAFSLSAKTDTNADKNHFLTEIVVYADQNKSMSSTQ
                        ** ****************************:;********************

ESQ71136.1        SVTQDDMKKSPVTNGNITDYLRSNPHVRYENSDQNGLQRGEIKPENISINGADYQQTTFF
WP_014391205.1    SVTQDDMKKSPVTNGNITDYLRSNPHVRYENSDQNGLQRGEIKPENISINGADYQQTTFF
WP_016534044.1    SVTQEDMKKSPVTNGNITDYLRSNPHVRYENSDQNGLQRGEIKPENISINGADYQQTTFF
1121_FepA_790aa   SVTQDDMKKSPVTNGNITDYLRSNPHVRYENSDQNGLQRGEIKPENISINGADYQQTTFF
WP_005756883.1    SVTQDDMKKSPVTNGNITDYLRSNPHVRYENSDQNGLQRGEIKPENISINGADYQQTTFF
                  ****:*******************************************************

ESQ71136.1        VDNVNINNDMGFGSDLFDGTMATVPFANHSQGYFFDANLLSSIVVHDSNVSASLGGFAGG
WP_014391205.1    VDNVNINNDMGFGSDLFDGTMATVPFANHSQGYFFDANLLSSIVVHDSNVSASLGGFAGG
WP_016534044.1    VDNVNINNDMGFGSDLFDGTMATVPFANHSQGYFFDANLLSSIVVHDSNVSASLGGFAGG
1121_FepA_790aa   VDNVNINNDMGFGSDLFDGTMATVPFANHSQGYFFDANLLSSIVVHDSNVSASLGGFAGG
WP_005756883.1    VDNVNINNDMGFGSDLFDGTMATVPFANHSQGYFFDANLLSSIVVHDSNVSASLGGFAGG
                  ************************************************************

ESQ71136.1        AVVAKTKQYDGKDQLKFSYRTTDASWAKFKVEDKDLERFKNAIPEGSVAEFQPKYSKHFF
WP_014391205.1    AVVAKTKQYDGKDRLKFSYRTTDASWAKFKVEDKDLERFKNAIPEGSVAEFQPKYSKHFF
WP_016534044.1    AVVAKTKQYDGKDRLKFSYRTTDASWAKFKVEDKDLERFKNAIPEGSVAEFQPKYSKRFF
1121_FepA_790aa   AVVAKTKQYDGKDRLKFSYRTTDASWAKFKVEDKDLERFKNAIPEGSVAEFQPKYSKHFF
WP_005756883.1    AVVAKTKQYDGKDRLKFSYRTTDASWAKFKVEDKDLERFKNAIPEGSVAEFQPKYSKHFF
                  *************:**********************************************:**

ESQ71136.1        NITAEKGLSENLGMVIGLSRRTSSIQQSRQINPQGDRDKQTHTRRSDNALLNFNLTPNDK
WP_014391205.1    NITAEKGLSENLGMVIGLSRRTSSIQQSRQINPQGDRDKQTHTRRSDNALLNFNLTPNDK
WP_016534044.1    NITAEKGLSENLGMVIGLSRRTSSIQQSRQINPQGDRDKQTHTRRSDNALLNFNLTPNDK
1121_FepA_790aa   NITAEKGLSENLGMVIGLSRRTSSIQQSRQINPQGDRDKQTHTPRSDNALLNFNLTPNDK
WP_005756883.1    NITAEKGLSENLGMVIGLSRRTSSIQQSRQINPQGDRDKQTHTPRSDNALLNFNLTPNDK
                  ************************************************************

ESQ71136.1        HRFELGFRYSNYREPKFFNTNIDSNVFDYHRAYGVTFSWINALQSGILTTTLAYDNFDDT
WP_014391205.1    HRFELGFRYSNYREPKFFNTNIDSNVFDYHRAYGVTFSWINALQSGILTTTLAYDNFDDT
WP_016534044.1    HRFELGFRYSNYREPKFFNTNIDSNVFDYHRAYGVTFSWINALQSGILTTTLAYDNFDDT
1121_FepA_790aa   HRFELGFRYSNYREPKFFNTNIDSNVFDYHRAYGVTFSWINALQSGILTTTLAYDNFDDT
WP_005756883.1    HRFELGFRYSNYREPKFFNTNIDSNVFDYHRAYGVTFSWINALQSGILTTTLAYDNFDDT
                  ************************************************************

ESQ71136.1        RKSASTSMKTII-EDENDYTLGGMGNSQLNQKNSHFSLEYAMNSFDLSHINHSISLGSVF
WP_014391205.1    RKSASTYMKTTLTDDGEEYTEGGMGNSQLNQKNLHTSLEYAMNPFNLGSIEHSVSLGGIY
WP_016534044.1    RKSASTYMKTTLTEEGEEYTEGGMGNSQLNQKNLHTSLEYAMNPFNLGSIEHSVSLGGIY
1121_FepA_790aa   RKSASTYMKTTLTEEGEEYTEGGMGNSQLNQKNLHTSLEYAMNPFNLGSIEHSVSLGGIY
WP_005756883.1    RKSASTYMKTTLTEEGEEYTEGGMGNSQLNQKNLHTSLEYAMNPFNLGSIEHSVSLGGIY
                  ****** ***  :  :: :** ************ * ****** *;*. *:**:***.::

ESQ71136.1        QHTQYRFHRESDAEAEIINRIDLEN------EKIEIKSSNLAKKGTVKTRYQNIALYVED
WP_014391205.1    QATKYRFTRHSDAVGELYTPNWLDNNSNDIYDELTLAQRNIAKKGTVKTRYQNIALYVED
WP_016534044.1    QATKYRFTRHSDAVGELYTPDWLNGNT----DKLILTQRNIAKKGTVKTRYQNIALYVED
1121_FepA_790aa   QATKYRFTRHSDAVGELYTPDWLNGNT----DKLILTQRNIAKKGTVKTRYQNIALYVED
WP_005756883.1    QATKYRFTRHSDAVGELYTPDWLNGNT----DKLILTQRNIAKKGTVKTRYQNIALYVED
                  * *;*** *;*** .*: .   *;.       ::: : . *;******************

ESQ71136.1        LMTWKNLEFRAGLRLERDDYLKNTNLAPRTVFRYKPFEDTAFSVGWNRYYGRSFASMKLS
WP_014391205.1    LMTWKNLEFRAGLRLERDDYLKNTNLAPRTVFRYKPFEDTAFSVGWNRYYGRSFASMKLS
WP_016534044.1    LMTWKNLEFRAGLRLERDDYLKNTNLAPRTVFRYKPFEDTAFSVGWNRYYGRSFASMKLS
1121_FepA_790aa   LMTWKNLEFRAGLRLERDDYLKNTNLAPRTVFRYKPFEDTAFSVGWNRYYGRSFASMKLS
WP_005756883.1    LMTWKNLEFRAGLRLERDDYLKNTNLAPRTVFRYKPFEDTAFSVGWNRYYGRSFASMKLS
                  ************************************************************
```

FIG. 16-2.

```
ESQ71136.1          EGIFKLDGHDTFRYKDLSQFKTPYSDELSFGVEQYVANLAFHLKYILRDNKQRIVLQEED
WP_014391205.1      EGIFKLDGHDTFRYKDLSQFKTPYSDELSFGVEQYVANLAFHLKYILHDNKQRIVLQEED
WP_016534044.1      EGIFKLDGHDTFRYKDLSQFKTPYSDELSFGVEQYVANLAFHLKYILRDNKQRIVLQEED
1121_FepA_790aa     EGIFKLDGHDTFRYKDLSQFKTPYSDELSFGVEQYVANLAFHLKYILRDNKQRIVLQEEE
WP_005756883.1      EGIFKLDGHDTFRYKDLSQFKTPYSDELSFGVEQYVANLAFHLKYILRDNKQRIVLQEED
                    ************************************************:*********:

ESQ71136.1          VMLNGEKKKLRYYQRGKDYKTNVLTFQINTQAPWELGPTRWTSAVAFDWLDSKAIDHGRG
WP_014391205.1      VMLNGEKKKLRYYQRGKDYKTNVLTFQISTQAPWEFGPTRWTSALAFDWLDSKAIDHGRG
WP_016534044.1      VMLNGERKKLRYYQRGKDYKTNVLTFQINTQAPWELGPTRWTSAVAFDWLDSKAIDHGRG
1121_FepA_790aa     VMLNGERKKLRYYQRGKDYKTNVLTFQINTQAPWELGPTRWTSAVAFDWLDSKAIDHGRG
WP_005756883.1      VMLNGEKKKLRYYQRGKDYKTNVLTFQINTQAPWELGPTRWTSAVAFDWLDSKAIDHGRG
                    ******:*****************************:******:***************

ESQ71136.1          YNGSTPVILDGRLMTYEQMLRKVNAYKETWGLRLNLDMFVPRFDLSWANTIYVKPPTTLF
WP_014391205.1      YNGSTPVILDGRLMTYEQMLRKVNAYKETWGLRLNLDMFVPKFDLSWANTIYVKPPTTLF
WP_016534044.1      YNGSTPVILDGRLMTYEQMLRKVNAYKETWGLRLNLDMFVPRFDLSWANTIYVKPPTTLF
1121_FepA_790aa     YNGSTPVILDGRLMTYEQMLRKVNAYKETWGLRLNLDMFVPIFDLSWANTIYVKPPTTLF
WP_005756883.1      YNGSTPVILDGRLMTYEQMLRKVNAYKETWGLRLNLDMFVPRFDLSWANTIYVKPPTTLF
                    ***************************************** *****************

ESQ71136.1          ERVSSNTPEVYRSYDYGTYTQWDTSLRWQPTFAEKHRPYIKLDVLNVLNKTRKGAGPNGQ
WP_014391205.1      ERVSSNTPEVYRSYDYGTYTQWDTSLRWQPTFAEKHRPYIKLDVLNVLNKTRKGAGPNGQ
WP_016534044.1      ERVSSNTPEVYRSYDYGTYTQWDTSLRWQPTFAEKHRPYIKLDVLNVLNKTRKGAGPNGQ
1121_FepA_790aa     ERVSSNTPEVYRSYDYGTYTQWDTSLRWQPTFAEKHRPYIKLDVLNVLNKTRKGAGPNGQ
WP_005756883.1      EHVSSSTPEVYRSYDYGTYTQWDTSLRWQPTFAEKHRPYIKLDVLNVLNKTRKGAGPNGQ
                    *:***.******************************************************

ESQ71136.1          DLGIYTPGREFWLEVGYEF
WP_014391205.1      DLGIYTPGREFWLEVGYEF
WP_016534044.1      DLGIYTPGREFWLEVGYEF
1121_FepA_790aa     DLGIYTPGREFWLEVGYEF
WP_005756883.1      DLGIYTPGREFWLEVGYEF
                    *******************
```

FIG. 17-1.

```
WP_071522773.1    MSFKHKTLALFVAHACCTSVLAENAATTLEPIVVSDLSHTTLNLDQNKLEKESPKDLKAI
WP_016534444.1    MSFKHKTLALFVAHACCTSALAENAATTLEPIVVSELSHTTLNLDQNKLEKESPKDLKAI
WP_005755819.1    MSFKHKTLALFVAHACCTSALAENVATTLEPIVVSDLSHTTLNLDQNKLEKESPKDLKAI
1121_PfhR_727aa   MSFKHKTLALFVAHACCTSALAENVATTLEPIVVSDLSHTTLNLDQNKLEKESPKDLKAI
EGP05580.1        MSFKHKTLALFVAHACCTSALAENAATTLEPIVVSDLSHTTLNLDQNKLEKESPKDLKAI
                  *******************.****.*********:*************************

WP_071522773.1    FATTPNINVIHTGHAQLGDIEIRGMGSSREIFATGANRVTMELDGMDISPSFYFGHSSRH
WP_016534444.1    FTTTPNINVIHTGHAQLGDIEIRGMGSSREIFATGANRVTMELDGMDISPSFYFGHSSRH
WP_005755819.1    FATTPNINVIHTGHAQLGDIEIRGMGSSREIFATGANRVTMELDGMDISPSFYFGHSSRH
1121_PfhR_727aa   FATTPNINVIHTGHAQLGDIEIRGMGSSREIFATGANRVTMELDGMDISPSFYFGHSSRH
EGP05580.1        FATTPNINVIHTGHAQLGDIEIRGMGSSREIFATGANRVTMELDGMDISPSFYFGHSSRH
                  *:**********************************************************

WP_071522773.1    GRQYFDPSDLKRVEVHKGPNSQGVAGHVRFQTKDPHDYLLPNQRTGAQLRAGYLGDSDAY
WP_016534444.1    GRQYFDPSDLKRVEIHKGPNSQGVAGHVRFQTKDPRDYLLPNQRTGAQLRAGYLGDSDAY
WP_005755819.1    GRQYFDPSDLKRVEIHKGPNSQGVAGHVRFQTKDPRDYLLPNQRTGAQLRAGYLGDSDAY
1121_PfhR_727aa   GRQYFDPSDLKRVEIHKGPNSQGVAGHVRFQTKDPRDYLLPNQRTGAQLRAGYLGDSDAY
EGP05580.1        GRQYFDPSDLKRVEIHKGPNSQGVAGHVRFQTKDPRDYLLPNQRTGAQLRAGYLGDSDAY
                  **************:*******************:*************************

WP_071522773.1    YVGITGAALLDEHSSALVSYTRRWFNEFNNKGGLDVTGSQRTKSNPSSGYSNAVNSKLRY
WP_016534444.1    YVGITGATLLDEHSSALVSYTRRWFNEFNNKGGLDVTGSQRTKSNPSSGYSNAVNSKLRY
WP_005755819.1    YVGITGATLLDEHSSALVSYTRRWFNEFNNKGGLDVTGSQRTKSNPSSGYSNAVNSKLRY
1121_PfhR_727aa   YVGITGATLLDEHSSALVSYTRRWFNEFNNKGGLDVTGSQRTKSNPSSGYSNAVNSKLRY
EGP05580.1        YVGITGATLLDEHSSALMSYTRRWFNEFNNKGGLDVTGSQRTKSNPSSGYSNAVNSKLRY
                  *******:*********:******************************************

WP_071522773.1    SPNDRHKFTLNLQHYDLKRTAYLEDSLGTTTTRRGTKTVHHNTNIQKNQRHAIAFSHDMQ
WP_016534444.1    SPNDRHKFTLNLQHYDLKRTAYLEDSLGTTTTRRGTKTVHHNTNIQKNQRHAIAFSHDMQ
WP_005755819.1    SPNDRHKFTLNLQHYDLKRTAYLEDSLGTTTTRRGTKTVHHNTNIQKNQRHAIAFSHDMQ
1121_PfhR_727aa   SPNDRHKFTLNLQHYDLKRTAYLEDSLGTTTTRRGTKTVHHNTNIQKNQRHAIAFSHDMQ
EGP05580.1        SPNDRHKFTLNLQHYDLKRTAYLEDSLGTTTTRRGTKTVHHNTNIQKNQRHAIAFSHDMQ
                  ************************************************************

WP_071522773.1    QTNHSIFDHLHWQIALQQTKSTSRNTGAVTSTSGSPPPSTPKFSQERSLDGFKTKTISLK
WP_016534444.1    QTT-AFFDHLHWQIALQQTKSTSRNTGVTSTSAPPPPSTPKFSQERSFDGFKTKTISLK
WP_005755819.1    QTT-AFFDHLHWQIALQQTKSTSRNTGAVTSTSASPPPSTPKFSQERSFDGFKTKTISLK
1121_PfhR_727aa   QTT-AFFDHLHWQIALQQTKSTSRNTGAVTNTSASPPPSTPKFSQERSLDGFKTKTISLK
EGP05580.1        QTT-AFFDHLHWQIALQQTKSTSRNTGAVTNTSASPPPSTPKFSQERSLDGFKTKTISLK
                  **. ::*******************:**.**. *************:************

WP_071522773.1    TEFNKSLGQHVVHELHYGLKLQYSQMQALRQTQSLNEQGSNTRTSAFFPTQQQWQSKLHL
WP_016534444.1    TEFNKSLGQHVVHELHYGLKLQYSQMQALRQTQSLNEQGSNTRTSAFFPTQQQWQSKFHL
WP_005755819.1    TEFNKSLGQHVVHELHYGLKLQYSQMQALRQTQSLNEQGSNTRTSAFFPTQQQWQSKLHL
1121_PfhR_727aa   TEFNKSIGQHVVHELHYGLKLQYSQMQALRQTQSLNEQGSNTRTSAFFPTQQQWQSKLHL
EGP05580.1        TEFNKSIGQHVVHELHYGLKLQYSQMQALRQTQSLNEQGSNTRTSAFFPTQQQWQSKLHL
                  ******:*****************************************************:**

WP_071522773.1    SDRISFGKSGLSLTPSIHLTQIRIKPKTENVSKKNREQLFTYKDTAIGYGLRVDYALNEA
WP_016534444.1    SDRISFGKSGLSLTPSIHLTQIRIKPKTENVSKKNREQLFTYKDTAIGYGLRVDYALNEA
WP_005755819.1    SDRISFGKSGLSLTPSIHLTQIRIKPKTENVSKKNREQLFTYKDTAIGYGLRVDYALNEA
1121_PfhR_727aa   SDRISFGKSGLSLTPSIHLTQIRIKPKTENVSKKNREQLFTYKDTAIGYGLRVDYALNEA
EGP05580.1        SDRISFGKSGLSLTPSIHLTQIRIKPKTENVSKKNREQLFTYKDTAIGYGLRVDYALNEA
                  ************************************************************
```

FIG. 17-2.

```
WP_071522773.1    NLLSLNYQHATRLPGYGENNAQSYGHWPAKPNPHLQPETSDGIELSWRSAGAIGQQTTTL
WP_016534444.1    NLLSLNYQHATRLPGYGENNAQSYGHWPAKPNPHLQPETSDGVELSWRSAGAIGQQTTTL
WP_005755819.1    NLLSLNYQHATRLPGYGENNAQSYGHWPAKPNPHLQPETSDGIELSWRSAGAIGQQTTTL
1121_PfhR_727aa   NLLSLNYQHATRLPGYGENNAQSYGHWPAKPNPHLQPETSDGIELSWRSAGAIGQQTTTL
EGP05580.1        NLLSLNYQHATRLPGYGENNAQSYGHWPAKPNPHLQPETSDGIELSWRSAGAIGQQTTTL
                  *****************************************:******************

WP_071522773.1    FYNRYNDLIYLDTTACYADRTGQVQVPCDLANEKGRSYSYGIEFDGKLNLDTIGFAQGTY
WP_016534444.1    FYNRYNDLIYLDTTACYADRTGQ--VPCDLANEKGRSYSYGIEFDGKLNLDTIGFAQGTY
WP_005755819.1    FYNRYNDLIYLDTTACYADRTGQ--VPCDLANEKGRSYSYGIEFDGKLNLDTIGFAQGTY
1121_PfhR_727aa   FYNRYNDLIYLDTTACYADRTGQ--VPCDLANEKGRSYSYGIEFDGKLNLDTIGFAQGTY
EGP05580.1        FYNRYNDLIYLDTTACYADRTGQ--VPCDLANEKGRSYSYGIEFDGKLNLDTIGFAQGTY
                  **********************  ************************************

WP_071522773.1    LNAGFAYSKGKTANKQPQGRLDPLTGFVGLGYQQPMDVWGIEGKLKFAAKKKTKDLPANQ
WP_016534444.1    LNAGFAYSKGKTANKQPQGRLDPLTGFVGLGYQQPMDVWGIEGKLKFAAKKKTKDLPANQ
WP_005755819.1    LNAGFAYSKGKTANKQPQGRLEPLTGFVGLGYQQPMDVWGIEGKLKFAAKKKTKDLPANQ
1121_PfhR_727aa   LNAGFAYSKGKTANKQPQGRLDPLTGFVGLGYQQPMDVWGIEGKLKFAAKKKTKDLPANQ
EGP05580.1        LNAGFAYSKGKTANKQPQGRLDPLTGFVGLGYQQPMDVWGIEGKLKFAAKKKTKDLPANQ
                  *********************:**************************************

WP_071522773.1    GFEGLPGYAVVDLTAYYNVTKQLYLGIGIYNVLDKKYARWAMARGDIKHGNYDKHTEAGR
WP_016534444.1    GFEGLPGYAVVDLTAYYNVTKQLYLGIGIYNVLDKKYARWAMARGDIKHGNYDKHTEAGR
WP_005755819.1    GFEGLPGYAVVDLTAYYNVTKQLYLGIGIYNVLDKKYARWAMARGDIKHGNYDKHTEAGR
1121_PfhR_727aa   GFEGLPGYAVVDLTAYYNVTKQLYLGIGIYNVLDKKYARWAMARGDIKHGNYDKHTEAGR
EGP05580.1        GFEGLPGYAVVDLTAYYNVTKQLYLGIGIYNVLDKKYARWAMARGDIKHGNYDKHTEAGR
                  ************************************************************

WP_071522773.1    HFGANIRYHF
WP_016534444.1    HFGANIRYHF
WP_005755819.1    HFGANIRYHF
1121_PfhR_727aa   HFGANIRYHF
EGP05580.1        HFGANIRYHF
                  **********
```

FIG. 18-1.

```
1135_PM0300_964aa      MRTTTIKFSAITLALLSYCGVILADSHQEATELDTITVSSQQDEMNIKEKKVGETVKTAS
WP_005753642.1         MRTTTIKFSAITLALLSYCGVILADSHQEATELDTITVSSQQDEMNIKEKKVGETVKTAS
WP_016534557.1         MRTTTIKFSAITLALLSYCGAILADSHQEATELDTITVSSQQDEMNIKEKKVGETVKTAS
WP_010906573.1         MRTTTIKFSAITLALLSYCGAILADSHQEATELDTITVSSQQDEMNIKEKKVGETVKTAS
AAQ14873.1             MRTTTIKFSAITLALLSYCGVILADSHQEATELDTITVSSQQDEMNIKEKKVGETVKTAS
1121_HgbA_968aa        MRTTTIKFSAITLALLSYCGAILADSHQEATELDTITVSSQQDEMNIKEKKVGETVKTAS
                       ********************.***************************************

1135_PM0300_964aa      QLKRQQVQDSRDLVRYETGVTVVEAGRFGSSGYAIRGVDENRVAITVDGLHQAETLSSQG
WP_005753642.1         QLKRQQVQDSRDLVRYETGVTVVEAGRFGSSGYAIRGVDENRVAITVDGLHQAETLSSQG
WP_016534557.1         QLKRQQVQDSRDLVRYETGVTVVEAGRFGSSGYAIRGVDENRVAITVDGLHQAETLSSQG
WP_010906573.1         QLKRQQVQDSRDLVRYETGVTVVEAGRFGSSGYAIRGVDENRVAITVDGLHQAETLSSQG
AAQ14873.1             QLKRQQVQDSRDLVRYETGVTVVEAGRFGSSGYAIRGVDENRVAITVDGLHQAETLSSQG
1121_HgbA_968aa        QLKRQQVQDSRDLVRYETGVTVVEAGRFGSSGYAIRGVDENRVAITVDGLHQAETLSSQG
                       ************************************************************

1135_PM0300_964aa      FKELFEGYGNFNNTRNSVEIETLKVAKIAKGADSVKVGSGSLGGAVLFETKDARDFLTEK
WP_005753642.1         FKELFEGYGNFNNTRNSVEIETLKVAKIAKGADSVKVGSGSLGGAVLFETKDARDFLTEK
WP_016534557.1         FKELFEGYGNFNNTRNSVEIETLKVAKIAKGADSVKVGSGSLGGAVLFETKDARDFLTEK
WP_010906573.1         FKELFEGYGNFNNTRNSVEIETLKVAKIAKGADSVKVGSGSLGGAVLFETKDARDFLTEK
AAQ14873.1             FKELFEGYGNFNNTRNSVEIETLKVAKIAKGADSVKVGSGSLGGAVLFETKDARDFLTEK
1121_HgbA_968aa        FKELFEGYGNFNNTRNSVEIETLKVAKIAKGADSVKVGSGSLGGAVLFETKDARDFLTEK
                       ************************************************************

1135_PM0300_964aa      DWHIGYKAGYSTADNQGLNAVTLAGRYQMFDALIMHSKRHGHELENYDYKNGRDIQGKER
WP_005753642.1         DWHIGYKAGYSTADNQGLNAVTLAGRYQMFDALIMHSKRHGHELENYDYKNGRDIQGKER
WP_016534557.1         DWHIGYKAGYSTADNQGLNAVTLAGRYQMFDALIMHSKRHGHELENYDYKNGRDIQGKER
WP_010906573.1         DWHIGYKAGYSTADNQGLNAVTLAGRYQMFDALIMHSKRHGHELENYDYKNGRDIQGKER
AAQ14873.1             DWHIGYKAGYSTADNQGLNAVTLAGRYQMFDALIMHSKRHGHELEIYDYKNGRDIQGKER
1121_HgbA_968aa        DWHIGYKAGYSTADNQGLNAVTLAGRYQMFDALIMHSKRHGHELENYDYKNGRDIQGKER
                       ******************************************** *************

1135_PM0300_964aa      EKADPYTITKESTLVKFSFSPTENHRFTVASDTYIQRSRGHDRSYSLQPQSNYFTYDEKE
WP_005753642.1         EKADPYTITKESTLVKFSFSPTENHRFTVASDTYIQRSRGHDRSYSLQPQSNYFTYDEKE
WP_016534557.1         EKADPYTITKESTLVKFSFSPTENHRFTVASDTYIQRSRGHDRSYSLQPQSNYFTYDEKE
WP_010906573.1         EKADPYTITKESTLVKFSFSPTENHRFTVASDTYIQRSRGHDRSYSLQPQSNYFTYDEKE
AAQ14873.1             EKADPYTITKESTLVKFSFSPTENHRFTVASDTYLQHSRGHDLSYNLVA-TTYIQLDEKE
1121_HgbA_968aa        EKADPYTITKESTLVKFSFSPTENHRFTVASDTYLQHSRGHDLSYNLVA-TTHIQLDEKE
                       **********************************:;***** **.*   :.::  ****

1135_PM0300_964aa      SRHANDLTKRKNVSFTYENYSVTPFWDTLKLSYSQQKIRTRAPTEDYCDGNEKCDSYKNP
WP_005753642.1         SRHANDLTKRKNVSFTYENYSVTPFWDTLKLSYSQQKIRTRAPTEDYCDGNEKCDSYKNP
WP_016534557.1         SRHANDLTKRKNVSFTYENYSVTPFWDTLKLSYSQQKIRTRAPTEDYCDGNEKCDSYKNP
WP_010906573.1         SRHANDLTKRKNVSFTYENYSITPFWDTLKLSYSQQKIRTRAPTEDYCDGNEKCDSYKNP
AAQ14873.1             SRHANDLTKRKNVSFTYENYTVTPFWDTLKLSYSQQRITTRAPTEDYCDGNEKCDSYKNP
1121_HgbA_968aa        SRHANDLTKRKNVSFTYENYTVTPFWDTLKLSYSQQRITTRAPTEDYCDGNEKCDSYKNP
                       ********************:*************** * *********************

1135_PM0300_964aa      LGLQLKDGKIVDPEGNQITLKGTGFNTEIVDKNGNPFPTTSGTNNAAFSNNIQLGPKEFW
WP_005753642.1         LGLQLKDGKIVDPEGNQITLKGTGFNTEIVDKNGNPFPTTSGTNNAAFSNNIQLGPKEFW
WP_016534557.1         LGLQLKDGKIVDPAGNQITLKGTGFNTEIVDKDGKPFPTTSGTNNAAFSNNLQLSPTGFW
WP_010906573.1         LGLQLKDGKIVDPAGNQITLKGTGFNTEIVDKDGKPFPTTSGTNNAAFSNNLQLSPTGFW
AAQ14873.1             LGLQLKEGKIVDRNGDPVNLQLVDGKHQVVDKAGKPFDVTSGTNYAAFSG-KQLGPSYFW
1121_HgbA_968aa        LGLQLKEGKIVDRNGDPVNLKLVDGKHQVVDKAGKPFDVASGTNYAAFSG-KELSPSSFW
                       ******:*****  *:  .*:  :  :  ***   :**  ****  ** *    *:*:* **
```

FIG. 18-2.

```
1135_PM0300_964aa    LDCSLFDCTQPFTVYNYQNGQYTPKQ--VELSEEITVNGKLYKTAKEERGVRNYLILPNS
WP_005753642.1       LDCSLFDCTQPFTVYNYQNGQYTPKQ--VELSEEITVNGKLYKTAKEERGVRNYLILPNS
WP_016534557.1       LDCTIFDCTKPFTVYNYKQNKYEPRE--VMLSEEITIDGKLYKTAKEESGVRNYLILPNS
WP_010906573.1       LDCTIFDCTKPFTVYNYKQNKYEPRE--VMLSEEITIDGKLYKTAKEESGVRNYLILPNS
AAQ14873.1           LECTVFDCSKPVTTYKYRYSTETPVKEDIQLNKTMEVNGKTFATYDM-GRERRYIILPNS
1121_HgbA_968aa      LDCSIFDCSKPINTYKYRYTSSEPTLQQITLNKTMEINGKTFATYDG---RGHYIILPNS
                     ::*::***::*...*:*:          :  *.: : ::** : * .   .*:*****

1135_PM0300_964aa    KGYLPYDYKERDLDSNTKQINLDLTKTFSTFNIENELLYGAIYSRTEKKMVNKAGYDGRN
WP_005753642.1       KGYLPYDYKERDLDSNTKQINLDLTKTFSTFNIENELLYGAIYSRTEKKMVNKAGYDGRN
WP_016534557.1       KGYLPYDYKERDLDSNTKQINLDLTKTFSTFNIENELLYGAIYSRTEKKMVNKAGYDGRN
WP_010906573.1       KGYLPYDYKERDLDSNTKQINLDLTKTFSTFNIENELLYGAIYSRTEKKMVNKAGYDGRN
AAQ14873.1           QGYLPLDYKERDLNTKTKQINLDLTKAFTLFEIENELSYGGVYAKTTNGVVNKAGYYGRN
1121_HgbA_968aa      KGYLPLDYKERDLNTKTKQINLDLTKAFTLFEIENELSYGGVYAKTTKEMVNKAGYYGRN
                     :****.*******::::*********:*:. *:***** **.:*:.* : :****** ***

1135_PM0300_964aa    PTWWADRILGKST---------NCNYNGLKCPRHEPLTSFLIPVEATTKSLYFSDNIKLH
WP_005753642.1       PTWWADRILGKST---------NCNYNGLKCPRHEPLTSFLIPVEATTKSLYFSDNIKLH
WP_016534557.1       PTWWADRILGKST---------NCNYNGLKCPRHEPLTSFLIPVEATTKSLYFSDNIKLH
WP_010906573.1       PTWWADRILGKST---------NCNYNGLKCPRHEPLTSFLIPVEATTKSLYFSDNIKLH
AAQ14873.1           PTWWAERTLGQSWNGTLRECKTSSSYNGMLCPRHEPLTSFLIPVEATTKSLYFADNIKLH
1121_HgbA_968aa      PTWWAERTLGQSW-GKLRECKTSSSYNGMLCPRHEPLTSFLIPVEATTKSLYFADNIKLH
                     *****:* **:*          ...***: **********************:******

1135_PM0300_964aa    NMLSVDLGYRYDDIKYQPEYIPGVTPKIADDMVKGIFIPLPKGEKVTTPWGAEYTKPLTQ
WP_005753642.1       NMLSVDLGYRYDDIKYQPEYIPGVTPKIADDMVKGIFIPLPKGEKVTTPWGAEYTKPLTQ
WP_016534557.1       NMLSVDLGYRYDDIKYQPEYIPGVTPKIADDMVKGIFIPLPKGEKIKIE-NYETTKPLTP
WP_010906573.1       NMLSVDLGYRYDDIKYQPEYIPGVTPKIADDMVKGIFIPLPKGEKIKIG-NYETTKPLTP
AAQ14873.1           NMLSVDLGYRYDDIKYQPEYIPGVTPKIADDMVKGLFIPLPEGEKVTVG-TVVFTKPLTP
1121_HgbA_968aa      NMLSVDLGYRYDDIKYQPEYIPGVTPKIADDMVKGLFIPLPEGEKVTVG-TMVFTKPLTQ
                     ***********************************:******:***:;***:.   *****

1135_PM0300_964aa    EQIRKNAEENIAYIAQEKRFKKHSYSLGATFDPLNFLRVQVKYSKGFRAPTSDELYFTFK
WP_005753642.1       EQIRKNAEENIAYIAQEKRFKKHSYSLGATFDPLNFLRVQVKYSKGFRAPTSDELYFTFK
WP_016534557.1       EQIRKNAEENIAYIAQEKRFKKHSYSLGATFDPLNFLRVQVKYSKGFRAPTSDELYFTFK
WP_010906573.1       EQIRKNAEENIAYIAQEKRFKKHSYSLGATFDPLNFLRVQVKYSKGFRAPTSDELYFTFK
AAQ14873.1           EQIRKNAEENIAYIAQGKRFKKHSYSLGTTFDPLNFLRVQVKYSKGFRAPTSDELYFTFK
1121_HgbA_968aa      AQIRKNAEENIAYIAQEKRFKKHSYSLGATFDPLNFLRVQVKYSKGFRAPTSDELYFTFK
                     ************** ***********.:************************

1135_PM0300_964aa    HPDFTILPNPVLKPEEAKNQEIALTVHDNWGFVSTSVFQTKYRHFIDLAYLGSRNLSNSV
WP_005753642.1       HPDFTILPNPVLKPEEAKNQEIALTVHDNWGFVSTSVFQTKYRHFIDLAYLGSRNLSNSV
WP_016534557.1       HPDFTILPNPVLKPEEAKNQEIALTVHDNWGFVSTSVFQTKYRHFIDLAYLGSRNLSNSV
WP_010906573.1       HPDFTILPNPVLKPEEAKNQEIALTVHDNWGFVSTSVFQTKYRHFIDLAYLGSRNLSNSV
AAQ14873.1           HPDFTILPNPVLKPEEAKNQEIALTVHDNWGFVSTSVFQTKYRHFIDLAYLGSRNLSNSV
1121_HgbA_968aa      HPDFTILPNPVLKPEEAKNQEIALTVHDNWGFVSTSVFQTKYRHFIDLAYLGSRNLSNSV
                     ************************************************************

1135_PM0300_964aa    GGQAQARDFQVYQNVNVDNAKVKGLEINARLNLGYFWHVLDGFNTSYKFTYQCGRLDGDR
WP_005753642.1       GGQAQARDFQVYQNVNVDNAKVKGLEINARLNLGYFWHVLDGFNTSYKFTYQRGRLDGDR
WP_016534557.1       GGQAQARDFQVYQNVNVDNAKVKGLEINARLNLGYFWHVLDGFNTSYKFTYQRGRLDGDR
WP_010906573.1       GGKAQARDFQVYQNVNVDNAKVKGVEINARLNLGYFWHVLDGFNTSYKFTYQRGRLDGDR
AAQ14873.1           GGQAQARDFQVYQNVNVDNAKVKGLEINARLNLGYFWHVLDGFNTSYKFTYQRGRLDGDR
1121_HgbA_968aa      GGQAQARDFQVYQNVNVDNAKVKGLEINARLNLGYFWHVLDGFNTSYKFTYQRGRLDGDR
                     **:******************:************************* *******
```

FIG. 18-3.

```
1135_PM0300_964aa      PMNAIQPKASVFGLGYDHKENKFGADLYITRVSEKKAKDTYNMFYKEQGYKDSAIRWRSD
WP_005753642.1         PMNAIQPKASVFGLGYDHKENKFGADLYITRVSEKKAKDTYNMFYKEQGYKDSAIRWRSD
WP_016534557.1         PMNAIQPKASVFGLGYDHKENKFGADLYITRVSEKKAKDTYNMFYKEQGYKDSAIRWRSD
WP_010906573.1         PMNAIQPKASVFGLGYDHKENKFGADLYITRVSEKKAKDTYNMFYKEQGYKDSAIRWRSD
AAQ14873.1             PMNAIQPKASVFGLGYDHKENKFGADLYITRVSEKKAKDTYNMFYKEQGYKDSAIRWRSD
1121_HgbA_968aa        PMNAIQPKASVFGLGYDHKENKFGADLYITRVSEKKAKDTYNMFYKEQGYKDSAVRWRSD
                       ************************************************:******

1135_PM0300_964aa      DYTLVDAVGYIKPIKNLTLQFGVYNLTDRKYLTWESARSIKPFGTSNLINQKTGAGINRF
WP_005753642.1         DYTLVDAVGYIKPIKNLTLQFGVYNLTDRKYLTWESARSIKPFGTSNLINQKTGAGINRF
WP_016534557.1         DYTLVDAVGYIKPIKNLTLQFGVYNLTDRKYLTWESARSIKPFGTSNLINQKTGAGINRF
WP_010906573.1         DYTLIDAVGYIKPIKNLTLQFGVYNLTDRKYLTWESARSIKPFGTSNLINQKTGAGINRF
AAQ14873.1             DYTLVDAVGYIKPIKNLTLQFGVYNLTERKYLTWESARSIKPFGTSNLINQKTGAGINRF
1121_HgbA_968aa        DYTLVDAVGYIKPIKNLTLQFGVYNLTDRKYLTWESARSIKPFGTSNLINQKTGAGINRF
                       ****:**********************:********************************

1135_PM0300_964aa      YSPGRNFKFSAEITF
WP_005753642.1         YSPGRNFKFSAEITF
WP_016534557.1         YSPGRNFKFSAEITF
WP_010906573.1         YSPGRNFKLSAEITF
AAQ14873.1             YSPGRNFKFSAEITF
1121_HgbA_968aa        YSPGRNFKFSAEITF
                       ********:******
```

FIG. 19-1.

```
WP_017861186.1      MQKSQPYPIHLGIFLMLGLPTWAFSQANLEKSTINKLETILVNESEEKNKFDENLIKTYL
AAU29202.1          MQKQQPYPIHLGIFLMLGLPTWAFSQANLEKSTINKLETILVNESEEKNKFDENLIKTYL
EGP04511.1          MQKQQPYPIHLGIFLMLGLPTWAFSQANLEKSTINKLETILVNESEEKNKFDENLIKTYL
1135_HasR_848aa     MQKQQPYPIHLGIFLMLGLPTWAFSQANLEKSTINKLETILVNESEEKNKFDENLIKTYL
WP_005752163.1      MQKQQPYPIHLGIFLMLGLPTWAFSQANLEKSTINKLETILVNESEEKNKFDENLIKTYL
                    ***.*******************************************************

WP_017861186.1      SSGSYSYLSQSDISTFRGSSVGDFLSGVPGVIVGNKRNSGALSVNIRGIANENRVPVWID
AAU29202.1          SSGSYSYLSQSDISTFRGSSVGDFLSGVPGVIVGNKRNSGALSVNIRGIANENRVPVWID
EGP04511.1          SSGSYSYLSQSDISTFRGSSVGDFLSGVPGVIVGNKRNSGALSVNIRGIANENRVPVWID
1135_HasR_848aa     SSGSYSYLSQSDISTFRGSSVGDFLSGVPGVIVGNKRNSGALSVNIRGIANENRVPVWID
WP_005752163.1      SSGSYSYLSQSDISTFRGSSVGDFLSGVPGVIAGNKRNSGALSVNIRGIANENRVPVWID
                    ********************************.***************************

WP_017861186.1      KGLQSVPSYQGYAGSSTRTYLDPDLISQVEIEKGPSLQMDATGATGGVVRVETLRWQDII
AAU29202.1          KGLQSVPSYQGYAGSSTRTYLDPDLISQVEIEKGPSLQMDATGATGGVVRVETLRWQDII
EGP04511.1          KGLQSVPSYQGYAGSSTRTYLDPDLISQVEIEKGPSLQMDATGATGGVVRVDTLRWQDII
1135_HasR_848aa     KGLQSVPSYQGYAGSSTRTYLDPDLISQVEIEKGPSLQMDATGATGGVVRVETLRWQDII
WP_005752163.1      KGLQSVPSYQGYAGSSTRTYLDPDLISQVEIEKGPSLQMDATGATGGVVRVETLRWQDII
                    **************************************************:*********

WP_017861186.1      PQGNKLGVRLKLGTMTNTVSPPPYYTRGGYQTKYISKCLSNHTGLCQTQTYAPNARYSSH
AAU29202.1          PQGKNWGVRLKLGTMANTVSPPPYYTRGGYQTKYISKCLSNHTGLCQTQTYAPNARYSSH
EGP04511.1          PQGKNWGVRLKLGTMTNTVSPPPYYTRGGYQTKYISKCLSNDTGLCQTQTYAPNARYSSH
1135_HasR_848aa     PQGKNWGVRLKLGTMTNTVSPPPYYTRGGYQTKYISKCLSNDTGLCQTQTYAPNARYSSH
WP_005752163.1      PQGKNWGVRLKLGTMTNTVSPPPYYTRGGYQTKYISKCLSNDTGLCQTQTYAPNARYSSH
                    ***:: *********.************************.*****************

WP_017861186.1      GFDLNAYNYSLAFANKWSNADLVLAYAKRPKQGNYFVGRHGQTPVIESIEFEEDSVEVKEP
AAU29202.1          GFDLNAYNYSLAFANKWQNADLVLAYAKRPKQGNYFVGRHGQTPVIESIEFEEDSVEVKEP
EGP04511.1          GFDLNAYNYSLAFANKWQNADLVLAYAKRPKQGNYFVGRHGQTPVIESIKFEEDSVEVKEP
1135_HasR_848aa     GFDLNAYNYSLAFANKWQNADLVLAYAKRPKQGNYFVGRHGQTPVIESIEFEEDSVEVKEP
WP_005752163.1      GFDLNAYNYSLAFANKWQNADLVLAYAKRPKQGNYFVGRHGQTPVIESIEFEEDSVEVKEP
                    ****************.********************************:***********

WP_017861186.1      RVHEDVEIGSLTFKENRSTLYRPGEEALNTSQDNTSYLAKINVYNDVHRLGLAYRHYHSR
AAU29202.1          RVHEDVEIGSLTFKENRSTLYRPGEEALNTSQDNTSYLAKINVYNDVHRLGLAYRHYHSR
EGP04511.1          RVHEDVEIGSLTFKENRSTLYRPGEEALNTSQDNTSYLAKINVYNDVHRLGLAYRHYHSR
1135_HasR_848aa     RVHEEVEIGSLTFKENRSTLYRPGEEALNTSQDNTSYLAKINVYNDVHRLGLAYRHYHSR
WP_005752163.1      RVHEEVEIGSLTFKENRSTLYRPGEEALNTSQDNTSYLAKINVYNDVHRLGLAYRHYHSR
                    ****:*******************************************************

WP_017861186.1      FGEIMSSILNFRAYGALQGEGTEVKVDSYHANYSYNPTTPYVNLSVNAYFTDSDSSNFTP
AAU29202.1          FGEIMSSILNFRAYGALQGEGTEVKVDSYHANYSYNSTTPYVNLSVNAYFTDSDSSNFTP
EGP04511.1          FGEIMSSILNFRAYGALQGEGTEVKVDSYHANYSYNPTTPYVNLNVNAYFTDSDSSNFTP
1135_HasR_848aa     FGEIMSSILNFRAYGALQGEGTEVKVDSYHANYSYNPTTPYVNLNVNAYFTDSDSSNFTP
WP_005752163.1      FGEIMSSILNFRAYGALQGEGTEVKVDSYHANYSYNPTTPYVNLNVNAYFTDSDSSNFTP
                    ***********************************.******.**************

WP_017861186.1      FIEEYGYSLSSRHAHFLVSKQKGLSIENTSIFQLNDKPFTLKYGLAHSYERIYQPRNAQA
AAU29202.1          FIEEYGYSLSSRHAHFLVSKQKGLSIENTSIFQLNDKPFTLKYGLAHSYERIYQPRNAQA
EGP04511.1          FIEEYGYSLSSRHAHFLVSKQKGLSIENTSIFQLNDKPFTLKYGLAHSYERIYQPRNAQA
1135_HasR_848aa     FIEEYGYSLSSRHAHFLVSKQKGLSIENTSIFQLNDKPFSLKYGLAHSYERIYQPRNAQA
WP_005752163.1      FIEEYGYSLSSRHAHFLVSKQKGLSIENTSIFQLNDKPFTLKYGLAHSYERIYQPRNAQA
                    ***************************************:*******************
```

FIG. 19-2.

```
WP_017861186.1    RVPAKGYPEDAIGPLYIRDGKRKEWSAFVAANYPITSWLKADIGLRYLQSTIYDYIVRTE
AAU29202.1        RVPAKGYPEDAIGPLYIRDGKRKEWSAFVAANYPITSWLKADIGLRYLQSTIYDYIVRTE
EGP04511.1        RVPAKGYPEDAIGPLYIRDGKRKEWSAFVAANYPINSWLKADIGLRYLQSTIYDYIVRTE
1135_HasR_848aa   RVPAKGYPEDAIGPLYIRDGKRKEWSAFVAANYPITSWLKADIGLRYLQSTIYDYIVRTE
WP_005752163.1    RVPAKGYPEDAIGPLYIRDGKRKEWSAFVAANYPITSWLKADIGLRYLQSTIYDYIVRTE
                  *********************************.*************************

WP_017861186.1    RVNIGGALVPNPNGSGNIWVEKYKDVVHKQAPVKNKGMSPIVMFTFEPINGVQIYTKYAE
AAU29202.1        RVNIGGALVPNPNGSGNIWVEKYKDVVHKQAPVKNKGMSPIVMFTFEPINGVQIYTKYAE
EGP04511.1        RVNIGGALVPNPNGPGNIWVEKYKDVVHKQAPVKNKGMSPIVMLTFEPINGVQIYTKYAE
1135_HasR_848aa   RVNIGGALVPNPNGSGNIWVEKYKDVVHKQAPVKNKGMSPIVMLTFEPINGVQIYTKYAE
WP_005752163.1    RVNIGGALVPNPNGSGNIWVEKYKDVVHKQAPVKNKGMSPIVMLTFEPINGVQIYTKYAE
                  ************** *******************************:************

WP_017861186.1    ALRSPSLFQATKGWSMSATEDNLEQLRPERAKNWEAGINLFYENLGGKDNILGFKLAYFN
AAU29202.1        ALRSPSLFQATKGWSMSATADNLEQLRPERAKNWEAGINLFYENLGGKDNILGFKLAYFN
EGP04511.1        ALRSPSLFQATKGWSMSATADNLEQLRPERAKNWEAGINLFYENLGGKDNILGFKLAYFN
1135_HasR_848aa   ALRSPSLFQATKGWSMSATADNLEQLRPERAQNWEAGINLFYENLGGKDNILGFKLAYFN
WP_005752163.1    ALRSPSLFQATKGWSMSATADNLEQLRPERAKNWEAGINLFYENLGGKDNILGFKLAYFN
                  *******************.***********:****************************

WP_017861186.1    NRIKDYLTRSYSPKDKVTQTINIQSAQFKGIELSAYYDMGKFYAKLAGTYYTKTKFCLTA
AAU29202.1        NRIKDYLTRSYSPKDKVTQTINIQSAQFKGIELSAYYDMGKFYAKLAGTYYTKTKFCLTA
EGP04511.1        NRIKDYLTRSYSPKDKVTQTINIQSAQFKGIELSAYYDMGKFYTKLAGTYYTKTKFCLTA
1135_HasR_848aa   NRIKDYLTRSYSPKDKVTQTINIQSAQFKGIELSAYYDMGKFYAKLAGTYYTKTKFCLTA
WP_005752163.1    NRIKDYLTRSYSPKDKVTQTINIQSAQFKGIELSAYYDMGKFYTKLAGTYYTKTKFCLTA
                  ******************************************:****************

WP_017861186.1    EQAGKGEQCNSGYVYRSNLNNAVPPRLNLHATLGTRLFEQKLDIGARYSYYSKRLVPVLS
AAU29202.1        EQAGKGEQCNSGYVYRSNLNNAVPPRLNLHATLGTRLFEQKLDIGARYSYYSKRLVPVLS
EGP04511.1        EQAGKGEQCNSGYVYRSNLNNAVPPRLNLHATLGTRLFEQKLDIGARYSYYSKRLVPVLS
1135_HasR_848aa   EQAGKGEQCNSGYVYRSNLNNAVPPRLNLHATLGTRLFEQKLDIGARYSYYSKRLVPVLS
WP_005752163.1    EQAGKGEQCNSGYVYRSNLNNAVPPRLNLHATLGTRLFEQKLDIGARYSYYSKRLVPVLS
                  ************************************************************

WP_017861186.1    AERFVNTSSIEWAPYSLVDLYANYNVSNNLKLTMTMDNVFNRYYLDINNMGLNTAPGRTL
AAU29202.1        AERFVNTSSIEWAPYSLVDLYANYNVSNNLKLTMTMDNVFNRYYLDINNTGLNTAPGRTL
EGP04511.1        AERFVNTSSIEWAPYSLVDLYANYNVSNNLKLTMTMDNVFNRYYLDINNMGLNTAPGRTL
1135_HasR_848aa   AERFVNTSSIEWAPYSLVDLYANYNVSNNLKLTMTMDNVFNRYYLDINNMGLNTAPGRTL
WP_005752163.1    AERFVNTSSIEWAPYSLVDLYANYNVSNNLKLTMTMDNVFNRYYLDINNMGLNTAPGRTL
                  ************************************************* **********

WP_017861186.1    HLGLEYRF
AAU29202.1        HLGLEYRF
EGP04511.1        HLGLEYRF
1135_HasR_848aa   HLGLEYRF
WP_005752163.1    HLGLEYRF
                  ********
```

FIG. 20-1.

```
WP_005751557.1      MKYPLSYKNIARSIPFLSFIAFPLYAQETTELEQITVQESATAEVNKTSPTVISKSATTI
1135_PM0741_784aa   MKYPLSYKNIARSIPFLSFIAFPLYAQETTELEQITVQESATAEVNKTSPTVISKSATTI
WP_016534554.1      MKYPLSYKNIARSIPFLSFIAFPLYAQETTELEQITVQESATAEVNKTSPTVISKSATTI
WP_064972816.1      MKYPLSYKNIARSIPFLSFIAFPLYAQETTELEQITVQESATAEVNKTSPTVISKSATTI
WP_074865020.1      MKYPLSYKNIARSIPFLSFIAFPLYAQETTELEQITVQESATAEVNKTSPTVISKSATTI
                    ************************************************************

WP_005751557.1      QNKMIRDTRDLVRYTTDVGISDNGRFLKGFAMRGVEDNRVGISIDGVSLPDSEENSLYAR
1135_PM0741_784aa   QNEMIRDTRDLVRYTTDVGISDNGRFLKGFAMRGVEDNRVGISIDGVSLPDSEENSLYAR
WP_016534554.1      QNEMIRDTRDLVRYTTDVGISDNGRFLKGFAMRGVEDNRVGISIDDVSLPDSEENSLYAR
WP_064972816.1      QNEMIRDTRDLVRYTTDVGISDNGRFLKGFAMRGVEDNRVGISIDGVSLPDSEENSLYAR
WP_074865020.1      QNEMIRDTRDLVRYTTDVGISDNGRFLKGFAMRGVEDNRVGISIDGVSLPDSEENSLYAR
                    **:*********************************************.***********

WP_005751557.1      YGNFNNSRLSIDPELIQTIDIVRGSDSFNAGSGSLGGGVNYNTLDPQHIVKAGNSVGALL
1135_PM0741_784aa   YGNFNNSRLSIDPELIQTIDIVRGSDSFNAGSGSLGGGVNYNTLDPQHIVKTGNSVGALL
WP_016534554.1      YGNFNNSRLSIDPELIQTIDIVRGSDSFNAGSGSLGGGVNYNTLDPQHIVKAGNSVGALL
WP_064972816.1      YGNFNNSRLSIDPELIQTIDIVRGSDSFNAGSGSLGGGVNYNTLDPQHIVKAGNSVGALL
WP_074865020.1      YGNFNNSRLSIDPELIQTIDIVRGSDSFNAGSGSLGGGVNYNTLDPQHIVKAGNSVGALL
                    **************************************************:********

WP_005751557.1      RGSYASKNREWVRTLGIGYVGEKFDALLMYSQRTGHEFKSRGSGPEFRYSSSQHPDPVTQ
1135_PM0741_784aa   RGSYASKNREWVRTLGIGYVGEKFDALLMYSQRTGHEFKSRGSGPEFRYSSSQHPDPVTQ
WP_016534554.1      RGSYASKNREWVRTLGIGYVGEKFDALLMYSQRTGHEFKSRGSGPEFRYSSSQHPDPVTQ
WP_064972816.1      RGSYASKNREWVRTLGIGYVGEKFDALLMYSQRTGHEFKSRGSGPEFRYSSSQHPDPVTQ
WP_074865020.1      RGSYASKNREWVRTLGIGYVGEKFDALLMYSQRTGHEFKSRGSGPEFRYSSSQHPDPVTQ
                    ************************************************************

WP_005751557.1      RFHNYLAKMNYQINDNQRIGLTLNGQTGGRYIDERSYTLMGSQWREADDQNERLNANLYY
1135_PM0741_784aa   RFHNYLAKMNYQINDQRIGLTLNGQTGGRYIDERSYTLMGSQWREADDQNERLNANLYY
WP_016534554.1      RFHNYLAKMNYQINDNQRIGLTLNGQTGGRYIDERSYTLMGSQWREADDQNERLNANLYY
WP_064972816.1      RFHNYLAKMNYQINDKQRIGLTLNGQTGGRYIDERSYTLMGSQWREADDQNERLNANLYY
WP_074865020.1      RFHNYLAKMNYQINDNQRIGLTLNGQTGGRYIDERSYTLMGSQWREADDQNERLNANLYY
                    ***************:********************************************

WP_005751557.1      IYAPSTGWLAYSKFDLDYQKTDLAAVNYKGGRHFTTDAKELNEIYDRRMKTVFTRGSVEL
1135_PM0741_784aa   IYAPSTGWLAYSKFDLDYQKTDLAAVNYKGGRHFTTDAKELNEIYDRRMKTVFTRGSVEL
WP_016534554.1      IYAPSTGWLAYSKFDLDYQKTDLAAVNYKGGRHFTTDAKELNEIYDRRMKTVFTRGSVEL
WP_064972816.1      IYAPSTGWLAYSKFDLDYQKTDLAAVNYKGGRHFTTDAKELNEIYDRRMKTVFTRGSVEL
WP_074865020.1      IYAPSTGWLAYSKFDLDYQKTDLAAVNYKGGRHFTTDAKELNEIYDRRMKTVFTRGSVEL
                    ************************************************************

WP_005751557.1      NAQPVHFYGEHTLTIKGYVSQRDFKNINQDRIGIGTNYDTQYHYTIQYPIRTKQYGLSLK
1135_PM0741_784aa   NAQPVHFYGEHTLTIKGYVSQRDFKNINQDRIGIGTNYDTQYHYTIQYPIRTKQYGLSLK
WP_016534554.1      NAQPVHFYGEHTLTIKGYVSQRDFKNINQDRIGIGTNYDTQYHYTIQYPIRTKQYGLSLK
WP_064972816.1      NAQPVHFYGEHTLTIKGYVSQRDFKNINQDRIGIGTNYDTQYHYTIQYPIRTKQYGLSLK
WP_074865020.1      NAQPVHFYGEHTLTIKGYVSQRDFKNINQDRIGIGTNYDTQYHYTIQYPIRTKQYGLSLK
                    ************************************************************

WP_005751557.1      DHVRWNDTFSSHLGLRYDHTKLKPKELNAPCSKACLEEGKPKPTRFSTVSTFAGLEAQLS
1135_PM0741_784aa   DHVRWNDTFSSHLGLRYDHTKLKPKELNAPCSKACLEEGKPKPTRFSTVSTFAGFEAQLS
WP_016534554.1      DHVRWNDTFSSHLGLRYDHTKLKPKELNAPCSNACLEEGKPKPTRFSTVSTFAGLEAQLS
WP_064972816.1      DHVRWNDTFSSHLGLRYDHTKLKPKELNAPCSKACLEEGKPKPTRFSTVSTFAGLEAQLS
WP_074865020.1      DHVRWNDTFSSHLGLRYDHTKLKPKELNAPCSKACLEEGKPKPTRFSTVSTFAGFEAQLS
                    ********************************:**********************:*****

WP_005751557.1      PSWMLGYNISTGYRVPTASEMFFSFTNAYGTWKSNPSLKPEKSINHTLSLKGNSEKGLLD
1135_PM0741_784aa   PSWMLGYNISTGYRVPTASEMFFSFTNAYGTWKSNPSLKPEKSINHTLSLKGNSEKGLLD
WP_016534554.1      PSWMLGYNISTGYRVPTASEMFFSFTNAYGTWKSNPSLKPEKSINHTLSLKGNSEKGLLD
WP_064972816.1      PSWMLGYNISTGYRVPTASEMFFSFTNAYGTWKSNPSLKPEKSINHTLSLKGNSEKGLLD
WP_074865020.1      PSWMLGYNISTGYRVPTASEMFFSFTNAYGTWKSNPSLKPEKSINHTLSLKGNSEKGLLD
                    ************************************************************
```

FIG. 20-2.

```
WP_005751557.1      LTLYQTNYRHFLFEQESLIQRTEIRYGQPYTYQSQEQQMVNLDKAKIYGVELKTHVNLDQ
1135_PM0741_784aa   LTLYQTNYRHFLFEQESLIQRTEMRYGRPYTYQSQEQQMVNLDKAKIYGVELKTHVNLDQ
WP_016534554.1      LTLYQTNYRHFLFEQESLIQRTEMRYGRPYTYQSQEQQMVNLDKAKIYGVELKTHVNLDQ
WP_064972816.1      LTLYQTNYRHFLFEQESLIQRTEMRYGRPYTYQSQEQQMVNLDKAKIYGVELKTHVNLDQ
WP_074865020.1      LTLYQTNYRHFLFEQESLIQRTEMRYGRPYTYQSQEQQMVNLDKAKIYGVELKTHVNLDQ
                    *********************:***:**********************************

WP_005751557.1      MIAVIPQGFKFYAALGYSKGKLSNNASLLSIQPLKIILGLDYEATNGKWAIFNRLTYLGE
1135_PM0741_784aa   MIAVIPQGFKFYAALGYSKGKLSNNASLLSIQPLKIILGLDYEATNGKWAIFNRLTYLGE
WP_016534554.1      MIAVIPQGFKFYAALGYSKGKLSNNASLLSIQPLKIILGLDYEATNGKWAIFNRLTYLGE
WP_064972816.1      MIAVIPQGFKFYAALGYSKGKLSNNASLLSIQPLKIILGLDYEATNGKWAIFNRLTYLGE
WP_074865020.1      MIAVIPQGFKFYAALGYSKGKLSNNASLLSIQPLKIILGLDYEATNGKWAIFNRLTYLGE
                    ************************************************************

WP_005751557.1      KRASDAKVYEIKRRCTEFVTETDPWSGEQITRCKKRELYPDLSTYKYLNKSAFVFDTFGY
1135_PM0741_784aa   KRASDAKVYEIKRRCTEFVTETDPWTGQQITRCKKRELYPDLSTYKHLNKSAFVFDTFGY
WP_016534554.1      KRASDAKVYEIKRRCTEFVTETDPWSGEQITRCKKRELYPDLSTYKHLNKSAFVFDTFGY
WP_064972816.1      KRASDAKVYEIKRRCTEFVTETDPWSGEQITRCKKRELYPDLSTYKHLNKSAFVFDTFGY
WP_074865020.1      KRASDAKVYEIKRRCTEFVTETDPWSGEQITRCKKRELYPDLSTYKHLNKSAFVFDTFGY
                    ************************:*:***:**********:************

WP_005751557.1      YKITDDITFRAGIYNLFNKKYHTWDALRGINANSTLNSVDREGKGLQRFYAPGRNYAASL
1135_PM0741_784aa   YKITDDITFRAGIYNLFNKKYHTWDALRGINANSTLNSVDREGKGLQRFYAPGRNYAASL
WP_016534554.1      YKITDDITFRAGIYNLFNKKYHTWDALRGINANSTLNSVDREGKGLQRFYAPGRNYAASL
WP_064972816.1      YKITDDITFRAGIYNLFNKKYHTWDALRGINANSTLNSVDREGKGLQRFYAPGRNYAASL
WP_074865020.1      YKITDDITFRAGIYNLFNKKYHTWDALRGINANSTLNSVDREGKGLQRFYAPGRNYAASL
                    ************************************************************

WP_005751557.1      EIRF
1135_PM0741_784aa   EIRF
WP_016534554.1      EIRF
WP_064972816.1      EIRF
WP_074865020.1      EIRF
                    ****
```

FIG. 21-1.

```
WP_050948957.1           -MNIIINKRIFLLVTFVGIQLNVTAKQNSSNSNREELLPIIVNTDEDSNKLPGRSVLKQK
WP_014391043.1           MDKNLMKGCVFLLIVGCGIQIGLA---SNPNPPDVDELLPIIVNADED--NKLPGRSVLKQK
WP_016533738.1           MDKNLMKGCVFLSIVGCGIQIGLA---SNPNPPDVDELLPIIVNADED--NKLPGRSVLKQK
1135_P1062_0207600_742aa MDKNLMKGCVFLSIVGCGIQIGLA---SNPNPPDVDELLPIIVNADED--NKLPGRSVLKQK
WP_025248456.1           MDKNLMKGCVFLSIVGCGIQIGLA---SNPNPPDVDELLPIIVNADED--NKLPGRSVLKQK
                           :::  :** :.  ***:.::  .*  . : :********:*** ************

WP_050948957.1           NIEQQQADNAANLINILPGVNMAGGFRPGGQTLNINGMGDAEDVRVQLDGATKSFEKYQQ
WP_014391043.1           NIDQQQADNAADLINILPGVNMAGGFRPGGQTLNINGMGDAEDVRVQLDGATKSFEKYQQ
WP_016533738.1           NIDQQQADNAADLINILPGVNMAGGFRPGGQTLNINGMGDAEDVRVQLDGATKSFEKYQQ
1135_P1062_0207600_742aa NIDQQQADNAADLINILPGVNMAGGFRPSGQTLNINGMGDAEDVRVQLDGATKSFEKYQQ
WP_025248456.1           NIDQQQADNAADLINILPGVNMAGGFRPGGQTLNINGMGDAEDVRVQLDGATKSFEKYQQ
                         **:********:****************.*******************************

WP_050948957.1           GSIFIEPELLRKVTVDKGNYSPQYGNGGFAGTVKFETRDARDFLKENQKIGGLLKYGNNS
WP_014391043.1           GSIFIEPELLRKVTVDKGNYSPQYGNGSFAGTVKFETKDATDFLKENQKIGGLFKYGNNS
WP_016533738.1           GSIFIEPELLRKVTVDKGNYSPQYGNGGFAGTVKFETKDATDFLKENQKIGGLFKYGNNS
1135_P1062_0207600_742aa GSIFIEPELLRKVTVDKGNYSPQYGNGGFAGTVKFETKDATDFLKENQKIGGLFKYGNNS
WP_025248456.1           GSIFIEPELLRKVTVDKGNYSPQYGNGGFAGTVKFETKDATDFLKENQKIGGLFKYGNNS
                         ***************************.********:** ************:******

WP_050948957.1           NNNQKTYSTALVLQNEQKNIDLLLFGSVRNAGDYKRPDNSKILFSKNNQKTGLIKVNWQI
WP_014391043.1           NNNQKTYSTALVLQNEQKNIDLLLFGSVRNASNYTRPDKSKILFSKNNQKSGLIKVNWQI
WP_016533738.1           NNNQKTYSTALVLQNEQKNIDLLLFGSVRNASNYTRPDKSKILFSKNNQKSGLIKVNWQI
1135_P1062_0207600_742aa NNNQKTYSTALVLQNEQKNIDLLLFGSVRNASNYTRPDKSKILFSKNNQKSGLIKVNWQI
WP_025248456.1           NNNQKTYSTALVLQNEQKNIDLLLFGSVRNASNYTRPDKSKILFSKNNQKSGLIKVNWQI
                         ******************************.:*.***:*********:**********

WP_050948957.1           TPEHLLTLSSVYGIHKGWEPWAAKRDVTSRPTETEIKRYGIDVAWKPKLVYRDQKDESYS
WP_014391043.1           TPEHLLTLSSVYGIHKGWEPWAAKRDVMSRPTEKEIKRYGIDVAWKRKLVYRDQKDESYS
WP_016533738.1           TPEHLLTLSSVYGIHKGWEPWAAKRDVMSRPTETEIKRYGIDVAWKRKLVYRDQKDESYS
1135_P1062_0207600_742aa TPEHLLTLSSVYGIHKGWEPWAAKRDVMSRPTETEIKHYGIDVAWKRKLVYRDQKDESYS
WP_025248456.1           TPEHLLTLSSVYGIHKGWEPWAAKRDVMSRPTETEIKHYGIDVAWKRKLVYRDQKDESYS
                         *************************** *****.***:***********:**********

WP_050948957.1           LKYRYLPENNKWINLSVQLSYSKTEQNDTRHEKVTSSFLGTLGNKSWITYSDLTFDISNT
WP_014391043.1           LKYRYLPENNKWINLSVQLSYSKTEQNDTRHEKVTSSFLGTLGNKSWITYSDLTFDISNT
WP_016533738.1           LKYRYLPENNKWINLSVQLSYSKTEQNDTRHEKVTSSFLGTLGNKSWITYSDLTFDISNT
1135_P1062_0207600_742aa LKYRYLPENNKWINLSVQLSYSKTEQNDTRHEKVTSSFLGTLGNKSWITYSDLTFDISNT
WP_025248456.1           LKYRYLPENNKWINLSVQLSYSKTEQNDTRHEKVTSSFLGTLGNKSWITYSDLTFDISNT
                         ************************************************************

WP_050948957.1           STLNIGRAEHELLFGLQWLKNTRNTLMYHKGKMNDKTYNYGYFQPYYMPSGRQYTQAFYL
WP_014391043.1           STLNIGRAEHELLFGLQWLKNKRNTLMYHKEGVKKADYNYGYFQPYYMPSGRQYTQAFYL
WP_016533738.1           STLNIGRAEHELLFGLQWLKNKRNTLMYHKEGVKKADYNYGYFQPYYMPSGRQYTHAFYL
1135_P1062_0207600_742aa STLNIGRAEHELLFGLQWLKNKRNTLMYHKGGVKKADYNYGYFQPYYMPSGRQYTQAFYL
WP_025248456.1           STLNIGRAEHELLFGLQWLKNKRNTLMYHKGGVKKADYNYGYFQPYYMPSGRQYTQAFYL
                         *********************.*******  ::. **********************:****

WP_050948957.1           QDQIKWKNIIFSTGARYDHINNIGQKNLAPQYNDISAGHNYSQKNYNGWSYYLGLKYDVN
WP_014391043.1           QDQIKWQNFLFTGGIRYDHINNIGQKNLAPRYNDISAGHNYSQKNYNGWSYYLGLKYDVN
WP_016533738.1           QDQIKWQNFLFTGGIRYDHINNIGQKNLAPRYNDISAGHDYSQKNYNGWSYYLGLKYDVN
1135_P1062_0207600_742aa QDQIKWQNFLFTGGIRYDHINNIGQKNLAPRYNDISAGHDYSQKNYNGWSYYLGLKYDVN
WP_025248456.1           QDQIKWQNFLFTGGIRYDHINNIGQKNLAPRYNDISAGHDYSQKNYNGWSYYLGLKYDVN
                         ******:*::*:* * **************:***********:***************

WP_050948957.1           HYLSLFTNFSRTWRAPVIDEQYETQYSKASVPATSLNLEKEMISQTRGGGIVTLNNLFQE
WP_014391043.1           HYLSLFTNFSKTWRAPVIDEQYETQYSQASVSATSLNLEKEMINQTRVGGIITLNHLFQE
WP_016533738.1           HYLSLFTNFSKTWRAPVIDEQYETQYSQASVSATSLNLEKEMINQTRVGGIITLNHLFQE
1135_P1062_0207600_742aa HYLSLFTNFSKTWRAPVIDEQYETQYSQASVSATSLNLEKEMINQTRVGGIITLNHLFQE
WP_025248456.1           HYLSLFTNFSKTWRAPVIDEQYETQYSRASVSATSLNLEKEMINQTRVGGIITLNHLFQE
                         **********:***************:***.*********** ***  *** :**:****
```

FIG. 21-2.

```
WP_050948957.1         DDTFQFRATYFYHRGKNEIFKTRGVNCVGNALDVDNKICPKIISNYRNLPGYVIQGAELE
WP_014391043.1         NDAFQFRTTYFYNRGKNEIFKTRGVNCVENALDVDNSVCPKIISNYRNLPGYVIQGAELE
WP_016533738.1         NDAFQFRTTYFYNRGKNEIFKTRGVNCVENALDVDNSVCPKIISNYRNLPGYVIQGAELE
1135_P1062_0207600_742aa  NDAFQFRTTYFYNRGKNEIFKTRGVNCVENALDVDNSVCPKIISNYRNLPGYVIQGAELE
WP_025248456.1         NDAFQFRTTYFYNRGKNEIFKTRGVNCVENALDVDNSVCPKIISNYRNLPGYVIQGAELE
                       :*:****:****:*************** ******.:***********************

WP_050948957.1         AYYQSTYLFGELTYSYVKGKRDTSPRNPWGKTSTWIAEIPPRKATATLGFNVPKYYLTVG
WP_014391043.1         AYYQSSYLFGGLTYSYVKGKRDTSPRNPWSKTSTWIAETPPRKATATLGFNIPEYYFTAG
WP_016533738.1         AYYQSSYLFGGLTYSYVKGKRDTSPRNPWSKTSTWIAETPPRKATATLGFNIPEYYFTAG
1135_P1062_0207600_742aa  AYYQSSYLFGGLTYSYVKGKRDTSPRNPWSKTSTWIAETPPRKAIATLGFNIPEYYFTAG
WP_025248456.1         AYYQSSYLFGGLTYSYVKGKRDTSPRNPWSKTSTWIAETPPRKATATLGFNIPEYYFTAG
                       ****:**** ******************.******* **** ******:*:**:*.*

WP_050948957.1         WRAEFVRPQDRSPSSRDPKASYYLSLPASPGYSLHNLFLSWTPEKIKGMNIKITVDNLFN
WP_014391043.1         WRAEFVRKQDRSPLSNDSKASYW-ALPSSKGYSLHSVFFSWSPTKIKGMNFKVTVDNLFN
WP_016533738.1         WRAEFVRKQDRSPLSNDSKASYW-ALPSSKGYSLHSVFFSWSPTKIKGMNFKVTVDNLFN
1135_P1062_0207600_742aa  WRAEFVRKQDRSPLSNDSKASYW-ALPSSKGYSLHSVFFSWSPTKIKGMNFKVTVDNLFN
WP_025248456.1         WRAEFVRKQDRSPLSNDSKASYW-ALPSSKGYSLHSVFFSWSPTKIKGMNFKVTVDNLFN
                       *******:***** *.*.****: :**:*:***** .**:*:*.* ******:*:*******

WP_050948957.1         RAYNPYLGELASGTGPNIKFSLSQKF
WP_014391043.1         RPYYPYLGELASGTGRNVKFSLTQQF
WP_016533738.1         RPYYPYLGELASGTGRNVKFSLTQQF
1135_P1062_0207600_742aa  RPYYPYLGELASGTGRNVKFSLTQQF
WP_025248456.1         RPYYPYLGELASGTGRNVKFSLTQQF
                       * * ***********:****:*:*
```

FIG. 22-1.

SEQ ID NO:43

ATGATTTCAAGAGGTTGTAAAGTAAATAAATTTTTTGCTGTTTTGATGATGTGTTGCATTCCGCA
AGTAGTTTGGGCAAATACAGAAAAGAAGCAAATTGTTTTTTTAGATGAAATTAGTGTGGAGTCGA
AAGGTGCTGCTTTTCGTAGCGATCCCCTTTCCGGCTTACCAAAACAAAATGACATTTTAGTCAGT
AAGCAAAAATTAAAAACAGGATCCAGTACATTAGGTAATGCGTTAGCGGGTGAACTCAGTGTACA
TAGTAATCAATTTGGTGGTGGATCCAGTGCACCTGTCGTTCGAGGACAGGAAGGCGTGCGTTTAA
AAATCTTACAAAATGGTTCTGATGTCATTGATATGTCTCAACTTTCTCCTGACCATGCGATTGGT
GTCGATACGTTATTGGCAGAGCAAGTCGAAATTGTACGTGGTGCCTCAACATTGTTATATGCCAA
TGCGTCACCTGCTGGTGTGATTAATGTAGTAGATAAACGCATTCCAACACAGCTTCCTCAAAAGG
GCTATGAAGTGGATTTCAACACGCGTTATAACACGAATAGTCATGAAAAATTGGTAACGGCTGCA
CTGACTTTCGGGTTAGGTAAGCACATTGCTTTACGGGTAGAAGAACTGTTACGTGGCTCAAATAA
TTACCATGTGCCAGCATTTAAGCTAGACAAAACATTAAATTATGTCCCCGATACTCAAAATAAAA
CGAAGTCAGGTAACTATGGTGTGGCTTTTATCGGTGAGCGAGGTTATGTCGGTTTTGCCTACAAT
CTTCGTCGTGAGAAATATGGGTTACCGGGACATAACCATAAGCTAGATAGTTGTGCTGCGCATAT
TTGGGGTGGCAATGTACGTAATGACTATTATTTAGGGCTTTATCCTCATTTAATGCATGATACGG
ATCTAGTAAATACGCATTTCCATTGTGGATCAAATCATGACATGGATGGAAAACACAGTCATGAT
CATCCGTACGGTCACGATCATGACCATTCTATTGCCGGTCCATTGATTGATTCTTATGCTAAACG
TTATGACATACGTGCTGAAGTCAAACAGCCGATGAAAGCGATTGAGAAAATCAAACTCAGTTATT
CGGAAACCCGTTATAAACACGATGAAAAGATGGCAATATCGCCGTGAATTTATTTAAAAATAAC
GGATATAACCTGCGCGTAGAAATTTTCCATACGCCCATAGCGGGGTTGAGTGGCGTTATAGGGGC
GCAGTATCAAACACAAACCAGCAGTGCGAATATTCCGCGTATTGCACCATGCTCAAATAATGCAA
GCGATCCTTGTCATAAGAAAAGCAACGCGATCCGTCCAAAATCACTAAGGGTGATCGTAAGTCA
TGGGCATTGATTGAAAATACTCAATCACAAATGAGTTTTTTTGCTATAGAACAATTGCGTTGGCA
AGATTTTTTATTTGAAATTGGTGTACGTACGGAAAAACAACGCATTGATATTGAATATGATCGCG
CTTGGCTGTTTAAAGTAAAGCGAAAGCTAGAAGGCTGTGATCCGAATTCGTTCTTTTATAGCCCA
TCAGGATGTCGTCAAGGCAGTTATCCAGCACCTGATTTTGCCTCTTATCATGATCGCGCGACCTC
TTATTCTGGTGCTATCAGTTGGAATATGACGCCTGACTACACCCTTTCTTTGACTTACTCACATA
ACGAACGTCACCCAACACCGATGGAATTGTATTACCACGGCAAACATTTAGCGACGGTGTCATTT
GAACATGGCAATCGTAATCTGAAAAAGAAGTTTCTGATAACTGGGAAGTCGGTCTTGCGTATCT
TGGTGACAAGCTAAGTTATAAAGTGAATGTATATTACAATGATTTTAAAAATCGGATTTTTAATC

FIG. 22-2.

AAACATTGAACAAATCCGGTAATTTATCTTTGAATCGTTATAATCAATCCAAAGCGAAATATTAT
GGTGTGGAAGGGCGTATTGACTATGCGTTGACACCTGAACTGCACATGGGACTTTTTGGTGATTA
TGTGCGTGGAAAACTGTATGATTTACCGCCAACGTACCGTGTCGATCATGTGGCGAATAGCTTAG
AACCCGTTCCTCAACCTGATCAAGACGCACCACGTGTCCCGCCAATGCGTTTAGGCTTTCGTGTG
AATATGGAGATGACTGAGAGTTTAACAAGTTCACTCGAATACACTTACGTTTATCAACAAAGAA
AGTAGCGCCGTTAGAAAATCAAACGGCTGCATATAGTTTATTAAATATCGGAGTGGATTATTCAC
GCCAAATAGCTGGGGTAAATTATCAATTATTTGTTCAAGCAAATAATGTGTTAAACCGTAAAGTT
TATTCTCATACTTCTTTTTTACCCTTTGTACCGCAGATGGGGCGTAATGTGACTTTAGGATTAAA
CATCCATTTCTAA

SEQ ID NO:44

MISRGCKVNKFFAVLMMCCIPQVVWANTEKKQIVFLDEISVESKGAAFRSDPLSGLPKQNDILVS
KQKLKTGSSTLGNALAGELSVHSNQFGGGSSAPVVRGQEGVRLKILQNGSDVIDMSQLSPDHAIG
VDTLLAEQVEIVRGASTLLYANASPAGVINVVDKRIPTQLPQKGYEVDFNTRYNTNSHEKLVTAA
LTFGLGKHIALRVEELLRGSNNYHVPAFKLDKTLNYVPDTQNKTKSGNYGVAFIGERGYVGFAYN
LRREKYGLPGHNHKLDSCAAHIWGGNVRNDYYLGLYPHLMHDTDLVNTHFHCGSNHDMDGKHSHD
HPYGHDHDHSIAGPLIDSYAKRYDIRAEVKQPMKAIEKIKLSYSETRYKHDEKDGNIAVNLFKNN
GYNLRVEIFHTPIAGLSGVIGAQYQTQTSSANIPRIAPCSNNASDPCHKKKQRDPSKITKGDRKS
WALIENTQSQMSFFAIEQLRWQDFLFEIGVRTEKQRIDIEYDRAWLFKVKRKLEGCDPNSFFYSP
SGCRQGSYPAPDFASYHDRATSYSGAISWNMTPDYTLSLTYSHNERHPTPMELYYHGKHLATVSF
EHGNRNLKKEVSDNWEVGLAYLGDKLSYKVNVYYNDFKNRIFNQTLNKSGNLSLNRYNQSKAKYY
GVEGRIDYALTPELHMGLFGDYVRGKLYDLPPTYRVDHVANSLEPVPQPDQDAPRVPPMRLGFRV
NMEMTESLTSSLEYTYVYQQKKVAPLENQTAAYSLLNIGVDYSRQIAGVNYQLFVQANNVLNRKV
YSHTSFLPFVPQMGRNVTLGLNIHF

FIG. 25.

```
ZAP               1  --------------SKRRDNYGLPGHNHKFDFCTGNIYGNK-RD---KYAYTYLYPHLIG      42
AHG81836.1      239  LSFVGEQGYIGASYSKRRDNYGLPGHNHKFDFCTGNIYGNK-RD---KYAYTYLYPHLIG     294
WP_005612269.1  231  LSFVGEQGYIGASYSKRRDNYGLPGHNHKFDFCIGNIYGNK-QG---KYAYTYLYPHLIG     286
WP_027074597.1  242  ISFIGERGYIGAAYSHRKDTYGLPGHNHKFDFCTGNIYGVD-RD---KHAHTYLYPHLLT     297
AHG73391.1      242  LSFVGERGYIGAAYNERTDTYGLPGHNHKFDECIGNIYNEV-RD---KYAYTYKYPHLLD     297
WP_021114857.1  252  LSFIGEKGYLGASYNQRKDRYGLPGHNHKFDTCIANIYDMRLQG---KHSYTNLYPHLMS     308
WP_026212957.1  232  LSYIGNQGHIGLAYSERRDKYGLVGHNHKFDNCEGNAFNTSRGLWGPERRYLIPYPHLMS     291
WP_028858792.1  274  LSYVGERGHIGVAYSEREDKYGLVGHNHKLDGCYGNVVYPQKNY--KNKPYLAAYPHLMG     331
WP_016534590.1  246  VAFIGERGYVGFAYNLRREKYGLPGHNHKLDSCAAHIWGGNVRN---DY-YLELYPHLMH     301
KDN24548.1      246  VSYIGDKGHIGVSYSRRQDKYGIPGHNHAYDNCIAHVLTPEAS---ISRYYLKAYPHLIQ     302
WP_027821676.1  249  VSWVGQNGHLGVSYSHRKDRYGLPGHNHMLDNCSGHVFDVTTAS-AVKRNYLLPYPHLIG     307

ZAP              43  EENIGSNPHFHCGTNHAEDGTHSHDNPFGHAHDHTHKGPWVQLES---------------      87
AHG81836.1      295  EENIGSNPHFHCGTNHAEDGTHSHDNPFGHDHDHTHPGPWVQLESKRFDVKAELRQPFKG     354
WP_005612269.1  287  EENIGSNPHFHCGTDHAEDGTHSHDNPFGHDHDHTHPGPWVQLESKRFDVKAELRQPFKG     346
WP_027074597.1  298  NELISENPHFHCGSDHGLDHNHSHDNPYGHKHDHTHKGPWVDLRSKRLDLKMELKQPFSG     357
AHG73391.1      298  EDLISHGPHFHCGTDHEMDAGHSHDNPYGHTHDHTHKGPWVDLKSKRIDVKSELLKPFRG     357
WP_021114857.1  309  DEMVTENPHFHCGTDYDLDPSHSHDHPYGHDHDHTHIGPWVQLHSKRIDIKGEIKQPLPN     368
WP_026212957.1  292  DEDMITSLHFHCGTNYDLDPSHSHEHVYGHKHDHTQKGPWVDMTSKTFSLQGEINQPIPS     351
WP_028858792.1  332  DEDLAESFHFHCDSDHNEDEPHSHDNPYGHDHDHTQGGPWVDMNSKSYYLQGELLEPIPA     391
WP_016534590.1  302  DTDL-VNTHFHCGSNHDMDGKHSHDHPYGHDHDHSIAGPLIDSYAKRYDIRAEVKQPMKA     360
KDN24548.1      303  NMDFSSSAHFHCGTDHAHDPGQSHEHPLGYEHDMTHPGPWIDMESERIDVRAQWEKPFKG     362
WP_027821676.1  308  DEDVNLSQHFHCHTEHSSNAKHSHDNVYGHKHDHGEPGPWIDMRVRRYDVRGEWRTQLPF     367
```

PROTEINS AND IMMUNIZING COMPOSITIONS CONTAINING *PASTEURELLA* PROTEINS AND METHODS OF USE

CROSS-REFERENCE TO RELATED APPLICATIONS

This application is a continuation of U.S. application Ser. No. 17/191,913, filed Mar. 4, 2021, which is a continuation of U.S. application Ser. No. 16/484,332, filed Aug. 7, 2019, now U.S. Pat. No. 10,967,056, and which is a § 371 U.S. National Stage of International Application No. PCT/US2018/017682, filed 9 Feb. 2018, which claims the benefit of U.S. Provisional Application No. 62/457,599, filed Feb. 10, 2017, the disclosures of which are incorporated by reference herein in their entireties.

SEQUENCE LISTING

This application contains a Sequence Listing electronically submitted via Patent Center to the United States Patent and Trademark Office in XML format entitled "0293000056US03", having a size of 105 kilobytes and created Sep. 18, 2023. This information contained in the Sequence Listing is incorporated by reference herein.

BACKGROUND

*Pasteurella* spp. are gram negative, facultatively anaerobic and pleomorphically rod shaped bacteria able to cause disease in a variety of animals as well as humans. Species of *Pasteurella* in domestic and wild animals have evolved a particular niche for mucosal membranes of the upper respiratory, mucosa of the oral cavity and lower genital tract. In farm animals, diseases are based on clinical symptoms and on the particular *Pasteurella* specie associated with disease. Today *Pasteurella multocida* and *Mannheimia haemolytica* are the two most widely recognized species of the Pasteurellaceae family associated with clinical disease in animal husbandry with particular reference to poultry, cattle, pigs and rabbits. The family Pasteurellaceae currently comprises five genera; *Pasteurella, Mannheimia, Actinobacillus, Haemophilus*, and *Lonepinella* and have been the subject of extensive reclassification (Angen et al. Int. J. Syst. Bacteriol. 49: 67-86 (1999). Recently *Pasteurella haemolytica* has been taxonomically reclassified as *Mannheimia haemolytica* based on ribosomal sequencing and DNA-DNA hybridization (Oystein et al. Int. J. Syst. Bacteriol. 49:6-86 (1999).

*Pasteurella multocida* is the etiological agent of avian pasteurellosis, commonly referred to as fowl cholera, a widely distributed and economically important disease of poultry, having a high incidence in chickens, turkeys, geese and ducks (Rhoades et al. Fowl Cholera. In: Adlam, C. F. and Rutter, J. M. (Eds.), *Pasteurella* and Pasteurellosis. Academic Press, London, pp. 95-113. 1989). The organism is also responsible for inducing clinical disease in wild birds, commercially raised game birds and Psittacines (Rhoades and Rimler, 1989, Fowl cholera. In *Pasteurella* and Pasteurellosis, pp. 95-113. Edited by C. F. Adlam & J. M. Rutter. London: Academic Press). All species of birds are susceptible to varying degrees. Heavy breeds appear more susceptible than light breeds, and adult birds and those in late growing phase appear more susceptible than younger birds (Jordan et al. Poultry Diseases. Ballierre Tindall, London, pp 42-50. 1990). Four capsular serogroups (A, B, D and F) are recognized among avian strains of *Pasteurella multocida* (Rhoades et al. Avian Dis. 31: 895-898 (1987). In domestic poultry, strains belonging to capsular type A are recognized as the primary agent of pasteurellosis (Rhoades and Rimler, 1987, Avian Dis 31, 895-898; Rhoades et al. Fowl Cholera. In: Adlam, C. F. and Rutter, J. M. (Eds.), *Pasteurella* and Pasteurellosis. Academic Press, London, pp. 95-113. 1989; Wilson et al. J. Clin. Microbiol. 31: 255-259 1993)). It has been shown that avian strains of *Pasteurella multocida* are genetically diverse as demonstrated by multilocus enzyme electrophoresis and DNA-DNA hybridization. Based on these findings *P. multocida* has now been subdivided into three subspecies, *multocida, septica* and *gallicida*.

The pathogenesis of *P. multocida* is poorly understood but is dependent on both host and pathogen specific factors. To date no single virulence factor has been associated with disease among strains. Virulence factors that have been studied to date include; capsule, endotoxin, outer membrane proteins, serum resistance, iron-acquisition systems, heat shock proteins, neuraminidase production, adhesion factors, antibody cleaving enzymes and the potential existence of cytopathic toxins.

Clinical manifestation of disease may range from peracute/acute to chronic infections, and may initially arise by the colonization of the upper respiratory tract, followed by invasion and septicaemia. During acute infections, few clinical signs are observed before death which is generally dominated by septicaemic lesions. In chronic forms of *P. multocida* infections, suppurative lesions may be widely distributed involving the mucous membranes of the respiratory tract, the pharynx, nasal passages, conjunctiva and adjacent tissues of the head.

Because of the ubiquitous nature of *P. multocida*, and the potential for great economic loss, commercial vaccines have been developed to protect against outbreaks of Fowl cholera in layer and breeder broiler operations throughout the US and abroad. Inactivated commercial Fowl cholera vaccines currently available rely on somatic serotypes to offer protection. Most inactivated vaccines contain, at a minimum, *Pasteurella multocida* strains of serotype 1 (also referred to as A:1), serotype 3 (also referred to as A:3), and serotype 4 (also referred to as A:4). Fowl cholera vaccines made with one serotype do not cross protect against other serotypes, e.g., a vaccine made using a serotype 1 strain does not protect against serotypes 3 or 4.

The ability of *Pasteurella multocida* to evade the natural defense mechanisms of the vertebrate host depends in part on its ability to obtain host iron, which in turn, directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host, reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is one of the most common and well-studied mechanisms for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

Divalent metal ions such as iron, cobalt, copper, magnesium, manganese, molybdenum, nickel, selenium, and zinc are trace elements often required for the survival of bacteria infecting both animal and human hosts. These trace metal elements are used by bacteria as cofactors for enzymes that catalyze biochemical reactions for various metabolic pathways required by the organism. The impact of iron on the pathogenesis of bacteria has been studied extensively. Iron is essential for nearly all life and is required for enzymatic and metabolic pathways of organisms at all phylogenic levels. It has been well-documented that during bacterial sepsis there is an alteration in the concentration of a number of metal ions in serum such as, iron, copper, and zinc. For instance, serum levels of zinc decrease from 10 percent to 60 percent with the onset of infection. Following the onset of infection, zinc is then redistributed from plasma to liver where it is bound to metallothionein. Decreases in serum iron of up to 50 percent have been described during infectious illness, whereas serum copper has been shown to increase in response to inflammatory stimuli. The alteration of these trace metal ions in serum may directly affect the severity or progression of any bacterial infection.

With so many basic functions relying on the availability of iron, bacteria have evolved a complex regulatory network for acquiring iron under varying physiological conditions. Under anaerobic conditions, iron is present in the soluble ferrous form (Fe II) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form (Fe III) and cannot pass through the outer membrane porins by passive diffusion. Instead, molecules called siderophores are secreted by bacteria, which have a high affinity for ferric iron. The ferric-siderophore complexes are recognized by receptors in the outer membrane collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferric-siderophore complexes across the outer membrane and through the periplasmic space. ABC transport systems present in the cytoplasmic membrane serve to transport the iron-siderophore complexes across the cytoplasmic membrane. Reductase enzymes reduce the ferric iron to its ferrous form, which dissociates it from the siderophore and releases iron into the cell.

Several species of pathogenic bacteria use additional mechanisms to obtain iron from mammalian hosts, including the direct binding of transferrin, heme, and other heme-containing compounds. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Beyond the role of iron as an essential nutrient for microbial survival, there are now many other well-defined transitional metals that play critical roles in bacterial survival, homeostasis, and pathogenesis such as iron, manganese, copper, zinc, magnesium, cobalt, and nickel (Waldron and Robinson and 2009; Porcheron; 2013). Iron, zinc and copper are the three most abundant divalent metal ions in mammals in descending order of concentration. The ability of a bacterium to utilize these transitional metals by finely regulated uptake or acquisition systems significantly contributes to the virulence of pathogenic bacteria. It is well known that bacteria within the same genus/species do not have the same uptake systems for the acquisition of transitional metals owing to the difference in pathogenicity from one strain of bacteria to another. These differences in the ability of bacteria to use different transitional metals based on expressed uptake systems may specifically direct what organ or tissue an organism can invade.

Little is known regarding the iron-acquisition by *Pasteurella multocida*; it has not been studied nearly to the extent of *E. coli* iron transport systems. The iron regulated proteins of *Pasteurella* have been investigated as potential immunogens as target antigens for different vaccine strategies in multiple animal species. It has been shown that these proteins provide protective efficacy against homologous challenge yet a combination of these proteins to provide heterologous protection has eluded researchers.

Glisson et al. (Avian Diseases 37:1074-1079, 1993) attempted to induce cross-protection across serotypes by preparing bacterins from *P. multocida* strains X-73 (serotype 1) and P-1059 (serotype 3) under iron-restricted culture conditions. They found that bacterins produced in medium low in iron did not consistently induce significant protection against heterologous challenge.

SUMMARY OF THE APPLICATION

We observed results similar to Glisson when growing two heterologous strains, one of serotype 3×4 and one of serotype 1, in iron-restricted medium and attempting a vaccination and challenge model with one strain as vaccine strain and the other as challenge strain (see Examples 6-9), i.e., some protection was observed when the vaccine and the challenge were different serotypes. However, when we compared field strains of pathogenic *Pasteurella multocida*, and particularly when we compared the patterns of metal regulated proteins present in these strains, we found two major patterns of metal regulated proteins predominate in these pathogenic strains. One pattern contains 2 or 3 major metal regulated proteins, and the other pattern contains 4 distinct metal regulated proteins. When the metal regulated proteins of these two pattern types were obtained from two *P. multocida* strains, one of serotype 2,5 and one of serotype 3,4, and combined and used to vaccinate animals, we observed heterologous protection across serotypes of *P. multocida*, including protection against a *P. multocida* of another serotype not represented in the two strains used to make the vaccine. This result was unexpected and surprising. We are not aware of any reports of this type of heterologous protection being observed in vaccines that protect against *P. multocida* infection.

Provided herein are compositions. In one embodiment, a composition includes an isolated protein having at least 80% similarity to amino acids 25-968 of SEQ ID NO:2, an isolated protein having at least 80% similarity to amino acids 27-790 of SEQ ID NO:4, an isolated protein having at least 80% similarity to amino acids 23-727 of SEQ ID NO:6, an isolated protein having at least 80% similarity to amino acids 25-964 of SEQ ID NO:8, an isolated protein having at least 80% similarity to amino acids 26-848 of SEQ ID NO:10, an isolated protein having at least 80% similarity to amino acids 27-784 of SEQ ID NO:12, an isolated protein having at least 80% similarity to amino acids 25-742 SEQ ID NO:14, an isolated protein having at least 80% similarity to amino acids 26-805 of SEQ ID NO:44, or a combination thereof. The composition protects an animal, such as a chicken, against challenge with *Pasteurella multocida*.

In another embodiment, a composition includes isolated proteins having molecular weights of 99 kDa, 81 kDa, and 80 kDa where the proteins are isolatable from a *Pasteurella multocida* when incubated in media that includes an iron chelator and not isolatable when grown in the media without the iron chelator, isolated proteins having molecular weights of 109 kDa, 89 kDa, and 87 kDa wherein the proteins are isolatable from a *P. multocida* when incubated in media comprising an iron chelator, where the proteins are expressed by the *P. multocida* when incubated in media without the iron chelator and expressed at an enhanced level during growth in media that includes an iron chelator. The composition protects an animal, such as a chicken, against challenge with *P. multocida*.

In one embodiment, a includes an isolated protein having at least 80% similarity to amino acids 26-805 of SEQ ID NO:44, wherein the composition protects a chicken against challenge with *P. multocida*.

A composition described herein can optionally include additional proteins, such as at least one isolated protein having a molecular weight of 249 kDa, 60 kDa, 42 kDa, 38 kDa, 27 kDa, 26 kDa, or 22 kDa, wherein the proteins are isolatable from the *P. multocida*.

In one embodiment, a composition includes an isolated whole cell that includes at least one of the proteins of a composition described herein. The composition protects an animal, such as a chicken, against challenge with *Pasteurella multocida*. In one embodiment, the whole cell is a cell engineered to express one or more of the proteins. In one embodiment, the cell is *E. coli*. Further provided is a composition that includes isolated antibody that specifically binds to a protein of a composition described herein. In one embodiment, the antibody is polyclonal antibody.

A composition described herein can further include a pharmaceutically acceptable carrier, an adjuvant, or a combination thereof.

Also provided are methods. In one embodiment, a method includes administering to a subject an amount of a composition described herein effective to induce the subject to produce antibody that specifically binds to at least one protein of the composition. In one embodiment, a method is for treating an infection in a subject, and includes administering an effective amount of the composition described herein to a subject having or at risk of having an infection caused by a *P. multocida*. In one embodiment, a method is for treating a symptom in a subject, and includes administering an effective amount of a composition described herein to a subject having or at risk of having an infection caused by a *P. multocida*. In one embodiment, a method is for decreasing colonization in a subject, and includes administering an effective amount of a composition described herein to a subject colonized by a *P. multocida*. In one embodiment, a method is for treating an infection in a subject, and includes administering an effective amount of a composition to a subject having or at risk of having an infection caused by a *P. multocida* wherein the composition includes antibody that specifically binds to a protein of a composition described herein. In one embodiment, a method is for treating a symptom in a subject, and includes administering an effective amount of a composition to a subject having or at risk of having an infection caused by a *P. multocida*, wherein the composition that includes antibody that specifically binds to a protein of a composition described herein. In one embodiment, a method is for decreasing colonization in a subject, and includes administering an effective amount of a composition to a subject colonized by a *P. multocida*, wherein the composition that includes antibody that specifically binds to a protein a composition described herein.

In one embodiment, the subject can be a mammal, such as a bovine, or an avian, such as a chicken or a turkey. In one embodiment, at least 700 micrograms (µg) to no greater than 1,200 µg of protein is administered.

Also provided are kits. In one embodiment, a kit is for detecting antibody that specifically binds a protein, and includes in separate containers (i) an isolated protein of the composition of claim 1 or 2, and (ii) a reagent that detects an antibody that specifically binds the protein. In one embodiment, a kit is for detecting a protein, and includes in separate containers (i) an antibody that specifically binds an isolated protein of a composition described herein, and a second reagent that specifically binds the protein.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 3. Table of proteins known to be in the reference challenge strains for serotype A:1 and serotype A:3 compared to the vaccine strain. Note the 8 proteins present in at least one of the reference strain genomes, but absent from the vaccine strain.

FIG. 6. Comparison of 38 expressed iron regulated proteins of 13 different isolates representing pattern types of FIG. 5. (+) indicates the protein is expressed, and (−) indicates the protein is not expressed at detectable levels. The ellipse identifies two potential vaccine targets that cover the majority of proteins.

FIGS. 8-1, 8-2, 9-1, 9-2, 10-1, 10-2, 11-1, 11-2, 12-1, 12-2, 13-1, 13-2, 14-1 and 14-2. The amino acid sequences of SEQ ID NOs:2, 4, 6, 8, 10, 12, and 14, and an example of a nucleotide sequence (SEQ ID NOs:1, 3, 5, 7, 9, 11, and 13, respectively) encoding each amino acid sequence.

FIGS. 15-1 and 15-2. Sequence alignment of SEQ ID NO:2 and four other sequences. WP_053521090.1 (SEQ ID NO:15), 1121_HgbA_968aa (SEQ ID NO:2), WP_005756141.1 (SEQ ID NO:16), AAQ14873.1 (SEQ ID NO:17), WP_061405928.1 (SEQ ID NO:18). All sequences are *P. multocida*, except WP_053521090.1 which is *Haemophilus influenzae*.

FIGS. 16-1 and 16-2. Sequence alignment of SEQ ID NO:4 and four other sequences. ESQ71136.1 (SEQ ID NO:19), WP_014391205.1 (SEQ ID NO:20), WP_016534044.1 (SEQ ID NO:21), 1121_FepA_790aa (SEQ ID NO:4), WP_005756883.1 (SEQ ID NO:22). All sequences are *P. multocida*.

FIGS. 17-1 and 17-2. Sequence alignment of SEQ ID NO:6 and four other sequences. WP_071522773.1 (SEQ ID NO:23), WP_016534444.1 (SEQ ID NO:24), WP_005755819.1(SEQ ID NO:25), 1121_PfhR_727aa (SEQ ID NO:6), EGP05580.1 (SEQ ID NO:26). All sequences are *P. multocida*.

FIGS. 18-1, 18-2 and 18-3. Sequence alignment of SEQ ID NO:8 and five other sequences. 1135_PM0300_964aa (SEQ ID NO:8), WP_005753642.1 (SEQ ID NO:27), WP_016534557.1 (SEQ ID NO:28), WP_010906573.1 (SEQ ID NO:29), AAQ14873.1 (SEQ ID NO:30), 1121_HgbA_968aa (SEQ ID NO:2). All sequences are *P. multocida*.

FIGS. 19-1 and 19-2. Sequence alignment of SEQ ID NO:10 and four other sequences. WP_017861186.1 (SEQ ID NO:31), AAU29202.1 (SEQ ID NO:32), EGP04511.1 (SEQ ID NO:33), 1135_HasR_848aa (SEQ ID NO:10), WP_005752163.1 (SEQ ID NO:34). All sequences are *P. multocida*.

FIGS. 20-1 and 20-2. Sequence alignment of SEQ ID NO:12 and four other sequences. WP_005751557.1 (SEQ ID NO:35), 1135_PM0741_784aa (SEQ ID NO:12), WP_016534554.1 (SEQ ID NO:36), WP_064972816.1 (SEQ ID NO:37), WP_074865020.1 (SEQ ID NO:38). All sequences are *P. multocida*.

FIGS. 21-1 and 21-2. Sequence alignment of SEQ ID NO:14 and four other sequences. WP_050948957.1 (SEQ ID NO:39), WP_014391043.1 (SEQ ID NO:40), WP_016533738.1 (SEQ ID NO:41), 1135_P1062_0207600_742aa (SEQ ID NO:14), WP_025248456.1 (SEQ ID NO:42). All sequences are *P. multocida*, except WP_050948957.1 which is *Haemophilus influenzae*.

FIGS. 22-1 and 22-2. The amino acid sequences of SEQ ID NO:44 and an example of a nucleotide sequence (SEQ ID NO:43) encoding the amino acid sequence. The first 78 nucleotides of SEQ ID NO:43 are predicted to encode the signal sequence of SEQ ID NO:44 (amino acids 1-26).

FIG. 25. Sequence alignment of the zinc affinity region of zinc acquisition proteins from *Mannheimia haemolytica* (ZAP, SEQ ID NO:45) and 10 other respiratory pathogens. AHG81836.1 (SEQ ID NO:46), WP_005612269.1 (SEQ ID NO:47), WP_027074597.1 (SEQ ID NO:48), AHG73391.1 (SEQ ID NO:49), WP_021114857.1 (SEQ ID NO:50), WP_026212957.1 (SEQ ID NO:51), WP_028858792.1

Figure 1:
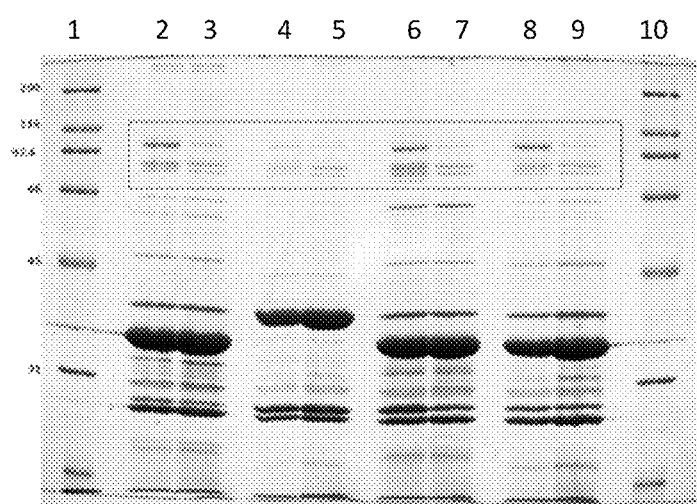
FIG. 1. SDS-PAGE gel of extract of bacteria grown under iron limiting and iron replete conditions. Lanes 1 and 10: Broad range molecular weight markers; Lane 2: Vaccine candidate MS061130 under iron restriction; Lane 3: Vaccine candidate strain under iron replete conditions. Lane 4: serotype 1 reference strain X-73 under iron limited conditions. Lane 5: X-73 under iron replete conditions. Lane 6: Serotype 3 reference strain P1059 under iron limiting conditions. Lane 7: P1059 under iron replete conditions. Lane 8: reference strain P-1662 under iron limiting conditions; lane 9: P-1662 under iron replete conditions. Note the similar molecular weights of the iron-regulated proteins as depicted within the rectangle.

(SEQ ID NO:52), WP_016534590.1 (SEQ ID NO:53), KDN24548.1 (SEQ ID NO:54), and WP_027021676.1 (SEQ ID NO:55).

DETAILED DESCRIPTION OF ILLUSTRATIVE EMBODIMENTS

In one aspect, this disclosure provides proteins and compositions including proteins. As used herein, "protein" refers to a polymer of amino acids linked by peptide bonds. Thus, for example, the terms peptide, oligopeptide, polypeptide, and enzyme are included within the definition of protein. This term also includes proteins that may include one or more post-expression modifications of the protein such as, for example, a glycosylation, an acetylation, a phosphorylation, and the like. The term protein does not connote a specific length of a polymer of amino acids. A protein may be isolatable directly from a natural source or can be prepared with the aid of recombinant, enzymatic, or chemical techniques. In the case of a protein that is naturally occurring, such a protein is typically isolated.

An "isolated" protein is one that has been removed from its natural environment. For instance, an isolated protein is a protein that has been removed from the cytoplasm or from the membrane of a cell, and many of the proteins, nucleic acids, and other cellular material of its natural environment are no longer present.

A protein characterized as "isolatable" from a particular source is a protein that, under appropriate conditions, is produced by the identified source, although the protein may be obtained from alternate sources using, for example, conventional recombinant, chemical, or enzymatic techniques. Thus, characterizing a protein as "isolatable" from a particular source does not imply any specific source from which the protein must be obtained or any particular conditions or processes under which the protein must be obtained.

A "purified" protein is one that is at least 60% free, preferably at least 75% free, and most preferably at least 90% free from other components with which they are naturally associated. Proteins that are produced outside the organism in which they naturally occur, e.g., through chemical or recombinant means, are considered to be isolated and purified by definition, since they were never present in a natural environment.

Generally, a protein may be characterized by molecular weight, amino acid sequence, mass fingerprint, nucleic acid that encodes the protein, immunological activity, or any combination of two or more such characteristics. The molecular weight of a protein, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Unless indicated otherwise, reference to molecular weight refers to molecular weight as determined by resolving a protein using an SDS polyacrylamide gel having a stacking gel of about 4% and a resolving gel of about 10% under reducing and denaturing conditions. In one embodiment, the molecular weight of a protein identified by SDS-PAGE includes molecular weights of 1, 2, 3, 4, or 5 kDa above and below the stated value.

The proteins described herein may be metal-regulated. As used herein, a "metal-regulated protein" is a protein that is expressed by a microbe at a greater level when the microbe is grown in low metal conditions compared to when the same microbe is grown in high metal conditions. Low metal and high metal conditions are described herein. For instance, certain metal-regulated proteins produced by P. multocida are not expressed at detectable levels during growth of the microbe in high metal conditions but are expressed at detectable levels during growth in low metal conditions. In one embodiment, a metal-regulated protein can be a siderophore receptor protein. Examples of metal-regulated proteins isolatable from a P. multocida after growth in low iron conditions include metal-regulated proteins having molecular weights of 104 kDa to 75 kDa. Specific examples of metal-regulated proteins isolatable from a P. multocida after growth in low iron conditions include proteins of 99 kDa, 81 kDa, and 80 kDa as determined by resolving a protein using an SDS polyacrylamide gel having a stacking gel of about 4% and a resolving gel of about 10% under reducing and denaturing conditions. In one embodiment, a low iron conditions is growth in the presence of 2,2'-dipyridyl. Examples of the iron regulated proteins having molecular weights of 99 kDa, 81 kDa, and 80 kDa, and nucleotide sequences encoding the proteins, are shown in FIGS. 10, 14, and 6, respectively. A specific example of metal-regulated proteins isolatable from a P. multocida after growth in low zinc conditions include a protein of 91 kDa as determined by resolving a protein using an SDS polyacrylamide gel having a stacking gel of about 4% and a resolving gel of about 10% under reducing and denaturing conditions. In one embodiment, a low zinc conditions is growth in the presence of N,N,N',N'-tetrakis(2-pyridylmethyl)ethylenediamine (TPEN) (Sigma-Aldrich, St. Louis MO). An example of the zinc regulated protein having a molecular weight of 91 kDa, and nucleotide sequences encoding the protein, is shown in FIG. 22.

The proteins described herein may be expressed at detectable levels during growth of the microbe in high metal conditions but expressed at higher levels during growth in low metal conditions. The expression of such proteins is referred to herein as "enhanced" during growth in low metal conditions. Typically, the increase in expression of a protein during growth in low metal conditions is between 50% and 500% compared to the expression of the protein during growth in high metal conditions.

Examples of metal-regulated proteins having enhanced expression and isolatable from P. multocida after growth in low iron conditions include metal-regulated proteins having molecular weights of and 114 kDa to 82 kDa. Specific examples of metal-regulated proteins isolatable from a P. multocida after growth in low iron conditions include proteins of 109 kDa, 89 kDa, and 87 kDa as determined by resolving a protein using an SDS polyacrylamide gel having a stacking gel of about 4% and a resolving gel of about 10% under reducing and denaturing conditions. Examples of the proteins having molecular weights of 109 kDa and nucleotide sequences encoding them are shown in FIGS. 8 and 11. Examples of the proteins having molecular weights of 89 kDa and 87 kDa, and nucleotide sequences encoding the proteins, are shown in FIGS. 13 and 9, respectively.

This disclosure also describes certain proteins that are not metal-regulated. Such proteins are expressed in the presence of a metal ion such as, for example, in the presence of ferric chloride, and also expressed when grown in low iron conditions. Examples of this type of protein isolatable from P. multocida have molecular weights of 254 kDa to 244 kDa, 65 kDa to 55 kDa, and 47 kDa to 17 kDa. Examples of molecular weights of this type of protein include 249 kDa, 60 kDa, 42 kDa, 38 kDa, 27 kDa, 26 kDa, and 22 kDa.

Additional examples of proteins include recombinantly-produced versions of proteins described herein. A recombinantly-produced protein may include the entire amino acid sequence translatable from an mRNA transcript. Alternatively, a recombinantly-produced protein can include a fragment of the entire translatable amino acid sequence. For example, a recombinantly-produced protein may lack a cleavable sequence at either terminus of the protein—e.g., a cleavable signal sequence at the amino terminus of the protein.

In one embodiment, a protein lacks one or more amino acids from the amino terminus of the protein encoded by a coding sequence obtained from a wild-type cell, e.g., the protein lacks a signal sequence. Thus, a fragment can lack at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, or at least 63 amino acids from the amino terminus of the protein. In one embodiment, a fragment of the protein depicted at SEQ ID NO:2 does not include amino acids 1-24. In one embodiment, a fragment of the protein depicted at SEQ ID NO:4 does not include amino acids 1-26. In one embodiment, a fragment of the protein depicted at SEQ ID NO:6 does not include amino acids 1-22. In one embodiment, a fragment of the protein depicted at SEQ ID NO:8 does not include amino acids 1-24. In one embodiment, a fragment of the protein depicted at SEQ ID NO:10 does not include amino acids 1-25. In one embodiment, a fragment of the protein depicted at SEQ ID NO:12 does not include amino acids 1-26. In one embodiment, a fragment of the protein depicted at SEQ ID NO:14 does not include amino acids 1-24. In one embodiment, a fragment of the protein depicted at SEQ ID NO:44 does not include amino acids 1-26.

Whether a protein is a metal-regulated protein, an enhanced protein, or a non-metal-regulated protein can be determined by methods useful for comparing the presence of proteins, including, for example, gel filtration, gel electrophoresis including sodium dodecyl sulfate-polyacrylamide gel electrophoresis (SDS-PAGE), capillary electrophoresis, mass spectrometry, isobaric tags for relative and absolute quantification (iTRAQ), and liquid chromatography including HPLC. Separate cultures of a microbe can be grown under high metal conditions and under low metal conditions, proteins may be isolated as described herein, and the proteins present in each culture can be resolved and compared. Typically, an equal amount of proteins from each culture is used. In one embodiment, the proteins can be resolved using an SDS polyacrylamide gel having a stacking gel of about 4% and a resolving gel of about 10% under reducing and denaturing conditions. For instance, 30 micrograms (g) of total protein from each culture may be used and loaded into wells of a gel. After running the gel and staining the proteins with Coomassie Brilliant Blue, the two lanes can be compared. When determining whether a protein is or is not expressed at a detectable level, 30 µg of total protein from a culture is resolved on an SDS-PAGE gel and stained with Coomassie Brilliant Blue using methods known in the art. A protein that can be visualized by eye is considered to be expressed at a detectable level, while a protein that cannot be visualized by eye is considered to not be expressed at a detectable level.

Alternatively, whether a protein is a metal-regulated protein or a non-metal-regulated protein can be determined using microarray-based gene expression analysis. Separate cultures of a microbe can be grown under high metal conditions and under low metal conditions, RNA can be extracted from cells of each culture, and differences in RNA expression in cells grown in high metal conditions versus RNA expression in cells grown in low metal conditions can be detected and compared. For example, labeled cDNA can be prepared from 8-10 µg of bacterial RNA using established protocols. The labeled cDNA can be applied to a microarray of a microbe's genome. Such microarrays are commercially available and evaluating gene expression using such arrays is routine.

The proteins described herein can have immunological activity. "Immunological activity" refers to the ability of a protein to elicit an immunological response in an animal. An immunological response to a protein is the development in an animal of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in an animal that inhibits or limits infection by *P. multocida*. Whether a protein has protective immunological activity can be determined by methods known in the art such as, for example, methods described in Examples 6-9 and 15-16. A protein may have seroactive activity. As used herein, "seroactive activity" refers to the ability of a candidate protein to react with antibody present in convalescent serum from an animal infected with a *P. multocida*.

A protein as described herein may have the characteristics of a reference protein. The characteristics can include, for example, molecular weight, mass fingerprint, amino acid sequence, or any combination thereof. In one embodiment, a protein can be obtained from a microbe. A microbe can express one, two, three, four, five, six, seven, eight, or nine of the proteins described herein. The reference protein can be isolatable from a gram negative microbe, preferably a member of the family Pasteurellaceae, including the genus *Pasteurella, Mannheimia*, or *Haemophilus*. A member of the genus *Pasteurella Mannheimia*, and *Haemophilus* is also referred to herein as *Pasteurella* spp., *Mannheimia* spp., and *Haemophilus* spp., respectively. In one embodiment, the reference protein is expressed by a *P. multocida*. In one embodiment, the *P. multocida* can be serotype 2,5 or serotype 3,4.

As used herein, a protein may be "structurally similar" to a reference protein if the amino acid sequence of the protein possesses a specified amount of sequence similarity and/or sequence identity compared to the reference protein. A protein also may be "structurally similar" to a reference protein if the protein exhibits a mass fingerprint possessing a specified amount of identity compared to a comparable mass fingerprint of the reference protein. Thus, a protein may be "structurally similar" to a reference protein if, compared to the reference protein, it possesses a sufficient level of amino acid sequence identity, amino acid sequence similarity, or a combination thereof. In one embodiment, a protein described herein can have an amino acid sequence that is structurally similar, as described below, to amino acids 25-968 of SEQ ID NO:2, amino acids 27-790 of SEQ ID NO:4, amino acids 23-727 of SEQ ID NO:6, amino acids 25-964 of SEQ ID NO:8, amino acids 26-848 of SEQ ID NO:10, amino acids 27-784 of SEQ ID NO:12, amino acids 25-742 of SEQ ID NO:14, or amino acids 26-805 of SEQ ID NO44.

Protein Sequence Similarity and Protein Sequence Identity

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein or any known metal-regulated protein, as appropriate. Examples of reference proteins include, but are not limited to, amino acids 25-968 of SEQ ID NO:2, amino acids 27-790 of SEQ ID NO:4, amino acids 23-727 of SEQ ID NO:6, amino acids 25-964 of SEQ ID NO:8, amino acids 26-848 of SEQ ID NO:10, amino acids 27-784 of SEQ ID NO:12, amino acids 25-742 of SEQ ID NO:14, and amino acids 26-805 of SEQ ID NO:44. A candidate protein is the protein being compared to the reference protein. A candidate protein can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison WI). Alternatively, proteins may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a protein containing deletions or additions of one or more contiguous or noncontiguous amino acids that do not eliminate a functional activity-such as, for example, immunological activity—of the protein are also contemplated.

Thus, as used herein, a protein as described herein and/or the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, a protein as described herein and/or the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

FIGS. 15-21 show Clustal Omega alignments for proteins having the amino acid sequences shown in SEQ ID NOs:2, 4, 6, 8, 10, 12, and 14. The alignments indicate amino acids that are conserved in the variants of each protein across different *P. multocida* strains and, for FIGS. 15 and 21, *Haemophilus influenzae*. In FIGS. 15-21 an asterisk (*) indicates positions which have a single, fully conserved residue, a colon (:) indicates conservation between groups of strongly similar properties as roughly equivalent to scoring >0.5 in the Gonnet PAM 250 matrix, and a period (.) indicates conservation between groups of weakly similar properties as roughly equivalent to scoring=<0.5 and >0 in the Gonnet PAM 250 matrix. A person of ordinary skill in the art can deduce from such data regions of the protein in which substitutions, particularly conservative substitutions, may be permitted without unduly affecting activity (immunological activity, protective immunological activity, or seroactive activity of the modified protein.

Consequently, a protein as described herein can include certain variants including, for example, homologous proteins that originate-biologically and/or recombinantly from microbial species or strains other than the microbial species or strain from which the protein was originally isolated and/or identified.

A protein described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of proteins on nickel columns. Such gene modification techniques and suitable additional sequences are well known in the molecular biology arts. A protein as described herein also may be designed so that certain amino acids at the C-terminus and/or N-terminus are deleted.

A protein described herein can include a "modification." A modification refers to a chemical or enzymatic derivatization at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified proteins as described herein may retain the biological activity—such as, for example, immunological activity—of the unmodified protein or may exhibit a reduced or increased biological activity compared to the unmodified protein.

A protein as described herein (including a biologically active analog thereof and/or a modification thereof) can include a native (naturally occurring), a recombinant, a chemically synthesized, or an enzymatically synthesized protein. For example, a protein as described herein may be prepared by isolating the protein from a natural source or may be prepared recombinantly by conventional methods including, for example, preparation as fusion proteins in bacteria or other host cells.

Polynucleotide Sequence Similarity and Polynucleotide Sequence Identity

Proteins as described herein also can be identified in terms of the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences.

As used herein, a polynucleotide as described herein and/or the nucleic acid sequence of one or more SEQ ID NOs:1, 3, 5, 7, 9, 11, 13, or 43, or a fragment thereof, can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence disclosed herein, such as SEQ ID NO:1, 3, 5, 7, 9, 11, 13, or 43, or a fragment thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes a nucleotide sequence described herein, for example, SEQ ID NO: 1, 3, 5, 7, 9, 11, or 13, or 43, or a fragment thereof. For example, two polynucleotide sequences can be compared using the Blastn program of the BLAST 2 search algorithm, as described by Tatusova et al., (*FEMS Microbiol Lett.*, 174:247-250 (1999)), and available on the world wide web at ncbi.nlm.nih.gov/BLAST/. The default values for all BLAST 2 search parameters may be used, including reward for match=1, penalty for mismatch=-2, open gap penalty=5, extension gap penalty=2, gap x dropoff=50, expect=10, wordsize=11, and filter on.

Finally, a polynucleotide as described herein can include any polynucleotide that encodes a protein as described herein. Thus, the nucleotide sequence of the polynucleotide may be deduced from the amino acid sequence that is to be encoded by the polynucleotide.

This disclosure also provides whole cell preparations of microbes. In one embodiment, the preparation includes a microbe that has been engineered to express the proteins described herein. For instance, a microbe can be engineered to express proteins having structural similarity with SEQ ID NOs:2, 4, 6, 8, 10, 12, 14, or 44, or a fragment thereof, or any subcombination of those eight proteins. The microbe can be any microbial cell that is amenable to genetic manipulation, including a gram negative or a gram positive microbe. Examples of gram negative microbes include, but are not limited to, *E. coli*, *Salmonella* spp., and *Pasteurella* spp., such as *P. multocida*.

In one embodiment, the preparation includes two or more populations of microbes. Each of the populations do not express all of SEQ ID NOs:2, 4, 6, 8, 10, 12, and 14, or a fragment thereof. Rather, each of the populations express a subset of the seven proteins, and the two or more populations when considered as a whole express the seven proteins. For instance, in one embodiment one population of microbe expresses SEQ ID NOs: 2, 4, and 6, and a second population of microbe expresses SEQ ID NOs:8, 10, 12, and 14, or a fragment thereof. A population can be a wild-type microbe or an engineered microbe. A preparation can include one or more wild-type microbes, one or more engineered microbes, or a combination of wild-type and engineered microbes. Examples of wild-type cells include members of the genus *Pasteurella*, such as *P. multocida*. In one embodiment, the cell is an attenuated *P. multocida*. The inventors have determined that administering certain types of *Pasteurella* strains as whole cells is expected to result in immunological properties that are different than the result of administering the individual strains separately. The different immunological properties include the ability to protect against *P. multocida* strains having a different serotype than the *P. multocida* cells administered to the animal. In one embodiment, one whole cell is *P. multocida* serotype 2,5 and a second whole cell is *P. multocida* serotype 3,4, and one expresses three of the seven proteins and the other expresses four of the seven proteins. In one embodiment, one of more of the populations of microbes can express SEQ ID NO:44, or a fragment thereof.

The cells present in a whole cell preparation may be inactivated such that the cells cannot replicate but the immunological activity of the proteins as described herein expressed by the microbe is maintained. Typically, the cells may be killed by exposure to agents such as glutaraldehyde, formalin, or formaldehyde.

Compositions

A composition can include one protein isolated described herein, at least two isolated proteins described herein, or a number of proteins that is an integer greater than two (e.g., at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20, and so on). In one embodiment, a composition including one protein described herein includes a protein identical to or having structural similarity with SEQ ID NO:44, or a fragment thereof. Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein in the section headed "Protein sequence similarity and protein sequence identity."

A recombinantly-produced protein may be expressed from a vector that permits expression of the protein when the vector is introduced into an appropriate host cell. A host cell may be constructed to produce one or more recombinantly-produced proteins as described herein and, therefore, can include one or more vectors that include at least one polynucleotide encoding a protein described herein. Thus, each vector can include one or more polynucleotides as described herein—i.e., a polynucleotide that encodes a protein as described herein. Methods for the genetic manipulation of microbes, such as *P. multocida*, are known and routine in the art.

Certain compositions such as, for example, those including recombinantly-produced proteins, can include a maximum number of proteins. In some embodiments, the maximum number of proteins can refer to the maximum total number of proteins. Certain compositions can include, for example, no more than 50 proteins such as, for example, no more than 40 proteins, no more than 30 proteins, no more than 25 proteins, no more than 20 proteins, no more than 17 proteins, no more than 16 proteins, no more than 15 proteins, no more than 14 proteins, no more than 13 proteins, no more than 12 proteins, no more than 11 proteins, no more than 10 proteins, no more than nine proteins, no more than eight proteins, no more than seven proteins, no more than six proteins, no more than five proteins, no more than four proteins, no more than three proteins, no more than two proteins, or no more than one protein. In other embodiments, a maximum number of recombinantly-produced proteins may be specified in a similar manner. In still other embodiments, a maximum number of non-recombinantly-produced proteins may be specified in a similar manner.

In one embodiment, a composition can include proteins isolatable from one microbe when the microbe is engineered to express one or more proteins identical to or having structural similarity with a protein described herein. In one embodiment, the microbe is engineered to express proteins identical to or having structural similarity with one of more of SEQ ID NOs:2, 4, 6, 8, 10, 12, 14, and 44, or a fragment thereof. In one embodiment, the microbe expresses a protein identical to or having structural similarity with SEQ ID NO:44, or a fragment thereof. In one embodiment, a composition can include proteins isolatable from two or more microbes. For instance, a composition can include proteins isolatable from two or more wild-type *P. multocida.*

In certain embodiments, a composition can include a preparation of whole cells. In one embodiment, the preparation is a whole cell that has been engineered to express one or more proteins identical to or having structural similarity with a protein described herein. In one embodiment, the microbe is engineered to express proteins identical to or have structural similarity with SEQ ID NOs:2, 4, 6, 8, 10, 12, and 14, or a fragment thereof. In one embodiment, the microbe is engineered to express proteins are identical to or have structural similarity with SEQ ID NOs:2, 4, 6, 8, 10, 12, 14, and 44, or a fragment thereof. In one embodiment, the microbe expresses a protein identical to or having structural similarity with SEQ ID NO: 44, or a fragment thereof. In one embodiment, the preparation is two or more populations of microbes where each of the populations express a subset of the proteins, e.g., the seven proteins (proteins identical to or having structural similarity with SEQ ID NOs:2, 4, 6, 8, 10, 12, and 14, or a fragment thereof), or the eight proteins (proteins identical to or having structural similarity with SEQ ID NOs:2, 4, 6, 8, 10, 12, 14, and 44, or a fragment thereof) and the two or more populations when considered as a whole express the seven proteins. In some of these embodiments, the whole cell can be a *P. multocida*, such as a wild-type *P. multocida*. In some embodiments, a composition can include whole cell preparations from two, three, four, five, or six strains.

Specific examples of compositions include, but are not limited to, the following. In one embodiment, a composition includes metal regulated proteins and enhanced proteins. The metal regulated proteins are isolatable from *P. multocida* after growth in low iron conditions and have molecular weights of 104 kDa to 75 kDa, such as 99 kDa, 81 kDa, and 80 kDa. The proteins can be, or have structural similarity with, a fragment of SEQ ID NOs:6, 10, or 14. The enhanced proteins are isolatable from *P. multocida* after growth in low iron conditions and have molecular weights of 156 kDa to 146 kDa, such as 151 kDa, and 114 kDa to 82 kDa, such as 109 kDa, 89 kDa, and 87 kDa. The proteins can be, or have structural similarity with, a fragment of SEQ ID NOs:2, 4, 8, or 12. Optionally, a composition can include non-metal regulated proteins that are isolatable from *P. multocida*. The non-metal regulated proteins can have molecular weights of 254 kDa to 244 kDa, such as 249 kDa, 65 kDa to 55 kDa, such as 60 kDa, and 47 kDa to 17 kDa, such as 42 kDa, 38 kDa, 27 kDa, 26 kDa, and 22 kDa. Another specific example of a composition is one that includes a protein that is, or has structural similarity with, a fragment of SEQ ID NO:44, or a fragment thereof.

Optionally, a protein described herein can be covalently bound to a carrier protein to improve the immunological properties of the protein. Useful carrier proteins are known in the art. The chemical coupling of a protein described herein can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, New York, NY (1988)).

A compositions described herein can include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site.

The concentration of LPS can be determined using routine methods known in the art. Such methods typically include measurement of dye binding by LPS (see, for instance, Keler and Nowotny, *Analyt. Biochem.*, 156, 189 (1986)) or the use of a Limulus amebocyte lysate(LAL) test (see, for instance, Endotoxins and Their Detection With the Limulus Amebocyte Lystate Test, Alan R. Liss, Inc., 150 Fifth Avenue, New York, NY (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX-ATE (Sigma Chemical Co., St. Louis, MO; see Sigma Technical Bulletin No. 210), and PYROTELL (Associates of Cape Cod, Inc., East Falmouth, MA). Typically, assay conditions include contacting the composition with a preparation containing a lysate of the circulating amebocytes of the horseshoe crab, Limulus polyphemus. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, MD, Catalog No. 235503), and Associates of Cape Cod, Inc., (Catalog No. E0005). In general, when a composition of the present invention is prepared by isolating proteins from a microbe, such as *P. multocida*, by a method as described herein (e.g., a method that includes disrupting and solubilizing the cells, and collecting the insoluble proteins), the amount of LPS in a composition of the present invention is less than the amount of LPS present in a mixture of same amount of the microbe that has been disrupted under the same conditions but not solubilized. Typically, the level of LPS in a composition of the present invention is decreased by, in increasing order of preference, at least 50%, at least 60%, at least 70%, at least 80%, or at least 90% relative to the level of LPS in a composition prepared by disrupting, but not solubilizing, the same microbe.

A composition described herein optionally further includes a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. Exemplary pharmaceutically acceptable carriers include buffer solutions and generally exclude blood products such as, for example, whole blood and/or plasma. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous, intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition of the present invention is administered in an amount sufficient to provide an immunological response to proteins or whole cells described herein. The amount of protein present in a composition can vary. For instance, the dosage of protein can be between 0.01 micrograms (μg) and 3000 milligrams (mg), typically between 100 μg and 2000 ug. When the composition is a whole cell preparation, the cells can be present at a concentration of $10^6$ bacteria/ml, $10^7$ bacteria/ml, $10^8$ bacteria/ml, or $10^9$ bacteria/ml. When a mixture of whole cells is administered (e.g., one population of cells expressing a subset of proteins and a second population expressing another subset of proteins) the ratio of populations can be 1:1. For an injectable composition (e.g. subcutaneous, intramuscular, etc.) the protein is preferably present in the composition in an amount such that the total volume of the composition administered is 0.5 ml to 5.0 ml, typically 1.0-3.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific proteins or cells chosen, the weight, physical condition and age of the animal, and the route of administration. Thus, the absolute weight of the protein or number of cells included in a given unit dosage form can vary, and depends upon factors such as the species, age, weight and physical condition of the animal, as well as the method of administration. Such factors can be determined by one skilled in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a protein or whole cell described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (available from under the tradename EMULSIGEN from MVP Laboratories, Ralston, Nebraska), ISA-70, RIBI and other substances known in the art.

In another embodiment, a composition including a pharmaceutically acceptable carrier can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Methods of Making

This disclosure also provides methods for obtaining the proteins and whole cells described herein. Proteins and whole cell preparations described herein may be obtained by incubating a microbe, such as *P. multocida*, under conditions that promote expression of one or more of the proteins described herein. The proteins and whole cells as described herein may be isolatable from a microbe engineered to recombinantly express one or more of the proteins. In one embodiment, a *P. multocida* of serotype 2,5 or serotype 3,4 is used. In addition, such microbes are readily obtainable by techniques routine and known in the art. The microbes may be derived from an infected animal as a field isolate, and used to obtain the proteins and/or the whole cell preparations as described herein, or stored for future use, for example, in a frozen repository at from −20° C. to −95° C., or from −40° C. to −50° C., in bacteriological media containing 20% glycerol, and other like media.

The present invention also includes compositions prepared by the processes disclosed herein. Typically, such conditions are low metal conditions. As used herein, the phrase "low metal conditions" refers to an environment, typically a bacteriological medium that contains amounts of a free metal that cause a microbe to express a metal regulated protein at a detectable level. As used herein, the phrase "high metal conditions" refers to an environment that contains an amount of a free metal that causes a microbe to express a metal-regulated protein at a decreased level compared to expression of the metal-regulated protein under low metal conditions. In some cases, "high metal conditions" can refer to an environment that causes a cell to fail to express one or more of the metal-regulated proteins described herein at a detectable level. In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron, copper, or zinc.

Low metal conditions are generally the result of the addition of a metal chelating compound to a bacteriological medium, the use of a bacteriological medium that contains low amounts of a metal, or a combination thereof. High metal conditions are generally present when a chelator is not present in the medium, when a metal is added to the medium, or a combination thereof. Examples of metal chelators include natural and synthetic compounds. Examples of natural compounds include plant phenolic compounds, such as flavonoids. Examples of flavonoids include the iron chelator myricetin. Examples of synthetic iron chelators include 2,2'-dipyridyl (also referred to in the art as 2,2'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as the catecholates and hydroxamates, and citrate.

In one embodiment, 2,2'-dipyridyl is used for the chelation of iron. Typically, 2,2'-dipyridyl is added to the media at a concentration of at least 0.0025 micrograms/milliliter (μg/ml), at least 0.025 μg/ml, or at least 0.25 μg/ml. High levels of 2,2'-dipyridyl can be μg/ml, 20 μg/ml, or 30 μg/ml.

Typically, TPEN is added to the media at a concentration of at least 25 micromolar (μM), at least 50 μM, or at least 70 μM. In one embodiment, TPEN can be 70 μM for expression of the polypeptide described herein, and higher levels may also be used.

It is expected that a *P. multocida* with a mutation in a fur gene will result in the constitutive expression of many, if not all, of the metal regulated proteins of the present invention. The production of a fur mutation in a *P. multocida* can be produced using routine methods including, for instance, electroporation and genetic constructs useful for gene knock-out in gram negative bacteria.

In one embodiment, the microbe, such as *P. multocida* used to make a composition described herein, e.g., a composition including isolated proteins or a composition including whole cells, may be produced using a *P. multocida* that has been engineered to recombinantly express one or more of the proteins described herein. In one embodiment, a *P. multocida* that expresses one or more of the proteins can be engineered to express the others. In one embodiment, such a *P. multocida* is incubated in the presence of low iron conditions, and the one or more recombinant proteins are expressed during the incubation in the low iron conditions. The result is a *P. multocida* that expresses iron-regulated proteins and the one or more recombinant proteins.

Many *Pasteurella* spp. are able to grow in low metal conditions in vitro in artificial media only after adaptation. For instance, a *Pasteurella* spp. can be adapted to low iron conditions in vitro by growth in the presence of low concentrations of an iron chelator and, after growth in a medium containing the chelator, gradually increasing the concentration of the chelator. For instance, a *Pasteurella* spp. can be adapted to growth in low iron conditions by adding 0.0025 μg/ml of 2,2'-dipyridyl to a medium, and gradually increasing the concentration of the chelator to a greater concentration, for instance 25 μg/ml.

The medium used to incubate the microbe is not critical, and conditions useful for the culture of *P. multocida* are known to the skilled person. The volume of medium used to incubate the microbe can vary. When a *P. multocida* microbe is being evaluated for the ability to produce the proteins described herein, the microbe can be grown in a suitable volume, for instance, 10 milliliters to 1 liter of medium. When a microbe is being grown to obtain proteins for use in, for instance, administration to animals, the microbe may be grown in a bioreactor to allow the isolation of larger amounts of proteins. Methods for growing microbes in a bioreactor are routine and known in the art. The conditions used for growing a microbe preferably include a metal chelator, more preferably an iron chelator, for instance 2,2'-dipyridyl, TPEN, or quercetin, a pH of between 6.5 and 7.5, preferably between 6.9 and 7.1, and a temperature of 37° C. When a fermentor is used, the culture may be purged with an appropriate gas to reduce dissolved oxygen content. Nitrogen is an example of such a gas. Dissolved oxygen may be regulated automatically or manually by agitation, the introduction of sterile air or pure oxygen to the culture.

In some aspects of the invention, a *P. multocida* may be harvested after growth. Harvesting includes concentrating the microbe into a smaller volume and suspending in a media different than the growth media. Methods for concentrating a microbe are routine and known in the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted. In one embodiment, bacterial cells may be concentrated into a pellet by, for instance, centrifugation, and the concentrated cells suspended in osmotic shock buffer (OMS; 7.26 grams/liter Tris-base and 0.93 grams/liter EDTA adjusted to a pH of 8.5). The ratio of cells to OMS may be 50 grams cell pellet, 60 grams cell pellet, or 70 grams cell pellet to 1 liter of OMS. The suspension of cells in OMS can be incubated at 2-8° C. for at least 24 hours, at least 48 hours, or at least 60 hours to remove excess endotoxin from the cells. In one embodiment, the incubation is for no greater than 72 hours. After the incubation the suspension is centrifuged again and the supernatant discarded to remove free endotoxin and any extracellular material, e.g., secreted proteins.

When the *P. multocida* is to be used as a whole cell preparation, the harvested cells may be processed using routine and known methods to inactivate the cells. Alternatively, when a *P. multocida* is to be used to prepare proteins of the present invention, the *P. multocida* may be disrupted using chemical, physical, or mechanical methods routine and known in the art, including, for example, french press, sonication, or homogenization. Preferably, homogenization is used. As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., proteins, nucleic acids, carbohydrates) into the aqueous phase of the buffer in which the microbe was disrupted, and the formation of aggregates of insoluble cellular materials. The conditions for solubilization preferably result in the aggregation of proteins of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the proteins described herein may be isolated by methods that are routine and known in the art, such as centrifugation, filtration, or a combination thereof. In one embodiment, the insoluble aggregates are isolated by filtration, such as tangential or crossflow filtration. Examples of a molecular weight cutoff to use with tangential filtration are 100 kDa or 300 kDa. In one embodiment, a tangential filtration system has a pore size of 0.2 microns. Tangential filtration may aid in removal of residual sarcosine from the protein suspension. Tangential filtration results in concentration of the protein suspension. Thus, the insoluble aggregates can be isolated at a significantly lower cost.

In one embodiment, the sarcosine is removed from the isolated proteins. Methods for removing sarcosine from the isolated proteins are known in the art, and include, for instance, diafiltration, precipitation, hydrophobic chromatography, ion-exchange chromatography, affinity chromatography, and ultra-filtration and washing the proteins in alcohol, such as isopropyl alcohol, by diafiltration. After isolation, the proteins suspended in buffer and stored at low temperature, for instance, −20° C. or below. In those aspects of the present invention where a whole cell preparation is to be made, after growth the microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated protein of the invention may be prepared recombinantly. When prepared recombinantly, a polynucleotide encoding the protein may be identified and cloned into an appropriate expression host. The recombinant expression host may be grown in an appropriate medium, disrupted, and the proteins isolated as described above.

Methods of Use

Also provided are methods of using the compositions described herein. The methods include administering to an animal an effective amount of a composition described herein. As used herein, an "effective amount" of a composition described herein is the amount able to elicit the desired response in the recipient. The composition can be administered at a time that maternal antibody may be present, for instance, as early as one day of age, or at a later time during the life of the animal. In one embodiment, the composition is administered before weaning, or at the time the animal is weaned (when the animal begins to be accustomed to food other than its mother's milk). The animal can be, for instance, fish, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, a dog or a cat), members of the family Cervidae (including, for instance, deer, elk, moose, caribou and reindeer), or a human. Examples of companion animals include dogs and cats. In one embodiment, an animal is a mouse. In one embodiment, an animal is a hooved animal.

The methods described herein refer to gram negative microbes. As used herein, a gram negative microbe includes, but is not limited to, members of the family Pasteurellaceae, such as *Pasteurella* spp. (including, for instance, *P. multocida* and *P. haemolytica*), *Photobacterium damsela* subsp., *piscicida* formerly known as *Pasteurella piscicida, Mannheimia* spp., and *Haemophilus* spp., members of the family Vibrionaceae (including, for instance, *Vibrio cholerae*), *Campylobacter* spp. (including, for instance, *C. jejuni*), members of the family Enterobacteriaceae (including, for instance, *Klebsiella* spp., *E. coli, Shigella* spp., *Salmonella* spp., *Proteus* spp., *Serratia* spp., and *Yersinia* spp.), and members of the family Pseudomonadaceae, preferably *Pseudomonas* spp., (including, for instance, *Pseudomonas aeruginosa*). Examples of *Klebsiella* spp. include *K. pneumoniae* and *K. oxytoca*. Examples of *Salmonella* spp. include *Salmonella enterica* serovars., Bredeney, Dublin, Agona, Blockley, *Enteriditis, Typhimurium*, Hadar, Heidelberg, Montevideo, Muenster, Newport senftenberg *Salmonella cholerasuis*, and *S. typhi*. Examples of strains of *P. multocida* include, for example, *P. multocida* serotypes 1 through 16 (serotype 1, 2, 3, 4, 5, 6, 7, 8, 9, 10, 11, 12, 13, 14, 15, or 16) or combinations thereof (for instance, 2,5, also referred to as 2×5 [both serotypes 2 and 5 are expressed by a *P. multocida*], or 3, 4 also referred to as 3×4 [both serotypes 3 and 4 are expressed by a *P. multocida*]). Examples of strains of *E. coli* include, for example, *E. coli* serotypes O1a, 02a, 078, and 0157; different O:H serotypes including 0104, 0111, 026, 0113, 091; hemolytic strains of enterotoxigenic *E. coli* such as K88$^+$, F4$^+$, F18ab$^+$, and F18ac$^+$; enteropathogenic (EPEC), enterohemorrhagic (EHEC), enteroinvasive (EIEC) and enteroaggregative (EAEC) strains of *E. coli*; and *E. coli* able to cause extraintestinal infections, such as uropathogenic strains. In one embodiment, the gram negative microbe is a pathogenic microbe. Respiratory pathogens such as *Bordetella* such species as *B. bronchiseptica, B. pertussis* and *B. parapertussis*, and *B. avium*.

In some embodiments, a method may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some embodiments annual boosters will not be necessary, as an animal will be challenged in the field by exposure to microbes expressing proteins having epitopes that are structurally related to epitopes present on proteins of the composition administered to the animal.

In one embodiment, a method includes making antibody to a protein described herein, for instance by inducing the production of antibody in an animal, or by recombinant techniques. The antibody produced includes antibody that specifically binds at least one protein present in the composition. In this embodiment, an "effective amount" is an amount effective to result in the production of antibody in the animal. Methods for determining whether an animal has produced antibodies that specifically bind a protein present in a composition of described herein can be determined using routine methods. Also provided is antibody that specifically binds to a protein described herein, and compositions including such antibodies.

As used herein, an antibody that can "specifically bind" a protein is an antibody that interacts with the epitope of the antigen that induced the synthesis of the antibody, or interacts with a structurally related epitope. At least some of the epitopes present in the proteins described herein are epitopes that are conserved in the proteins of different species and different genera of microbes. Accordingly, antibody produced using a protein described herein is expected to bind to proteins expressed by more than one species of microbe, and provide broad spectrum protection against gram negative microbes.

In one embodiment, a method includes treating an infection in an animal, caused by a gram negative microbe. As used herein, the term "infection" refers to the presence of a gram negative microbe in an animal's body, which may or may not be clinically apparent. Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of a composition described herein to an animal having, or at risk of having, an infection caused by a gram negative microbe, and determining whether the number of microbes causing the infection has decreased. In this embodiment, an "effective amount" is an amount effective to reduce the number of the specified microbes in an animal or reduce the likelihood that the animal experiences a clinically-evident infection compared to an animal to which the composition is not administered. Methods for determining whether an infection is caused by a gram negative microbe are routine and known in the art, as are methods for determining whether the infection has decreased. The successful treatment of a gram negative microbial infection in an animal is disclosed in Examples 15-16, which demonstrates that a composition described herein made from two *P. multocida* strains, one serotype 2×5 and one serotype 3×4, protected chickens from challenge with a *P. multocida* of serotype 1.

In another embodiment, a method includes treating one or more symptoms or clinical signs of certain conditions in an animal that may be caused by infection by a gram negative microbe. The method includes administering an effective amount of a composition described herein to an animal having or at risk of having a condition, or exhibiting symptoms and/or clinical signs of a condition, and determining whether at least one symptom and/or clinical sign of the condition is changed, preferably, reduced. In one embodiment, the animal has a condition caused by a member of the family Pasteurellaceae, such as *Pasteurella* spp.

(including, for instance, *P. multocida*, *P. haemolytica*, and *P. anatipestifer*), *Mannheimia* spp., or *Haemophilus* spp. Examples of conditions include, but are not limited to, fowl cholera, new duck disease, Bovine Respiratory Disease Complex (also referred to as shipping fever pneumonia, or simply pneumonia), hemorrhagic septicemia in cattle, buffalo and bison in tropical and subtropical areas; pneumonia and atrophic rhinitis in swine; snuffles in rabbits; and mastitis and pneumonia in sheep. *Mannheimia haemolytica*, also known as *Pasteurella haemolytica*, can cause fibrinous pleuropneumonia involved in the shipping fever complex in cattle, septicemia in newborn and pneumonia and mastitis in adult sheep. *Haemophilus* spp. can cause Glasser's disease in swine, fowl coryza in chickens, contagious equine metritis. *P. multocida* can cause fowl cholera which, in the peracute form, is one of the most virulent and highly infectious diseases of poultry. *P. anatipestifer* can cause new duck disease (also known as duck septicaemia or infectious serositis).

Treatment of symptoms and/or clinical signs associated with conditions caused by infection by a gram negative microbe can be prophylactic or, alternatively, can be initiated after the development of a condition described herein. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Symptoms and/or clinical signs caused by a gram negative microbial infection are known to the person skilled in the art. Examples of symptoms and/or clinical signs include, but are not limited to, pneumonia, depression and toxemia, fever, serious to mucopurulent nasal discharge, moist cough, a rapid, shallow respiratory rate, abscesses and lesions in the lungs of cattle and swine; acute septicemia, joint infections and arthritis in poultry and wildfowl; turbinate atrophy in swine; superficial abscesses in cats; bite wound infections in humans, usually from dog or cat bites. Treatment initiated after the development of a condition may result in decreasing the severity of the symptoms or signs of one of the conditions, or completely removing the symptoms or signs. In this embodiment, an "effective amount" is an amount effective to prevent the manifestation of symptoms or signs of a disease, decrease the severity of the symptoms or signs of a disease, and/or completely remove the symptoms or signs.

Also provided is a method for decreasing colonization by a gram negative microbe, for instance blocking the attachment sites of a gram negative microbe, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioles, alveoli), digestive system (for instance, mouth, salivary glands, esophagus, liver, stomach, large and small intestine), excretory system (for instance, kidney, ureter, bladder, and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a sub-colonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition described herein to an animal colonized by, or at risk of being colonized by, a gram negative microbe. In this embodiment, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's respiratory tract by a microbe can be determined by measuring the presence of the microbe in the animal's specimens from the lower respiratory tract by tracheal swab, transtracheal wash, or bronchoalveolar lavage. It is expected that decreasing the colonization of an animal by a microbe will reduce transmission of the microbe to other animals of the same or different species.

Also provided is the use of such antibody to target a microbe expressing a protein having an epitope structurally related to an epitope present on a protein described herein. A composition described herein can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24):10029-33; Daugherty et al., Nucleic Acids Res., 1991, 19(9):2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a protein having an epitope structurally related to an epitope present on a protein described herein.

Animal models are available for experimentally evaluating the compositions described herein. These models are commonly accepted models for the study of disease caused by gram negative microbes. In those cases where a gram negative microbe causes disease in an animal, for instance a cow or a chicken, the natural host can be used to experimentally evaluate the compositions described herein.

However, protection in an animal model is not the only way to assess whether a composition can confer protection to an animal against infection by a gram negative microbe. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in conferring protection against infection such as, for example, complement fixation, opsonization, neutralization, and/or agglutination. Moreover, some subclasses of antibodies are better than others at specific functions; for example, or complement fixation the following hierarchy exists for human IgG subclasses: IgG3>IgG1>IgG2>IgG4.

Antibody immunological functions can be studied in a variety of ways. For instance, Western blots are used to identify antigen-specific binding based on size of separated proteins, while the standard enzyme-linked immunosorbant assay (ELISA) is used to produce quantitative information about antibody titers within serum. Antibody surface binding studies are used to determine whether antibody in serum are able to recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against microbial infection. However, one skilled in the art further recognizes that a lack of antibody binding in an assay such as, for example, a Western blot, ELISA, or surface binding assay does not mean that the assayed antigen fails to provide immunological activity against microbial infection.

Antibodies can mediate bacterial death by blocking the acquisition of nutrients or initiating complement-mediated membrane perforation that leads to osmotic lysis. Bactericidal antibodies can be assayed by mixing serum with live cultures and measuring for the presence of viable bacteria under appropriate conditions known to those skilled in the art. Techniques such as opsonophagocytosis assays (OPA), in which antibody and complement-bound bacteria are combined with human or mouse phagocytes to determine levels of bacterial killing, are useful for studying antibody function. A similar oxidative burst assay can be used to assess the level of reactive oxygen species (ROS) by fresh human or mouse neutrophils following interaction with antibody and complement-bound bacteria.

In some cases, one can determine that a protein described herein possesses cell-mediated immunological activity against a gram negative microbe and, therefore, the protein may exhibit immunological activity in the absence of inducing the production of antibodies. Cytotoxic or CD8 T cells primarily kill infected cells directly through various effector mechanisms, while helper CD4 T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated CD4' T cell, a memory CD8+ T cell, etc. In addition, cytokines and other products of T cells can be studied by isolating the T cells from lymphoid tissue and restimulating them with cognate antigen. Following antigen stimulation the T cells produce cytokines that may be visualized by, for example, intracellular cytokine staining coupled with flow cytometry, or collecting the cell supernatants and using Luminex bead technology to measure 15-25 cytokines simultaneously.

Thus, in addition to animal models, those of ordinary skill in the art recognize that immunological activity commensurate with the methods described herein may correlate with any one or more of the following: Western blot data showing that serum from animals exposed to a microbial pathogen contains antibody that specifically binds to a protein described herein, Western blot data showing that serum from animals exposed to protein described herein contains antibody that specifically binds to a gram negative microbe, cell surface binding assays demonstrating that antibody that specifically binds to a protein described herein specifically binds to a gram negative microbe, opsonophagocytosis data, and cytokine induction.

Also provided is a method for detecting antibody that specifically binds proteins described herein. These methods are useful in, for instance, detecting whether an animal has antibody that specifically binds a protein described herein, and diagnosing whether an animal may have a condition caused by a microbe expressing proteins that share epitopes with the proteins described herein. Such diagnostic systems may be in kit form. The methods include contacting an antibody with a preparation that includes a protein described herein to result in a mixture. The antibody may be present in a biological sample, for instance, blood, milk, or colostrum. The method further includes incubating the mixture under conditions to allow the antibody to specifically bind the protein to form a protein:antibody complex. As used herein, the term "protein:antibody complex" refers to the complex that results when an antibody specifically binds to a protein. The preparation that includes the proteins described herein may also include reagents, for instance a buffer, that provide conditions appropriate for the formation of the protein:antibody complex. The protein:antibody complex is then detected. The detection of antibodies is known in the art and can include, for instance, immunofluorescence or peroxidase. The methods for detecting the presence of antibodies that specifically bind to proteins described herein can be used in various formats that have been used to detect antibody, including radioimmunoassay and enzyme-linked immunosorbent assay.

Kits

Also provided are kits. In one embodiment, a kit is for detecting antibody that specifically binds a protein described herein. The antibody detected may be obtained from an animal suspected of having an infection caused by a gram negative microbe. In another embodiment, a kit is for detecting a protein described herein. In yet another embodiment, a kit is for using a protein described herein, such as using a protein to produce antibody, treat a condition, or treat an infection.

The kit includes at least one of the proteins described herein (e.g., one, at least two, at least three, etc.), or an antibody described herein in a suitable packaging material in an amount sufficient for at least one assay or use. Optionally, other reagents such as buffers and solutions are also included. For instance, a kit may also include a reagent to permit detection of an antibody that specifically binds to a protein described herein, such as a detectably labeled secondary antibody designed to specifically bind to an antibody obtained from an animal. Instructions for use of the packaged antibody or protein are also typically included. As used herein, the phrase "packaging material" refers to one or more physical structures used to house the contents of the kit. The packaging material is constructed by routine methods, generally to provide a sterile, contaminant-free environment. The packaging material may have a label which indicates that the proteins can be used for detecting antibody that specifically binds a protein described herein, or using a protein described herein. In addition, the packaging material contains instructions indicating how the materials within the kit are employed to detect the antibody or administer a protein to an animal. As used herein, the term "package" refers to a container such as glass, plastic, paper, foil, and the like, capable of holding within fixed limits the proteins, and other reagents, for instance a secondary antibody. Thus, for example, a package can be a microtiter plate well to which microgram quantities of proteins have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

Example 1

Selection and Preparation of Type Strains

*Pasteurella multocida* strains X-73, P-1059 and P-1662 are reference strains for serotype A:1, A:3 and A:4, respectively. Serotypes A:1, A:3, and A:4 are also referred to as serotypes 1, 3, and 4, respectively. Each of these strains was obtained from the USDA National Veterinary Services Laboratory (NVSL) (Ames, IA) as a lyophilized culture. The cultures were resuspended in sterile saline, streaked for isolation using a sterile inoculating loop onto trypticase soy agar(TSA)+5% sheep blood (Becton Dickenson, Sparks MD), and incubated overnight at 37° C. Several isolated colonies were picked from the plate with a sterile inoculating loop and transferred to a cryobank tube (Copan diagnostics, Murrietta CA) containing polystyrene beads for the purpose of cryopreservation. The cryobank tubes were then stored at <−60° C.

Example 2

Preparation of *Pasteurella multocida* Isolate

A *Pasteurella multocida*, serotype 3×4 was originally isolated from the liver and lungs of a 44 week old turkey breeder hen under natural field conditions showing clinical signs of Pasteurellosis. The isolate was plated on a tryptic soy agar (TSA) plus 5% sheep blood. After initial isolation, the organism was passed 5 times in non-animal-based Trypticase Soy Broth (naTSB) (EM Science, Darmstadt, Germany) (supplemented with 18 µg/ml 2,2' Dipyridyl (DP) (Sigma Aldrich, St. Louis, MO) and 6 g/l Yeast Extract (Becton Dickenson, Sparks, MD). Briefly, colonies were picked and inoculated into 500 ml naTSB and the culture was incubated for 16 hours and 25 minutes at 37° C. on a table-top shaker set at 105 revolutions per minute (RPM). The following morning, 25 ml of the overnight culture was transferred to 500 ml fresh naTSB and incubated for 8 hours at the same temperature and agitation. Five ml of the culture was transferred to 500 ml fresh naTSB and incubated for 15 hours in the same conditions as above. Fifty ml of this culture was transferred to 500 ml fresh naTSB and incubated in the same manner for 4 hours. Four bottles containing 900 ml naTSB each were each inoculated with 100 ml of the previous media and incubated for 3 hours and 45 minutes. The four liters of culture was aseptically dispensed into sterile 500 ml Nalgene jars and centrifuged in a Beckman model J2-21 centrifuge (Beckman Coulter, Brea CA) at 3500 rpm or approximately 1350×g for 20 minutes to pellet the bacterial cells. The supernatant was aseptically removed by aspiration and the cell pellets were resuspended in a total of 500 ml of naTSB containing 20% glycerol as a cryo-preservative. The cell suspension was then dispensed into 243 vials at 2 ml per vial and frozen at <−60° C. This frozen Master Seed was designated MS061130.

A working seed was prepared from the above frozen Master Seed. Briefly, 1-25 µl of the frozen seed was inoculated into 100 ml modified tryptose phosphate broth (mTPB) containing 6 g/l yeast extract. The culture was incubated for 13 hours at 37° C. on a table-top shaker until the culture reached an optical density (O.D.) of 0.6 to 0.8 on a Spectronic 20D spectrophotometer (Thermo Fisher Scientific, Mississauga, Ontario, Canada) set at 540 or 630 nm. The culture was transferred, 10 ml into 90 ml mTPB with 18 µg/ml 2, 2' dipyridyl and incubated for 2-3 hours at 37° C. with agitation. The culture was transferred and grown in the same manner two additional times as above. When the culture reached on O.D. of 0.8, the cells were centrifuged at approx. 3500 rpm for 20 minutes, the supernatant was aseptically removed by aspiration, and the culture was resuspended in the original volume of fresh mTPB. Sterile glycerol was added to reach 20% final concentration. The culture was mixed well, dispensed into sterile cryogenic vials at 2 ml per vial, and stored frozen at <−60° C.

Example 3

Production of Metal Regulated Proteins

*Pasteurella multocida* Type strains (X-73, P-1059, and P-1662) and the vaccine candidate strain (MS061130) of example 2 were grown in iron limiting and iron replete conditions in order to show differential membrane protein expression.

Each of the frozen type strain cultures from example 1 and the working seed isolate from example 2 were inoculated into 10 ml of porcine brain heart infusion broth (BD-Difco, Sparks MD)+6 g yeast extract (pBHI) and incubated overnight at 37□C with agitation. Two of the cultures did not grow directly in broth and so were first inoculated onto TSA+blood agar plates and incubated overnight at 37□C prior to transferring colonies to pBHI. Five ml of each overnight culture was transferred to 100 ml fresh pBHI containing either 20 µg/ml FeCl$_3$ or DP for iron-replete or iron-deplete conditions, respectively. The cultures were incubated at 37° C. for 7 hours and 30 minutes with agitation on a table top shaker (Barnstead, Dubuque IA). Bottles displayed turbidity indicating strong growth after incubation, and the cultures were then transferred, 50 ml into 500 ml of fresh pBHI containing either FeCl$_3$ or DP and incubated for 15 hours at 37° C., with agitation.

The cultures were processed to isolate outer membrane proteins. Briefly, the cultures were centrifuged for 20 minutes at approximately 11,000×g in a Beckman floor model centrifuge equipped with a JA-10 rotor (Beckman Coulter, Brea CA). The supernatant was decanted and discarded. The cell pellet was resuspended in 35 ml of Osmotic Shock Buffer (OMS) containing 7.26 grams/liter Tris-base and 0.93 grams/liter EDTA adjusted to a pH of 8.5, and the cell suspension was frozen at −80° C. for 3 hours to help weaken the cell wall structure. The cell suspension was then thawed and sonicated (Branson sonifier, model 102c) (Branson Ultrasonics, Danbury, CT) for 90 seconds in an ice water bath to prevent excessive heating of the disrupted cell suspension. Cell debris was removed by centrifugation at approximately 37,000×g for 20 minutes. Sodium lauroyl sarcosyl was added to the retained supernatant to reach a concentration of 3% v/v and the protein suspension was allowed to solubilize for 18-24 hours at 4° C. with slight agitation. Insoluble membrane proteins were collected by centrifugation at 37,000×g for at least two hours. The pellet was resuspended in tris buffered water and the resulting antigen was measured for protein content via the bicinchoninic acid (BCA) assay (Pierce BCA protein assay, ThermoFisher Scientific, Waltham MA) according to the manufacturer instructions.

Example 4

Test for Metal Regulated Protein Pattern Coverage by SDS-Page and Analysis of Protein Banding Cell extracts, derived from each isolate grown under iron restriction, were size-fractionated on SDS-PAGE gels using a 4% stacking gel and 10% resolving gel. Samples for electrophoresis were prepared by combining 30 µg of sample with 30 µl of SDS reducing sample buffer (62.5 mM Tris-HCL pH 6.8, 20% glycerol, 2% SDS, 5% beta-mercaptoethanol) boiled for 4 minutes. A sample of each extract was resolved on a 10% SDS-PAGE gel per standard methods and visualized by Coomassie Blue staining (FIG. 1). The vaccine candidate strain (MS061130) was compared to the type strains on SDS-PAGE gels. Specific attention was given to the banding patterns in the regions between 66 and 116 kDa. The vaccine candidate strain demonstrated bands overlapping with type strains, as shown in FIG. 1, and was considered a strong candidate for further protection studies.

Example 5

Production of Metal Regulated Proteins

Two separate antigen compositions were prepared at production scale using a single Master Seed MS061130 strain of *Pasteurella multocida* designated as antigen A and antigen B. This was done to evaluate the consistency of the manufacturing process.
Fermentation A cryogenic vial of the working seed of example 2 was thawed at 30-35° C. for 10-15 minutes and 0.1 ml of the thawed cell suspension was added to 250 ml of 37° C. mTPB. The culture was incubated for 6.5 hours at 37° C. on a tabletop shaker set at 70 rpm. After incubation, 25 ml of the culture was transferred to 300 ml of mTPB plus 18 µg/ml DP to restrict iron. This second culture was incubated for approximately 2 hours at 37° C. shaking at 70 rpm. The culture was transferred 250 ml into 3 liters of the above media, and the culture was incubated for approximately 3 hours at 37□C shaking at 70 rpm until an OD of 1 was reached (as measured at 540 nm). The entire culture was used to inoculate a 130 liter fermentor (Bio-Service, Easton, PA) charged with 70 liters of mTPB+18 µg/ml DP and 0.5 ml/l antifoam (MAZU DF 204 Chem/Serv, Minneapolis, MN). The parameters of the fermentation were as follows: Dissolved oxygen (DO) was maintained at 20% (target 15-30%) by automatic agitation control and airflow sparge set at 60 liters per minute (LPM) and 5 pounds per square inch (PSI) back pressure. The culture was incubated with agitation controlled automatically by controlling dissolved oxygen at 20%. The pH was controlled automatically between 6.9 and 7.1 by the automatic titration of 50% sodium hydroxide or 10% hydrochloric acid. The temperature was maintained at 37□C. The culture was allowed to grow in this manner for approximately 5 hours until an optical density of 4.21 at 540 nm was reached as measured by a Beckman DU600 spectrophotometer (Beckman Instruments, Fullerton, CA). The entire expansion culture was transferred to a 1200 liter fermentation vessel (New Brunswick Scientific, Edison, NJ) charged with 989 1 of mTPB plus DP and antifoam as listed above. The fermentation conditions were as follows: Airflow was set to 300 LPM and back pressure set at 5 PSI. Agitation was initially set to 100 RPM and then controlled by dissolved oxygen set point of 20% with a range of 15-30%. The culture was allowed to grow for another 5 hours until growth plateaued, as measured by optical density measurements being steady at approximately 2.5 at 540 nm at a 1:100 dilution for 1.5 hours. Growth was suspended by adjusting the culture pH to 8.7 and the temperature to 23° C. until harvest.

Harvest

The Bacterial Cells were Collected by Tangential Flow Filtration.

The bacterial fermentation was concentrated and washed using a Pall Filtron Tangential Flow Maxisette-25 (Pall Filtron Corporation, Northboro, MA) equipped with two 30 ft$^2$ Alpha 300-K open channel filters, catalog No. AS300C5, (Pall Filtron) connected to a Waukesha Model U-60 feed pump (Waukesha Chemy-Burrell, Delevan, Wis.) set at about 44 Hz. The original culture volume of 1078 liters was reduced to approximately 100 liters into a process tank (Lee Industries, model 2000LBDT) using a filter inlet pressure of 30 psi and a retentate pressure of 12-14 psi. The retentate (100 liters) was adjusted to 200 liters using sterile Osmotic Shock Buffer (OMS) containing 7.26 grams/liter Tris-base and 0.93 grams/liter EDTA adjusted to a pH of 8.5. The EDTA in the OMS serves to remove LPS from the cell wall, while the elevated pH prevents much of the proteolytic degradation after freezing and disruption. Protease inhibitors may be used instead, or in addition to, an elevated pH. The retentate was concentrated back down to approximately 65 liters and the system was flushed with 20 liters of OMS. The retentate was mixed thoroughly while in the 200-liter tank using a bottom mount magnetically driven mixer.

The retentate was sterilely dispensed (3.5 liters) into sterile 4 liter NALGENE containers No. 2122 in a biosafety cabinet and placed into a −20° C. freezer for storage. Freezing the bacterial pellet serves to weaken the cell wall structure making downstream disruption more efficient. The pellet mass was calculated by centrifuging 30 ml samples of the fermented culture and final harvest. Briefly, pre-weighted 50 ml NALGENE conical tubes were centrifuged at 39,000×g for 90 minutes in a BECKMAN J2-21 centrifuge using a JA-21 rotor (Beckman Instruments, Palo Alto Calif.). At the end of the run, the supernatant was poured off and the tubes were weighed again. The pellet mass was calculated for each stage. The fermentation process yielded a wet pellet mass of 3.7 kilograms.

Alternative methods for bacterial harvest can be used. Bacterial harvest may be performed by the use of hollow fiber filter methods. Bacterial culture is harvested using filter cartridges ranging in size from 0.6 μM to 750 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Disruption

Sixty five Liters of frozen bacterial cell slurry in OMS were thawed at 4° C. (3.7 kg of pellet mass). The liquid culture suspension from each container was aseptically aspirated into a steam in place 150 liter jacketed process tank (Lee, Model Style U). The cell suspension was disrupted by homogenization. Briefly, the 150 liter tank containing the bacterial suspension was connected to an Avestin model EF-C500B Homogenizer (Avestin, Inc. Ottawa, ON, Canada). A 250 liter jacketed process tank (empty) (Lee, Model 259LU) with a top mounted mixer (Eastern, Model TME-1/2, EMI Incorporated, Clinton, CT) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of the pass, fluid was circulated at 60 psi via a Waukesha model 10DO pump (Waukesha) through the homogenizer (500 gallons/hour) and back to the tank of origin, while the homogenizer pressure was adjusted to 15,000 psi. Prior to homogenization, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The starting % T was 86.65 at a 1:100 dilution. The cell slurry was passed once through the homogenizer, and the resulting % T was 89.9 at a 1:100 dilution.

After homogenization, 1 liter Sodium Lauroyl Sarcosinate (Hamposyl L-30, Chem Serv, Minneapolis, MN) was aseptically passed to the 81 liters of homogenized slurry for solubilization. The jacketed vessel removed from the homogenizer and was kept on a chiller loop at 5□C mixing at 30% mixer speed. After 29 hours, 121 ml of formaldehyde was added as a preservative, followed by a 2 liter wash of OMS. Solubilization continued for a total of 46 hours and 16 minutes. This time period was important for complete solubilization. It was discovered that increasing the solubilization time in OMS at an elevated pH (8.0-8.5) that metal regulated proteins aggregated together forming large insoluble aggregates that were easily removed by centrifugation.

Protein Harvest

The aggregated metal regulated proteins within the solubilized process fluid were collected by centrifugation using T-1 SHARPLES, (Alfa Laval Separations, Warminster, Pa.). Briefly, the tank of solubilized homogenate was fed into twelve Sharples with a feed rate of 170 ml/minute at 11 psi. The first pass protein collected on the bowls of the Sharples was discarded. This consists of large cell debris and cell wall material. The effluent was collected into a second 250 liter jacketed process tank through a closed sterile loop allowing for multiple passes through the centrifuges while maintaining a closed system. The temperature during centrifugation was kept at 4° C. The solubilized homogenate was passed an additional 7 times across the centrifuges, at a feed rate of 150 ml/minute and a pressure of 21 PSI. Protein was collected after each pass. The protein was collected, resuspended and dispensed in 7.46 liters Tris-buffer pH 8.5. Twenty five ml of formaldehyde (Sigma) was added, to reach 0.3% concentration, as a preservative.

Alternative methods for protein harvest can be used. For example, the desired proteins can be harvested by the use of hollow fiber filter methods. Proteins can be harvested using filter cartridges ranging in size from 5 kDa to 0.2 µM; preferably with a 50 kDa to 750 kDa cartridge. Culture is reduced in volume from 2-20× and subsequently washed 1-5× by diafiltration with buffer prior to storage at 4° C. or freezing at −20° C.

Diafiltration

The protein suspension was washed by diafiltration at 4° C. to remove any contaminating sarcosine that may have been bound to the protein. Briefly, the 8640 ml of protein was sterilely aspirated into a 200 liter process tank containing 50 liters sterile Tris-buffer, pH 8.5, equipped with a bottom mount Dayton mixer, Model 2Z846 (Dayton Electric, Chicago, Ill.) rotating at 125 rev/minute. The process tank was sterilely connected to a MILLIPORE PELLICON TANGENTIAL FLOW FILTER assembly (Millipore Corporation), equipped with a 25 ft2 screen-channel series Alpha 10K Centrasette filter (Pall Filtron) connected to a Waukesha Model U30 feed pump. The 59 liter protein solution was brought to 150 liters by adding TBW, concentrated down to 35 liters, brought up to a volume of 110 liters of TBW and then concentrated down to 10.4 L final antigen volume. The protein concentrate was aseptically dispensed (3.5 liters) into sterile 4 liter NALGENE containers and placed into a −20° C. freezer for storage.

This process produced a composition containing metal regulated proteins with a decrease in the amount of LPS and very little to no sarcosine residue. The protein was examined by SDS-PAGE for purity and banding profile, and also examined for bacterial contamination, residual sarcosine and LPS. The banding profile of the finished product showed consistent patterns as examined by electrophoresis. The composition was tested for sarcosine by the use of a modified agar gel diffusion test in which sheep red blood cells (5%) were incorporated into an agar base (1.5%). Wells were cut into the agar and samples of the finished product along with control samples of known concentrations of sarcosine at 0.05, 0.1, 0.2, 0.3, 0.4, 0.5 1.0 and 2.0% were placed into the wells. The gel was incubated at 25° C. for 24 hours and the degree of hemolysis was determined compared to the controls. The process removes the level of detectable sarcosine below 0.05%, which at this concentration showed minimal hemolysis in control samples. The concentration of LPS is examined by a Limulus amebocyte lysate (LAL) test available under the tradename PYROTELL (Associates of Cape Cod, Inc., East Falmouth, Mass.).

Example 6

Preparation of Immunizing Compositions Derived from *Pasteurella multocida*

Three vaccine serials consisting of the same antigen was prepared from the Master Seed MS061130 of Example 5. Please Note: two antigen preparation representing two separate fermentation processes were used to prepare two antigen lots designated as antigen A and antigen B. Thus, The first vaccine serial was prepared using a mixture of antigen A and antigen B, the second vaccine serial was prepared only using antigen A, and the third vaccine serial was prepared using only antigen B.

The vaccine compositions consisting of antigen A, B and A+B were prepared in the following constituents: 44.44% aqueous protein suspension in 0.1% formalized saline, (standardized to 150 μg protein per chicken dose) 50% Drakeol 6 mineral oil (VOPAK USA, Inc, Kirkland, WA), 3.0% Span 85 and 2.56% Tween 85 (Ruger Chemicals, Hillside, NJ). Briefly the Mineral Oil and Span 85 were combined and dispensed into a vessel equipped with a high-speed emulsifier (IKA model Process pilot 2000/4 or equivalent). Antigen, Tween 85 and 0.1% formalized saline was dispensed into a second vessel. The emulsifier was set at 60 hz, and the aqueous solution was pumped into the oil, which was pre-cooled to 7° C. The vaccine was continuously stirred as it was pumped into sterile bottles.

Example 7

Vaccination of Chickens

Leghorn type Specific Pathogen Free (SPF) chickens (Hy-Vac, Adel, IA) were vaccinated with the compositions of example 6. Briefly, 74 specific pathogen free (SPF) leghorn chickens were obtained at 11 weeks of age (WOA) and were allowed to acclimate for one week prior to vaccination. Birds were divided into 3 groups designated as Antigen A+B (21 Birds), Antigen A (21 birds), Antigen B (21 Birds and a group of non-vaccinated controls (11 Birds). Birds were identified by colored leg bands. At 12 WOA, all birds in groups Antigen A+B, Antigen A and Antigen B were vaccinated with 0.25 ml of the appropriate vaccine intramuscularly in the breast. A group of 11 chickens received no vaccine and served as the control group. At 15 weeks of age or twenty one days post second vaccination all vaccinated birds received a second vaccination

Example 8

Preparation and Administration of Challenge Organism

One day prior to challenge, one cryogenic bead of *Pasteurella multocida*, strain X-73 of example 1, was aseptically removed from the frozen stock and spread onto two TSA II plates with 5% sheep blood (Becton Dickenson) which were then streaked for isolation of colonies. The plates were incubated for 16-19 hours at 37□C. On day 14 or 14 days post second vaccination several colonies from the sheep blood agar plate were scraped from the blood plate and suspended in a sterile 13×100 test tube. Colonies were added or the suspension diluted with tryptose broth to obtain a % T of 71-75% at 630 nm using a Spectronics 20D (ThermoFisher) spectrophotometer. The suspension was serially diluted in tryptose broth to 1:100,000 dilution. This dilution was dispensed into serum vials for challenge.

Twenty chickens of each vaccinated group and 10 chickens of the control group were inoculated intramuscularly in the breast with 0.5 ml of the above diluted challenge. The extra chickens from the vaccinated and the control group were removed at this time.

Example 9

Challenge Results

The results, shown in FIG. 2, are an average of three separate challenge studies conducted with the three serials. The term Prevented Fraction (PF) is the complement of the Risk Ratio (RR) and has long been used by epidemiologists as an expression of the preventative role of a protective factor, or the preventative success of an implemented program of intervention (Miettinen, 1974, Am J Epidemiol 99:

325-332) (Field Epidemiology, Oxford University Press, 2002, pp 147-7). Prevented Fraction PF=1-p2/p1, where p2=affected fraction in the vaccinated group, and p1=affected fraction in the unvaccinated or placebo group. Veterinary fowl cholera vaccines are expected to routinely demonstrate a PF of 53% or greater, preferably 62.5% or greater Vaccines that demonstrate a PF of less than 53% demonstrate protection.

Figure 2:
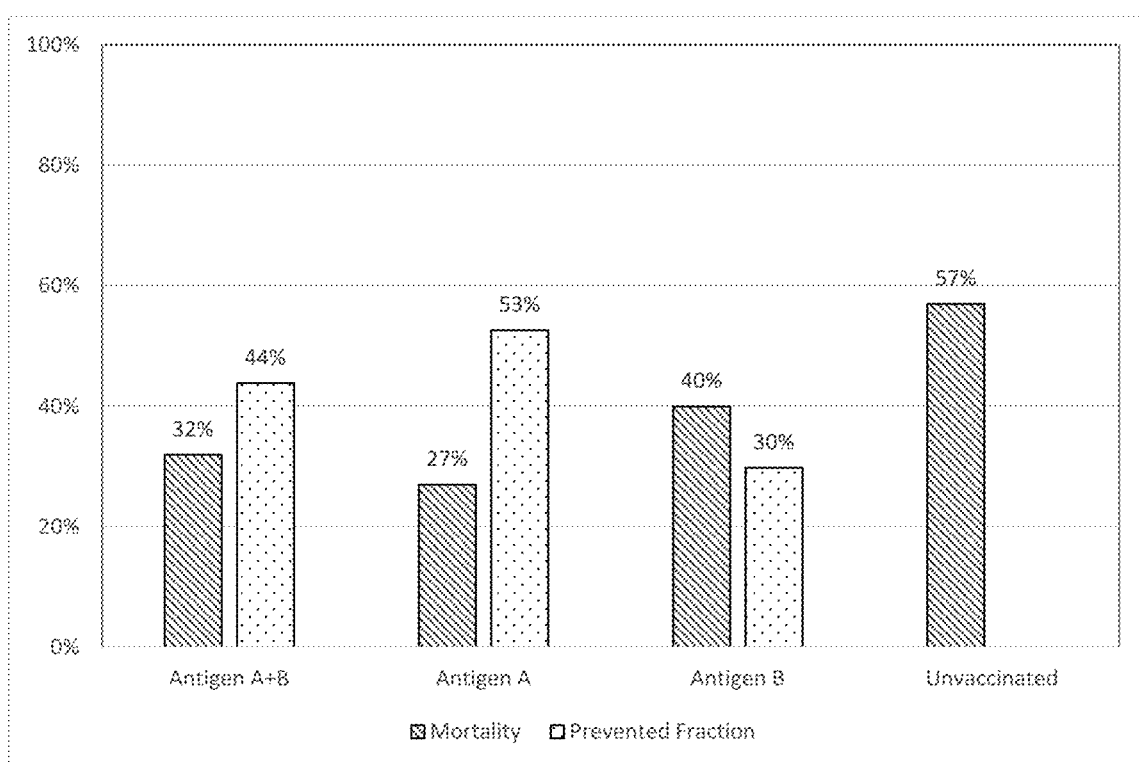
FIG. 2. Efficacy of three *Pasteurella multocida* vaccine serials produced from a single strain against challenge with heterologous *Pasteurella* serotype 1. Three vaccine serials consisting of the same antigen were prepared from the Master Seed MS061130. Note: two antigen preparation representing two separate fermentation processes were used to prepare two antigen lots designated as antigen A and antigen B. The first vaccine serial was prepared using a mixture of antigen A and antigen B, the second vaccine serial was prepared only using antigen A, and the third vaccine serial was prepared using only antigen B.

Table 1 presents mortality data from FIG. 2 and the calculations for Prevented Fraction for Antigen B of FIG. 2. Vaccine efficacy or prevented fraction was calculated to be 30%, indicating that vaccination prevented 30% of the cases that might have otherwise occurred among vaccinated birds had they not been vaccinated. These calculations were repeated for antigens A and A+B to obtain the prevented fraction for each vaccine.

TABLE 1

|  | DEAD | NOT DEAD | TOTAL | RISK |
|---|---|---|---|---|
| Vaccinated Antigen B | 40% | 60% | 100% | 40% |
| Not Vaccinated | 57% | 43% | 100% | 57% |
| TOTAL | 97% | 103% |  |  |

Relative Risk = 40/57 = .70 or 70%
Vaccine Efficacy = (57 − 40)/57 = 0.3 or 30%

The difference between vaccinates and controls are significant (p<0.05) for two of the three vaccinate groups, but the prevented fraction was 53%, 30%, and 44% for antigen 1, antigen 2, and the combined antigen, respectively. While the vaccine met the 53% PF level in one case, it could not be demonstrated consistently, and therefore is inadequately effective for a commercial fowl cholera vaccine. Based upon the banding profiles observed in example 4, we expected very good protection. Unfortunately, the protection observed was less than expected. These unexpected results suggest that bands visually appearing to overlap on a SDS-PAGE gel as shown in FIG. 1 are not enough to confer the desired protection level.

Example 10

Known Genome Analysis

Current known genomes were surveyed for potential metal regulated proteins. Several strains of *Pasteurella multocida* have full or partial genome sequences available in the public domain. The Universal Protein Resource (Uniprot) is a comprehensive resource for protein sequence and annotation data. At the time of the search, the full or partial sequence data of serotype 1 reference strain X-73 and the serotype 3 reference strain P-1059 were present in this database. For each of these organisms, we searched the database for all proteins having molecular weights between 50 kilodaltons and 150 kilodaltons that had any annotation reference to iron uptake. The identified proteins were organized into a table (FIG. 3), where those of different strains having a similarity of greater than or equal to 95% were grouped together. Fourteen distinct proteins were identified among these strains.

The proteins were compared to expressed metal regulated proteins of the previous vaccine candidate (MS061130) as identified by MALDI-TOF analysis. There were eight proteins that appeared to be absent from the vaccine candidate, but were identified in additional genomes of other *Pasteurella multocida* strains derived from avian species. (See FIGS. 3 and 4).

Figure 4:
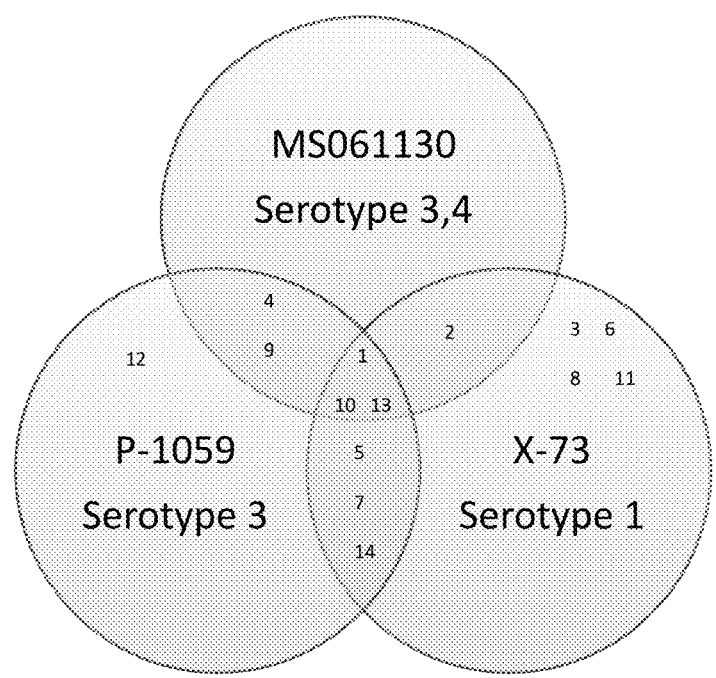
FIG. 4. Venn diagram illustrating outer membrane proteins missing from the vaccine strain (MS061130). Numbers correlate to the protein identification numbers of FIG. 3.

These results demonstrated that our vaccine candidate (MS061130) was potentially missing 7 desirable proteins that were identified by genomic analysis of additional strains of *Pasteurella*. This same observation was seen in the analysis of the genome of the challenge strain that was used in example 9 which also had the seven protein subset that was not present in the MS061130 vaccine candidate. Thus, the vaccine strain described in Examples 6-9 was missing 7 proteins that were present in the challenge strain (FIG. 3). The Venn diagram in FIG. 4 illustrates the number of proteins present in relevant challenge strains P1059 and X73 that are not present in the vaccine strain MS061130. These observations led us to hypothesize that a combination of two or more strains with comprehensive siderophore receptor coverage of the seven protein subset would provide a higher degree of protective efficacy as well show cross protection independent of serotype.

Example 11

Comparison of Iron-Restricted Protein Banding Patterns in Wild and Type Strains of *Pasteurella multocida*

Figure 5:
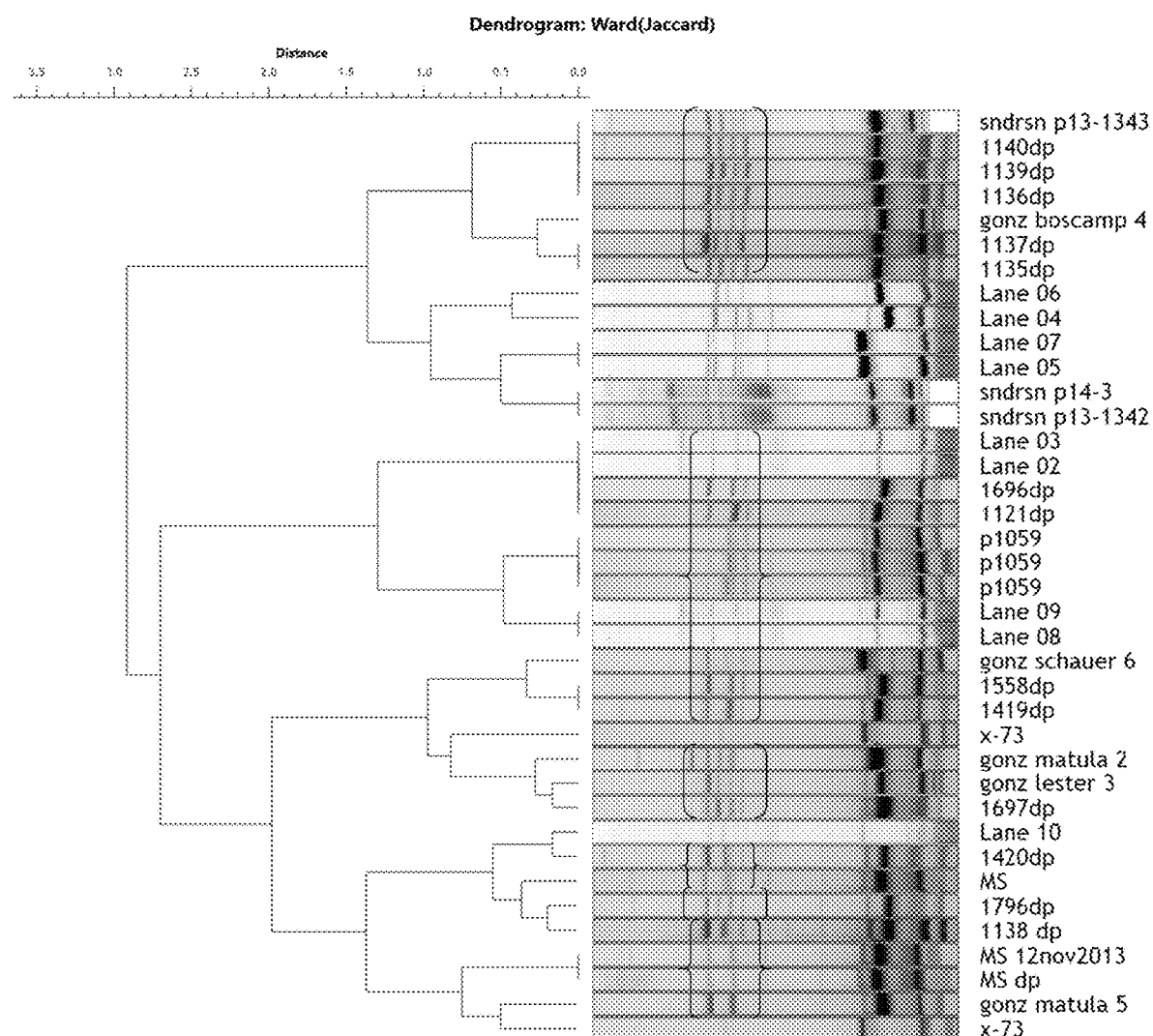
FIG. 5. Dendogram of metal regulated protein banding patterns of 30+ clinical field isolates and reference strains of *Pasteurella multocida*. Note the two major banding patterns as depicted as a four band pattern in brackets[ ], and a three band pattern in braces{ }. Most other strains appear to be variations on these two patterns.
Figure 7:
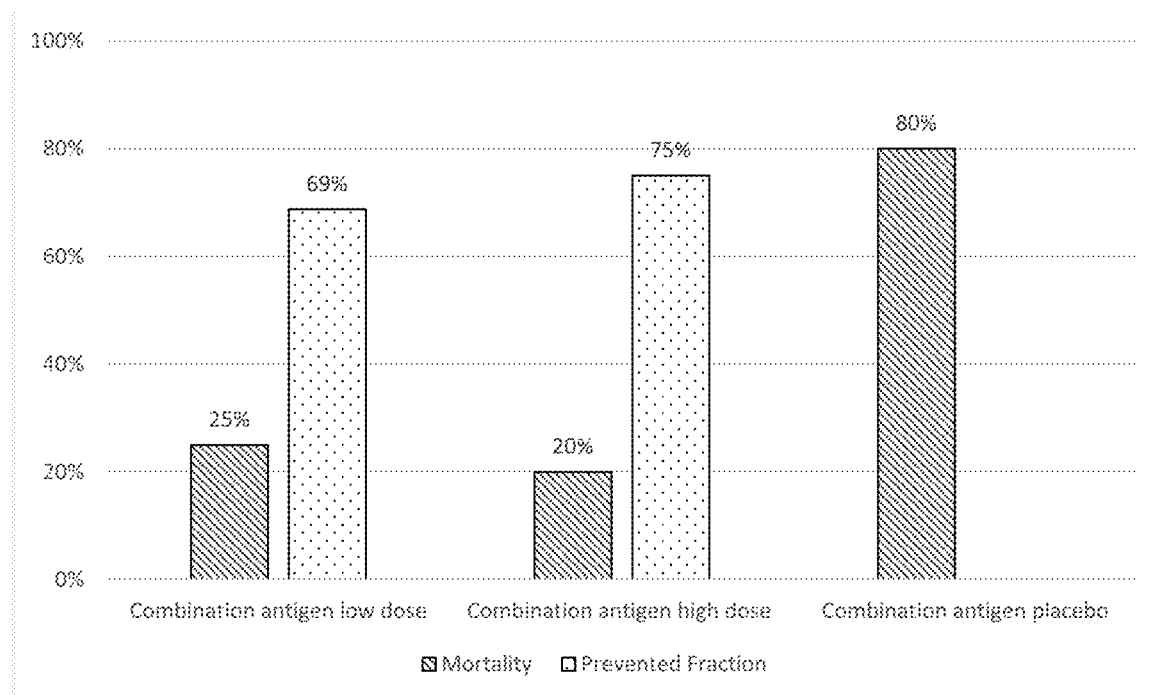
FIG. 7. Vaccine efficacy using a vaccine composed of two Master seed strains challenged with *Pasteurella* serotype 1 in chickens showing heterologous protection.

In order to more fully understand metal regulated proteins in *Pasteurella*, thirty three type strains and clinical field strains of *Pasteurella multocida* were grown in iron-restricted medium and processed to purify membrane bound proteins in the manner of example 3. The resulting protein compositions were analyzed for metal regulated protein banding patterns on Sodium Dodecyl Sulfate-poly-acrylimide gel electrophoresis (SDS-PAGE) gels (Criterion TGX Stain-free gels, Bio-Rad laboratories, Hercules, CA). The individual lanes were compared and grouped using Phoretix 1D, a 1-dimensional gel analysis program (TotalLab, Newcastle upon Tyne, UK). A dendogram was created with Phoretix 1D software showing banding pattern similarities as illustrated in FIG. 5. The analysis of the type strains and clinical field isolates revealed two predominant patterns of expressed metal regulated proteins; a four-band pattern as marked by the brackets [ ], and a three-band pattern as shown by braces{ }. Other strains appear to have variations on these two patterns, missing one or two protein bands.

Example 12

Analysis of Proteins by MALDI-TOF

Thirteen isolates were chosen from example 11 as representative of the various band patterns observed in FIG. 5. Each protein band in the molecular weight range of 75,000 to 115,000 from these thirteen isolates of example 11 were excised from the SDS-PAGE gels for protein identification analysis via Matrix Assisted Laser Desorption Time of Flight mass spectrometry (MALDI-TOF MS) and peptide mass fingerprinting. The peptide masses were compared to a database (Uniprot, in this case) containing known protein sequences of the genome. This was achieved by using computer programs that translate the known genome of the organism into proteins, then theoretically cut the proteins into peptides, and calculate the absolute masses of the peptides from each protein. They then compare the masses of the peptides of the unknown protein to the theoretical peptide masses of each protein encoded in the genome. The results are statistically analyzed to find the best match. The identities of these proteins were grouped in a greater than 93 percent similarity and the results are shown in the table in FIG. 6. A total of 38 bands from the 13 isolates were analyzed and were identified to be one of seven proteins as indicated by their molecular weight in FIG. 6. Two of the isolates (1121 and 1135, indicated by the ellipse in FIG. 6), when combined, expressed all seven protein bands. These two strains were chosen for a new combination vaccine because together they expressed all the proteins of the remaining eleven isolates in FIG. 6, and also were representative of the two major banding patterns identified in FIG. 5.

Example 13

Pasteurella Culture Seed Preparation

Master seed stocks of Pasteurella multocida strains 1121 and 1135 from example 12 and FIG. 6 were prepared. Strain 1121 was identified to be serotype 3×4 and strain 1135 was identified to be serotype 2×5. These isolates were isolated from turkeys that had died from avian Pasteurellosis. Typically, the liver or lung was swabbed and the resulting swab was streaked to 5% sheep blood agar plate and incubated at 37° C. for 24 hours. A Master Seed was prepared by inoculating the isolate into pBHI containing 6 g/l yeast extract and 12 ug/ml DP. The culture was then successively transferred into the above media with 18 µg/ml DP for five more passes to adapt the organisms to an iron-restricted environment and to maximize growth and expression of desired proteins. The cultures were concentrated by centrifugation for 30 minutes at 7,000 rpm (Beckman Coultier, Brea, CA) and resuspended in fresh pBHI containing 20% glycerol (as a cryoprotectant) but no DP. The resulting Master Seeds were aliquoted in 2.2 ml volumes into 3 ml cryovials and stored at or below −60° Celsius. The isolates were given the identification numbers PM1121 20140911 and PM1135 20140925 and established as Master Seeds MS1121 and MS1135, respectively. The Master Seeds were then expanded into working seeds that were used for the production of metal regulated proteins.

Example 14

Production of Metal Regulated Proteins

Pasteurella multocida can be grown under controlled fermentation conditions so as to express proteins, including proteins associated with the outer membrane. The bacteria can then be harvested and the proteins isolated, purified, and used as immunogens in a composition.
Fermentation:
A cryogenic vial of the working seed of strain 1135 (1 ml at $10^9$ CFU/ml) of example 13 was used to inoculate 300 ml of 37° C. modified porcine brain heart infusion media (pBHI) (BD Difco) containing 6 g/l yeast extract (BD). The culture was incubated at 35-38° C. while shaking at 30-400 rpm for 5 hours, at which point was transferred to 1500 ml of modified pBHI containing 22 ug/ml DP to restrict available iron. The culture was incubated at 37° C. for 2 hours and 38 minutes until it reached an optical density greater than or equal to 0.6. The entire culture was transferred to 15 liters of modified pBHI plus 22 ug/ml DP in an 18 liter flask. This culture was incubated for approximately 2 hours and 30 minutes and reached an optical density of 0.75 at 540 nm. The culture was then transferred to a 300 liter fermentor containing 270 liters of modified pBHI with 22 µg DP to maintain iron restriction, and 40 ml per liter of a 50% glucose solution as a carbon source. The culture was incubated at 35-38° C. with agitation controlled by dissolved oxygen content which was maintained at or above 30%. The culture grew to an optical density, as measured by a Beckman series 600 spectrophotometer, of approximately 5.4. At the end of fermentation, the culture pH was adjusted above 8.5 and the temperature adjusted at or below 15° C.
Harvest of Whole Cells:
The whole cell bacterial suspension was concentrated to approximately 1/10 volume by tangential flow filtration with a Pall Filtron Tangential Flow Maxisette-25 (Pall Filtron) equipped with two 30 ft² Alpha 300-K open channel filters, catalog No. AS300C5, (Pall Filtron) connected to a Waukesha Model U-60 feed pump (Waukesha Chemy-Burrell, Delevan, Wis.) set at about 44 Hz. The culture was further washed with Tris-buffered saline, and then concentrated to ~45 liters of whole cell suspension. A subsample of the cell suspension was dried and weighed to yield a final dried pellet weight. The final whole cell suspension was then frozen at −20°.
Whole Cell Disruption.
The whole cell suspension was thawed at 5-7° C. for 3 days. Individual containers of whole cell were pooled and mixed in a sterile tank equipped with a mixer set at 40%. The liquid cell suspension was disrupted by homogenization. Briefly, the suspended whole cell was passed twice through an Avestin homogenizer, model Emulsiflix C500B, (Avestin, Inc., Ottawa, Canada) at a pressure of 15,000-18,000 pounds per square inch (PSI) until a 1:100 dilution of homogenate reached 80 percent transparency (% T at 540 nm) on a Beckman series 600 Spectrophotometer (Beckman instruments, Brea, CA). A second process tank was connected to the homogenizer such that the fluid could be passed back and forth through the homogenizer for multiple passes while maintaining a closed system. Sodium lauroyl sarcosinate (Hamposyl L-30, Chattem Chemicals, Chattanooga, TN) was added at 3% volume/volume to the disrupted cell homogenate to solubilize the cell membrane and non-membrane proteins. Solubilization continued for approximately 72 hours at 2-7° C. Cell debris was removed by centrifugation utilizing a Sharples T1 continuous centrifuge set at 11 PSI.
Protein Harvest:
The protein suspension was washed with 800 liters of Tris-buffered water (TBW) (pH 7.4) containing 0.2% formalin by continuous wash tangential flow filtration (Maxisette 300 kDa filter, Pall corp, NY, NY). The protein was further washed with 100 liter of TBW containing formalin and 10% ethanol. Following the ethanol wash, the protein suspension was further washed with 200 liters of TBW plus formalin (0.2%) to remove the ethanol. When the remaining TBW was washed from the system, the volume was reduced by continued filtration until the final antigen volume was approximately 20 liters. The final antigen lot 1135-A0001 was then inactivated with the 0.2% formalin with continuous mixing at 33° C. for 93 hours.
The working seed of strain 1121 was used to prepare antigen lot 1121-A0001 in the same manner as strain 1135.

Example 15

Preparation of Vaccine

The antigens prepared in Example 14 were used to prepare two 20 liter water in oil vaccines with 50% mineral oil as adjuvant and tween/span emulsifier as described in example 6. Briefly, 10,145 ml of Drakeol 6 mineral oil and 609 ml Span 85, as an emulsifier, were added to a sterile vessel equipped with a Silverson model 150UHSLS mixer (Silverson Machines, East Longmeadow, MA). The mixer was set to 52 hz and the adjuvant phase recirculation was set at 2.5 liters per minute. The aqueous phase ingredients were added to a second vessel: Tween 85 (517 ml), 540 ml of antigen lot 1121-A0001, 1420 ml of antigen lot 1135-A0001 and 7010 ml of phosphate buffered saline, pH 7.4, —was slowly added over the course of 20 minutes. The vaccines were formulated to contain 100 μg total antigen (50 ug from each strain) per 0.25 ml dose, and 200 μg total antigen (100 μg of each strain), respectively. These two antigens, combined, represent the 7 proteins, of example 12 and FIG. 6, required for increased heterologous serotype protection.

Example 16

Vaccination and Challenge Model

The vaccines prepared in example 15 was used in a vaccination challenge model against type 1 challenge in SPF chickens. Briefly, 60 SPF leghorn chickens, both males and females, were obtained from Valo BioMedia (Adel, IA). The chickens were sorted by sex, and divided into three groups of 20 birds of mixed hens and roosters, each group with equal numbers of males and females. The birds were identified by numbered wing bands; each bird received identical numbers on the left and right wing to preserve identity. One group was vaccinated with 0.25 ml of the 200 μg vaccine of example 14. A second group was vaccinated with 0.25 ml of the 100 μg vaccine of example 14. A third group was vaccinated with a placebo containing the oil adjuvant in phosphate buffered saline (PBS) in place of the antigen. All birds were vaccinated subcutaneously in the back of the neck at 12 and 15 weeks of age, and all birds were challenged intramuscular in the breast at 17 weeks of age with approximately 6,000 cfu of the serotype 1 challenge strain X-73 prepared in the manner of example 8. The results of the study are shown in FIG. 7. It is clear that the level of protection is vastly improved with a preventive fraction of 69 and 75 percent and a p-value of 0.001 and <0.0004 for the 100 μg and 200 μg vaccinated groups, respectively. These results clearly show that the combination of two antigens, expressing all seven proteins of FIG. 6, confer increased prevented fraction against heterologous challenge in a chicken vaccination and challenge model.

Example 17

Zinc and Respiratory Pathogens

In our previous research (data not shown) we have shown that many gram-negative pathogens express a novel protein under zinc restriction. An abundance of these bacteria are respiratory pathogens. Some of these pathogens include *Moraxella catarrhalis, Haemophilus parasuis, Mannheimia haemolytica, Acinetobacter baumannii, Pasteurella multocida, Bordetella pertussis*, and *Actinobacillus pleuropneumonia* (Stork et al. PLoS Pathogens, 6(7), e1000969 2010). It has been reported that this Zinc acquisition protein is a transmembrane beta-barrel protein now identified as ZnuD located in the outer cell wall that utilizes a single surface exposed loop containing two cysteines that when brought together by a disulfide linkage forms a cluster of histidines that can interact with a zinc ion (Stork et al., PLoS Pathogens, 6(7), e1000969. 2010). ZnuD thereby acts as a scavenger protein used for the acquisition of zinc sequestered by the host organism.

All these ZnuD homologs contain His- and Asp-rich regions that have been identified in the binding of zinc. This suggests that zinc acquisition mechanisms are important for bacteria residing in the respiratory tract. The current explanation is that unbound zinc concentration within the mucosal tract is too low to allow for simple diffusion across the bacterial membrane via porin proteins (Stork et al., PLoS Pathogens, 6(7), e1000969 2010). Thereby, proteins such as ZnuD are required to scavenge for zinc. This scavenging not only includes unbound zinc, but also the stripping of sequestered zinc from proteins such as calprotectin (Liu et al., Cell host & microbe, 11(3), pp 227-239. 2012). This theory has been supported by the detection of convalescent antibodies towards ZnuD from healthy carriers, which allows the assumption that ZnuD is expressed by bacteria that reside in the respiratory tract (Stork et al., PLoS Pathogens, 6(7), e1000969. 2010). The goal of this experiment was to identify, clone and evaluate the efficacy of a zinc acquisition protein of *Pasteurella multocida*. If a ZnuD homolog is expressed in *Pasteurella multocida*, it offers another possible target for vaccine development currently unexplored for controlling this respiratory pathogen.

Example 18

Genomic Sequencing of *Pasteurella Multocida* P-1059

The isolate of *Pasteurella multocida* used for this study was reference strain P-1059 of example 1. The genomic DNA was isolated from the *Pasteurella multocida* isolate using the Invitrogen by Life Technologies ChargeSwitch gDNA Mini Bacteria Kit (Life Technologies, Carlsbad, CA, product number: CS1 1301). Prior to extraction of genomic DNA, a fresh culture of the isolate was grown on Trypticase Soy Agar II with 5% Sheep Blood (Becton, Dickinson and Company, Franklin Lakes, NJ, product code: 221261) overnight at 37° C. The procedure followed the manufacturer protocol. The final yield was 33.7 μg of genomic DNA, which was stored at −20° C. until sequencing. The genomic DNA was submitted to ACGT, Inc. for sequencing (Wheeling, IL). Genbank reference sequences CP004752 and CP004753 were used in the assembly of the complete genomic sequence of the isolate.

Example 19

Possible Target Genes

After receiving the complete genomic sequence of the isolate, tblastn alignments were performed with the National Center for Biotechnology Information (NCBI) database to identify the possible genes of interest based on homology towards ZnuD (GenBank AAF62323.1). A blastx search was used to identify the proteins translated by the homologous genes found with the tblastn alignment. Pairwise sequence alignments of the identified ZnuD homologues and ZnuD zinc affinity region were performed using EMBOSS Matcher (Rice et al., Trends in genetics, 16(6), pp 276-277. 2000).).

Example 20

Expression of a Zinc Acquisition Protein

To identify the zinc acquisition protein of *Pasteurella multocida* we used the sequence of the zinc acquisition protein of *Mannheimia haemolytica* previously identified in our laboratory. Briefly, the expression of the target protein was evaluated by supplementing Bacto Brain Heart Infusion, Porcine culture medium (BHI) (Becton, Dickinson and Company, Franklin Lakes, NJ, product code: 256110) used for bacterial cell growth with TPEN (Tokyo Chemical Industry Co., Ltd., Portland, OR, product code: T1487). A titration of TPEN over a range of 0-100 µM during bacterial growth was used. The BHI media containing the various concentrations of TPEN were inoculated with a starter culture of the isolate in BHI containing no TPEN. The inoculum volume was 1 percent of the total volume of the final culture. The cultures were allowed to grow with vigorous agitation at 37° C. to an $OD_{540}$ of 1.0, unless bacteria were unable to grow at certain concentrations.

Once an OD of 1.0 was obtained, the bacteria were pelleted by centrifugation at 7,000×g for 10 minutes. An outer membrane preparation was performed on the pelleted bacteria to isolate the integral membrane proteins within the outer membrane following a procedure described by (Molloy et al., European Journal of Biochemistry, 267(10), pp 2871-2881. 2000) with modifications. The bacteria pellet was re-suspended in 30 ml of 60 mM Tris-HCl (Sigma-Aldrich, St. Louis, MO, product code: T3253) and 2.5 mM EDTA (EMD, Billerica, MA, product code: EX0539-3), pH 8.5. The bacteria were then lysed by sonication using a Sonifier S-450A analog ultrasonic processor with a ½" diameter Tipped Bio-Horn attached to a102-C converter (Branson Ultrasonics Corporation, Danbury, CT, product code: 101-063-198, 101-47-037, and 101-135-066 respectively) for 1 minute and 30 seconds on ice at a power setting of 9 and a duty cycle of 90. The sample was clarified by centrifugation at 39,000×g and 4° C. for 20 minutes to remove large cell debris. To remove the inner membrane, peptidoglycan, and proteins not found within the outer membrane, Hamposyl L-30 (Chattem Chemicals, Inc., Chattanooga, TN, product code: BD2099) was added to the supernatant at a final concentration of 1% and incubated for 16 hours at 4° C. while rocking end-over-end. The outer membrane was pelleted by centrifugation at 39,000×g and 4° C. for 2 hours. The outer membrane pellet was washed and re-suspended in 25 mM Tris-HCl buffered water, pH 7.2.

The integral membrane proteins were visualized by SDS-PAGE. Prior to the electrophoresis, a BCA (Thermo Fisher Scientific Inc., Rockford, IL, product code: 23225) was performed to quantify the protein within each sample as to allow for equivalent protein loads of 30 µg. Samples were brought up to equal volume prior to the addition of 3× loading buffer (New England BioLabs Inc., Ipswich, MA, product number: B7703S). The samples were compared on the gel to look for expression of the target protein.

Example 21

Protein Identification

The banding profile from the outer membrane preparation was analyzed by Matrix-assisted Laser Desorption/Ionization Mass Spectrometry (MALDI) to determine if any of the bands of interest match the genes identified by BLAST homology. The bands were cut out of the gel with a scalpel and sent to the Mayo Clinic Proteomics Core facility to be analyzed.

Example 22

Structure Modeling

Swiss Model was used to create a 3-D structural model of zinc acquisition protein of *Mannheimia haemolytica* based on homology sequencing (Arnold et al., Bioinformatics, (22), pp 195-201. 2006).). The PDB template used to create the protein model was 4epaA. The extracellular loop (ECL) sequence positions were identified using the 3-D structural model obtained from Swiss Model (Arnold et al., Bioinformatics, (22), pp 195-201. 2006).), Prediction of TransMembrane Beta-Barrel Proteins (Bagos et al., BMC Bioinformatics, 5(29). 2004).), Orientations of Proteins in Membranes (OMP) database and Positioning of Proteins in Membranes (PPM) server (Lomize et al., Nucleic Acids Res, 40(Database issue):D370-6. 2012).

Example 23

Target Gene Identification

Once the proteins within the banding profile were identified, they were compared to the proteins of interest identified by BLAST homology. One protein within the banding profile matched a protein identified by the BLAST homology. The protein was identified as OMR family outer membrane iron receptor (GenBank: EDN73812.1) also referred to as the zinc acquisition protein in this paper. The target gene was located at nucleotides 1,160,319 . . . 1,162,691 within the genome. The signal peptide was identified using SignalP 4.1 (Petersen et al., Nature methods, 8(10), pp 785-786. 2011)). The nucleotide and amino acid sequences of the zinc acquisition protein identified in *Pasteurella multocida* is shown in FIG. 22.

Example 24

The Homology of the Zinc Acquisition Protein Across Respiratory Pathogens

Using the sequence of the acquisition protein of *Mannheimia haemolytica* (data not shown) the homology of zinc acquisition protein across respiratory pathogens, particularly the zinc affinity region, was determined with the protein blast search tool established by NCBI. Ten different species of bacteria were found to contain a zinc acquisition protein homologue with greater than 49% identity. All species identified are respiratory pathogens. Aligning the homologous proteins to the zinc affinity region of ZAP using Clustal Omega highlights strikingly similar amino acid motifs. All the homologues contain two cysteines and multiple histidines and aspartic acids. The amino acid motifs are emphasized in FIG. 25 using GLAM2. The spatial arrangement of the cysteines, histidines, and aspartic acids remain constant across the homologues.

TABLE 2

| Strain | Accession Number | % Identity | % Similarity |
|---|---|---|---|
| Bibersteinia trehalosi | AHG81836.1 | 98 | 97 |
| Actinobacillus pleuropneumoniae | WP_005612269.1 | 93 | 95 |
| Mannheimia granulomatis | WP_027074597.1 | 75 | 82 |
| Mannheimia varigena | AHG73391.1 | 72 | 79 |
| Haemophilus parasuis | WP_021114857.1 | 62 | 78 |
| Moraxella boevrei | WP_026212957.1 | 53 | 69 |
| Psychrobacter phenylpyruvicus | WP_028858792.1 | 54 | 69 |
| Pasteurella multocida | WP_016534590.1 | 58 | 72 |
| Moraxella bovoculi | KDN24548.1 | 52 | 67 |
| Conchiformibius steedae | WP_027021676.1 | 49 | 64 |

The results show that multiple respiratory pathogens indeed show a degree of homology to the zinc acquisition protein of Mannheimia Haemolytica ranging from 49 to 98 percent identity.

Example 25

Expression and Identification of a Zinc Acquisition Protein

Cloning

The *Pasteurella multocida* zinc gene was PCR amplified from genomic DNA of strain P-1059 and inserted into plasmid vector pQE-T7-2 (Qiagen; Hilden, Germany) using Gibson assembly methods. The assembled plasmid was then transformed in to NEB T7 Express Competent *E. coli* (New England Biolabs; Ipswitch, MA; catalog #C2566H) for clonal selection and expression.

Expression

A starter culture of LB broth containing 50 µg/mL kanamycin was inoculated with a clone containing the recombinant plasmid. Culture was grown to an OD540 of 0.6 and then transferred to fresh LB broth. The new culture was allowed to grow again to an OD540 of 0.6. Expression was then induced with 1 mM IPTG and incubated an additional 16 hours. The cells were collected by centrifugation and stored at −80° C. until processing.

Inclusion Body Purification

Figure 24:
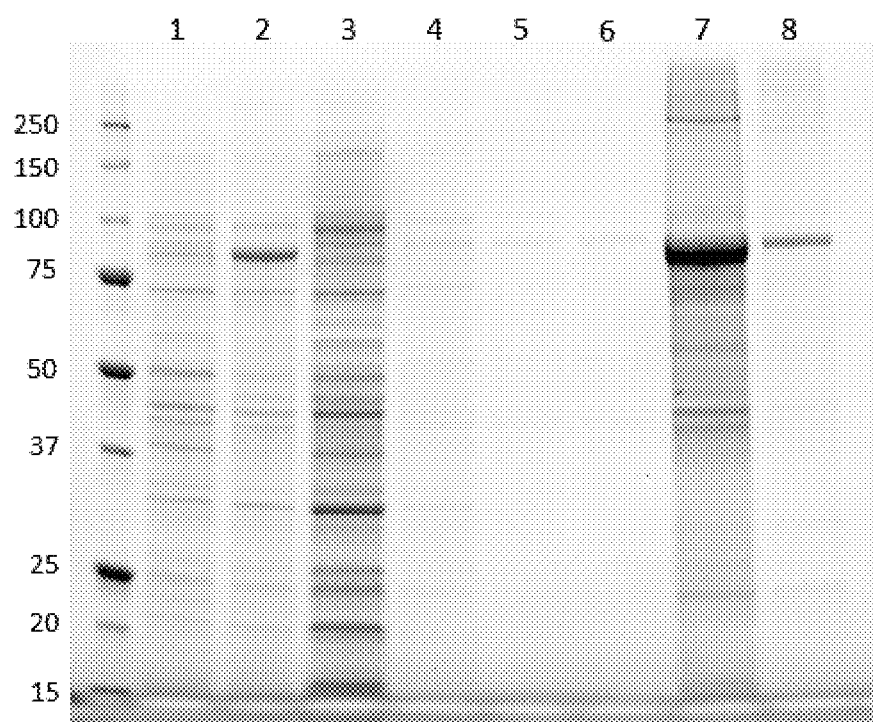
FIG. 24. Gel image showing the inclusion body preparation of *Pasteurella multocida* recombinant zinc acquisition protein. Lane 1: Un-Induced Whole Cell, lane 2: Induced Whole Cell, Lane 3: Lysed Cell Supernatant, Lane 4: 1× Bugbuster Wash, L:ane 5: 1/10× Bugbuster Wash, Lane 6: TBW Wash, Lane 7: Solubilized Inclusion Bodies and Lane 8: Pellet Post Solubilization showing the recombinant protein with a molecular weight of 90.85 kDa.

Cells were thawed and resuspended in BugBuster Protein Extraction Reagent (Merck Millipore; Billerica, MA; catalog #70584-4). 10 µL of Lysonase Bioprocessing Reagent (Merck Millipore; Billerica, MA; catalog #71230) was added and the suspension was incubated for 1 hour at ambient temperature. The suspension was then sonicated (Branson Sonifier, model 102c; Branson Ultrasonics, Danbury, CT) for 30 seconds using a micro tip, output 6, at a 90% duty cycle. The lysate was centrifuged at 16000×g for 20 minutes to collect the insoluble material. The pellet was washed three times: first with BugBuster, second with 1/10× BugBuster, and third with tris-buffered water. The inclusion body prep was solubilized in tris-buffered saline containing 8 M urea and 1 mM dithiothreitol at pH 8.0, yielding 10 mg recombinant protein. FIG. 24 shows the different stages of expression of the zinc acquisition protein run on a 10% Criterion stain free-free TGX Gel run at 300V (Bio-Rad, Hercules, CA) to include: the un-induced whole cell preparation, the induced whole cell preparation, the lysed cell supernatant, 1× bugbuster wash, 1/10× bugbuster wash, the solubilized inclusion bodies and the pellet post solubilization.

Example 26

Vaccine-Mediated Protection of a Novel Recombinant Zinc Protein of *Pasteurella multocida* in a Chicken Sepsis Model The purpose of the following experimental study was to evaluate the protective efficacy of a recombinant zinc protein (rZinc) against a virulent challenge of *Pasteurella multocida* in a chicken sepsis model. The efficacy of the rZinc protein of example 25 was compared to the efficacy of the *Pasteurella multocida* SRP extract composition of example 14 compared to non-vaccinated controls. Briefly, 30 SPF leghorn chickens, (males), were obtained from Valo BioMedia (Adel, IA). The chickens divided into three groups of 10 birds each. The birds were identified by colored leg bands. Treatment groups were designated as Group-A (Placebo), Group-B (rZinc protein) and Group C (*Pasteurella multocida* protein extract). The outcome parameter used to evaluate vaccine efficacy in this experiment was total mortality between vaccinates compared to the non-vaccinated Placebo group. Food and water was supplied ad libitum to all chickens.

Example 27

Preparation of the Immunizing Compositions

The vaccines (SRP extract and rZinc) were prepared from the protein compositions of examples 14 and 25 by diluting the antigen into phosphate buffered saline (PBS) containing 8.0 g/l NaCl, 0.2 g/l KCl, 1.44 g/l $Na_2HPO_4$ and 0.24 g/l $KH_2PO_4$ pH 7.4. Each vaccine was prepared by emulsifying the following ingredients: 44.44% aqueous protein suspension in 0.1% formalized saline, 50% Drakeol 6 mineral oil (VOPAK USA, Inc, Kirkland, WA), 3.0% Span 85 and 2.56% Tween 85 (Ruger Chemicals, Hillside, NJ). The final bird dose for each vaccine composition (rZinc and SRP extract) was 250 µg and 400 µg administered in a volume of 0.5 ml and 0.25 ml respectively. The placebo was prepared by replacing the antigen with physiological saline and emulsifying the suspension using the above formulation in a dose volume of 0.5 ml. All birds were vaccinated subcutaneously at 14 and 17 weeks of age (21-day interval).

Example 28

Challenge and Results

Figure 23:
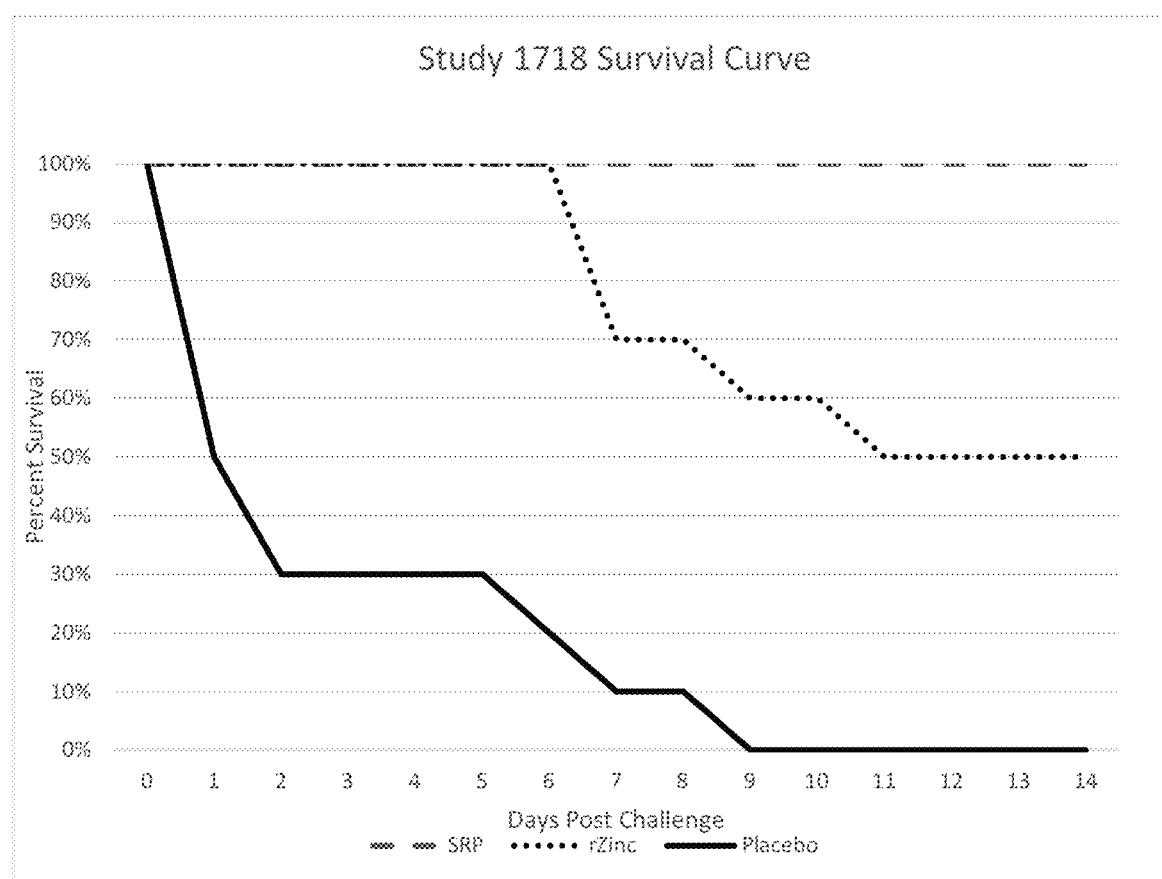
FIG. 23. The percent survival of chickens challenged with *Pasteurella multocida* comparing a recombinant zinc (rZinc) protein to SRP extract. The results clearly show the efficacy of both the *Pasteurella multocida* SRP extract and the rZinc protein compared to non-vaccinated Placebo controls.

At 19 weeks of age all birds were challenged intramuscularly in the breast with 5450 Colony Forming Units (CFU) of *Pasteurella multocida* (serotype 1) strain X-73 prepared as described example 8. Birds were observed for mortality for 14 days following challenge. The results clearly demonstrate the efficacy of both the *Pasteurella multocida* SRP Extract and the rZinc vaccines having a percent survival of 100% and 50% respectively, in contrast to the non-vaccinated controls having no survivors (FIG. 23). The recombinant zinc protein in this study was evaluated at a single concentration of 250 µg, showing a 50% survival rate (p=0.0325) against a virulent challenge.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising a bacterium, the bacterium comprising:
   (i) a protein having at least 90% similarity to amino acids 25-968 of SEQ ID NO: 2, a protein having at least 90% similarity to amino acids 27-780 of SEQ ID NO:4, and a protein having at least 90% similarity to amino acids 23-727 of SEQ ID NO:6; or
   (ii) a protein having at least 90% similarity to amino acids 25-964 of SEQ ID NO: 8, a protein having at least 90% similarity to amino acids 26-848 of SEQ ID NO:10, a protein having at least 90% similarity to amino acids 27-784 of SEQ ID NO:12, and a protein having at least 90% similarity to amino acids 25-742 of SEQ ID NO:14; and
   an adjuvant.

2. The composition of claim 1, wherein the bacterium is *E. coli, Pasteurella, Actinobacillus, Haemophilus*, or *Lonepinella*.

3. The composition of claim 1, wherein the bacterium further comprises a protein having at least 90% amino acid sequence identity to amino acids 26-805 of SEQ ID NO:44.

4. The composition of claim 2, wherein the bacterium is engineered to express the protein having at least 90% amino acid sequence identity to amino acids 26-805 of SEQ ID NO:44.

5. The composition of claim 1, wherein the composition comprises the bacterium comprising (i) the protein having at least 90% similarity to amino acids 25-968 of SEQ ID NO:2, the protein having at least 90% similarity to amino acids 27-780 of SEQ ID NO:4, and the protein having at least 90% similarity to amino acids 23-727 of SEQ ID NO: 6; and the bacterium comprising (ii) the protein having at least 90% similarity to amino acids 25-964 of SEQ ID NO:8, the protein having at least 90% similarity to amino acids 26-848 of SEQ ID NO:10, the protein having at least 90% similarity to amino acids 27-784 of SEQ ID NO: 12, and the protein having at least 90% similarity to amino acids 25-742 of SEQ ID NO: 14.

6. The composition of claim 5, wherein the bacterium is inactivated.

7. A method comprising: administering to a subject an amount of the composition of claim 1 effective to induce the subject to produce antibody that specifically binds to at least one protein of the composition.

8. A method for treating an infection in a subject, the method comprising: administering an effective amount of the composition of claim 1 to a subject having or at risk of having an infection caused by a *P. multocida*.

9. A method for treating a symptom in a subject, the method comprising: administering an effective amount of the composition of claim 1 to a subject having or at risk of having an infection caused by a *P. multocida*.

10. A method for decreasing colonization in a subject, the method comprising: administering an effective amount of the composition of claim 1 to a subject colonized by a *P. multocida*.

11. The composition of claim 1, wherein the bacterium is gram negative.

12. The method of claim 1, wherein the bacterium is engineered to express at least one of the proteins of (i) or at least one of the proteins of (ii).

13. The composition of claim 1, wherein the composition comprises the bacterium comprising the proteins of (i) and the bacterium comprising the proteins of (ii).

14. A composition comprising two or more bacteria, wherein each bacterium expresses a subset of proteins selected from
- a protein having at least 90% similarity to amino acids 25-968 of SEQ ID NO:2,
- a protein having at least 90% similarity to amino acids 27-780 of SEQ ID NO:4,
- a protein having at least 90% similarity to amino acids 23-727 of SEQ ID NO:6,
- a protein having at least 90% similarity to amino acids 25-964 of SEQ ID NO:8,
- a protein having at least 90% similarity to amino acids 26-848 of SEQ ID NO:10,
- a protein having at least 90% similarity to amino acids 27-784 of SEQ ID NO:12, and
- a protein having at least 90% similarity to amino acids 25-742 of SEQ ID NO:14; and
- an adjuvant, wherein the two or more bacteria when considered as a whole express all of proteins, and wherein each bacterium of the two or more bacteria express at least two of the proteins.

15. The method of claim 14, wherein at least one of the bacteria are engineered to express at least one of the proteins.

* * * * *

```
                         SEQUENCE LISTING

Sequence total quantity: 55
SEQ ID NO: 1            moltype = DNA  length = 2906
FEATURE                 Location/Qualifiers
source                  1..2906
                        mol_type = genomic DNA
                        organism = Pasteurella multocida
SEQUENCE: 1
atgcgtacaa caacaataaa attttctgca attacattgg cattattgag ttattgtggg    60
gctattttgg cggatagtca tcaagaggcg actgaacttg atacgattac cgtttcttct   120
caacaagatg agatgaatat taaagagaaa aaagtcggtg aaactgtgaa aacggcgagt   180
caattgaaac gccagcaagt acaggatagt cgtgatcttg tgcgctatga aaccggtgtg   240
actgtggtag aagctggacg ttttgggtcg agcggttatg ccattcgtgg tgtggatgag   300
aaccgagtgg caattacagt agatggctta catcaagcag aaaccctttc ttctcaaggt   360
tttaaagaat tatttgaagg ttacggcaat tttaacaata cccgaaatag tgtggaaatt   420
gagacgttga aagtcgctaa aatcgcgaaa ggtgctgatt ctgtaaaagt gggtagtggt   480
tctttgggag gcgctgtact ttttgaaaca aaagatgcca gagatttcct gactgaaaaa   540
gattggcata tcggctataa agcgggctac tcaacggcag ataatcaggg attaaatgca   600
gtgactcttg caggtcgcta tcaaatgttt gatgcattga ttatgcattc taagcgacat   660
ggacatgaat tagaaaatta tgactataaa aatggcagag atattcaagg aaagaaaga   720
gagaaagcgg atcctatac gattacgaaa gaagtacat tagtgaaatt ctcttttcg    780
ccaacagaaa atcatcgttt tacagtcgct tctgatactt atcttcagca ttcccgcgga   840
catgatcttt catacaatct tgttgcaaca acacatattc agttagatga gaaagaatct   900
cgtcatgcaa atgatctgac aaaacgtaaa aatgttcct ttacttatga aattatact   960
gttacgccat tttgggatac gctcaagtta agctattcac aacaaagaat tacaacaaga  1020
gcaagaacag aagattactg tgatggtaat gaaaaatgtg actcttataa aatccttta  1080
gggcttcaat taaaagaggg aaaaatcgtt gatcgtaatg gcgatcctgt taatttgaag  1140
cttgttgatg gtaaacatca agttgtagat aaagctggta agcctttga tgtagcctct  1200
ggaactaatt atgcggcttt ctcaggtaaa gaattaagtc cttcttcttt ttggttagat  1260
tgctctattt ttgattgttc taagcctatc aatacttata aatatcgcta tacctcttcg  1320
gagccaactt tgcagcaaat tacttaaat aaaaccattg aaattaatgg aaagacattt  1380
gctacttatg atgggcgtgg acactatatt attttaccaa attctaaagg ttacttgcct  1440
ttggattata aagagcgtga tttaaataca aagacgaaac aaattaattt agatttaaca  1500
aaagcattta ctctctttga gattgaaaat gaactttcct atggtggtgt ttacgcgaaa  1560
acgaccaagg aaatggtgaa taaagcagga tattatgggc gtaatcctac ttggtgggcg  1620
gagagaacgt tagggcaatc atggggaaaa ttgagagagt gtaagacaag ttcttcatat  1680
aatgggatgc tatgtcctcg tcatgaacca ttaacctcct tcttaattcc ggtagaagca  1740
acaactaagt ctttatattt tgcagacaat atcaagttgc acaatatgtt aagtgtagat  1800
ttaggtttatc gttatgatga tattaaatat cagccagaat atattcctgg tgtgacacct  1860
aaaattgcag atgatatgt aaaagggtta tttattccat tacctgaagg tgaaaaagta  1920
actgtaggga caatggtatt cacaaaacca ctcactcagg cgcaaattcg taagaatgcg  1980
gaggaaaata ttgcttatat tgcacaagaa aaacgcttta agaacattc ttattctctt  2040
ggtgcaacgt tcgatcctct gaattttta cgagtacaag taaaatattc aaaagggttt  2100
agggccccga cttcggatga actttatttt accttaagc atccagattt tacgattta  2160
ccgaaccccg tgttgaaacc agaggaagca aaaaatcaag agattgcatt aacagtgcac  2220
gataattggg gatttgttag cacaagtgtt ttccaaacaa agtatcgtca ttttattgat  2280
ttagcgtatt taggttcaag aaatttatcg aattccgtgg gagggcaggc acaagcaaga  2340
gatttccaag tttatcaaaa tgtcaatgtc gataatgcca aggttaaagg acttgaaatt  2400
aatgcacgtt tgaatttggg atatttctgg catgtgttgg atggatttaa tacgagctat  2460
aaattcactt accaacgtgg tcgtttggat ggcgatcgtc caatgaatgc gattcagcct  2520
aaagcttctg ttttggttt aggctatgat cataagaaa ataaatttgg cgctgattta  2580
tatatcacac gtgtgagtga aaaaaagcga aagacactta taatatgttc tataaagaac  2640
agggatataa agatagtgct gttcgttgga gaagtgatga ctatacgcta gttgatgcgg  2700
ttggttatat taaccgatt aagaatttaa cgttacagtt tggcgtttat aatttgacag  2760
accgtaaata cttgacatgg gaatctgctc gttcgattaa accatttggt acaagtaatt  2820
taattaatca gaaacaggc gcaggaatta atcgtttta ctcaccaggt cgtaatttta  2880
aatttagtgc cgaaattacc ttctaa                                       2906

SEQ ID NO: 2            moltype = AA  length = 968
FEATURE                 Location/Qualifiers
source                  1..968
                        mol_type = protein
                        organism = Pasteurella multocida
SEQUENCE: 2
MRTTTIKFSA ITLALLSYCG AILADSHQEA TELDTITVSS QQDEMNIKEK KVGETVKTAS    60
QLKRQQVQDS RDLVRYETGV TVVEAGRFGS SGYAIRGVDE NRVAITVDGL HQAETLSSQG   120
FKELFEGYGN FNNTRNSVEI ETLKVAKIAK GADSVKVGSS SLGGAVLFET KDARDFLTEK   180
```

-continued

```
DWHIGYKAGY STADNQGLNA VTLAGRYQMF DALIMHSKRH GHELENYDYK NGRDIQGKER  240
EKADPYTITK ESTLVKFSFS PTENHRFTVA SDTYLQHSRG HDLSYNLVAT THIQLDEKES  300
RHANDLTKRK NVSFTYENYT VTPFWDTLKL SYSQQRITTR ARTEDYCDGN EKCDSYKNPL  360
GLQLKEGKIV DRNGDPVNLK LVDGKHQVVD KAGKPFDVAS GTNYAAFSGK ELSPSSFWLD  420
CSIFDCSKPI NTYKYRYTSS EPTLQQITLN KTMEINGKTF ATYDGRGHYI ILPNSKGYLP  480
LDYKERDLNT KTKQINLDLT KAFTLFEIEN ELSYGGVYAK TTKEMVNKAG YYGRNPTWWA  540
ERTLGQSWGK LRECKTSSSY NGMLCPRHEP LTSFLIPVEA TTKSLYFADN IKLHNMLSVD  600
LGYRYDDIKY QPEYIPGVTP KIADDMVKGL FIPLPEGEKV TVGTMVFTKP LTQAQIRKNA  660
EENIAYIAQE KRFKKHSYSL GATFDPLNFL RVQVKYSKGF RAPTSDELYF TFKHPDFTIL  720
PNPVLKPEEA KNQEIALTVH DNWGFVSTSV FQTKYRHFID LAYLGSRNLS NSVGGQAQAR  780
DFQVYQNVNV DNAKVKGLEI NARLNLGYFW HVLDGFNTSY KFTYQRGRLD GDRPMNAIQP  840
KASVFGLGYD HKENKFGADL YITRVSEKKA KDTYNMFYKE QGYKDSAVRW RSDDYTLVDA  900
VGYIKPIKNL TLQFGVYNLT DRKYLTWESA RSIKPFGTSN LINQKTGAGI NRFYSPGRNF  960
KFSAEITF                                                           968

SEQ ID NO: 3            moltype = DNA  length = 2373
FEATURE                 Location/Qualifiers
source                  1..2373
                        mol_type = genomic DNA
                        organism = Pasteurella multocida
SEQUENCE: 3
atggaatccg caaaaaatcc actcaaaaag acgacacttg cactcctctg ttgttctacc  60
gccttctcgc tttccgcaaa aaccgatacg aacgccgata aaaatcactt tctgacggaa  120
attgtcgtgt atgcggatca aaataaatca atgagttcaa cacagagtgt cactcaagat  180
gacatgaaaa aaagccctgt cacaaatggt aatattactg actatttacg ttcaaatccg  240
catgtgcgtt atgagaatag cgatcaaaat ggattgcaac gaggtgaaat taaacccgaa  300
aacatttcaa ttaatggtgc agattatcag cagaccactt tttttgtcga taatgtaaat  360
atcaataatg atatgggatt tggtagtgat ctttttgacg gcaccatggc aacagtcccc  420
tttgccaatc attctcaagg ctactttttt gatgccaatc tgctctcttc aattgtagtg  480
catgacagta atgtttctgc cagcttagga ggatttgcgg ggggagccgt cgtggcgaaa  540
accaaacaat atgatgggaa agatcggtta aaatttagtt atcgtacaac tgatgcctca  600
tgggcaaaat ttaaagtaga agacaaagat cttgaacgtt ttaaaaatgc gattcctgaa  660
ggatcggtcg ccgaatttca acctaagtat tctaaacact tttcaatat cacggcagaa  720
aaagggttaa gtgaaaattt aggtatggtg atcggattaa gtcgtagaac atcaagtatc  780
caacaatcac gtcaaattaa tccacaaggt gatcgtgata aacaaacaca tacaagacgt  840
tcagacaatg cgttactgaa ttttaatctg acaccaaacg acaaacaccg tttcgaactc  900
ggtttcagat actcaaatta tcgtgagcgt aaattcttta atactaatat agacagtaat  960
gtttttgact atcaccgtgc ttatggtgtg actttctctt ggataaacgc ccttcagtct  1020
ggcattctca cgacgacact cgcctatgat aactttgatg acacgagaaa atcagcgtca  1080
acttatatga aaacgacgct cactgaagag ggtgaggaat ataccgaagg tggaatgggt  1140
aacagtcaat tgaaccaaaa aaatttacat acgtcacttg aatatgcgat gaatcctttt  1200
aatttaggtt caatagaaca ctctgtatca ttaggcggta tttatcaagc aacgaaatat  1260
cgctttacgc gacattcaga tgcagtcggt gaattgtata ctcctgattg gttaaatggt  1320
aatacagata aacttatatt gacgcaacgt aacatagcca aaaaagggac cgtaaaaaca  1380
cgttatcaaa atatcgcact ttacgtggaa gatttaatga cgtggaaaaa tctcgaattt  1440
cgggcgggac ttcgtcttga acgtgatgat tatttaaaaa acacgaattt ggcgccaaga  1500
accgtttttc gttataaacc atttgaagac accgcattca gtgtgggttg gaaccgttac  1560
tacggacgtt cctttgcctc aatgaaatta tctgaaggta tcttcaaatt agatggtcat  1620
gataccttcc gttacaaaga ccttagccaa tttaaaaccc cttattcaga cgaactgagc  1680
tttggtgtag aacaatatgt tgctaatctc gcctttcact tgaaatacat tttacgtgat  1740
aacaaacaac gtattgtttt acaagaagaa gaggtcatgt taaatggaga aaggaaaaaa  1800
ctccgctatt accaacgagg aaaagactac aaaacgaatg tgttaacctt ccaaattaac  1860
acacaagcgc cttgggagct tggtccaaca cgctggacaa gtgcagtggc atttgattgg  1920
ttagatagca aagctatcga tcatggcagg ggctataacg gttcgacacc tgtgatttta  1980
gacgggaaat taatgactta tgagcaaatg ttgaaaaaag tcaatgctta caaagaaaca  2040
tggggtctac gtttaaatct tgacatgttt gttccaatat ttgatctttc ttgggctaat  2100
acaatctatg tcaaaccacc aacaacctta accgaacgcg ttagcagtaa tacacctgag  2160
gtatatcgta gctatgatta tggtacttat acacaatggg ataccagtct tcgctggcag  2220
ccaactttcg cagaaaaaca ccgtccttat attaaattag atgtacttaa tgtgttaaat  2280
aaaacacgta aaggcgcggg tccaaatgga caagatctcg gcatctacac ccccggtcgt  2340
gagttctggc ttgaagttgg ttacgaattc taa                               2373

SEQ ID NO: 4            moltype = AA  length = 790
FEATURE                 Location/Qualifiers
source                  1..790
                        mol_type = protein
                        organism = Pasteurella multocida
SEQUENCE: 4
MESAKNPLKK TTLALLCCST AFSLSAKTDT NADKNHFLTE IVVYADQNKS MSSTQSVTQD  60
DMKKSPVTNG NITDYLRSNP HVRYENSDQN GLQRGEIKPE NISINGADYQ QTTFFVDNVN  120
INNDMGFGSD LFDGTMATVP FANHSQGYFF DANLLSSIVV HDSNVSASLG GFAGGAVVAK  180
TKQYDGKDRL KFSYRTTDAS WAKFKVEDKD LERFKNAIPE GSVAEFQPKY SKHFFNITAE  240
KGLSENLGMV IGLSRRTSSI QQSRQINPQG DRDKQTHTRR SDNALLNFNL TPNDKHRFEL  300
GFRYSNYRER KFFNTNIDSN VFDYHRAYGV TFSWINALQS GILTTTLAYD NFDDTRKSAS  360
TYMKTTLTEE GEEYTEGGMG NSQLNQKNLH TSLEYAMNPF NLGSIEHSVS LGGIYQATKY  420
RFTRHSDAVG ELYTPDWLNG NTDKLILTQR NIAKKGTVKT RYQNIALYVE DLMTWKNLEF  480
RAGLRLERDD YLKNTNLAPR TVFRYKPFED TAFSVGWNRY YGRSFASMKL SEGIFKLDGH  540
DTFRYKDLSQ FKTPYSDELS FGVEQYVANL AFHLKYILRD NKQRIVLQEE EVMLNGERKK  600
LRYYQRGKDY KTNVLTFQIN TQAPWELGPT RWTSAVAFDW LDSKAIDHGR GYNGSTPVIL  660
```

```
DGKLMTYEQM  LKKVNAYKET  WGLRLNLDMF  VPIFDLSWAN  TIYVKPPTTL  TERVSSNTPE   720
VYRSYDYGTY  TQWDTSLRWQ  PTFAEKHRPY  IKLDVLNVLN  KTRKGAGPNG  QDLGIYTPGR   780
EFWLEVGYEF                                                               790

SEQ ID NO: 5             moltype = DNA   length = 2184
FEATURE                  Location/Qualifiers
source                   1..2184
                         mol_type = genomic DNA
                         organism = Pasteurella multocida
SEQUENCE: 5
atgtcattca aacataaaac actggcgctt tttgtcgcac atgcttgctg cacttctgcc   60
ttagcagaaa acgtggctac cacgttagaa cccatcgtgg tttctgatct cagtcatacc  120
acgctgaacc ttgatcaaaa taagcttgaa aaagaaagtc caaaagattt aaaagctatt  180
tttgccacaa cgccaaatat taatgttatc catacggcaa atgcacaatt aggcgatatt  240
gaaattcgcg gtatgggaag cagccgagaa atctttgcta ccggcgcaaa ccgcgtcaca  300
atggaattag acggtatgga cattagcccg agttttatt ttggcacag ctcacgccat  360
ggtcggcaat attttgatcc cagtgatcta aaacgtgttg agattcataa aggtccaaac  420
agtcaaggcg tggcagggca tgttcgtttc caaacgaaag atcctcgtga ttatctctta  480
cctaaccaac gtacaggtgc acaacttcgt gctggctatt taggcgatag tgatgcttat  540
tatgttggga taactggtgc cactttattg gatgaacaca gtagtgcttt agtgagctat  600
acacgacgct ggtttaatga atttaataat aagggaggct ggatgtcac aggtagtcaa  660
cgtactaaaa gcaatccttc cagtggttat agtaatgcag taaacagtaa attacgctat  720
tcaccaaatg accgccataa atttacgctg aatttgcaac attatgattt aaaacgcacc  780
gcctatttag aagatagctt aggaacaacg acaacacgac gtggcacaaa aacagttcat  840
cataatacca acattcagaa aaatcagcgt catgctattg ctttcagtca tgacatgcaa  900
caaaccacgg catttttga tcacctgcac tggcaaattg cgttacaaca aacgaaaagc  960
acgagccgta atacagggc agtcacgaat acatcagcat ctcctcccc aagtacgcca 1020
aaatttagcc aagagcgttc acttgatggc tttaaaacca aaaccatcag cttaaaaacg 1080
gaattcaata aaagcattgg gcaacatgtc gtacatgaac ttcactatgg actaaaatta 1140
caatatgacc taaatcaagc tttacgccaa acacaatccc taaacgaaca agggagtaac 1200
actcgaacca gcgcctttt cccgacacag caacaatggc aaagtaaact ccatctttcc 1260
gatcggatca gttttggtaa atctggttta agcttgacac catccataca tctcacacag 1320
attagaatca accgaaaac agaaaatgta tcgaagaaaa accgtgaaca attatttact 1380
tacaaggata ccgccattgg ttacgtctg cgtgttgatt atgcactcaa tgaagcgaat 1440
ttactgagtc tgaactatca gcacgccact cgcttacccg gctatggtga aaacaatgcg 1500
caaagctatg gacactggcc agcaaaaccg aaccctcatc tacagccaga acctcagat 1560
ggtattgaat taagttggcg tagtgcgggg gcgattggtc aacaaccac gaccttgttc 1620
tataaccgtt acaatgactt aatttatctc gataccacgg catgttatgc tgaccgaaca 1680
ggtcaagtgc cttgtgattt agcaaatgaa aaaggacgta gttatagcta tggaataaga 1740
ttcgacggta aactcaatct tgatacgatc ggcttcgctc aaggaacata tttaaatgct 1800
ggcttcgctt acagcaaagg gaagaccgcg aacaagcaac cacaaggacg tcttgatccc 1860
ctaacaggct tgtcggtct tggctaccaa cagccaatgg atgtttgggg cattgaaggt 1920
aaactgaaat ttgccgcgaa gaaaaaaact aaagacttac ccgccaatca aggttttgaa 1980
ggcttaccgg gctatgctgt agttgatctt accgccattt ataatgtgac gaaacagctt 2040
tatcttggca tcggcatcta taatgtgcta gataaaaaat atgctcgctg gcaatggca 2100
agaggcgaca ttaaacatgg taactatgac agcacactg aagcaggtcg tcattttggt 2160
gccaatattc gttaccactt ttaa                                         2184

SEQ ID NO: 6             moltype = AA   length = 727
FEATURE                  Location/Qualifiers
source                   1..727
                         mol_type = protein
                         organism = Pasteurella multocida
SEQUENCE: 6
MSFKHKTLAL  FVAHACCTSA  LAENVATTLE  PIVVSDLSHT  TLNLDQNKLE  KESPKDLKAI   60
FATTPNINVI  HTGHAQLGDI  EIRGMGSSRE  IFATGANRVT  MELDGMDISP  SFYFGHSSRH  120
GRQYFDPSDL  KRVEIHKGPN  SQGVAGHVRF  QTKDPRDYLL  PNQRTGAQLR  AGYLGDSDAY  180
YVGITGATLL  DEHSSALVSY  TRRWFNEFNN  KGGLDVTGSQ  RTKSNPSSGY  SNAVNSKLRY  240
SPNDRHKFTL  NLQHYDLKRT  AYLEDSLGTT  TTRRGTKTVH  HNTNIQKNQR  HAIAFSHDMQ  300
QTTAFFDHLH  WQIALQQTKS  TSRNTGAVTN  TSASPPPSTP  KFSQERSLDG  FKTKTISLKT  360
EFNKSIGQHV  VHELHYGLKL  QYSQMQALRQ  TQSLNEQGSN  TRTSAFFPTQ  QQWQSKLHLS  420
DRISFGKSGL  SLTPSIHLTQ  IRIKPKTENV  SKKNREQLFT  YKDTAIGYGL  RVDYALNEAN  480
LLSLNYQHAT  RLPGYGENNA  QSYGHWPAKP  NPHLQPETSD  GIELSWRSAG  AIGQQTTTLF  540
YNRYNDLIYL  DTTACYADRT  GQVPCDLANE  KGRSYSYGIE  FDGKLNLDTI  GFAQGTYLNA  600
GFAYSKGKTA  NKQPQGRLDP  LTGFVGLGYQ  QPMDVWGIEG  KLKFAAKKKT  KDLPANQGFE  660
GLPGYAVVDL  TAYYNVTKQL  YLGIGIYNVL  DKKYARWAMA  RGDIKHGNYD  KHTEAGRHFG  720
ANIRYHF                                                              727

SEQ ID NO: 7             moltype = DNA   length = 2895
FEATURE                  Location/Qualifiers
source                   1..2895
                         mol_type = genomic DNA
                         organism = Pasteurella multocida
SEQUENCE: 7
atgcgtacaa caacaataaa atttctgca attacattgg cattattgag ttattgtggg   60
gtcatttggg cggatagtca tcaagaggcg actgaacttg tacgattac cgtttcttct  120
caacaagatg agatgaatat taagagaaa aaagtcggtg aaactgtgaa aacggcgagt  180
caattgaaac gccagcaagt acaggatagt cgtgatcttg tgcgctatga aaccggtgtg  240
actgtggtag aagctggacg ttttgggtcg agcggttatg ccattcgtgg tgtggatgag  300
```

```
aaccgagtgg caattacagt agatggctta catcaagcag aaaccctttc ttctcaaggt    360
tttaaagaat tattcgaagg ttacggcaat tttaacaata cccgaaatag tgtggaaatt    420
gagacgttga aagtcgctaa aatcgcgaaa ggtgctgatt ctgtaaaagt gggtagtggg    480
tctttgggag gcgctgtact ttttgaaaca aaagatgcca gagatttcct gactgaaaaa    540
gattggcata tcggctataa agcgggctac tcaacggcaa ataatcaggg attaaatgca    600
gtgactcttg caggtcgcta tcaaatgttt gatgcattga ttatgcattc taagcgacat    660
ggacatgaat tagaaaatta tgactataaa aatggcagag atattcaagg aaagaaaga     720
gagaaagcgg atccttatac gattacgaaa gaagtacat  tagtgaaatt ctcttttcg     780
ccaacagaaa atcatcgttt tacagtcgtc tctgatactt ataacaacg  ttctcgtggc    840
catgatcgct cttattcttt acagcctcaa tctaattatt tcacatatga cgagaaagaa    900
tcgcgtcatg caaatgattt gacaaaacgt aaaaatgttt cttttactta tgaaaactat    960
agcgtaactc cattttggga tacgctaaaa ttgagttatt cacaacaaaa gatcagaaca   1020
agagcaagaa cagaagatta ttgtgatggt aatgaaaaat gtgattccta taaaaatcca   1080
ttagggcttc agttgaaaga tggcaaaatt gttgatccag agggaaatca gattacttta   1140
aaaggaacag gatttaatac agaaatagtt gataaaaatg gtaacccatt tcctacgaca   1200
tctggtacta ataatgcagc atttagtaat aatattcagt taggacctaa agaattttgg   1260
ttagattgtt ctcttttga  ttgtactcag ccatttactg tttataacta tcaaaatggt   1320
caatatacgc caaaacaagt tgagttatct gaagaaatca ctgtcaatgg taaattatat   1380
aaaacagcta aagaagaaag aggtgttagg aactatttaa ttttacctaa ttcaaaaggt   1440
tatttaccat atgattacaa agaaagagat cttgattcaa atacaaaaca aatcaatttg   1500
gatttaacaa aaacattttc gacttttaat atagaaaatg aattattata cggtgccatt   1560
tattcacgta cagagaagaa aatggttaat aaagcaggtt acgatgggag aaatcctaca   1620
tggtgggctg atagaatttt agggaagagt acgaattgta actataatgg actgaaatgt   1680
cctcgtcatg aaccttttaac ttctttctta attccagtag aagcgacaac caagtctcta   1740
tatttttcag ataatatcaa attcacaac  atgttgagtg tagatttagg ttatcgttat   1800
gacgatatta aatatcaacc agaatatatt cctggtgtaa cacctaaaat tgcagatgat   1860
atggtgaaag gtatttttat tccattacct aagggagaaa aagtaacaac accttggggg   1920
gccgaatata caaaaccact cacacaggaa caaattcgta agaatgcgga ggaaaatatt   1980
gcttatattg cacaagaaaa acgctttaaa aaacattctt attctcttgg tgcaacgttc   2040
gatcctctga atttttacg  agtacaagta aaatattcaa aagggtttag agccccgact   2100
tcggatgaac tttattttac ctttaagcat ccagattttta cgatttttacc gaaccccgtg   2160
ttgaaaccag aggaagcaaa aaatcaagag attgcattaa cagtgcacga taattggga    2220
tttgttagca caagtgtttt ccaaacaaag tatcgtcatt ttattgattt agcgtattta   2280
ggttcaagaa atttatcgaa ttccgtggga gggcaggcac aagcaagaga tttccaagtt   2340
tatcaaaatg tcaatgtcga taatgccaag gttaaaggac ttgaaattaa tgcacgtttg   2400
aatttgggat atttctggca tgtgttggat ggatttaata cgagctataa attcacttac   2460
caatgtggtc gtttggatgg cgatcgtcca atgaatgcga ttcagcctaa agcttctgtt   2520
tttggtttag gctatgatca taagaaaaat aaatttggcg ctgatttata tatcacacgt   2580
gtgagtgaa  aaaaagcgaa agacacctat aaatatgttct ataaagaaca gggtataaa    2640
gatagtgcta ttcgttggag aagtgatgac tatacgctag ttgatgcggt tggttatatt   2700
aaaccgatta gaatttaac gttacagttt ggcgtttata atttgacaga ccgtaaatac   2760
ttgacatggg aatctgctcg ttcgattaaa ccatttggta caagtaattt aattaatcag   2820
aaaacaggcg caggaattaa tcgttttttac tcaccaggtc gtaattttaa atttagtgcc   2880
gaaattacct tctaa                                                   2895

SEQ ID NO: 8           moltype = AA  length = 964
FEATURE                Location/Qualifiers
source                 1..964
                       mol_type = protein
                       organism = Pasteurella multocida
SEQUENCE: 8
MRTTTIKFSA ITLALLSYCG VILADSHQEA TELDTITVSS QQDEMNIKEK KVGETVKTAS     60
QLKRQQVQDS RDLVRYETGV TVVEAGRFGS SGYAIRGVDE NRVAITVDGL HQAETLSSQG    120
FKELFEGYGN FNNTRNSVEI ETLKVAKIAK GADSVKVGSG SLGGAVLFET KDARDFLTEK    180
DWHIGYKAGY STADNQGLNA VTLAGRYQMF DALIMHSKRH GHELENYDYK NGRDIQGKER    240
EKADPYITTK ESTLVKFSFS PTENHRFTVA SDTYIQRSRG HDRSYSLQPQ SNYFTYDEKE    300
SRHANDLTKR KNVSFTYENY SVTPFWDTLK LSYSQQKIRT RARTEDYCDG NEKCDSYKNP    360
LGLQLKDGKI VDPEGNQITL KGTGFNTEIV DKNGNPFPTT SGTNNAAFSN NIQLGPKEFW    420
LDCSLFDCTQ PFTVYNYQNG QYTPKQVELS EEITVNGKLY KTAKEERGVR NYLILPNSKG    480
YLPYDYKERD LDSNTKQINL DLTKTFSTFN IENELLYGAI YSRTEKKMVN KAGYDGRNPT    540
WWADRILGKS TNCNYNGLKC PRHEPLTSFL IPVEATTKSL YFSDNIKLHN MLSVDLGYRY    600
DDIKYQPEYI PGVTPKIADD MVKGIFIPLP KGEKVTTPWG AEYTKPLTQE QIRKNAEENI    660
AYIAQEKRFK KHSYSLGATF DPLNFLRVQV KYSKGFRAPT SDELYFTFKH PDFTILPNPV    720
LKPEEAKNQE IALTVHDNWG FVSTSVFQTK YRHFIDLAYL GSRNLSNSVG GQAQARDFQV    780
YQNVNVDNAK VKGLEINARL NLGYFWHVLD GFNTSYKFTY QCGRLDGDRP MNAIQPKASV    840
FGLGYDHKEN KFGADLYITR VSEKKAKDTY NMFYKEQGYK DSAIRWRSDD YTLVDAVGYI    900
KPIKNLTLQF GVYNLTDRKY LTWESARSIK PFGTSNLINQ KTGAGINRFY SPGRNFKFSA    960
EITF                                                                964

SEQ ID NO: 9           moltype = DNA  length = 2547
FEATURE                Location/Qualifiers
source                 1..2547
                       mol_type = genomic DNA
                       organism = Pasteurella multocida
SEQUENCE: 9
atgcaaaaac agcaacctta tcccattcac cttgggattt tttgatgtt gggtttacca     60
acatgggcgt tcagtcaagc taatttagag aaatcaacaa tcaataaatt ggaaacgatt    120
ttggtcaatg agagtgaaga gaaaaataaa ttcgatgaga atttgatcaa aacttatctg    180
tcttcggggtt cttattctta tttatcgcaa tcggatatca gtacgttcag aggtagctcg    240
```

-continued

```
gtaggggatt tcctctctgg tgtaccagga gttattgtgg gaaataagcg taatagcggc  300
gctttatccg ttaatattcg aggaattgcg aatgaaaatc gtgtgcctgt ttggatagat  360
aaaggtctac aatcggtacc ctccttaccaa ggttatgcag gttcttcaac tcgaacctat  420
ttagatcccg atttgatcag ccaagtcgag attgaaaaag gtccctcttt gcaaatggac  480
gcaacaggcg cgacgggagg ggtagtgaga gtagagactt tacgttggca agatatattt  540
cctcaaggga aaaattgggg cgtgcgtttg aaactaggga cgatgactaa caccgtatca  600
cctcccccTT attatacaag aggaggatat caaactaagt atattagtaa atgtctttct  660
aatgatactg gtttatgtca aacacaaaca tatgcaccaa atgcacgcta ttcttctcat  720
ggctttgatt tgaatgcata caattatagc ctggcttttg ctaataaatg gcaaaatgct  780
gatcttgtac ttgcgtatgc aaaacgtaaa cagggcaact attttgttgg gcgtcatgga  840
caaaccccag tgattgaatc cattgaattt gaggaagatt cagtagaagt caaagagcct  900
cgcgttcatg aagaggttga aattggttca ttaacatttta agaaaatcg cagcacctta  960
tatcgaccgg gtgaagaagc cctgaatacc tcacagata atacctctta tctcgctaaa 1020
ataaatgtct acaatgatgt tcatcgttta gggttagcgt atcgccatta tcatagccgt 1080
tttggtgaga ttatgagctc aattttgaat ttcagagcgt atggcgcatt gcaaggtgaa 1140
gggacagaag tcaaagtcga tagctatcat gcaaattata gctataaccc aacgacacct 1200
tatgtgaatt tgaatgttaa tgcatatttt actgacagtg attcgtctaa ttttacccca 1260
tttattgaag aatatggtta ctctttatcc agtcgtcatg cccattttct ggtttctaag 1320
cagaaagggt taagtattga aaatactagc attttccagc ttaacgacaa accgtttagt 1380
ttaaaatatg gtcttgcgca tagttatgaa cggatttatc aaccacgtaa tgctcaagca 1440
cgtgtgagag ctaaagggta tccagaagat gcgattggtc cactttatat tcgagatggt 1500
aagcgtaaag aatggagcgc ttttgttgct gcgaactatc caatcacttc gtggttaaaa 1560
gccgacatcg ggctacgtta tcttcaatct actatttatg attatattgt gagaacggaa 1620
agagtgaata ttggagggggc acttgtgcct aatccaaatg gatccggtaa tatttgggtg 1680
gaaaaatata aagatgttgt gcataaacag gcgccagtga aaaataaagg catgtcgcca 1740
attgtgatgc tcacatttga acctattaac ggagtacaaa tttatacgaa atatgcagaa 1800
gcattgcgtt cgccaagttt attccaagca actaaaggct ggtccatgag tgcgacggca 1860
gataatctag aacaattgag acctgaacga gcccaaaatt gggaggcggg tattaacttg 1920
ttttatgaaa atctaggtgg taaggacaat attcttggtt ttaaattggc gtattttaat 1980
aataggataa agattatttt gacgcggagt tattcgccta aagataaggt gacgcagaca 2040
attaatatac aaagtgcaca atttaaagga attgagttat cagcgtatta tgatatgggg 2100
aaattttacg caaaattagc tggtacatat tacacaaaaa cgaaattttg tttaacagca 2160
gaacaagcag gcaaggaga gcaatgtaat tcaggttatg tatatcgtag taatttaaat 2220
aatgccgttc ctccgcgttt aaatttacat gcgactttag gaacccgttc gtttgaacaa 2280
aaactcgata ttggtgcgcg ctatagttac tacagtaagc gattagtacc agtgctttct 2340
gcagaacgtt ttgttaacac atcaagtatt gagtgggcgc ttattccctt agtagattta 2400
tatgccaatt acaatgtgtc taataaccta aaacttacga tgaccatgga taatgtgttt 2460
aatcgctatt atttagatat caataatatg ggattaaata ccgcaccggg tagaacattg 2520
catttaggat tagaatatcg gttttag                                     2547

SEQ ID NO: 10          moltype = AA  length = 848
FEATURE                Location/Qualifiers
source                 1..848
                       mol_type = protein
                       organism = Pasteurella multocida
SEQUENCE: 10
MQKQQPYPIH LGIFLMLGLP TWAFSQANLE KSTINKLETI LVNESEEKNK FDENLIKTYL  60
SSGSYSYLSQ SDISTFRGSS VGDFLSGVPG VIVGNKRNSG ALSVNIRGIA NENRVPVWID 120
KGLQSVPSYQ GYAGSSTRTY LDPDLISQVE IEKGPSLQMD ATGATGGVVR VETLRWQDII 180
PQGKNWGVRL KLGTMTNTVS PPPYYTRGGY QTKYISKCLS NDTGLCQTQT YAPNARYSSH 240
GFDLNAYNYS LAFANKWQNA DLVLAYAKRK QGNYFVGRHG QTPVIESIEF EEDSVEVKEP 300
RVHEEVEIGS LTFKENRSTL YRPGEEALNT SQDNTSYLAK INVYNDVHRL GLAYRHYHSR 360
FGEIMSSILN FRAYGALQGE GTEVKVDSYH ANYSYNPTTP YVNLNVNAYF TDSDSSNFTP 420
FIEEYGYSLS SRHAHFLVSK QKGLSIENTS IFQLNDKPFS LKYGLAHSYE RIYQPRNAQA 480
RVRAKGYPED AIGPLYIRDG KRKEWSAFVA ANYPITSWLK ADIGLRYLQS TIYDYIVRTE 540
RVNIGGALVP NPNGSGNIWV EKYKDVVHKQ APVKNKGMSP IVMLTFEPIN GVQIYTKYAE 600
ALRSPSLFQA TKGWSMSATA DNLEQLRPER AQNWEAGINL FYENLGGKDN ILGFKLAYFN 660
NRIKDYLTRS YSPKDKVTQT INIQSAQFKG IELSAYYDMG KFYAKLAGTY YTKTKFCLTA 720
EQAGKGEQCN SGYVYRSNLN NAVPPRLNLH ATLGTRLFEQ KLDIGARYSY YSKRLVPVLS 780
AERFVNTSSI EWAPYSLVDL YANYNVSNNL KLTMTMDNVF NRYYLDINNM GLNTAPGRTL 840
HLGLEYRF                                                          848

SEQ ID NO: 11          moltype = DNA  length = 2355
FEATURE                Location/Qualifiers
source                 1..2355
                       mol_type = genomic DNA
                       organism = Pasteurella multocida
SEQUENCE: 11
atgaaatatc ccttaagcta taaaaatata gcaaggtcca ttcctttttct ctcattcatt  60
gcgtttcctc tgtatgcgca agaaacgact gaattagaac aaattacagt acaagaaagc 120
gcaaccgctg aagtgaacaa aacctcacca acagtgatca gcaaaagcgc cacgaccatt 180
caaaacgaaa tgattcgaga caccagagat ttagtccgct acacaacgga tgtagggatt 240
agcgataatg ggcgtttttt gaaaggcttt gcgatgcgag cgttgaaga taaccgcgtt 300
ggtatcagta ttggtggtgt ttctttgcct gattcagaag aaaactcact gtatcgcgt 360
tatggtaact ttaataattc ccgcctaagc attgatcctg aattaattca aaccattgat 420
attgtacgcg gctcagattc ctttaatgca ggcagcggtt cattaggtgg cggtgtgaat 480
tataacactt tagatccaca acatattgtt aaaacaggta attccgttgg tgctttacta 540
cgaggcagtt atgccagtaa aaatcgtgaa tgggttcgta cttagggat aggctatgtt 600
ggcgaaaaat ttgatgcctt attgatgtat tcacaacgca cagggcacga gtttaaaagt 660
```

```
cgtggttcag gtcctgaatt tcggtattcc agtagccagc atcccgatcc tgtgacacaa    720
cgcttccaca attatctcgc taaaatgaat tatcaaatta atgacaaaca acgtattggt    780
ttaacgctga atgggcaaac agggggggcgt tacattgatg agcgttctta tacgttaatg    840
ggctcacaat ggcgtgaagc cgatgatcaa aacgaacggt tgaatgcaaa cttatattat    900
atttatgcac caagcacggg atggttagcc tacagtaaat ttgatttaga ttatcaaaag    960
accgatctag cagcagttaa ctataaaggc ggacgccatt tcacgacaga tgctaaagag   1020
ctgaacgaaa tttatgatcg ccgtatgaaa accgtgttta cgcgcggcag tgtagaactc   1080
aatgcacaac ctgtacattt ctatggtgaa catactttaa ccatcaaagg ctatgttagt   1140
cagcgtgatt tcaaaaatat caatcaagat cgtatcggta ttggcacaac ctacgacaga   1200
caataccact atacgattca atatcctatt agaaccaagc agtacgggct ttctttgaaa   1260
gatcatgtgc gctggaatga taccttctca agccatttag gtttacgtta tgaccataca   1320
aaactaaaac caaaggaact caatgcacct tgtagcaaag cctgtttaga agaaggaaaa   1380
cctaaaccga cccgtttctc taccgttagc acatttgcgg gatttgaggc acaactcagc   1440
ccctcatgga tgttaggcta caatattagc accggttatc gtgtaccaac ggcttcagaa   1500
atgttcttca gctttaccaa tgcgtatggc acgtggaaat ctaacccgag cttgaaaccc   1560
gaaaaaagta ttaaccatac actctctttg aaaggcaata tgaaaaaggg cttgcttgat   1620
ctcaccctct atcaaacaaa ctatcgtcat ttcttatttg aacaagaaag tttaattcaa   1680
cgtaccgaaa tgcgctatgg acgccctat acttaccaaa gccaagaaca acaaatggtg   1740
aacttagata aagcaaaaat ttatggtgtg aaattgaaaa cccatgtcaa tttagatcag   1800
atgatcgctg tgataccaca aggctttaag ttctacgccg cgctcggtta tagcaaaggt   1860
aaactctcga ataacgccag cctactttcc attcaaccgc ttaaaattat tctggggttg   1920
gattatgaag caacaaacgg caaatgggct attttcaacc gcctaaccta tttgggtgaa   1980
aaagagctca gtgatgcgaa agtgtatgaa attaaacgtc gctgtactga atttgtgaca   2040
gaaacagatc cttggactgg tcaacaaatt actcgctgta aaaacgggaa attgtatcca   2100
gatttatcta cttataaaca cttaaataaa tctgcttttg tgtttgatac ttttggttat   2160
tacaagatca cggacgatat cacgttccga gctggcatt ataatctgtt taataaaaaa   2220
taccacactt gggatgcctt acgtggtatt aatgccaata gtacgctaaa ttcagttgac   2280
cgtgaaggga aagggttaca acgcttctat gcgcccggac gtaactatgc ggcttcccctt   2340
gaaatccgtt tctaa                                                    2355

SEQ ID NO: 12         moltype = AA  length = 784
FEATURE               Location/Qualifiers
source                1..784
                      mol_type = protein
                      organism = Pasteurella multocida
SEQUENCE: 12
MKYPLSYKNI ARSIPLFLSFI AFPLYAQETT ELEQITVQES ATAEVNKTSP TVISKSATTI    60
QNEMIRDTRD LVRYTTDVGI SDNGRFLKGF AMRGVEDNRV GISIDGVSLP DSEENSLYAR   120
YGNFNNSRLS IDPELIQTID IVRGSDSFNA GSGSLGGGVN YNTLDPQHIV KTGNSVGALL   180
RGSYASKNRE WVRTLGIGYV GEKFDALLMY SQRTGHEFKS RGSGPEFRYS SSQHPDPVTQ   240
RFHNYLAKMN YQINDKQRIG LTLNGQTGGR YIDERSYTLM GSQWREADDQ NERLNANLYY   300
IYAPSTGWLA YSKFDLDYQK TDLAAVNYKG GRHFTTDAKE LNEIYDRRMK TVFTRGSVEL   360
NAQPVHFYGE HTLTIKGYVS QRDFKNINQD RIGIGTNYDT QYHYTIQYPI RTKQYGLSLK   420
DHVRWNDTFS SHLGLRYDHT KLKPKELNAP CSKACLEEGK PKPTRFSTVS TFAGFEAQLS   480
PSWMLGYNIS TGYRVPTASE MFFSFTNAYG TWKSNPSLKP EKSINHTLSL KGNSEKGLLD   540
LTLYQTNYRH FLFEQESLIQ RTEMRYGRPY TYQSQEQQMV NLDKAKIYGV ELKTHVNLDQ   600
MIAVIPQGFK FYAALGYSKG KLSNNASLLS IQPLKIILGL DYEATNGKWA IFNRLTYLGE   660
KRASDAKVYE IKRRCTEFVT ETDPWTGQQI TRCKKRELYP DLSTYKHLNK SAFVFDTFGY   720
YKITDDITFR AGIYNLFNKK YHTWDALRGI NANSTLNSVD REGKGLQRFY APGRNYAASL   780
EIRF                                                                784

SEQ ID NO: 13         moltype = DNA  length = 2229
FEATURE               Location/Qualifiers
source                1..2229
                      mol_type = genomic DNA
                      organism = Pasteurella multocida
SEQUENCE: 13
atggataaaa aatttaatgaa gggatgtgta ttcttatcaa tagtcggttg cggtatccaa    60
ataggggctag catcaaatcc aaatcctcca gatgtggatg agttattacc tattattgtg   120
aatgctgatg aagataataa attaccaggt cgttctgtat taaaacagaa aaatatcgat   180
caacaacaag cagataatgc tgctgactta ataaatatt tgcctggtgt aaatatggcg   240
ggaggatttc gccctagtgg tcaaacatta atatttaatg aatgggtgaa tgctgaagat   300
gttagagtta aactagacgg cgcaacaaaa agtttcgaaa aatatcaaca aggctctatt   360
tttattgaac ctgagttatt aagaaaggtg acagtagaca aaggaaatta ttctcctcaa   420
tatggcaatg gtggctttgc tggtactgta aaatttgaaa caaagatgc aactgatttt   480
ttgaaagaaa atcagaaaat aggtggatta tttaaatatg gaataatag caataataac   540
caaaaaactt atagtacagc cctagtttta cagaatgaac aaaaaaatat tgatttgtta   600
ttatttggtt ctgtaagaaa tgcaagcaat tatacaagac ctgataaaag taaaatcttt   660
ttttcaaaaa acaatcaaaa aagtggatta ataaagtaa attggcaaat tactcctgga   720
catttattaa ctttatccag tgtttatggc attcataaag ggtgggaacc ttgggcagca   780
aaagagatg tgatgtcgag accaacagaa acagaaataa acactatgg gattgatgtt   840
gcgtggaaac gtaaacttgt ttatcgagat caaaagatg aaagttattc attgaaatat   900
cgctattac ctgaaaataa taagtggatt aaatttatctg ttcagctgag ttatagtaaa   960
acagaacaga attacttcg ccatgagaaa cacttcttt cattccttag tacattagga  1020
aatattggc gtgctgagca tgaactacta tttggtttac agtggttaaa aaataaaga   1140
aatccctta tgtatcataa aggggagtc aagaaggcag actataatta tggctatttt  1200
cagcctattt atatgcctcc tggacgccag tatacacaag cattttattt acaagatcaa  1260
ataaaatggc agaaatttcct ctttacagga gggataagat atgaccatat caataatata  1320
```

```
gggcagaaaa atttagcgcc acgatataat gatatctctg caggacatga ttatagccag    1380
aaaaattata atggttggtc ttattattta ggtcttaagt atgatgtaaa tcattattta    1440
agtttattta cgaattttag taaaacttgg cgagccctg ttattgatga acagtatgag     1500
acacaatata gtcaagcttc tgtatctgcg acttctttaa atttagaaaa agaaatgatt    1560
aatcaaacca gagtgggtgg aattattact ctcaatcatc tatttcagga aaatgatgct    1620
tttcaattta gaactactta ttttacaat cgcggcaaga atgaaatctt caaaacgaga     1680
ggagttaatt gcgtagaaaa tgctttagat gttgataata gtgtttgtcc taaaattatt    1740
agtaattacc gtaatttacc tggttatgtt attcaaggag cggaattaga agcttattat    1800
caatcatcgt atttatttgg tggactgaca tattcttatg taaaggaaa acgcgatact    1860
tcaccaagaa atccatggag taaaacatct acatggatcg cagaaacatc acctagaaaa    1920
gcaatcgcta ctttaggttt taatattccg gaatatatt ttacggcagg ttggcgtgct    1980
gagtttgtga aaagcaaga tagatcacca ctatctaatg attctaaagc atcatattgg     2040
gcattacctt cttcaaaagg atatagccta catagtgtat tcttctcttg gagtcctaca    2100
aagattaaag aatgaatttc caagttact gttgataatt tatttaaccg accctattat     2160
ccttacttag gagaattagc ttcaggaaca ggtaggaatg tcaaatttag cctgactcag    2220
caattttaa                                                             2229

SEQ ID NO: 14          moltype = AA   length = 742
FEATURE                Location/Qualifiers
source                 1..742
                       mol_type = protein
                       organism = Pasteurella multocida
SEQUENCE: 14
MDKNLMKGCV FLSIVGCGIQ IGLASNPNPP DVDELLPIIV NADEDNKLPG RSVLKQKNID     60
QQQADNAADL INILPGVNMA GGFRPSGQTL NINGMGDAED VRVQLDGATK SFEKYQQGSI    120
FIEPELLRKV TVDKGNYSPQ YGNGGFAGTV KFETKDATLF LKENQKIGGL PKYGNNSNNN    180
QKTYSTALVL QNEQKNIDLL LFGSVRNASN YTRPDKSKIL FSKNNQKSGL IKVNWQITPE    240
HLLTLSSVYG IHKGWEPWAA KRDVMSRPTE TEIKHYGIDV AWKRKLVYRD QKDESYSLKY    300
RYLPENNKWI NLSVQLSYSK TEQNDTRHEK VTSSFLGTLG NKSWITYSDL TFDISNTSTL    360
NIGRAEHELL FGLQWLKNKR NTLMYHKGGV KKADYNYGYF QPYYMPSGRQ YTQAFYLQDQ    420
IKWQNFLFTG GIRYDHINNI GQKNLAPRYN DISAGHDYSQ KNYNGWSYYL GLKYDVNHYL    480
SLFTNFSKTW RAPVIDEQYE TQYSQASVSA TSLNLEKEMI NQTRVGGIIT LNHLFQENDA    540
FQFRTTYFYN RGKNEIFKTR GVNCVENALD VDNSVCPKII SNYRNLPGYV IQGAELEAYY    600
QSSYLFGGLT YSYVKGKRDT SPRNPWSKTS TWIAETSPRK AIATLGFNIP EYYFTAGWRA    660
EFVRKQDRSP LSNDSKASYW ALPSSKGYSL HSVFFSWSPT KIKGMNFKVT VDNLFNRPYY    720
PYLGELASGT GRNVKFSLTQ QF                                              742

SEQ ID NO: 15          moltype = AA   length = 968
FEATURE                Location/Qualifiers
source                 1..968
                       mol_type = protein
                       organism = Haemophilus influenzae
SEQUENCE: 15
VLLMLSQPTN QPTNQPTNQN SNASEQLEQI NVLGSDNNND NTPPKIAETV KTASQLKRQQ     60
VQDSRDLVRY ETGVTVVEAG RFGSSGYAIR GVDENRVAIT VDGLHQAETL SSQGFKELFE    120
GYGNFNNTRN SVEIETLKVA KIAKGADSVK VGSGSLGGAV LFETKDARDF LTEKDWHIGY    180
KAGYSTADNQ GLNAVTLAGR YQMFDALIMH SKRHGHELEN YDYKNGRDIQ GKEREKADPY    240
TITKESTLVK FSFSPTENHR FTVASDTYLQ HSRGHDFSYN LVKTTYIHKD EEELRHTNDL    300
TKRKNVSFTY ENYTVTPFWD TLKLSYSQQR ITTRARTEDY CDGNEKCDSY KNPLGLQLKN    360
GQIVDRDGNP VNLKLINGRH KVVDKNNKLF GLTDEDNNAA FDGKQLGLSG FWFDCTVFDC    420
DKPVRTYKYK YSSSNPAVEN VELNKFMQVN GKRFATYEDK IQSSEKRYVI LPNSKGYLPL    480
DYKERDLNTK TKQINLDLTK AFTLFEIENE LSYGGVYAKT TKEMVNKAGY YGRNPTWWAE    540
RTLGQDLSGN QHNCNTNSSY NGMLCPRHEP LTSFLIPVEA TTKSLYFSDN IKLHNMLSVD    600
LGYRYDDIKY QPEYIPGVTP KIADDMVKGI FIPLPKGEKI KIGNYETTKP LTPEQIRKNA    660
EENIAYIAQE KRFKKHSYSL GATFDPLNFL RVQVKYSKGF RAPTSDELYF TFKHPDFTIL    720
PNPVLKPEEA KNQEIALTVH DNWGFVSTSV FQTKYRHFID LAYLGSRNLS NSVGGQAQAR    780
DFPQVYQNVN VDNAKVKGLEI NARLNLGYFW HVLDGFNTSY KFTYQRGRLD GDRPMNAIQP    840
KASVFGLGYD HKENKFGADL YITRVSEKKA KDTYNMFYKE EKKKDSAIHW RSDDYTLVDF    900
VTYIKPVKNV TLQFGIYNLT DRKYLTWESA RSIKPFGTSN LINQQTGAGI NRFYSPGRNY    960
KLSAEITF                                                             968

SEQ ID NO: 16          moltype = AA   length = 968
FEATURE                Location/Qualifiers
source                 1..968
                       mol_type = protein
                       organism = Pasteurella multocida
SEQUENCE: 16
MRTTTIKFSA ITLALLSYCG AILADSHQEA TELDTITVSS QQDEMNIKEK KVGETVKTAS      60
QLKRQQVQDS RDLVRYETGV TVVEAGRFGS SGYAIRGVDE NRVAITVDGL HQAETLSSQG    120
FKELFEGYGN FNNTRNSVEI ETLKVAKIAK GADSVKVGSG SLGGAVLFET KDARDFLTEK    180
DWHIGYKAGY STADNQGLNA VTLAGRYQMF DALIMHSKRH GHELENYDYK NGRDIQGKER    240
EKADPYTITK ESTLVKFSFS PTENHRFTVA SDTYLQHSRG HDLSYNLVAT THIQLDEKES    300
RHANDLTKRK NVSFTYENYT VTPFWDTLKL SYSQQRITTA ARTEDYCDGN EKCDSYKNPL    360
GLQLKEGKIV DRNGDPVNLK LVDGKHQVVG KAGKPFDVAS GTNYAAFSGK ELSPSSFWLD    420
CSIFDCSKPI NTYKYRYTSS EPTLQQITLN KTMEINGKTF ATYDGRGHYI ILPNSKGYLP    480
LDYKERDLNT KTKQINLDLT KAFTLFEIEN ELSYGGVYAK TTKEMVNKAG YYGRNPTWWA    540
ERTLGQSWGK LRECKTSSSY NGMLCPRHEP LTSFLIPVEA TTKSLYFADN IKLHNMLSVD    600
LGYRYDDIKY QPEYIPGVTP KIADDMVKGL FIPLPKGEKV TVGTMVFTKP LTQAQIRKNA    660
EENIAYIAQE KRFKKHSYSL GATFDPLNFL RVQVKYSKGF RAPTSDELYF TFKHPDFTIL    720
```

```
PNPVLKPEEA KNQEIALTVH DNWGFVSTSV FQTKYRHFID LAYLGSRNLS NSVGGQAQAR   780
DFQVYQNVNV DNAKVKGLEI NARLNLGYFW HVLDGFNTSY KFTYQRGRLD GDRPMNAIQP   840
KASVFGLGYD HKENKFGADL YITRVSEKKA KDTYNMFYKE QGYKDSAVRW RSDDYTLVDA   900
VGYIKPIKNL TLQFGVYNLT DRKYLTWESA RSIKPFGTSN LINQKTGAGI NRFYSPGRNF   960
KFSAEITF                                                           968

SEQ ID NO: 17           moltype = AA   length = 971
FEATURE                 Location/Qualifiers
source                  1..971
                        mol_type = protein
                        organism = Pasteurella multocida
SEQUENCE: 17
MRTTTIKFSA ITLALLSYCG VILADSHQEA TELDTITVSS QQDEMNIKEK KVGETVKTAS    60
QLKRQQVQDS RDLVRYETGV TVVEAGRFGS SGYAIRGVDE NRVAITVDGL HQAETLSSQG   120
FKELFEGYGN FNNTRNSVEI ETLKVAKIAK GADSVKVGSG SLGGAVLFET KDARDFLTEK   180
DWHIGYKAGY STADNQGLNA VTLAGRYQMF DALIMHSKRH GHELEIYDYK NGRDIQGKER   240
EKADPYTITK ESTLVKFSFS PTENHRFTVA SDTYLQHSRG HDLSYNLVAT TYIQLDEKES   300
RHANDLTKRK NVSFTYENYT VTPFWDTLKL SYSQQRITTR ARTEDYCDGN EKCDSYKNPL   360
GLQLKEGKIV DRNGDPVNLQ LVDGKHQVVD KAGKPFDVTS GTNYAAFSGK QLGPSYFWLE   420
CTVFDCSKPV TTYKYRYSTE TPVKEDIQLN KTMEVNGKTF ATYDMGRERR YIILPNSQGY   480
LPLDYKERDL NTKTKQINLD LTKAFTLFEI ENELSYGGVY AKTTNGVVNK AGYYGRNPTW   540
WAERTLGQSW NGTLRECKTS SSYNGMLCPR HEPLTSFLIP VEATTKSLYF ADNIKLHNML   600
SVDLGYRYDD IKYQPEYIPG VTPKIADDMV KGLFIPLPEG EKVTVGTVVF TKPLTPEQIR   660
KNAEENIAYI AQGKRFKKHS YSLGTTFDPL NFLRVQVKYS KGFRAPTSDE LYFTFKHPDF   720
TILPNPVLKP EEAKNQEIAL TVHDNWGFVS TSVFQTKYRH FIDLAYLGSR NLSNSVGGQA   780
QARDFQVYQN VNVDNAKVKG LEINARLNLG YFWHVLDGFN TSYKFTYQRG RLDGDRPMNA   840
IQPKASVFGL GYDHKENKFG ADLYITRVSE KKAKDTYNMF YKEQGYKDSA IRWRSDDYTL   900
VDAVGYIKPI KNLTLQFGVY NLTERKYLTW ESARSIKPFG TSNLINQKTG AGINRFYSPG   960
RNFKFSAEIT F                                                       971

SEQ ID NO: 18           moltype = AA   length = 971
FEATURE                 Location/Qualifiers
source                  1..971
                        mol_type = protein
                        organism = Pasteurella multocida
SEQUENCE: 18
MRTTTIKFSA ITLALLSYCG AILADSHQEA TELDTITVSS QQDEMNIKEK KVGETVKTAS    60
QLKRQQVQDS RDLVRYETGV TVVEAGRFGS SGYAIRGVDE NRVAITVDGL HQAETLSSQG   120
FKELFEGYGN FNNTRNSVEI ETLKVAKIAK GADSVKVGSG SLGGAVLFET KDARDFLTEK   180
DWHIGYKAGY STADNQGLNA VTLAGRYQMF DALIMHSKRH GHELENYDYK NGRDIQGKER   240
EKADPYTITK ESTLVKFSFS PTENHRFTVA SDTYLQHSRG HDLSYNLVAT THIQLDEKES   300
RHANDLTKRK NVSFTYENYT VTPFWDTLKL SYSQQRITTR ARTEDYCDGN EKCDSYKNPL   360
GLQLKEGKIV DRNGDPVNLQ LVDGKHQVVD KAGKPFDVTS GTNYAAFSGK QLGPSYFWLE   420
CTVFDCSKPV TTYKYRYSTE TPVKEDIQLN KTMEVNGKTF ATYDMGRERR YIILPNSQGY   480
LPLDYKERDL NTKTKQINLD LTKAFTLFEI ENELSYGGVY AKTTKEMVNK AGYYGRNPTW   540
WAERTLGQSW NGTLRECKTS SSYNGMLCPR HEPLTSFLIP VEATTKSLYF ADNIKLHNML   600
SVDLGYRYDD IKYQPEYIPG VTPKIADDMV KGLFIPLPEG EKVTVGTVVF TKPLTPEQIR   660
KNAEENIAYI AQEKRFKKHS YSLGATFDPL NFLRVQVKYS KGFRAPTSDE LYFTFKHPDF   720
TILPNPVLKP EEAKNQEIAL TVHDNWGFVS TSVFQTKYRH FIDLAYLGSR NLSNSVGGQA   780
QARDFQVYQN VNVDNAKVKG LEINARLNLG YFWHVLDGFN TSYKFTYQRG RLDGDRPMNA   840
IQPKASVFGL GYDHKENKFG ADLYITRVSE KKAKDTYNMF YKEQGYKDSA VRWRSDDYTL   900
VDAVGYIKPI KNLTLQFGVY NLTDRKYLTW ESARSIKPFG TSNLINQKTG AGINRFYSPG   960
RNFKLSAEIT F                                                       971

SEQ ID NO: 19           moltype = AA   length = 792
FEATURE                 Location/Qualifiers
source                  1..792
                        mol_type = protein
                        organism = Pasteurella multocida
SEQUENCE: 19
MEKIDMESAK NPLKKTTLAL LCCSTAFSLS AKTDTNADKN HFLTEIVVYA DQNKSMSSTQ    60
SVTQDDMKKS PVTNGNITDY LRSNPHVRYE NSDQNGLQRG EIKPENISIN GADYQQTTFF   120
VDNVNINNDM GFGSDLFDGT MATVPFANHS QGYFFDANLL SSIVVHDSNV SASLGGFAGG   180
AVVAKTKQYD GKDQLKFSYR TTDASWAKFK VEDKDLERFK NAIPEGSVAE FQPKYSKHFF   240
NITAEKGLSE NLGMVIGLSR RTSSIQQSRQ INPQGDRDKQ THTRRSDNAL LNFNLTPNDK   300
HRFELGPRYS NYRERKFFNT NIDSNVFDYH RAYGVTFSWI NALQSGILTT TLAYDNFDDT   360
RKSASTSMKT IIEDENDYTL GGMGNSQLNQ KNSHFSLEYA MNSFDLSHIN HSISLGSVFQ   420
HTQYRPHRES DAEAEIINRI DLENEKIEIK SSNLAKKGTV KTRYQNIALY VEDLMTWKNL   480
EFRAGLRLER DDYLKNTNLA PRTVFRYKPF EDTAFSVGWN RYYGRSFASM KLSEGIFKLD   540
GHDTFRYKDL SQFKTPYSDE LSFGVEQYVA NLAFHLKYIL RDNKQRIVLQ EEDVMLNGEK   600
KKLRYYQRGK DYKTNVLTFQ INTQAPWELG PTRWTSAVAF DWLDSKAIDH GRGYNGSTPV   660
ILDGKLMTYE QMLKKVNAYK ETWGLRLNLD MFVPRFDLSW ANTIYVKPPT TLTERVSSNT   720
PEVRSYDYG TYTQWDTSLR WQPTFAEKHR PYIKLDVLNV LNKTRKGAGP NGQDLGIYTP   780
GREFWLEGVY EF                                                      792

SEQ ID NO: 20           moltype = AA   length = 794
FEATURE                 Location/Qualifiers
source                  1..794
                        mol_type = protein
```

```
                        organism = Pasteurella multocida
SEQUENCE: 20
MESAKNPLKK TTLALLCCST AFSLSAKTDT DSDKNHFLTE IVVYADQNKS MSSTQSVTQD    60
DMKKSPVTNG NITDYLRSNP HVRYENSDQN GLQRGEIKPE NISINGADYQ QTTFFVDNVN   120
INNDMGFGSD LFDGTMATVP FANHSQGYFF DANLLSSIVV HDSNVSASLG GFAGGAVVAK   180
TKQYDGKDRL KFSYRTTDAS WAKFKVEDKD LERFKNAIPE GSVAEFQPKY SKHFFNITAE   240
KGLSENLGMV IGLSRRTSSI QQSRQINPQG DRDKQTHTRR SDNALLNFNL TPNDKHRFEL   300
GFRYSNYRER KFFNTNIDSN VFDYHRAYGV TFSWINALQS GILTTTLAYD NFDDTRKSAS   360
TYMKTTLTDD GEEYTEGGMG NSQLNQKNLH TSLEYAMNPF NLGSIEHSVS LGGIYQATKY   420
RFTRHSDAVG ELYTPNWLDN NSNDIYDELT LAQRNIAKKG TVKTRYQNIA LYVEDLMTWK   480
NLEFRAGLRL ERDDYLKNTN LAPRTVFRYK PFEDTAFSVG WNRYYGRSFA SMKLSEGIFK   540
LDGHDTFRYK DLSQFKTPYS DELSFGVEQY VANLAFHLKY ILHDNKQRIV LQEEDVMLNG   600
EKKKLRYYQR GKDYKTNVLT FQISTQAPWE FGPTRWTSAL AFDWLDSKAI DHGRGYNGST   660
PVILDGKLMT YEQMLKKVNA YKETWGLRLN LDMFVPKFDL SWANTIYVKP PTTLTERVSS   720
NTPEVYRSYD YGTYTQWDTS LRWQPTFAEK HRPYIKLDVL NVLNKTRKGA GPNGQDLGIY   780
TPGREFWLEV GYEF                                                    794

SEQ ID NO: 21           moltype = AA   length = 790
FEATURE                 Location/Qualifiers
source                  1..790
                        mol_type = protein
                        organism = Pasteurella multocida
SEQUENCE: 21
MEYAKNPLKK TTLALLCCST AFSLSAKTDT NADKNHFLTE IVVYADQNKS MSSTQSVTQE    60
DMKKSPVTNG NITDYLRSNP HVRYENSDQN GLQRGEIKPE NISINGADYQ QTTFFVDNVN   120
INNDMGFGSD LFDGTMATVP FANHSQGYFF DANLLSSIVV HDSNVSASLG GFAGGAVVAK   180
TKQYDGKDRL KFSYRTTDAS WAKFKVEDKD LERFKNAIPE GSVAEFQPKY SKRFFNITAE   240
KGLSENLGMV IGLSRRTSSI QQSRQINPQG DRDKQTHTRR SDNALLNFNL TPNDKHRFEL   300
GFRYSNYRER KFFNTNIDSN VFDYHRAYGV TFSWINALQS GILTTTLAYD NFDDTRKSAS   360
TYMKTTLTEE GEEYTEGGMG NSQLNQKNLH TSLEYAMNPF NLGSIEHSVS LGGIYQATKY   420
RFTRHSDAVG ELYTPDWLNG NTDKLILTQR NIAKKGTVKT RYQNIALYVE DLMTWKNLEF   480
RAGLRLERDD YLKNTNLAPR TVFRYKPFED TAFSVGWNRY YGRSFASMKL SEGIFKLDGH   540
DTFRYKDLSQ FKTPYSDELS FGVEQYVANL AFHLKYILRD NKQRIVLQEE DVMLNGERKK   600
LRYYQRGKDY KTNVLTFQIN TQAPWELGPT RWTSAVAFDW LDSKAIDHGR GYNGSTPVIL   660
DGKLMTYEQM LKKVNAYKET WGLRLNLDMF VPRFDLSWAN TIYVKPPTTL TERVSSNTPE   720
VYRSYDYGTY TQWDTSLRWQ PTFAEKHRPY IKLDVLNVLN KTRKGAGPNG QDLGIYTPGR   780
EFWLEVGYEF                                                         790

SEQ ID NO: 22           moltype = AA   length = 790
FEATURE                 Location/Qualifiers
source                  1..790
                        mol_type = protein
                        organism = Pasteurella multocida
SEQUENCE: 22
MESAKNPLKK TTLALLCCST AFSLSAKTDT NADKNHFLTE IVVYADQNKS MSSTQSVTQD    60
DMKKSPVTNG NITDYLRSNP HVRYENSDQN GLQRGEIKPE NISINGADYQ QTTFFVDNVN   120
INNDMGFGSD LFDGTMATVP FANHSQGYFF DANLLSSIVV HDSNVSASLG GFAGGAVVAK   180
TKQYDGKDRL KFSYRTTDAS WAKFKVEDKD LERFKNAIPE GSVAEFQPKY SKHFFNITAE   240
KGLSENLGMV IGLSRRTSSI QQSRQINPQG DRDKQTHTRR SDNALLNFNL TPNDKHRFEL   300
GFRYSNYRER KFFNTNIDSN VFDYHRAYGV TFSWINALQS GILTTTLAYD NFDDTRKSAS   360
TYMKTTLTEE GEEYTEGGMG NSQLNQKNLH TSLEYAMNPF NLGSIEHSVS LGGIYQATKY   420
RFTRHSDAVG ELYTPDWLNG NTDKLILTQR NIAKKGTVKT RYQNIALYVE DLMTWKNLEF   480
RAGLRLERDD YLKNTNLAPR TVFRYKPFED TAFSVGWNRY YGRSFASMKL SEGIFKLDGH   540
DTFRYKDLSQ FKTPYSDELS FGVEQYVANL AFHLKYILRD NKQRIVLQEE DVMLNGEKKK   600
LRYYQRGKDY KTNVLTFQIN TQAPWELGPT RWTSAVAFDW LDSKAIDHGR GYNGSTPVIL   660
DGKLMTYEQM LKKVNAYKET WGLRLNLDMF VPRFDLSWAN TIYVKPPTTL TEHVSSSTPE   720
VYRSYDYGTY TQWDTSLRWQ PTFAEKHRPY IKLDVLNVLN KTRKGAGPNG QDLGIYTPGR   780
EFWLEVGYEF                                                         790

SEQ ID NO: 23           moltype = AA   length = 730
FEATURE                 Location/Qualifiers
source                  1..730
                        mol_type = protein
                        organism = Pasteurella multocida
SEQUENCE: 23
MSFKHKTLAL FVAHACCTSV LAENAATTLE PIVVSDLSHT TLNLDQNKLE KESPKDLKAI    60
FATTPNINVI HTGHAQLGDI EIRGMGSSRE IFATGANRVT MELDGMDISP SFYFGHSSRH   120
GRQYFDPSDL KRVEVHKGPN SQGVAGHVRF QTKDPHDYLL PNQRTGAQLR AGYLGDSDAY   180
YVGITGAALL DEHSSALVSY TRRWFNEFNN KGGLDVTGSQ RTKSNPSSGY SNAVNSKLRY   240
SPNDRHKFTL NLQHYDLKRT AYLEDSLGTT TTRRGTKTVH HNTNIQKNQR HAIAFSHDMQ   300
QTNHSIFDHL HWQIALQQTK STSRNTGAVT STSGSPPPST PKFSQERSLD GFKTKTISLK   360
TEFNKSLGQH VVHELHYGLK LQYSQMQALR QTQSLNEQGS NTRTSAFFPT QQQWQSKLHL   420
SDRISFGKSG LSLTPSIHLT QIRIKPKTEN VSKKNREQLF TYKDTAIGYG LRVDYALNEA   480
NLLSLNYQHA TRLPGYGENN AQSYGHWPAK PNPHLQPETS DGIELSWRSA GAIGQQTTTL   540
FYNRYNDLIY LDTTACYADR TGQVQVPCDL ANEKGRSYSY GIEFDGKLNL DTIGFAQGTY   600
LNAGFAYSKG KTANKQPQGR LDPLTGFVGL GYQQPMDVWG IEGKLKFAAK KKTKDLPANQ   660
GFEGLPGYAV VDLTAYYNVT KQLYLGIGIY NVLDKKYARW AMARGDIKHG NYDKHTEAGR   720
HFGANIRYHF                                                         730
```

```
SEQ ID NO: 24           moltype = AA  length = 727
FEATURE                 Location/Qualifiers
source                  1..727
                        mol_type = protein
                        organism = Pasteurella multocida
SEQUENCE: 24
MSFKHKTLAL FVAHACCTSA LAENAATTLE PIVVSELSHT TLNLDQNKLE KESPKDLKAI    60
FTTTPNINVI HTGHAQLGDI EIRGMGSSRE IFATGANRVT MELDGMDISP SFYFGHSSRH   120
GRQYFDPSDL KRVEIHKGPN SQGVAGHVRF QTKDPRDYLL PNQRTGAQLR AGYLGDSDAY   180
YVGITGATLL DEHSSALVSY TRRWFNEFNN KGGLDVTGSQ RTKSNPSSGY SNAVNSKLRY   240
SPNDRHKFTL NLQHYDLKRT AYLEDSLGTT TTRRGTKTVH HNTNIQKNQR HAIAFSHDMQ   300
QTTAFFDHLH WQIALQQTKS TSRNTGTVTS TSAPPPPSTP KFSQERSFDG FKTKTISLKT   360
EFNKSLGQHV VHELHYGLKL QYSQMQALRQ TQSLNEQGSP TRTSAFFPTQ QQWQSKFHLS   420
DRISFGKSGL SLTPSIHLTQ IRIKPKTENV SKKNREQLFT YKDTAIGYGL RVDYALNEAN   480
LLSLNYQHAT RLPGYGENNA QSYGHWPAKP NPHLQPETSD GVELSWRSAG AIGQQTTTLF   540
YNRYNDLIYL DTTACYADRT GQVPCDLANE KGRSYSYGIE FDGKLNLDTI GFAQGTYLNA   600
GFAYSKGKTA NKQPQGRLDP LTGFVGLGYQ QPMDWGIEG KLKFAAKKKT KDLPANQGFE   660
GLPGYAVVDL TAYYNVTKQL YLGIGIYNVL DKKYARWAMA RGDIKHGNYD KHTEAGRHFG   720
ANIRYHF                                                            727

SEQ ID NO: 25           moltype = AA  length = 727
FEATURE                 Location/Qualifiers
source                  1..727
                        mol_type = protein
                        organism = Pasteurella multocida
SEQUENCE: 25
MSFKHKTLAL FVAHACCTSA LAENVATTLE PIVVSDLSHT TLNLDQNKLE KESPKDLKAI    60
FATTPNINVI HTGHAQLGDI EIRGMGSSRE IFATGANRVT MELDGMDISP SFYFGHSSRH   120
GRQYFDPSDL KRVEIHKGPN SQGVAGHVRF QTKDPRDYLL PNQRTGAQLR AGYLGDSDAY   180
YVGITGATLL DEHSSALVSY TRRWFNEFNN KGGLDVTGSQ RTKSNPSSGY SNAVNSKLRY   240
SPNDRHKFTL NLQHYDLKRT AYLEDSLGTT TTRRGTKTVH HNTNIQKNQR HAIAFSHDMQ   300
QTTAFFDHLH WQIALQQTKS TSRNTGAVTS TSASPPPSTP KFSQERSFDG FKTKTISLKT   360
EFNKSLGQHV VHELHYGLKL QYSQMQALRQ TQSLNEQGSN TRTSAFFPTQ QQWQSKLHLS   420
DRISFGKSGL SLTPSIHLTQ IRIKPKTENV SKKNREQLFT YKDTAIGYGL RVDYALNEAN   480
LLSLNYQHAT RLPGYGENNA QSYGHWPAKP NPHLQPETSD GIELSWRSAG AIGQQTTTLF   540
YNRYNDLIYL DTTACYADRT GQVPCDLANE KGRSYSYGIE FDGKLNLDTI GFAQGTYLNA   600
GFAYSKGKTA NKQPQGRLEP LTGFVGLGYQ QPMDWGIEG KLKFAAKKKT KDLPANQGFE   660
GLPGYAVVDL TAYYNVTKQL YLGIGIYNVL DKKYARWAMA RGDIKHGNYD KHTEAGRHFG   720
ANIRYHF                                                            727

SEQ ID NO: 26           moltype = AA  length = 727
FEATURE                 Location/Qualifiers
source                  1..727
                        mol_type = protein
                        organism = Pasteurella multocida
SEQUENCE: 26
MSFKHKTLAL FVAHACCTSA LAENAATTLE PIVVSDLSHT TLNLDQNKLE KESPKDLKAI    60
FATTPNINVI HTGHAQLGDI EIRGMGSSRE IFATGANRVT MELDGMDISP SFYFGHSSRH   120
GRQYFDPSDL KRVEIHKGPN SQGVAGHVRF QTKDPRDYLL PNQRTGAQLR AGYLGDSDAY   180
YVGITGATLL DEHSSALMSY TRRWFNEFNN KGGLDVTGSQ RTKSNPSSGY SNAVNSKLRY   240
SPNDRHKFTL NLQHYDLKRT AYLEDSLGTT TTRRGTKTVH HNTNIQKNQR HAIAFSHDMQ   300
QTTAFFDHLH WQIALQQTKS TSRNTGAVTN TSASPPPSTP KFSQERSLDG FKTKTISLKT   360
EFNKSIGQHV VHELHYGLKL QYSQMQALRQ TQSLNEQGSN TRTSAFFPTQ QQWQSKLHLS   420
DRISFGKSGL SLTPSIHLTQ IRIKPKTENV SKKNREQLFT YKDTAIGYGL RVDYALNEAN   480
LLSLNYQHAT RLPGYGENNA QSYGHWPAKP NPHLQPETSD GIELSWRSAG AIGQQTTTLF   540
YNRYNDLIYL DTTACYADRT GQVPCDLANE KGRSYSYGIE FDGKLNLDTI GFAQGTYLNA   600
GFAYSKGKTA NKQPQGRLDP LTGFVGLGYQ QPMDWGIEG KLKFAAKKKT KDLPANQGFE   660
GLPGYAVVDL TAYYNVTKQL YLGIGIYNVL DKKYARWAMA RGDIKHGNYD KHTEAGRHFG   720
ANIRYHF                                                            727

SEQ ID NO: 27           moltype = AA  length = 964
FEATURE                 Location/Qualifiers
source                  1..964
                        mol_type = protein
                        organism = Pasteurella multocida
SEQUENCE: 27
MRTTTIKFSA ITLALLSYCG VILADSHQEA TELDTITVSS QQDEMNIKEK KVGETVKTAS    60
QLKRQQVQDS RDLVRYETGV TVVEAGRFGS SGYAIRGVDE NRVAITVDGL HQAETLSSQG   120
FKELFEGYGN FNNTRNSVEI ETLKVAKIAK GADSVKVGSG SLGGAVLFET KDARDFLTEK   180
DWHIGYKAGY STADNQGLNA VTLAGRYQMF DALIMHSKRH GHELENYDYK NGRDIQGKER   240
EKADPYTITK ESTLVKFSFS PTENHRFTVA SDTYIQRSRG HDRSYSLQPQ SNYFTYDEKE   300
SRHANDLTKR KNVSFTYENY SVTPFWDTLK LSYSQQKIRT RARTEDYCDG NEKCDSYKNP   360
LGLQLKDGKI VDPEGNQITL KGTGFNTEIV DKNGNPFFPT SGTNNAAFSN NIQLGPKEFW   420
LDCSLFDCTQ PFTVYNYQNG QYTPKQVELS EEITVNGKLY KTAKEERGVR NYLILPNSKG   480
YLPYDYKERD LDSNTKQINL DLTKTFSTFN IENELLYGAI YSRTEKKMVN KAGYDGRNPT   540
WWADRILGKS TNCNYNGLKC PRHEPLTSFL IPVEATTKSL YFSDNIKLHN MLSVDLGYRY   600
DDIKYQPEYI PGVTPKIADD MVKGIFIPLP KGEKVTTPWG AEYTKPLTQE QIRKNAEENI   660
AYIAQEKRFK KHSYSLGATF DPLNFLRVQV KYSKGFRAPT SDELYFTKH PDFTILPNPV   720
LKPEEAKNQE IALTVHDNWG FVSTSVFQTK YRHFIDLAYL GSRNLSNSVG GQAQARDFQV   780
```

```
YQNVNVDNAK VKGLEINARL NLGYFWHVLD GFNTSYKFTY QRGRLDGDRP MNAIQPKASV  840
FGLGYDHKEN KFGADLYITR VSEKKAKDTY NMFYKEQGYK DSAIRWRSDD YTLVDAVGYI  900
KPIKNLTLQF GVYNLTDRKY LTWESARSIK PFGTSNLINQ KTGAGINRFY SPGRNFKFSA  960
EITF                                                               964

SEQ ID NO: 28           moltype = AA  length = 963
FEATURE                 Location/Qualifiers
source                  1..963
                        mol_type = protein
                        organism = Pasteurella multocida
SEQUENCE: 28
MRTTTIKFSA ITLALLSYCG AILADSHQEA TELDTITVSS QQDEMNIKEK KVGETVKTAS  60
QLKRQQVQDS RDLVRYETGV TVVEAGRFGS SGYAIRGVDE NRVAITVDGL HQAETLSSQG  120
FKELFEGYGN FNNTRNSVEI ETLKVAKIAK GADSVKVGSG SLGGAVLFET KDARDFLTEK  180
DWHIGYKAGY STADNQGLNA VTLAGRYQMF DALIMHSKRH GHELENYDYK NGRDIQGKER  240
EKADPYTITK ESTLVKFSFS PTENHRFTVA SDTYIQRSRG HDRSYSLQPQ SNYFTYDEKE  300
SRHANDLTKR KNVSFTYENY SVTPFWDTLK LSYSQQKIRT RARTEDYCDG NEKCDSYKNP  360
LGLQLKDGKI VDPAGNQITL KGTGFNTEIV DKDGKPFPTT SGTNNAAFSN NLQLSPTGFW  420
LDCTIFDCTK PFTVYNYKQN KYEPREVMLS EEITIDGKLY KTAKEESGVR NYLILPNSKG  480
YLPYDYKERD LDSNTKQINL DLTKTFSTFN IENELLYGAI YSRTEKKMVN KAGYDGRNPT  540
WWADRILGKS TNCNYNGLKC PRHEPLTSFL IPVEATTKSL YFSDNIKLHN MLSVDLGYRY  600
DDIKYQPEYI PGVTPKIADD MVKGIFIPLP KGEKIKIENY ETTKPLTPEQ IRKNAEEENIA  660
YIAQEKRFKK HSYSLGATFD PLNFLRVQVK YSKGFRAPTS DELYFTFKHP DFTILPNPVL  720
KPEEAKNQEI ALTVHDNWGF VSTSVFQTKY RHFIDLAYLG SRNLSNSVGG QAQARDFQVY  780
QNVNVDNAKV KGLEINARLN LGYFWHVLDG FNTSYKFTYQ RGRLDGDRPM NAIQPKASVF  840
GLGYDHKENK FGADLYITRV SEKKAKDTYN MFYKEQGYKD SAIRWRSDDY TLVDAVGYIK  900
PIKNLTLQFG VYNLTDRKYL TWESARSIKP FGTSNLINQK TGAGINRFYS PGRNFKFSAE  960
ITF                                                               963

SEQ ID NO: 29           moltype = AA  length = 963
FEATURE                 Location/Qualifiers
source                  1..963
                        mol_type = protein
                        organism = Pasteurella multocida
SEQUENCE: 29
MRTTTIKFSA ITLALLSYCG AILADSHQEA TELDTITVSS QQDEMNIKEK KVGETVKTAS  60
QLKRQQVQDS RDLVRYETGV TVVEAGRFGS SGYAIRGVDE NRVAITVDGL HQAETLSSQG  120
FKELFEGYGN FNNTRNSVEI ETLKVAKIAK GADSVKVGSG SLGGAVLFET KDARDFLTEK  180
DWHIGYKAGY STADNQGLNA VTLAGRYQMF DALIMHSKRH GHELENYDYK NGRDIQGKER  240
EKADPYTITK ESTLVKFSFS PTENHRFTVA SDTYIQRSRG HDRSYSLQPQ SNYFTYDEKE  300
SRHANDLTKR KNVSFTYENY SITPFWDTLK LSYSQQKIRT RARTEDYCDG NEKCDSYKNP  360
LGLQLKDGKI VDPAGNQITL KGTGFNTEIV DKDGKPFPTT SGTNNAAFSN NLQLSPTGFW  420
LDCTIFDCTK PFTVYNYKQN KYEPREVMLS EEITIDGKLY KTAKEESGVR NYLILPNSKG  480
YLPYDYKERD LDSNTKQINL DLTKTFSTFN IENELLYGAI YSRTEKKMVN KAGYDGRNPT  540
WWADRILGKS TNCNYNGLKC PRHEPLTSFL IPVEATTKSL YFSDNIKLHN MLSVDLGYRY  600
DDIKYQPEYI PGVTPKIADD MVKGIFIPLP KGEKIKIGNY ETTKPLTPEQ IRKNAEEENIA  660
YIAQEKRFKK HSYSLGATFD PLNFLRVQVK YSKGFRAPTS DELYFTFKHP DFTILPNPVL  720
KPEEAKNQEI ALTVHDNWGF VSTSVFQTKY RHFIDLAYLG SRNLSNSVGG KAQARDFQVY  780
QNVNVDNAKV KGVEINARLN LGYFWHVLDG FNTSYKFTYQ RGRLDGDRPM NAIQPKASVF  840
GLGYDHKENK FGADLYITRV SEKKAKDTYN MFYKEQGYKD SAIRWRSDDY TLIDAVGYIK  900
PIKNLTLQFG VYNLTDRKYL TWESARSIKP FGTSNLINQK TGAGINRFYS PGRNFKLSAE  960
ITF                                                               963

SEQ ID NO: 30           moltype = AA  length = 971
FEATURE                 Location/Qualifiers
source                  1..971
                        mol_type = protein
                        organism = Pasteurella multocida
SEQUENCE: 30
MRTTTIKFSA ITLALLSYCG VILADSHQEA TELDTITVSS QQDEMNIKEK KVGETVKTAS  60
QLKRQQVQDS RDLVRYETGV TVVEAGRFGS SGYAIRGVDE NRVAITVDGL HQAETLSSQG  120
FKELFEGYGN FNNTRNSVEI ETLKVAKIAK GADSVKVGSG SLGGAVLFET KDARDFLTEK  180
DWHIGYKAGY STADNQGLNA VTLAGRYQMF DALIMHSKRH GHELEIYDYK NGRDIQGKER  240
EKADPYTITK ESTLVKFSFS PTENHRFTVA SDTYLQHSRG HDLSYNLVAT TYIQLDEKES  300
RHANDLTKRK NVSFTYENYT VTPFWDTLKL SYSQQRITTR ARTEDYCDGN EKCDSYKNPL  360
GLQLKEGKIV DRNGDPVNLQ LVDGKHQVVD KAGKPFDVTS GTNYAAFSGK QLGPSYFWLE  420
CTVFDCSKPV TTYKYRYSTE TPVKEDIQLN KTMEVNGKTF ATYDMGRERR YIILPNSQGY  480
LPLDYKERDL NTKTKQINLD LTKAFTLFEI ENELSYGGVY AKTTNGVVNK AGYYGRNPTW  540
WAERTLGQSW NGTLRECKTS SSYNGMLCPR HEPLTSFLIP VEATTKSLYF ADNIKLHNML  600
SVDLGYRYDD IKYQPEYIPG VTPKIADDMV KGLFIPLPEG EKVTGTVVF TKPLTPEQIR  660
KNAEENIAYI AQGKRFKKHS YSLGTTFDPL NFLRVQVKYS KGFRAPTSDE LYFTFKHPDF  720
TILPNPVLKP EEAKNQEIAL TVHDNWGFVS TSVFQTKYRH FIDLAYLGSR NLSNSVGGQA  780
QARDFQVYQN VNVDNAKVKG LEINARLNLG YFWHVLDGFN TSYKFTYQRG RLDGDRPMNA  840
IQPKASVFGL GYDHKENKFG ADLYITRVSE KKAKDTYNMF YKEQGYKDSA IRWRSDDYTL  900
VDAVGYIKPI KNLTLQFGVY NLTERKYLTW ESARSIKPFG TSNLINQKTG AGINRFYSPG  960
RNFKFSAEIT F                                                      971

SEQ ID NO: 31           moltype = AA  length = 848
FEATURE                 Location/Qualifiers
```

```
source                  1..848
                        mol_type = protein
                        organism = Pasteurella multocida
SEQUENCE: 31
MQKSQPYPIH LGIFLMLGLP TWAFSQANLE KSTINKLETI LVNESEEKNK FDENLIKTYL    60
SSGSYSYLSQ SDISTFRGSS VGDFLSGVPG VIVGNKRNSG ALSVNIRGIA NENRVPVWID   120
KGLQSVPSYQ GYAGSSTRTY LDPDLISQVE IEKGPSLQMD ATGATGGVVR VETLRWQDII   180
PQGNKLGVRL KLGTMTNTVS PPPYYTRGGY QTKYISKCLS NHTGLCQTQT YAPNARYSSH   240
GFDLNAYNYS LAFANKWSNA DLVLAYAKRK QGNYFVGRHG QTPVIESIEF EEDSVEVKEP   300
RVHEDVEIGS LTFKENRSTL YRPGEEALNT SQDNTSYLAK INVYNDVHRL GLAYRHYHSR   360
FGEIMSSILN FRAYGALQGE GTEVKVDSYH ANYSYNPTTP YVNLSVNAYF TDSDSSNFTP   420
FIEEYGYSLS SRHAHFLVSK QKGLSIENTS IFQLNDKPFT LKYGLAHSYE RIYQPRNAQA   480
RVRAKGYPED AIGPLYIRDG KRKEWSAFVA ANYPITSWLK ADIGLRYLQS TIYDYIVRTE   540
RVNIGGALVP NPNGSGNIWV EKYKDVVHKQ APVKNKGMSP IVMFTFEPIN GVQIYTKYAE   600
ALRSPSLFQA TKGWSMSATE DNLEQLRPER AKNWEAGINL FYENLGGKDN ILGFKLAYFN   660
NRIKDYLTRS YSPKDKVTQT INIQSAQFKG IELSAYYDMG KFYAKLAGTY YTKTKFCLTA   720
EQAGKGEQCN SGYVYRSNLN NAVPPRLNLH ATLGTRLFEQ KLDIGARYSY YSKRLVPVLS   780
AERFVNTSSI EWAPYSLVDL YANYNVSNNL KLTMTMDNVF NRYYLDINNM GLNTAPGRTL   840
HLGLEYRF                                                          848

SEQ ID NO: 32           moltype = AA   length = 848
FEATURE                 Location/Qualifiers
source                  1..848
                        mol_type = protein
                        organism = Pasteurella multocida
SEQUENCE: 32
MQKQQPYPIH LGIFLMLGLP TWAFSQANLE KSTINKLETI LVNESEEKNK FDENLIKTYL    60
SSGSYSYLSQ SDISTFRGSS VGDFLSGVPG VIVGNKRNSG ALSVNIRGIA NENRVPVWID   120
KGLQSVPSYQ GYAGSSTRTY LDPDLISQVE IEKGPSLQMD ATGATGGVVR VETLRWQDII   180
PQGNKWGVRL KLGTMANTVS PPPYYTRGGY QTKYISKCLS NHTGLCQTQT YAPNARYSSH   240
GFDLNAYNYS LAFANKWQNA DLVLAYAKRK QGNYFVGRHG QTPVIESIEF EEDSVEVKEP   300
RVHEDVEIGS LTFKENRSTL YRPGEEALNT SQDNTSYLAK INVYNDVHRL GLAYRHYHSR   360
FGEIMSSILN FRAYGALQGE GTEVKVDSYH ANYSYNSTTP YVNLSVNAYF TDSDSSNFTP   420
FIEEYGYSLS SRHAHFLVSK QKGLSIENTS IFQLNDKPFT LKYGLAHSYE RIYQPRNAQA   480
RVRAKGYPED AIGPLYIRDG KRKEWSAFVA ANYPITSWLK ADIGLRYLQS TIYDYIVRTE   540
RVNIGGALVP NPNGSGNIWV EKYKDVVHKQ APVKNKGMSP IVMFTFEPIN GVQIYTKYAE   600
ALRSPSLFQA TKGWSMSATA DNLEQLRPER AKNWEAGINL FYENLGGKDN ILGFKLAYFN   660
NRIKDYLTRS YSPKDKVTQT INIQSAQFKG IELSAYYDMG KFYAKLAGTY YTKTKFCLTA   720
EQAGKGEQCN SGYVYRSNLN NAVPPRLNLH ATLGTRLFEQ KLDIGARYSY YSKRLVPVLS   780
AERFVNTSSI EWAPYSLVDL YANYNVSNNL KLTMTMDNVF NRYYLDINNT GLNTAPGRTL   840
HLGLEYRF                                                          848

SEQ ID NO: 33           moltype = AA   length = 848
FEATURE                 Location/Qualifiers
source                  1..848
                        mol_type = protein
                        organism = Pasteurella multocida
SEQUENCE: 33
MQKQQPYPIH LGIFLMLGLP TWAFSQANLE KSTINKLETI LVNESEEKNK FDENLIKTYL    60
SSGSYSYLSQ SDISTFRGSS VGDFLSGVPG VIVGNKRNSG ALSVNIRGIA NENRVPVWID   120
KGLQSVPSYQ GYAGSSTRTY LDPDLISQVE IEKGPSLQMD ATGATGGVVR VDTLRWQDII   180
PQGKNWGVRL KLGTMTNTVS PPPYYTRGGY QTKYISKCLS NDTGLCQTQT YAPNARYSSH   240
GFDLNAYNYS LAFANKWQNA DLVLAYAKRK QGNYFVGRHG QTPVIESIKF EEDSVEVKEP   300
RVHEDVEIGS LTFKENRSTL YRPGEEALNT SQDNTSYLAK INVYNDVHRL GLAYRHYHSR   360
FGEIMSSILN FRAYGALQGE GTEVKVDSYH ANYSYNPTTP YVNLNVNAYF TDSDSSNFTP   420
FIEEYGYSLS SRHAHFLVSK QKGLSIENTS IFQLNDKPFT LKYGLAHSYE RIYQPRNAQA   480
RVRAKGYPED AIGPLYIRDG KRKEWSAFVA ANYPINSWLK ADIGLRYLQS TIYDYIVRTE   540
RVNIGGALVP NPNGPGNIWV EKYKDVVHKQ APVKNKGMSP IVMLTFEPIN GVQIYTKYAE   600
ALRSPSLFQA TKGWSMSATA DNLEQLRPER AKNWEAGINL FYENLGGKDN ILGFKLAYFN   660
NRIKDYLTRS YSPKDKVTQT INIQSAQFKG IELSAYYDMG KFYTKLAGTY YTKTKFCLTA   720
EQAGKGEQCN SGYVYRSNLN NAVPPRLNLH ATLGTRLFEQ KLDIGARYSY YSKRLVPVLS   780
AERFVNTSSI EWAPYSLVDL YANYNVSNNL KLTMTMDNVF NRYYLDINNM GLNTAPGRTL   840
HLGLEYRF                                                          848

SEQ ID NO: 34           moltype = AA   length = 848
FEATURE                 Location/Qualifiers
source                  1..848
                        mol_type = protein
                        organism = Pasteurella multocida
SEQUENCE: 34
MQKQQPYPIH LGIFLMLGLP TWAFSQANLE KSTINKLETI LVNESEEKNK FDENLIKTYL    60
SSGSYSYLSQ SDISTFRGSS VGDFLSGVPG VIAGNKRNSG ALSVNIRGIA NENRVPVWID   120
KGLQSVPSYQ GYAGSSTRTY LDPDLISQVE IEKGPSLQMD ATGATGGVVR VETLRWQDII   180
PQGKNWGVRL KLGTMTNTVS PPPYYTRGGY QTKYISKCLS NDTGLCQTQT YAPNARYSSH   240
GFDLNAYNYS LAFANKWQNA DLVLAYAKRK QGNYFVGRHG QTPVIESIEF EEDSVEVKEP   300
RVHEEVEIGS LTFKENRSTL YRPGEEALNT SQDNTSYLAK INVYNDVHRL GLAYRHYHSR   360
FGEIMSSILN FRAYGALQGE GTEVKVDSYH ANYSYNPTTP YVNLNVNAYF TDSDSSNFTP   420
FIEEYGYSLS SRHAHFLVSK QKGLSIENTS IFQLNDKPFT LKYGLAHSYE RIYQPRNAQA   480
RVRAKGYPED AIGPLYIRDG KRKEWSAFVA ANYPITSWLK ADIGLRYLQS TIYDYIVRTE   540
```

-continued

```
RVNIGGALVP NPNGSGNIWV EKYKDVVHKQ APVKNKGMSP IVMLTFEPIN GVQIYTKYAE  600
ALRSPSLFQA TKGWSMSATA DNLEQLRPER AKNWEAGINL FYENLGGKDN ILGFKLAYFN  660
NRIKDYLTRS YSPKDKVTQT INIQSAQFKG IELSAYYDMG KFYTKLAGTY YTKTKFCLTA  720
EQAGKGEQCN SGYVYRSNLN NAVPPRLNLH ATLGTRLFEQ KLDIGARYSY YSKRLVPVLS  780
AERFVNTSSI EWAPYSLVDL YANYNVSNNL KLTMTMDNVF NRYYLDINNM GLNTAPGRTL  840
HLGLEYRF                                                           848

SEQ ID NO: 35          moltype = AA  length = 784
FEATURE                Location/Qualifiers
source                 1..784
                       mol_type = protein
                       organism = Pasteurella multocida
SEQUENCE: 35
MKYPLSYKNI ARSIPFLSFI AFPLYAQETT ELEQITVQES ATAEVNKTSP TVISKSATTI  60
QNKMIRDTRD LVRYTTDVGI SDNGRFLKGF AMRGVEDNRV GISIDGVSLP DSEENSLYAR  120
YGNFNNSRLS IDPELIQTID IVRGSDSFNA GSGSLGGGVN YNTLDPQHIV KAGNSVGALL  180
RGSYASKNRE WVRTLGIGYV GEKFDALLMY SQRTGHEFKS RGSGPEFRYS SSQHPDPVTQ  240
RFHNYLAKMN YQINDNQRIG LTLNGQTGGR YIDERSYTLM GSQWREADDQ NERLNANLYY  300
IYAPSTGWLA YSKFDLDYQK TDLAAVNYKG GRHFTTDAKE LNEIYDRRMK TVFTRGSVEL  360
NAQPVHFYGE HTLTIKGYVS QRDFKNINQD RIGIGTNYDT QYHYTIQYPI RTKQYGLSLK  420
DHVRWNDTFS SHLGLRYDHT KLKPKELNAP CSKACLEEGK PKPTRFSTVS TFAGLEAQLS  480
PSWMLGYNIS TGYRVPTASE MFFSFTNAYG TWKSNPSLKP EKSINHTLSL KGNSEKGLLD  540
LTLYQTNYRH FLFEQESLIQ RTEIRYGQPY TYQSQEQQMV NLDKAKIYGV ELKTHVNLDQ  600
MIAVIPQGFK FYAALGYSKG KLSNNASLLS IQPLKIILGL DYEATNGKWA IFNRLTYLGE  660
KRASDAKVYE IKRRCTEFVT ETDPWSGEQI THCKKRELYP DLSTYKYLNK SAFVFDTFGY  720
YKITDDITFR AGIYNLFNKK YHTWDALRGI NANSTLNSVD REGKGLQRFY APGRNYAASL  780
EIRF                                                               784

SEQ ID NO: 36          moltype = AA  length = 784
FEATURE                Location/Qualifiers
source                 1..784
                       mol_type = protein
                       organism = Pasteurella multocida
SEQUENCE: 36
MKYPLSYKNI ARSIPFLSFI AFPLYAQETT ELEQITVQES ATAEVNKTSP TVISKSATTI  60
QNEMIRDTRD LVRYTTDVGI SDNGRFLKGF AMRGVEDNRV GISIDDVSLP DSEENSLYAR  120
YGNFNNSRLS IDPELIQTID IVRGSDSFNA GSGSLGGGVN YNTLDPQHIV KAGNSVGALL  180
RGSYASKNRE WVRTLGIGYV GEKFDALLMY SQRTGHEFKS RGSGPEFRYS SSQHPDPVTQ  240
RFHNYLAKMN YQINDNQRIG LTLNGQTGGR YIDERSYTLM GSQWREADDQ NERLNANLYY  300
IYAPSTGWLA YSKFDLDYQK TDLAAVNYKG GRHFTTDAKE LNEIYDRRMK TVFTRGSVEL  360
NAQPVHFYGE HTLTIKGYVS QRDFKNINQD RIGIGTNYDT QYHYTIQYPI RTKQYGLSLK  420
DHVRWNDTFS SHLGLRYDHT KLKPKELNAP CSNACLEEGK PKPTRFSTVS TFAGLEAQLS  480
PSWMLGYNIS TGYRVPTASE MFFSFTNAYG TWKSNPSLKP EKSINHTLSL KGNSEKGLLD  540
LTLYQTNYRH FLFEQESLIQ RTEMRYGRPY TYQSQEQQMV NLDKAKIYGV ELKTHVNLDQ  600
MIAVIPQGFK FYAALGYSKG KLSNNASLLS IQPLKIILGL DYEATNGKWA IFNRLTYLGE  660
KRASDAKVYE IKRRCTEFVT ETDPWSGEQI TRCKKRELYP DLSTYKHLNK SAFVFDTFGY  720
YKITDDITFR AGIYNLFNKK YHTWDALRGI NANSTLNSVD REGKGLQRFY APGRNYAASL  780
EIRF                                                               784

SEQ ID NO: 37          moltype = AA  length = 784
FEATURE                Location/Qualifiers
source                 1..784
                       mol_type = protein
                       organism = Pasteurella multocida
SEQUENCE: 37
MKYPLSYKNI ARSIPFLSFI AFPLYAQETT ELEQITVQES ATAEVNKTSP TVISKSATTI  60
QNEMIRDTRD LVRYTTDVGI SDNGRFLKGF AMRGVEDNRV GISIDGVSLP DSEENSLYAR  120
YGNFNNSRLS IDPELIQTID IVRGSDSFNA GSGSLGGGVN YNTLDPQHIV KAGNSVGALL  180
RGSYASKNRE WVRTLGIGYV GEKFDALLMY SQRTGHEFKS RGSGPEFRYS SSQHPDPVTQ  240
RFHNYLAKMN YQINDKQRIG LTLNGQTGGR YIDERSYTLM GSQWREADDQ NERLNANLYY  300
IYAPSTGWLA YSKFDLDYQK TDLAAVNYKG GRHFTTDAKE LNEIYDRRMK TVFTRGSVEL  360
NAQPVHFYGE HTLTIKGYVS QRDFKNINQD RIGIGTNYDT QYHYTIQYPI RTKQYGLSLK  420
DHVRWNDTFS SHLGLRYDHT KLKPKELNAP CSKACLEEGK PKPTRFSTVS TFAGFEAQLS  480
PSWMLGYNIS TGYRVPTASE MFFSFTNAYG TWKSNPSLKP EKSINHTLSL KGNSEKGLLD  540
LTLYQTNYRH FLFEQESLIQ RTEMRYGRPY TYQSQEQQMV NLDKAKIYGV ELKTHVNLDQ  600
MIAVIPQGFK FYAALGYSKG KLSNNASLLS IQPLKIILGL DYEATNGKWA IFNRLTYLGE  660
KRASDAKVYE IKRRCTEFVT ETDPWSGEQI TRCKKRELYP DLSTYKHLNK SAFVFDTFGY  720
YKITDDITFR AGIYNLFNKK YHTWDALRGI NANSTLNSVD REGKGLQRFY APGRNYAASL  780
EIRF                                                               784

SEQ ID NO: 38          moltype = AA  length = 784
FEATURE                Location/Qualifiers
source                 1..784
                       mol_type = protein
                       organism = Pasteurella multocida
SEQUENCE: 38
MKYPLSYKNI ARSIPFLSFI AFPLYAQETT ELEQITVQES ATAEVNKTSP TVISKSATTI  60
QNEMIRDTRD LVRYTTDVGI SDNGRFLKGF AMRGVEDNRV GISIDGVSLP DSEENSLYAR  120
YGNFNNSRLS IDPELIQTID IVRGSDSFNA GSGSLGGGVN YNTLDPQHIV KAGNSVGALL  180
```

```
RGSYASKNRE WVRTLGIGYV GEKFDALLMY SQRTGHEFKS RGSGPEFRYS SSQHPDPVTQ    240
RFHNYLAKMN YQINDNQRIG LTLNGQTGGR YIDERSYTLM GSQWREADDQ NERLNANLYY    300
IYAPSTGWLA YSKFDLDYQK TDLAAVNYKG GRHFTTDAKE LNEIYDRRMK TVFTRGSVEL    360
NAQPVHFYGE HTLTIKGYVS QRDFKNINQD RIGIGTNYDT QYHYTIQYPI RTKQYGLSLK    420
DHVRWNDTFS SHLGLRYDHT KLKPKELNAP CSKACLEEGK PKPTRFSTVS TFAGLEAQLS    480
PSWMLGYNIS TGYRVPTASE MFFSFTNAYG TWKSNPSLKP EKSINHTLSL KGNSEKGLLD    540
LTLYQTNYRH FLFEQESLIQ RTEMRYGRPY TYQSQEQQMV NLDKAKIYGV ELKTHVNLDQ    600
MIAVIPQGFK FYAALGYSKG KLSNNASLLS IQPLKIILGL DYEATNGKWA IFNRLTYLGE    660
KRASDAKVYE IKRRCTEFVT ETDPWSGEQI TRCKKRELYP DLSTYKHLNK SAFVFDTFGY    720
YKITDDITFR AGIYNLFNKK YHTWDALRGI NANSTLNSVD REGKGLQRFY APGRNYAASL    780
EIRF                                                                 784

SEQ ID NO: 39          moltype = AA   length = 745
FEATURE                Location/Qualifiers
source                 1..745
                       mol_type = protein
                       organism = Haemophilus influenzae
SEQUENCE: 39
MNIIINKRIF LLVTFVGIQL NVTAKQNSSN SNREELLPII VNTDEDSNKL PGRSVLKQKN     60
IEQQQADNAA NLINILPGVN MAGGFRPGGQ TLNINGMGDA EDVRVQLDGA TKSFEKYQQG    120
SIFIEPELLR KVTVDKGNYS PQYGNGGFAG TVKFETRDAR DFLKENQKIG GLLKYGNNSN    180
NNQKTYSTAL VLQNEQKNID LLLFGSVRNA GDYKRPDNSK ILFSKNNQKT GLIKVNWQIT    240
PEHLLTLSSV YGIHKGWEPW AAKRDVTSRP TETEIKRYGI DVAWKRKLVY RDQKDESYSL    300
KYRYLPENNK WINLSVQLSY SKTEQNDTRH EKVTSSFLGT LGNKSWITYS DLTFDISNTS    360
TLNIGRAEHE LLFGLQWLKN TRNTLMYHKG KMNDKTYNYG YFQPYYMPSG RQYTQAFYLQ    420
DQIKWKNIIF STGARYDHIN NIGQKNLAPQ YNDISAGHNY SQKNYNGWSY YLGLKYDVNH    480
YLSLFTNFSR TWRAPVIDEQ YETQYSKASV PATSLNLEKE MISQTRGGGI VTLNNLFQED    540
DTFQFRATYF YHRGKNEIFK TRGVNCVGNA LDVDNKICPK IISNYRNLPG YVIQGAELEA    600
YYQSTYLFGE LTYSYVKGKR DTSPRNPWGK TSTWIAEIPP RKATATLGFN VPKYYLTVGW    660
RAEFVRRQDR SPSSRDPKAS YYLSLPASRG YSLHNLFLSW TPEKIKGMNI KITVDNLFNR    720
AYNPYLGELA SGTGRNIKFS LSQKF                                          745

SEQ ID NO: 40          moltype = AA   length = 742
FEATURE                Location/Qualifiers
source                 1..742
                       mol_type = protein
                       organism = Pasteurella multocida
SEQUENCE: 40
MDKNLMKGCV FLLIVGCGIQ IGLASNPNPP DVDELLPIIV NADEDNKLPG RSVLKQKNID     60
QQQADNAADL INILPGVNMA GGFRPGGQTL NINGMGDAED VRVQLDGATK SFEKYQQGSI    120
FIEPELLRKV TVDKGNYSPQ YGNGSFAGTV KFETKDATDF LKENQKIGGL FKYGNNSNNN    180
QKTYSTALVL QNEQKNIDLL LFGSVRNASN YTRPDKSKIL FSKNNQKSGL IKVNWQITPE    240
HLLTLSSVYG IHKGWEPWAA KRDVMSRPTE KEIKRYGIDV AWKRKLVYRD QKDESYSLKY    300
RYLPENNKWI NLSVQLSYSK TEQNDTRHEK VTSSFLGTLG NKSWITYSDL TFDISNTSTL    360
NIGRAEHELL FGLQWLKNKR NTLMYHKEGV KKADYNYGYF QPYYMPSGRQ YTQAFYLQDQ    420
IKWQNFLFTG GIRYDHINNI GQKNLAPRYN DISAGHDYSQ KNYNGWSYYL GLKYDVNHYL    480
SLFTNFSKTW RAPVIDEQYE TQYSQASVSA TSLNLEKEMI NQTRVGGIIT LNHLFQENDA    540
FQFRTTYFYN RGKNEIFKTR GVNCVENALD VDNSVCPKII SNYRNLPGYV IQGAELEAYY    600
QSSYLFGGLT YSYVKGKRDT SPRNPWSKTS TWIAETPPRK ATATLGFNIP EYYFTAGWRA    660
EFVRRQDRSP LSNDSKASYW ALPSSKGYSL HSVFFSWSPT KIKGMNFKVT VDNLFNRPYY    720
PYLGELASGT GRNVKFSLTQ QF                                             742

SEQ ID NO: 41          moltype = AA   length = 742
FEATURE                Location/Qualifiers
source                 1..742
                       mol_type = protein
                       organism = Pasteurella multocida
SEQUENCE: 41
MDKNLMKGCV FLSIVGCGIQ IGLASNPNPP DVDELLPIIV NADEDNKLPG RSVLKQKNID     60
QQQADNAADL INILPGVNMA GGFRPGGQTL NINGMGDAED VRVQLDGATK SFEKYQQGSI    120
FIEPELLRKV TVDKGNYSPQ YGNGGFAGTV KFETKDATDF LKENQKIGGL FKYGNNSNNN    180
QKTYSTALVL QNEQKNIDLL LFGSVRNASN YTRPDKSKIL FSKNNQKSGL IKVNWQITPE    240
HLLTLSSVYG IHKGWEPWAA KRDVMSRPTE TEIKRYGIDV AWKRKLVYRD QKDESYSLKY    300
RYLPENNKWI NLSVQLSYSK TEQNDTRHEK VTSSFLGTLG NKSWITYSDL TFDISNTSTL    360
NIGRAEHELL FGLQWLKNKR NTLMYHKEGV KKADYNYGYF QPYYMPSGRQ YTHAFYLQDQ    420
IKWQNFLFTG GIRYDHINNI GQKNLAPRYN DISAGHDYSQ KNYNGWSYYL GLKYDVNHYL    480
SLFTNFSKTW RAPVIDEQYE TQYSQASVSA TSLNLEKEMI NQTRVGGIIT LNHLFQENDA    540
FQFRTTYFYN RGKNEIFKTR GVNCVENALD VDNSVCPKII SNYRNLPGYV IQGAELEAYY    600
QSSYLFGGLT YSYVKGKRDT SPRNPWSKTS TWIAETPPRK ATATLGFNIP EYYFTAGWRA    660
EFVRRQDRSP LSNDSKASYW ALPSSKGYSL HSVFFSWSPT KIKGMNFKVT VDNLFNRPYY    720
PYLGELASGT GRNVKFSLTQ QF                                             742

SEQ ID NO: 42          moltype = AA   length = 742
FEATURE                Location/Qualifiers
source                 1..742
                       mol_type = protein
                       organism = Pasteurella multocida
SEQUENCE: 42
MDKNLMKGCV FLSIVGCGIQ IGLASNPNPP DVDELLPIIV NADEDNKLPG RSVLKQKNID     60
```

-continued

```
QQQADNAADL INILPGVNMA GGFRPGGQTL NINGMGDAED VRVQLDGATK SFEKYQQGSI  120
FIEPELLRKV TVDKGNYSPQ YGNGGFAGTV KFETKDATDF LKENQKIGGL FKYGNNSNNN  180
QKTYSTALVL QNEQKNIDLL LFGSVRNASN YTRPDKSKIL FSKNNQKSGL IKVNWQITPE  240
HLLTLSSVYG IHKGWEPWAA KRDVMSRPTE TEIKHYGIDV AWKRKLVYRD QKDESYSLKY  300
RYLPENNKWI NLSVQLSYSK TEQNDTRHEK VTSSFLGTLG NKSWITYSDL TFDISNTSTL  360
NIGRAEHELL FGLQWLKNKR NTLMYHKGGV KKADYNYGYF QPYYMPSGRQ YTQAFYLQDQ  420
IKWQNFLFTG GIRYDHINNI GQKNLAPRYN DISAGHDYSQ KNYNGWSYYL GLKYDVNHYL  480
SLFTNFSKTW RAPVIDEQYE TQYSRASVSA TSLNLEKEMI NQTRVGGIIT LNHLFQENDA  540
FQFRTTYFYN RGKNEIFKTR GVNCVENALD VDNSVCPKII SNYRNLPGYV IQGAELEAYY  600
QSSYLFGGLT YSYVKGKRDT SPRNPWSKTS TWIAETPPRK ATATLGFNIP EYYFTAGWRA  660
EFVRKQDRSP LSNDSKASYW ALPSSKGYSL HSVFFSWSPT KIKGMNFKVT VDNLFNRPYY  720
PYLGELASGT GRNVKFSLTQ QF                                            742

SEQ ID NO: 43          moltype = DNA  length = 2418
FEATURE                Location/Qualifiers
source                 1..2418
                       mol_type = genomic DNA
                       organism = Pasteurella multocida
SEQUENCE: 43
atgatttcaa gaggttgtaa agtaaataaa ttttttgctg ttttgatgat gtgttgcatt  60
ccgcaagtag tttgggcaaa tacagaaaag aagcaaattg ttttttaga tgaaattagt  120
gtggagtcga aaggtgctgc ttttcgtagc gatccccttt ccggcttacc aaaacaaaat  180
gacattttag tcagtaagca aaaattaaaa acaggatcca gtacattagg taatgcgtta  240
gcgggtgaac tcagtgtaca tagtaatcaa tttggtggtg gatccagtgc acctgtcgtt  300
cgaggacagg aaggcgtgcg tttaaaaatc ttacaaaatg gttctgatgt cattgatatg  360
tctcaacttt ctcctgacca tgcgattggt gtcgatacgt tattggcaga gcaagtcgaa  420
attgtacgtg gtgcctcaac attgttatat gccaatgcgt cacctgctgg tgtgattaat  480
gtagtagata aacgcattcc aacacagctt cctcaaaagg gctatgaagt ggatttcaac  540
acgcgttata acacgaatag tcatgaaaaa ttggtaacgg ctgcactgac tttcgggtta  600
ggtaagcaca ttgctttacg ggtagaagaa ctgttacgtg gctcaaataa ttaccatgtg  660
ccagcattta agctagacaa aacattaaat tatgtccccg atactcaaaa taaaacgaag  720
tcaggtaact atggtgtggc ttttatcggt gagcgaggtt atgtcggttt tgcctacaat  780
cttcgtcgtg agaaatatgg gttaccggga cataaccata agctagatag ttgtgctgcg  840
catatttggg gtggcaatgt acgtaatgac tattatttag ggctttatcc tcatttaatg  900
catgatacgg atctagtaaa tacgcatttc cattgtggat caaatcatga catggatgga  960
aaacacagtc atgatcatcc gtacggtcac gatcatgacc attctattgc cggtccattg  1020
attgattctt atgctaaacg ttatgacata cgtgctgaag tcaaacagcc gatgaaagcg  1080
attgagaaaa tcaaactcag ttattcggaa acccgttata aacacgatga aaaagatggc  1140
aatatcgccg tgaatttatt taaaaataac ggatataacc tgcgcgtaga aattttccat  1200
acgcccatag cggggttgag tggcgttata ggggcgcagt atcaaacaca aaccagcagt  1260
gcgaatattc cgcgtattgc accatgctca aataatgcaa gcgatccttg tcataagaaa  1320
aagcaacgcg atccgtccaa aatcactaag ggtgatcgta agtcatgggc attgattgaa  1380
aatactcaat cacaaatgag tttttttgct atagaacaat tgcgttggca agatttttta  1440
tttgaaattg gtgtacgtac ggaaaaacaa cgcattgata ttgaatatga tcgcgcttgg  1500
ctgtttaaag taaagcgaaa gctagaaggc tgtgatccga attcgttctt ttatagccca  1560
tcaggatgtc gtcaaggcag ttatccagca cctgattttg cctcttatca tgatcgcgcg  1620
acctcttatt ctggtgctat cagttggaat atgacgcctg actacaccct ttctttgact  1680
tactcacata acgaacgtca cccaacaccg atggaattgt attaccacgg caaacattta  1740
gcgacggtgt catttgaaca tggcaatcgt aatctgaaaa aagaagtttc tgataactgg  1800
gaagtcggtc ttgcgtatct tggtgacaag ctaagttata aagtgaatgt atattacaat  1860
gattttaaaa atcggatttt taatcaaaca ttgaacaaat ccggtaattt atctttgaat  1920
cgttataatc aatccaaagc gaaatattat ggtgtggaag ggcgtattga ctatgcgttg  1980
acacctgaac tgcacatggg actttttggt gattatgtgc gtggaaaact gtatgattta  2040
ccgccaacgt accgtgtcga tcatgtggcg aatagcttag aacccgttcc tcaacctgat  2100
caagacgcac cacgtgtccc gccaatgcgt ttaggctttc gtgtgaatat ggagatgact  2160
gagagtttaa caagttcact cgaatacact tacgtttatc aacaaaagaa agtagcgccg  2220
ttagaaaatc aaacggctgc atatagttta ttaaatatcg gagtggatta ttcacgccaa  2280
atagctgggg taaattatca attatttgtt caagcaaata atgtgttaaa ccgtaaagtt  2340
tattctcata cttctttttt accctttgta ccgcagatgg ggcgtaatgt gactttagga  2400
ttaaacatcc atttctaa                                                 2418

SEQ ID NO: 44          moltype = AA  length = 805
FEATURE                Location/Qualifiers
source                 1..805
                       mol_type = protein
                       organism = Pasteurella multocida
SEQUENCE: 44
MISRGCKVNK FFAVLMMCCI PQVVWANTEK KQIVFLDEIS VESKGAAFRS DPLSGLPKQN  60
DILVSKQKLK TGSSTLGNAL AGELSVHSNQ FGGGSSAPVV RGQEGVRLKI LQNGSDVIDM  120
SQLSPDHAIG VDTLLAEQVE IVRGASTLLY ANASPAGVIN VVDKRIPTQL PQKGYEVDFN  180
TRYNTNSHEK LVTAALTFGL GKHIALRVEE LLRGSNNYHV PAFKLDKTLN YVPDTQNKTK  240
SGNYGVAFIG ERGYVGFAYN LRREKYGLPG HNHKLDSCAA HIWGGNVRND YYLGLYPHLM  300
HDTDLVNTHF HCGSNHDMDG KHSHDHPYGH DHDHSIAGPL IDSYAKRYDI RAEVKQPMKA  360
IEKIKLSYSE TRYKHDEKDG NIAVNLFKNN GYNLRVEIFH TPIAGLSGVI GAQYQTQTSS  420
ANIPRIAPCS NNASDPCHKK KQRDPSKITK GDRKSWALIE NTQSQMSFFA IEQLRWQDFL  480
FEIGVRTEKQ RIDIEYDRAW LFKVKRKLEG CDPNSFFYSP SGCRQGSYPA PDFASYHDRA  540
TSYSGAISWN MTPDYTLSLT YSHNERHPTP MELYYHGKHL ATVSFEHGNR NLKKEVSDNW  600
EVGLAYLGDK LSYKVNVYYN DFKNRIFNQT LNKSGNLSLN RYNQSKAKYY GVEGRIDYAL  660
TPELHMGLFG DYVRGKLYDL PPTYRVDHVA NSLEPVPQPD QDAPRVPPMR LGFRVNMEMT  720
```

```
ESLTSSLEYT YVYQQKKVAP LENQTAAYSL LNIGVDYSRQ IAGVNYQLFV QANNVLNRKV    780
YSHTSFLPFV PQMGRNVTLG LNIHF                                         805

SEQ ID NO: 45           moltype = AA  length = 87
FEATURE                 Location/Qualifiers
source                  1..87
                        mol_type = protein
                        organism = Mannheimia haemolytica
SEQUENCE: 45
SKRRDNYGLP GHNHKFDFCT GHIYGNKRDK YAYTYLYPHL IGEENIGSNP HFHCGTNHAE    60
DGTHSHDNPF GHAHDHTHKG PWVDLES                                       87

SEQ ID NO: 46           moltype = AA  length = 790
FEATURE                 Location/Qualifiers
source                  1..790
                        mol_type = protein
                        organism = Bibersteinia trehalosi
SEQUENCE: 46
MFNKKLLAVL ISAQFSPLVW ANNNDVAVLD EVSVVGSTPS ISQGSEVTLL KVSDKIIAGK    60
EFKKRSATLG NALAAELGVH SNPFGGGASK PIIRGQEGAR IRILQNGSDV IDMSNLSPDH   120
AVVADSLLAK QVEILRGSST LLYASSSPAG IVNVVDKRIP TEIPEKGYEV ELNSRFDTAA   180
KEKVGALGAT FGIGKHIAVR AEGLTRHSDN YRVPGINLGE RLNYVPDTYN KSKVGTLGLS   240
FVGEQGYIGA SYSKRRDNYG LPGHNHKFDF CTGHIYGNKR DKYAYTYLYP HLIGEENIGS   300
NPHFHCGTNH AEDGTHSHDN PFGHDHDHTH PGPWVDLESK RFDVKAELRQ PFKGIDKIKV   360
SYADADYYHD EKDAGVLATR YHKQLKKDQD YGKPVNIFKN RGKNARLEIY HAPLDGLTGV   420
WGVQYQTQKS SMHAPKDREV KFPLVENTNK QMSLFGIEQY MWDNFALEFA GRVEKQKIEI   480
EYDRNEIKRL QDHYRISGGK QVEPDLSPYN QNAYAYSGTL NWFFHPDYQL SFTASHNERF   540
PTPMELYYHG QHIATNSFEY GNKDLKKEQS NNVELGLGYQ TERVGYKVNV YYNHFKNYIY   600
NENLFRENQL FMRRYNQAKA RFYGIEAEAS YRFNNKYQAT IFGDMVRGWL TNLPPLTVNS   660
DYSVFKDYLP KDAKPGEDYL IYRADQNTPR TPPVRLGFRF NAEFTPNWSG DLELIRTFTQ   720
RRTSQLEYIT EGNTMLNIGV AYSNKWKDLD YKISLNGTNL LNQPVYIHTS YHQFVPQMGR   780
NFILGMEMKF                                                          790

SEQ ID NO: 47           moltype = AA  length = 782
FEATURE                 Location/Qualifiers
source                  1..782
                        mol_type = protein
                        organism = Actinobacillus pleuropneumoniae
SEQUENCE: 47
MLISAQFSPL VWANNNDVAV LDEVSVVGST PSISQGSEVT LLKVSDKIIA GKEFKKRSAT    60
LGNALAAELG VHSNPFGGGA SKPIIRGQEG ARIRILQNGS DVIDMSNLSP DHAVVADSLL   120
AKQVEILRGS STLLYASSSP AGIVNVVDKR IPTEIPEKGY EVELNSRFDT AAKEKVGALG   180
ATFGIGKHIA VRAEGLTRHS DNYRVPGINL GERLNYVPDT YNKSKVGTLG LSFVGEQGYI   240
GASYSKRRDN YGLPGHNHKF DFCIGHIYGN KQGKYAYTYL YPHLIGEENI GSNPHFHCGT   300
DHAEDGTHSH DNPFGHDHDH THPGPWVDLE SKRFDVKAEL RQPFKGIDKI KVSYADADYY   360
HDEKDAGVLA TRYHKQLKKD QDYGKPVNIF KNRGKNARLE IYHAPLGGLT GVWGVQYQTQ   420
KSSMHAPKDR EVKFPLVENT NKQMSLFGIE QYMWDNFALE FAGRVEKQKI EIEYDRNEIK   480
RLQDHYRISG GKQVEPDLSP YNQNAYAYSS TLNWFFHPDY QLSFTASHNE RFPTPMELYY   540
HGQHIATNSF EYGNKDLKKE QSNNVELGLG YQTERVGYKV NVYYNHFKNY IYNENLFREN   600
QLFMRRYNQA KARFYGIEAE ASYRFNNKYQ ATIFGDMVRG WLTNLPPLTV NSDYSVFKDY   660
LPKDAKPGED YLIYRADQNT PRTPPVRLGF RFNAEFTPNW SGDLELIRTF TQRRTSQLEY   720
ITEGNTMLNI GVAYSNKWKD LDYKISLNGT NLLNQPVYIH TSYHQFVPQT GRNFILVVNV   780
KF                                                                  782

SEQ ID NO: 48           moltype = AA  length = 790
FEATURE                 Location/Qualifiers
source                  1..790
                        mol_type = protein
                        organism = Mannheimia granulomatis
SEQUENCE: 48
MTNKTILALL ISAHLSSLAL AQTKEDIAVL EEVSVIGNSD TPVVAQGSEV TILKVSDKII    60
DGKEFKKRSA TLGNALAAEL GVHSNPFGGG ASKPIIRGQE GARIKILQNG AEVVDMSSLS   120
PDHAVVADSL LASKVEVLRG SSTLLYTSSS PAGVVNVVDK RIPTSIPEKG YEVELNSRFD   180
TVSKERLGVI GATVGLGQHV ALRVEGLNRH SDNYRVKSLQ LGESLNYVPD TYNRSRVGTM   240
GISFIGERGY IGAAYSHRKD TYGLPGHNHK FDFCTGHIYG VDRDKHAHTY LYPHLLTNEL   300
ISENPHFHCG SDHGLDHNHS HDNPYGHKHD HTHKGPWVDL RSKRLDLKME LKQPFSGIEK   360
LRLSHTDVNY YHDEKDAGVL LTFLHKQLKK DKDYGKPVNI YKNRGKNSRL EFYHTPVGGL   420
TGVWGLQYQT QKSSMNAPKD REVRFPLIEN NNKQLSLFGI EQYMWDNFAL ELAGRIEKQK   480
IEIDYDLNEI KRLQDFYRIS GGAQVEPDLS PYNKTAYAYS GTLNWFFHPN YQLSFTASHN   540
ERHPTPMELY YHGQHLATSS FEYGNKDLKK EQSNNVELGL GYQGEKFGYK TTVYYNHFKN   600
YIFNENLYRE NQLFMRRYSQ AKARFYGLEA EMSYRFNDKY QATLFGDMVR GWLTDLPPVK   660
VGGIHKEHLP KDAKPGETYL LYRADMNTPR TPPVRLGLRL NAQFNENWAG EAEFYRMFSQ   720
RRLSQLEYPT NGHSMLNLGL SYSNKFKNAE YKISLNGTNL LNQAVYIHTS YHQFVSQPGR   780
NFILGLEMKF                                                          790

SEQ ID NO: 49           moltype = AA  length = 790
FEATURE                 Location/Qualifiers
source                  1..790
                        mol_type = protein
```

```
                          organism = Mannheimia sp.
SEQUENCE: 49
MTNKTLLAVL ISAHLSTLAL AQTNEDVAVL DEVSVIGNTA TPVIAQGSEV TLLKVSDKII      60
EGKEFKKRSA TLGNALSAEL GVHSNPFGGG ASKPIIRGQE GARIKILQNG SDVVDMSSLS     120
PDHAVVADSL LASQVEVLRG SSTLLYTSSS PAGVVNVVDK RIPTIVPEKG YEVELNSRFD     180
TASKERLGVL GATLGLGQHV ALRVEGLARH SDNYRVKSLQ LGERLNYVPD TYNRSRVGTV     240
GLSFVGERGY IGAAYNERTD TYGLPGHNHK FDECIGHIYN EVRDKYAYTY KYPHLLDEDL     300
ISHGPHFHCG TDHEMDAGHS HDNPYGHTHD HTHKGPWVDL KSKRIDVKGE LLKPFRGLDK     360
IRASYTDVNY YHDEKDAGSV STFVNKQLKK DQNYGKPVNI YKNRGKNSRL EFYHSPIGGL     420
TGVWGVQYQT QKSSMNAPND REVRFPLVEN NNKQLSLFAI EQYMWDNFAL ELAGRIEKQK     480
IEIDYDLEEI RRLQKFYSES GGRQVEPDLS PYDKTAYAYS GTFNWFFHPD YQLSFTVSHN     540
ERHPTPMELY YHGPHLATSS FEYGNKDLKK EQSNNVELGL SYQGEKFGYK TTVYYNHFKN     600
YIFNENLYRE NQLFMRRYSQ AKARFYGLEA EMSYRFNEQY QATIFGDMVR GWLTDLPPVK     660
VGGIHKHHLP KDAKPGETYL LYRADMNTPR TPPLRLGLRV NAQFNENWAG EAEFYRMFSQ     720
RRLSQLEYPT KGHSMLNLGL SYSNKFKNAE YKISLNGTNL LNQPIYIHTS YHPFVSQPGR     780
NFILGVEVKF                                                           790

SEQ ID NO: 50           moltype = AA  length = 817
FEATURE                 Location/Qualifiers
source                  1..817
                        mol_type = protein
                        organism = Haemophilus parasuis
SEQUENCE: 50
MINNRTTEQQ NNRTTEQQNN RTTAFSLAFS LLLCCLGINA EQLELDEISV MGKVPEGNSI      60
SFLKVSDAII DGEKFKNRSA TLGNALSSEL GVHSTPFGGG ASAPIIRGQE GVRVKILQNN     120
ADVVDMSNIS PDHAITADTL LANQVEILRG ASTLLYASSS PAGIVNIVDQ RIPNKMPKKG     180
YEVTLSSRFD TASKEKVYAL GTTIGIGKHL ALRLEGLDRQ SQNYKVPQIK LGETLNYVPD     240
TYHQSKVGTI GLSFIGEKGY LGASYNQRKD RYGLPGHNHK FDTCIAHIYD MRLQGKHSYT     300
NLYPHLMSDE MVTENPHFHC GTDYDLDPSH SHDHPYGHDH DHTHIGPWVD LHSKRIDIKG     360
EIKQPLPMLD KIQLSYAQTD YYHDEKDAGK SGDTINPNRV DKSKDFGKPV NIFKNQGKNA     420
RLEFFHTPIG GLTGMFGVQY QTLQSSANTP SNREVQWPLV DNRNKQISLF ALEQYAWDNF     480
AIELGLRTEK QNIHIDYDLA KIQKQQKFNE RTYGKQVDPD LSDYDEKAIS YTGAFNWFFH     540
PDYQLSFTAS HNERLPTPME LYYHGQHLAT NSFEYGNKDL KKEISNNFEL GLGYHTEKLD     600
YKLSTYYNNF DNYIYNETLY RSNNLFMRRY NQAKATFYGL KEGIINYRFTP DYQFSVFGDM     660
VKGKLKQLPD IKGLNDVYGE PILNPDYDPE YDEPEDQYYR PYLGKEMIKQ ADRVSPRLPP     720
IRLGARFNAQ LTENLSGSVE WMKVFTQNKV SKLESSTKGY QLLNASLNYR RQIKGVEYTV     780
SLTGNNLLNQ AVYIHNSYHP YVPQMGRNFI LGLDLSF                             817

SEQ ID NO: 51           moltype = AA  length = 825
FEATURE                 Location/Qualifiers
source                  1..825
                        mol_type = protein
                        organism = Moraxella boevrei
SEQUENCE: 51
MAVLASSSMS VFANDSSPET TLDTIVIEAT SANKVNSLAF AESQKASDMV ISKERLKSKS      60
ATLGNALAGE SGIHSNPFGG GASAPVIRGQ EGVRVKILQN GSAVADMSTV SPDHVVAVDT     120
LLASRVEVVR GASTLMHANA SPAGVINVVD GRIPDKMPTG ITGETMLRFN SGSDEKLATA     180
GISAPLNDNF VLRLEAMGRD ANPYNVPAIN FGEVLNYLPD SYNKSTVGTL GLSYIGNQGH     240
IGLAYSERRD KYGLVGHNHK FDNCEGHAFN TSRGLWGPER RYLIPYPHLM SDEDMITSLH     300
FHCGTNYDLD PSHSHEHVYG HKHDHTQKGP WVDMTSKTFS LQGEINQPIP SIDKIRLTAS     360
HSNYEHQEYD DGKQIPDPSK GKIFVKGNTS YWDNQGLSSK LSIYQSPTDR LSFVWGFDNQ     420
RNKTHALIPS PNEKAGNRRL LVKNTQKTHS IFGLSEYKIG NVKLHTALRQ ERTRIPVEYN     480
MDEIKAQLAN GIGTQELPDL TPYKSNATSY AMGAIWDINP KLRLDTTFSH NERTPTPMEL     540
YYHGKHLATN SFLYGNKDLN KEKSDNGELG LTFKGDKWRV KGSIYANKFD NYIHPENLYK     600
SGNLTMRRFT QSKAKLRGAE LEIGYQFNPN LNVSLFGDMV RGKLYGFSPI TGGNLYEKVK     660
VIDPNCDLEK DDPDYEDFCI DIENKVVGKD TITRPDRTPP RLSPDRIGMR INGEYGNFSP     720
SLEFIRVFDQ NRTSNSVAAK YNSECTHHQY GNERLCPIPI QEDATKGYNL LNVGLDYHNY     780
FKGLQYTVSL NANNLLNEKV YIHNSFLPFV PQQGRNFSLA LTTKF                    825

SEQ ID NO: 52           moltype = AA  length = 869
FEATURE                 Location/Qualifiers
source                  1..869
                        mol_type = protein
                        organism = Psychrobacter phenylpyruvicus
SEQUENCE: 52
MKIKPLSYAV SAIMLSYLSH TPMAQAAVSS KTVTDTQDQK QTPSQQASET DSTPDSASNP      60
IAIFDTITVP PSSTHVPSSL AFDNAQKASD VVIDNEKLRH RSATLGNALA DELGVHSNPF     120
GGGSSAPVVR GQEGVRVKIL QNGMDAIDMS TLSPDHVVGV DTLLADKVEL IRGASTLLYS     180
NASPAGVINV VDGRIPTEVP EGYTGEATLR FNENNDERVA TAGITFGLTD NVALRVEGLT     240
RKANEYEVPE INLGDKLNYL PDSQNKSNVG TIGLSYVGER GHIGVAYSER EDKYGLVGHN     300
HKLDGCYGHV VYPQKNYKNK PYLAAYPHLM GDEDLAESFH FHCDSDHNED EPHSHDNPYG     360
HDHDHTQGGP WVDMNSKSYY LQGELLEPIP AIEKVRLNVA YHDYHHEEHD HGKTIPDPAK     420
GERFVKAQPS YFDNQGYNAK LEAYHTPTEH LQGVWGIQSQ SHKSSALIPS KEEHPQNRRP     480
LVENKHRQFS VFGVEQYKLN DWLFEAGLRY EHSKIPVTYN LDEIEAQNKI LGQLLKPEQP     540
DLTPYQESAF SYALGAIWDM TPEYRLDMSY SHNERLPTPM ELYYHGKNLA TNSFLYGNKD     600
LDKEESDNFE LGIQFTGDKW RYKASAYSNH FDNYVHAENL HKDGNLYMRR MTQSKAKIQG     660
LEAEVGYEYL PGHSATLFGD YVRGKLYGFA PVYGNEIKSQ NEVIKYMPPE ECGASPGDDV     720
YEEWCGYPDY EVIGIDKVER PERNAPRMSP LRLGLRLNNE YNDNWSTSLD FTRVFAQNKT     780
STATVVNIPR DESRLKVTEV PEDSTSGYSL LNVGVDYKNT WDNAKHPVDY TLSLRANNLL     840
```

```
DEYIYVHNSF LPYVPQMGRN FMLSLNVEF                                              869

SEQ ID NO: 53           moltype = AA  length = 805
FEATURE                 Location/Qualifiers
source                  1..805
                        mol_type = protein
                        organism = Pasteurella multocida
SEQUENCE: 53
MISRGCKVNK FFAVLMMCCI PQVVWANTEK KQIVFLDEIS VESKGAAFRS DPLSGLPKQN   60
DILVSKQKLK TGSSTLGNAL AGELSVHSNQ FGGGSSAPVV RGQEGVRLKI LQNGSDVIDM  120
SQLSPDHAIG VDTLLAEQVE IVRGASTLLY ANASPAGVIN VVDKRIPTQL PQKGYEVDFN  180
TRYNTNSHEK LVTAALTFGL GKHIALRVEE LLRGSNNYHV PAFKLDKTLN YVPDTQNKTK  240
SGNYGVAFIG ERGYVGFAYN LRREKYGLPG HNHKLDSCAA HIWGGNVRND YYLELYPHLM  300
HDTDLVNTHF HCGSNHDMDG KHSHDHPYGH DHDHSIAGPL IDSYAKRYDI RAEVKQPMKA  360
IEKIKLSYSE TRYKHDEKDG NIAVNLFKNN GYNLRVEIFH TPIAGLSGVI GAQYQTQTSS  420
ANIPRIALCS NNASDPCHKK KQRDPSKITK GDRKSWALIE NTQSQMSFFA IEQLRWQDFL  480
FEIGVRTEKQ RIDIEYDRAW LFKVKRKLEG CDPNSFFYSP SGCRQGSYPA PDFASYHDRA  540
TSYSGAISWN MTPDYTLSLT YSHNERHPTP MELYYHGKHL ATVSFEHGNR NLKKEVSDNW  600
EVGLAYLGDK LSYKVNVYYN DFKNRIFNQT LNKSGNLSLN RYNQSKAKYY GVEGRIDYAL  660
TPELHMGLFG DYVRGKLYDL PPTYRVDHVA NSLEPVPQPD QDAPRVPPMR LGFRVNMEMT  720
ESLTSSLEYT YVYQQKKVAP LENQTAAYSL LNIRVDYSRQ IAGVNYQLFV QANNVLNRKV  780
YSHTSFLPFV PQMGRNVTLG LNIHF                                       805

SEQ ID NO: 54           moltype = AA  length = 826
FEATURE                 Location/Qualifiers
source                  1..826
                        mol_type = protein
                        organism = Moraxella bovoculi
SEQUENCE: 54
MVNLYSRPTV LALSIALVSL SAHADDTATK TEVTLDTLNA VVKGGMQTTS TLKKPSDMII   60
RRDTLQQRSA TLGNALAGEL GIHSNPFGGG ASKPIIRGQD GVRVKILQNG TDVIDMSALS  120
PDHVAADTL LASRVELVRG AGTLLYGTAS QAGVVNVIDE RIPSRMPQGN IKEKIEGETL  180
LRYNTGSNEK VVTASLNMGV GQNVAVRVEG LTRRADDYEV PGFQSDVMLD YLPDSHNKST  240
VGTVGVSYIG DKGHIGVSYS RRQDKYGIPG HNHAYDNCIA HVLTPEASIS RYYLKAYPHL  300
IQNMDFSSSA HFHCGTDHAH DPGQSHEHPL GYEHDHTHPG PWIDMESERI DVRAQWEKPF  360
KGLDKIALSF TSSDYYHEEN DHEVEKLDKY TGRLQTINNK PGYFGNQGKN VRVEFHHTPV  420
KDVSGLWGMQ WQKQESFAHL PHEREEGQRY PLIANTNKQV SVFGLERWQA NDKWAFEFGT  480
RFEKQSIPID YSEDKLDRYR PKPECWDWGF SSGCLPAPNY EEPDLTTYKE KATSYSIGTT  540
WDFKPDYRLS ATYSHNERLP TPMELYYHGK HLATHSFEFG NIGLDKEKSN NLDLGISFSG  600
DKWSYAVNAY HSRFKNYIYN ENVYREGNLF MRRHNQAKAD FYGLEGMVTY NMDNHAISLF  660
GDLVRGKLKD LPNAYAKAYY CDGAYTTTKP EDTEENMQRC NYNYFTDDFN YSYEPIIAQP  720
NMPTPRLPPA RLGLRWQGDL SANWSADAEY MHVFGQNRIS KLESATASYD MLNLGLGYHN  780
HWGNVDYTLS LRANNVLDEK VYIHNSFLPF VPQMGRNFSL SANFKF                826

SEQ ID NO: 55           moltype = AA  length = 850
FEATURE                 Location/Qualifiers
source                  1..850
                        mol_type = protein
                        organism = Conchiformibius steedae
SEQUENCE: 55
MFSRMLILPL LLGLGANAAY AEQNTSPAKP ATEDNEGKTL PAMQGVGKRR DTAQPFSGNR   60
KASDMVISQE KLKSRSANLG EALAGELGIH GNPFGGGASA PVIRGQEGVR VKILQGGSDV  120
VDMSALSPDH AVAADTLLAQ QVEVLRGTST LAYAAASPAG VINITDKRIP DRLPAKGWEA  180
ETGVRFDTAA KEKALTAGAT FGIGKHFAVR AEGLERKSDD YRVPGINLGE TLKYVPDTYN  240
RSHTGTLGVS WVGQNGHLGV SYSHRKDRYG LPGHNHMLDN CSGHVFDVTT ASAVKRNYLL  300
PYPHLIGDED VNLSQHFHCH TEHSSNAKHS HDNVYGHKHD HGEPGPWIDM RVRRYDVRGE  360
WRTQLPFLEK IRLTSAYTDY YHDEKNDGKV YISPDDPEGW RERKLKDAAA RKGKPDIILK  420
NKGLNTRLEF FHRFGSVWNG MAGVQYQTQR SSARRVMPPM IGGERYINER NPLVDNTNKQ  480
LSLFALQQYR RGNWLAEGGV RWEKQRIPIR YDHDLLAQYV KPGTQQPDLK PYSQKALSYS  540
GSLLWDFKPG YRLSLTASHN ERLPTPMELY YHGKHLATNS FEYGNKDLKK ERSNNYEIGL  600
RYFGDKWDYK LSVYHNRFKN YIYNENLYRS GNLFIRRNTQ AQGRFHGVEG EVSYRFKPTH  660
QVTLFGDMVR GRLFGLSPVY GDKIYREYEC VDEDGLEDTC FEVVGREKIE RPDRHAPRVP  720
PTRLGLRLNS QWGDNWTASL EYARVWAQNR TAVSQFPRER DDEDDEDEDE GNPKPRQQKL  780
YAEPVLEDPT SGYHLLNAGI AYRKRIGKAD YRVSLDAFNL LNKKVYIHNS HLPYVPRPGR  840
NFVFGVNVSF                                                        850
```